(12) United States Patent
Sawyers et al.

(10) Patent No.: US 7,709,517 B2
(45) Date of Patent: *May 4, 2010

(54) DIARYLHYDANTOIN COMPOUNDS

(75) Inventors: Charles L. Sawyers, New York, NY (US); Michael E. Jung, Los Angeles, CA (US); Charlie D. Chen, Los Angeles, CA (US); Samedy Ouk, Costa Mesa, CA (US); Derek Welsbie, Northridge, CA (US); Chris Tran, New York, NY (US); John Wongvipat, Nanuet, NY (US); Dongwon Yoo, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 592 days.

This patent is subject to a terminal disclaimer.

(21) Appl. No.: 11/433,829

(22) Filed: May 15, 2006

(65) Prior Publication Data

US 2007/0004753 A1    Jan. 4, 2007

Related U.S. Application Data

(60) Provisional application No. 60/680,835, filed on May 13, 2005, provisional application No. 60/750,351, filed on Dec. 15, 2005, provisional application No. 60/756,552, filed on Jan. 6, 2006, provisional application No. 60/786,837, filed on Mar. 29, 2006.

(51) Int. Cl.
*A61K 31/4166* (2006.01)
*C07D 233/02* (2006.01)

(52) U.S. Cl. .................. 514/392; 548/300.1; 548/316.4; 548/317.1; 548/321.1; 514/385; 514/386

(58) Field of Classification Search .............. 548/300.1, 548/316.4, 317.1, 321.1; 514/385, 386, 392; 544/358, 359, 370; 546/184, 192, 207, 210
See application file for complete search history.

(56) References Cited

U.S. PATENT DOCUMENTS

| | | | |
|---|---|---|---|
| 3,823,240 A | 7/1974 | Sauli | |
| 3,984,430 A | 10/1976 | Curran | |
| 4,097,578 A | 6/1978 | Perronnet et al. | |
| 4,234,736 A | 11/1980 | Bernauer et al. | |
| 4,304,782 A | 12/1981 | Dumont et al. | |
| 4,312,881 A | 1/1982 | Wootton | |
| 4,399,216 A | 8/1983 | Axel et al. | |
| 4,407,814 A | 10/1983 | Bernauer et al. | |
| 4,427,438 A | 1/1984 | Nagano et al. | |
| 4,473,393 A | 9/1984 | Nagpal | |
| 4,482,739 A | 11/1984 | Bernauer et al. | |
| 4,559,157 A | 12/1985 | Smith et al. | |
| 4,608,392 A | 8/1986 | Jacquet et al. | |
| 4,749,403 A | 6/1988 | Liebl et al. | |
| 4,820,508 A | 4/1989 | Wortzman | |
| 4,859,228 A | 8/1989 | Prisbylla | |
| 4,873,256 A | 10/1989 | Coussediere et al. | |
| 4,938,949 A | 7/1990 | Borch et al. | |
| 4,944,791 A | 7/1990 | Schröder et al. | |
| 4,992,478 A | 2/1991 | Geria | |
| 5,010,182 A | 4/1991 | Brake et al. | |
| 5,069,711 A | 12/1991 | Fischer et al. | |
| 5,071,773 A | 12/1991 | Evans et al. | |
| 5,166,358 A | 11/1992 | Seuron et al. | |
| 5,411,981 A | 5/1995 | Gaillard-Kelly et al. | |
| 5,434,176 A | 7/1995 | Claussner et al. | |
| 5,556,983 A | 9/1996 | Claussner et al. | |
| 5,589,497 A | 12/1996 | Claussner et al. | |
| 5,614,620 A | 3/1997 | Liao et al. | |
| 5,627,201 A | 5/1997 | Gaillard-Kelly et al. | |
| 5,646,172 A | 7/1997 | Claussner et al. | |
| 5,656,651 A | 8/1997 | Sovak et al. | |
| 5,705,654 A | 1/1998 | Claussner et al. | |
| 5,750,553 A | 5/1998 | Claussner et al. | |
| RE35,956 E | 11/1998 | Gaillard-Kelly et al. | |
| 5,958,936 A | 9/1999 | Claussner et al. | |
| 5,985,868 A | 11/1999 | Gray | |
| 6,087,509 A | 7/2000 | Claussner et al. | |
| 6,107,488 A | 8/2000 | Bouchet et al. | |
| 6,235,910 B1 | 5/2001 | Beller et al. | |
| 6,242,611 B1 | 6/2001 | Claussner et al. | |
| 6,307,030 B1 | 10/2001 | French et al. | |
| 6,472,415 B1 | 10/2002 | Sovak et al. | |
| 6,479,063 B2 | 11/2002 | Weisman et al. | |
| 6,489,163 B1 | 12/2002 | Roy et al. | |
| 6,506,607 B1 | 1/2003 | Shyjan | |
| 6,828,471 B2 | 12/2004 | Sawyers et al. | |
| 7,271,188 B2 | 9/2007 | Tachibana et al. | |
| 2002/0133833 A1 | 9/2002 | Sawyers et al. | |
| 2004/0009969 A1 | 1/2004 | Cleve et al. | |
| 2004/0116417 A1 | 6/2004 | Boubia et al. | |
| 2005/0153968 A1 | 7/2005 | Bi et al. | |
| 2007/0249697 A1 | 10/2007 | Tachibana et al. | |

FOREIGN PATENT DOCUMENTS

| | | |
|---|---|---|
| AU | 217893 | 6/1958 |
| DE | 2102605 | 7/1971 |
| EP | 0017976 A2 | 10/1980 |
| EP | 0017976 A3 | 10/1980 |
| EP | 0017976 B1 | 6/1983 |

(Continued)

OTHER PUBLICATIONS

International Search Report issued in PCT Application No. PCT/US06/11417 dated Jul. 3, 2006.

(Continued)

*Primary Examiner*—Golam M Shameem
(74) *Attorney, Agent, or Firm*—Venable LLP; Michael A. Gollin; Lars H. Genieser

(57) ABSTRACT

The present invention relates to diarylhydantoin compounds, including diarylthiohydantoins, and methods for synthesizing them and using them in the treatment of hormone refractory prostate cancer.

13 Claims, 29 Drawing Sheets

FOREIGN PATENT DOCUMENTS

| | | |
|---|---|---|
| EP | 0 002 259 B1 | 10/1984 |
| EP | 033123 A2 | 9/1989 |
| EP | 362179 | 4/1990 |
| EP | 0 494 819 A1 | 1/1992 |
| EP | 0 578 516 A1 | 5/1993 |
| EP | 0 580 459 A1 | 5/1993 |
| EP | 0572191 A1 | 12/1993 |
| EP | 0 580 459 B1 | 1/1994 |
| EP | 0 494 819 B1 | 7/1996 |
| EP | 0 721 944 B1 | 1/2001 |
| EP | 1 790 640 A | 5/2007 |
| FR | 2 693 461 A1 | 1/1994 |
| FR | 2 715 402 A1 | 1/1994 |
| FR | 2 845 348 A1 | 10/2002 |
| JP | 2019363 A | 1/1990 |
| WO | WO 90/13646 | 11/1990 |
| WO | WO 97/00071 | 1/1997 |
| WO | WO 97/19064 | 5/1997 |
| WO | WO 97/19931 | 6/1997 |
| WO | WO 00/17163 | 3/2000 |
| WO | WO 02/053155 A1 | 7/2002 |
| WO | WO 02/081453 A1 | 10/2002 |
| WO | WO 03/029245 A1 | 4/2003 |
| WO | WO 2003/057220 A1 | 7/2003 |
| WO | WO 03/093243 A1 | 11/2003 |
| WO | WO 03/096980 | 11/2003 |
| WO | WO 2004/031160 A2 | 4/2004 |
| WO | WO 2004/070050 A2 | 8/2004 |
| WO | WO 2005/059109 | 6/2005 |
| WO | WO 2005/060661 | 7/2005 |
| WO | WO 05/089752 | 9/2005 |
| WO | WO 2005/099693 | 10/2005 |
| WO | WO 06/010642 | 2/2006 |
| WO | WO 2006/028226 A1 | 3/2006 |
| WO | WO 2006/124118 A1 | 11/2006 |
| WO | WO 2007/126765 | 11/2007 |
| WO | WO 2007/127010 | 11/2007 |
| WO | WO 2008/119015 A2 | 10/2008 |

OTHER PUBLICATIONS

Wallen et al., "Androgen Receptor Gene Mutations in Hormone-Refractory Prostate Cancer", J. Pathology 1999, vol. 189, pp. 559-563.
Lu et al. "Molecular Mechanisms of Androgen-Independent Growth of Human Prostate Cancer LNCaP-AI Cells", Endocrinology 1999, vol. 140, No. 11, pp. 5054-5059.
Karp et al., Cancer Res. 56: 5547-5556.
Ausubel et al., Current Protocols in Molecular Biology, Wiley Interscience Publishers, (1995).
Sambrook et al., Molecular Cloning: A Laboratory Manual 2$^{nd}$ edition (1989) Cold Spring Harbor Laboratory Press, Cold Spring Harbor, N.Y.
Chang et al., Science 240 (4850), 324-326 (1988).
NM_000044<http://www.ncbi.nlm.nih.gov:80/entrez/viewer.fcgi?cmd=Retrieve&db=nucleotide&list_uids=21322251&dopt=GenBank&term=sapiens+AR+androgen+receptor+prostate+cancer&qty=1>gi:21322251, printed Oct. 24, 2007.
*Mammalian Cell Biotechnology: a Practical Approach*, M. Butler, ed. (IRL Press, 1991).
Graham and van der Eb, Virology, 52:456-467.
Keown et al., Methods in Enzymology, 185:527-537 (1990).
Mansour et al., Nature, 336:348-352 (1988).
Muller et al., 1991, Mol. & Cell. Bio. 11:1785.
Urlaub et al., Proc. Natl. Acad. Sci. USA, 77:4216 (1980).
Stinchcomb et al., Nature, 282:39 (1979).
Kingsman et al., Gene, 7: 141 (1979).
Tschumper et al., Gene, 10: 157 (1980).
Jones, Genetics, 85:12 (1977).

Feldman, B.J. & Feldman, D. The development of androgen-independent prostate cancer. Nat Rev Cancer 1, 34-45 (2001).
Gelmann, E.P. Molecular biology of the androgen receptor. J Clin Oncol 20, 3001-15 (2002).
Balk, S. P. Androgen receptor as a target in androgen-independent prostate cancer. Urology 60, 132-8; discussion 138-9 (2002).
Taplin, M.E. et al. Selection for androgen receptor mutations in prostate cancers treated with androgen antagonist. Cancer Res 59, 2511-5 (1999).
Taplin, M.E. et al. Androgen receptor mutations in androgen-independent prostate cancer: Cancer and Leukemia Group B Study 9663. J Clin Oncol 21, 2673-8 (2003).
Visakorpi, T. et al. In vivo amplification of the androgen receptor gene and progression of human prostate cancer. Nat Genet 9, 401-6 (1995).
Taplin, M.E. et al. Mutation of the androgen-receptor gene in metastatic androgen-independent prostate cancer. N Engl J Med 332, 1393-8 (1995).
Veldscholte, J. et al. A mutation in the ligand binding domain of the androgen receptor of human LNCaP cells affects steroid binding characteristics and response to anti-androgens. Biochem Biophys Res Commun 173, 534-40 (1990).
Matias, P.M. et al. Structural basis for the glucocorticoid response in a mutant human androgen receptor (AR(ccr)) derived from an androgen-independent prostate cancer. J Med Chem 45, 1439-46 (2002).
Craft, N., Shostak, Y., Carey, M. & Sawyers, C.L. A mechanism for hormone-independent prostate cancer through modulation of androgen receptor signaling by the HER-2/neu tyrosine kinase. Nat Med 5, 280-5 (1999).
Gioeli, D. et al. Androgen receptor phosphorylation. Regulation and identification of the phosphorylation sites. J Biol Chem 277, 29304-14 (2002).
Kato, S. et al. Activation of the estrogen receptor through phosphorylation by mitogen-activated protein kinase. Science 270, 1491-4 (1995).
Font de Mora, J. & Brown, M. AIB1 is a conduit for kinase-mediated growth factor signaling to the estrogen receptor. Mol Cell Biol 20, 5041-7 (2000).
Tremblay, A., Tremblay, G.B., Labrie, F. & Giguere, V. Ligand-independent recruitment of SRC-1 to estrogen receptor beta through phosphorylation of activation function AF-1. Mol Cell 3, 513-9 (1999).
Gregory, C.W. et al. A mechanism for androgen receptor-mediated prostate cancer recurrence after androgen deprivation therapy. Cancer Res 61, 4315-9 (2001).
Li, P. et al. Heterogeneous expression and functions of androgen receptor co-factors in primary prostate cancer. Am J Pathol 161, 1467-74 (2002).
Glass, C.K. & Rosenfeld, M.G. The coregulator exchange in transcriptional functions of nuclear receptors. Genes Dev 14, 121-41 (2000).
Raffo, A.J. et al. Overexpression of bcl-2 protects prostate cancer cells from apoptosis in vitro and confers resistance to androgen depletion in vivo. Cancer Res 55, 4438-45 (1995).
McDonnell, T.J. et al. Expression of the protooncogene bcl-2 in the prostate and its association with emergence of androgen-independent prostate cancer. Cancer Res 52, 6940-4 (1992).
Kinoshita, H. et al. Methylation of the androgen receptor minimal promoter silences transcription in human prostate cancer. Cancer Res 60, 3623-30 (2000).
Shang, Y., Myers, M. & Brown, M. Formation of the androgen receptor transcription complex. Mol Cell 9, 601-10 (2002).
Zhau, H.Y. et al. Androgen-repressed phenotype in human prostate cancer. Proc Natl Acad Sci U S A 93,15152-7 (1996).
Wainstein, M.A. et al. CWR22: androgen-dependent xenograft model derived from a primary human prostatic carcinoma. Cancer Res 54, 6049-52 (1994).
Ellis, W.J. et al. Characterization of a novel androgen-sensitive, prostate-specific antigen-producing prostatic carcinoma xenograft: LuCaP 23. Clin Cancer Res 2, 1039-48 (1996).
Horoszewicz, J.S. et al. LNCaP model of human prostatic carcinoma. Cancer Res 43, 1809-18 (1983).

Klein, K.A. et al. Progression of metastatic human prostate cancer to androgen independence in immunodeficient SCID mice. Nat Med 3, 402-8 (1997).

Perou, C.M. et al. Molecular portraits of human breast tumors. Nature 406, 747-52 (2000).

Gregory, C.W., Johnson, R.T., Jr., Mohler, J.L., French, F.S. & Wilson, E.M. Androgen receptor stabilization in recurrent prostate cancer is associated with hypersensitivity to low androgen. Cancer Res 61, 2892-8. (2001).

Huang, Z.Q., Li, J. & Wong, J. AR possess an intrinsic hormone-independent transcriptional activity. Mol Endocrinol 16, 924-37 (2002).

Matias, P.M. et al. Structural evidence for ligand specificity in the binding domain of the human androgen receptor. Implications for pathogenic gene mutations. J Biol Chem 275, 26164-71 (2000).

Lobaccaro, J.M. et al. Molecular modeling and in vitro investigations of the human androgen receptor DNA-binding domain: application for the study of two mutations. Mol Cell Endocrinol 116, 137-47 (1996).

Migliaccio, A. et al. Steroid-induced androgen receptor-oestradiol receptor beta-Src complex triggers prostate cancer cell proliferation. Embo J 19, 5406-17 (2000).

Kousteni, S. et al. Nongenotropic, sex-nonspecific signaling through the estrogen or androgen receptors: dissociation from transcriptional activity. Cell 104, 719-30 (2001).

Manolagas, S.C., Kousteni, S. & Jilka, R.L. Sex steroids and bone. Recent Prog Horm Res 57, 385-409 (2002).

DePrimo, S.E. et al. Transcriptional programs activated by exposure of human prostate cancer cells to androgen. Genome Biol 3, RESEARCH0032 (2002).

Masiello, D., Cheng, S., Bubley, G.J., Lu, M.L. & Balk, S.P. Bicalutamide functions as an androgen receptor antagonist by assembly of a transcriptionally inactive receptor. J Biol Chem 277, 26321-6 (2002).

Edwards, J., Krishna, N.S., Grigor, K.M. & Bartlett, J.M. Androgen receptor gene amplification and protein expression in hormone refractory prostate cancer. Br J Cancer 89, 552-6 (2003).

Laitinen, S., Karhu, R., Sawyers, C.L., Vessella, R.L. & Visakorpi, T. Chromosomal aberrations in prostate cancer xenografts detected by comparative genomic hybridization. Genes Chromosomes Cancer 35, 66-73 (2002).

Grad, J.M., Dai, J.L., Wu, S. & Burnstein, K.L. Multiple androgen response elements and a Myc consensus site in the androgen receptor (AR) coding region are involved in androgen-mediated up-regulation of AR messenger RNA. Mol Endocrinol 13, 1896-911 (1999).

Craft, N. et al. Evidence for clonal outgrowth of androgen-independent prostate cancer cells from androgen-dependent tumors through a two-step process. Cancer Res 59,5030-6 (1999).

Ellwood-Yen, K. et al. Myc-driven murine prostate cancer shares molecular features with human prostate tumors. Cancer Cell 4, 223-38 (2003).

Wang, S. et al. Prostate-specific deletion of the murine Pten tumor suppressor gene leads to metastatic prostate cancer. Cancer Cell 4, 209-21 (2003).

Shiau, A.K. et al. The structural basis of estrogen receptor/coactivator recognition and the antagonism of this interaction by tamoxifen. Cell 95, 927-37 (1998).

Norris, J.D. et al. Peptide antagonists of the human estrogen receptor. Science 285, 744-6 (1999).

Baek, S.H. et al. Exchange of N-CoR corepressor and Tip60 coactivator complexes links gene expression by NF-kappaB and beta-amyloid precursor protein. Cell 110, 55-67 (2002).

Shang, Y. & Brown, M. Molecular determinants for the tissue specificity of SERMs. Science 295, 2465-8 (2002).

Schellhammer, P.F. et al. Prostate specific antigen decreases after withdrawal of antiandrogen therapy with bicalutamide or flutamide in patients receiving combined androgen blockade. J Urol 157, 1731-5 (1997).

Sack, J.S. et al. Crystallographic structures of the ligand-binding domains of the androgen receptor and its T877A mutant complexed with the natural agonist dihydrotestosterone. Proc Natl Acad Sci U S A 98, 4904-9 (2001).

Zhou, Z.X., Sar, M., Simental, J.A., Lane, M.V. & Wilson, E.M. A ligand-dependent bipartite nuclear targeting signal in the human androgen receptor. Requirement for the DNA-binding domain and modulation by NH2-terminal and carboxyl-terminal sequences. J Biol Chem 269, 13115-23 (1994).

Chen, C.D., Welsbie, D.S., Tran, C., Baek, S.H., Chen, R., Vessella, R., Rosenfeld, M.G., and Sawyers, C.L., Molecular determinants of resistance to antiandrogen therapy, Nat. Med., 10: 33-39, 2004.

*The Pharmacological Basis of Therapeutics,* Goodman and Gilman, eds., Macmillan Publishing Co., New York.

The Practice of Medicinal Chemistry, Camille G. Wermuth et al., Ch 31, (Academic Press, 1996).

Design of Prodrugs, edited by H. Bundgaard, (Elsevier, 1985).

A Textbook of Drug Design and Development, P. Krogsgaard-Larson and H. Bundgaard, eds. Ch 5, pp. 113-191 (Harwood Academic Publishers, 1991).

Remington: The Science and Practice of Pharmacy, $19^{th}$ Edition, Gennaro (ed.) 1995, Mack Publishing Company, Easton, PA.

Teutsch, G.; Goubet, F.; Battmann, T.; Bonfils, A.; Bouchoux, F.; Cerede, E.; Gofflo, D.; Gaillard-Kelly, M.; Philibert. D. ..*J. Steroid Biochem. Molec. Biol.* 1994, 48, 111-119.

Van Dort, M. E.; Robins, D. M.; Wayburn, B. *J. Med. Chem.* 2000, 43, 3344-3347.

Homma,S., et al., "Differential levels of human leukocyte antigen-class I, multidrug-resistance 1 and androgen receptor expressions in untreated prostate cancer cells: the robustness of prostate cancer", Oncol. Rep. 18 (2), 343-346 (2007).

Cai,C., et al., "c-Jun has multiple enhancing activities in the novel cross talk between the androgen receptor and Ets variant gene 1 in prostate cancer", Mol. Cancer Res. 5 (7), 725-735 (2007).

Su,Q.R., et al., "Polymorphisms of androgen receptor gene in childhood and adolescent males with first-onset major depressive disorder and associationwith related symptomatology", Int. J. Neurosci. 117 (7), 903-917 (2007).

Brockschmidt,F.F., et al., "The two most common alleles of the coding GGN repeat in the androgen receptor gene cause differences in protein function", J. Mol. Endocrinol. 39 (1), 1-8 (2007).

Hamilton-Reeves,J.M., et al, "Isoflavone-rich soy protein isolate suppresses androgen receptor expression without altering estrogen receptor-beta expression or serum hormonal profiles in men at high risk of prostate cancer", J. Nutr. 137 (7), 1769-1775 (2007).

Sweet,C.R., et al., "A unique point mutation in the androgen receptor gene in a family with complete androgen insensitivity syndrome", Fertil. Steril. 58 (4), 703-707 (1992).

Batch,J.A., et al., "Androgen receptor gene mutations identified by SSCP in fourteen subjects with androgen insensitivity syndrome", Hum. Mol. Genet. 1 (7), 497-503 (1992).

Wooster,R., et al., "A germline mutation in the androgen receptor gene in two brothers with breast cancer and Reifenstein syndrome", Nat. Genet. 2 (2), 132-134 (1992).

Saunders,P.T., et al., "Point mutations detected in the androgen receptor gene of three men with partial androgen insensitivity syndrome", Clin. Endocrinol. (Oxf) 37 (3), 214-220 (1992).

Zoppi,S., et al. "Amino acid substitutions in the DNA-binding domain of the human androgen receptor are a frequent cause of receptor-binding positive androgen resistance", Mol. Endocrinol. 6 (3), 409-415 (1992).

International Search Report issued in PCT Application PCT/US2005/005529, mailed on Nov. 10, 2005.

International Search Report issued in PCT Application PCT/US2004/042221, mailed on Jun. 20, 2005.

Wang, Long G., et al., "Overexpressed androgen receptor linked to p21WAF1 silencing may be responsible for androgen independence and resistance to apoptosis of a prostate cancer cell line", Cancer Research 61 (20), pp. 7544-7551 (Oct. 15, 2001).

Shi, Xu-Bao, et al., "Functional analysis of 44 mutant androgen receptors from human prostate cancer", Cancer Research 62 (5), pp. 1496-1502 (Mar. 1, 2002).

Navone, N. M., et al., "Model Systems of Prostate Cancer: Uses and Limitations" Cancer Metastasis, Kluwer Academic Publishers, Dordrecht, NL, 17 (4), 1999, pp. 361-371.

Extended European Search Report issued in European Patent Application No. EP 06748863.5, mailed on Feb. 12, 2009.

International Search Report issued in International Application No. PCT/US2007/007854, mailed on Apr. 15, 2008.

Written Opinion issued in International Application No. PCT/US2007/007854, mailed on Apr. 15, 2008.

S.Ouk et al., "Development Of Androgen Receptor Inhibitors For Hormone-refractory Prostate Cancer", Prostate Cancer Foundation Meeting, Scottsdale, AZ, Sept. 29-Oct. 1, 2005.

Cousty-Berlin, et al., "Preliminary Pharmacokinetics and Metabolism of Novel Nonsteroidal Antiandrogens in the Rat: Relation of their Systemic Activity to the Formation of a Common Metabolite," *J. Steroid Biochem. Molec. Biol.*, vol. 51, No. 1/2, pp. 47-55 (1994).

Feher, et al., "BHB: A Simple Knowledge-Based Scoring Function to Improve the Efficiency of Database Screening," *J. Chem. Inf. Comput. Sci.*, vol. 43, pp. 1316-1327 (2003).

Foury, et al., "Control of the Proliferation of Prostate Cancer Cells by an Androgen and Two Antiandrogens. Cell Specific Sets of Responses," *J. Steroid Biochem. Molec. Biol.*, vol. 66, No. 4, pp. 235-240 (1998).

Goubet, et al., Conversion of a Thiohydantoin to he Corresponding Hydantoin via a Ring-Opening/Ring Closure Mechanism, *Tetrahedron Letters*, vol. 37, No. 43, pp. 7727-7730 (1996).

Karvonen, et al., "Interaction of Androgen Receptors with Androgen Response Element in Intact Cells," *The Journal of Biological Chemistry*, vol. 272, No. 25, pp. 15973-15979 (1997).

Kemppainen, et al., "Distinguishing Androgen Receptor Agonists and Antagonists: Distinct Mechanisms of Activation by Medroxyprogesterone Acetate and Dihydrotestosterone," *Mol. Endocrinol.*, vol. 13, pp. 440-454 (1999); mend.endojournals.org,.

Marhefka, et al., "Homology Modeling Using Multiple Molecular Dynamics Simulations and Docking Sudies of the Human Androgen Receptor Ligand Binding Domain Bound to Testosterone and Nonsteroidal Ligands," *J. Med. Chem.*, vol. 44, No. 11, pp. 1729-1740 (2001).

Matias, et al., "Local Inhibition of Sebaceous Gland Growth by Topically Applied RU 58841," *NY Acad. Sci.*, vol. 761, pp. 56-65 (1995).

Sderholm, et al., "Three-Dimensional Structure—Activity Relationships of Nonsteroidal Ligands in Complex with Androgen Receptor Ligand-Binding Domain," *J. Med. Chem.*, vol. 48, No. 4, pp. 917-925 (2005).

Sperry, et al., Androgen binding profiles of two distinct nuclear androgen receptors in Atlantic croaker (*Micropogonias undulates*), *Journal of Steroid Biochemistry & Molecular Biology*, vol. 73, pp. 93-103 (2000).

Zarghami, et al., "Steroid hormone regulation of prostate-specific antigen gene expression in breast cancer," *British Journal of Cancer*, vol. 75, No. 4, pp. 579-588 (1997).

International Search Report issued in PCT Application PCT/US2007/07485, mailed on Sep. 4, 2008.

Written Opinion issued in PCT Application PCT/US2007/07485, mailed on Sep. 4, 2008.

International Search Report issued in International Application No. PCT/US2008/012149 mailed on Apr. 29, 2009.

Written Opinion issued in International Application No. PCT/US2008/012149, mailed on Apr. 29, 2009.

Office Action issued in U.S. Appl. No. 10/590,445, mailed on Mar. 2, 2009.

International Search Report issued in International Application No. PCT/US2007/007854, mailed on Apr. 15, 2008.

International Search Report issued in PCT Application No. PCT/US2004/042221, mailed on Jun. 20, 2005.

Written Opinion issued in PCT Application No. PCT/US2004/042221, mailed on Jun. 20, 2005.

Written Opinion issued in PCT Application No. PCT/US2005/005529, mailed on Nov. 10, 2005.

Written Opinion issued in PCT Application No. PCT/US2006/011417, mailed on Jul. 3, 2006.

Data Sheet from U.S. Patent and Trademark Office (USPTO) File Wrapper for U.S. Appl. No. 08/807,760.

Notice of References Cited from U.S. Patent and Trademark Office (USPTO) File Wrapper for U.S. Appl. No. 08/807,760.

Office Action of Jan. 18, 1994 from U.S. Patent and Trademark Office for U.S. Appl. No. 08/064,257.

Office Action (paper No. 7) from U.S. Patent and Trademark Office for U.S. Appl. No. 08/064,257.

Office Action (paper No. 10) from U.S. Patent and Trademark Office for U.S. Appl. No. 08/064,257.

Office Action of Aug. 14, 1992 from U.S. Patent and Trademark Office for U.S. Appl. No. 07/819,110.

Notice of References Cited of Jul. 24, 1992 from U.S. Patent and Trademark Office for U.S. Appl. No. 07/819,110.

Office Action of Feb. 22, 1993 from U.S. Patent and Trademark Office for U.S. Appl. No. 07/819,110.

Office Action of Sep. 2, 1993 from U.S. Patent and Trademark Office for U.S. Appl. No. 07/819,110.

Office Action of Jun. 1, 1994 from U.S. Patent and Trademark Office for U.S. Appl. No. 07/819,110.

M.J. Linja et al., "Amplification and overexpression of androgen receptor gene in hormone-refractory prostate cancer", Cancer Research, vol. 61 (May 1, 2001) pp. 3550-3555.

J. Holzbeierlein et al., "Gene Expression Analysis of Human Prostate Carcinoma during Hormonal Therapy Identifies Androgen-Responsive Genes and Mechanisms of Therapy Resistance", Am. J. Pathology, vol. 164, No. 1 (Jan. 2004) pp. 217-227.

C.D. Chen et al., "Molecular determinants of resistance to antiandrogen therapy", Nature Medicine, vol. 10, No. 1 (Jan. 2004) pp. 33-39.

Office Action of Jul. 23, 2008 from U.S. Patent and Trademark Office for U.S. Appl. No. 10/590,445.

Karp et al., "Prostate Cancer Prevention: Investigational Approaches and Opportunities", Cancer Res., v. 56 (Dec. 15, 1996) pp. 5547-5556.

Graham and van der Eb, "A new technique for the assay of infectivity of human adenovirus 5 DNA", Virology, v. 52(2) (Apr. 1973) pp. 456-467.

P.J. Creaven et al., "Pharmacokinetics and Metabolism of Nilutamide", Supp. Urology, vol. 37, No. 2 (Feb. 1991) pp. 13-19.

Singh et al., "*Androgen Receptor Antagonists (Antiandrogens): Structure-Activity Relationships*", Current Medicinal Chemistry, 2000, 7, pp. 211-247.

Bohl et al., "*Structural basis for antagonism and resistance of bicalutamide in prostate cancer*", Proc. Nat. Acad. Sci., 2005, v. 102(17), pp. 6201-6206.

Nam et al., "Action of the Src Family Kinase Inhibitor, Dasatinib (BMS-354825), on Human Prostate Cancer Cells", Cancer Res., 2005, v. 65(20), pp. 9185-9189.

Burnstein et al. Androgen Glucocorticoid Regulation of Androgen Receptor cDNA Expression. *Molecular and Cellular Endocrinology*. 1995. v. 115, pp. 177-186.

Cinar et al. Androgen Receptor Mediates the Reduced Tumor Growth, Enhanced Androgen Responsiveness, and Selected Target Gene Transactivation in Human Prostate Cancer Cell Line. *Cancer Research*. 2001. v. 61. pp. 7310-7317.

Szelei et al. Androgen-Induced Inhibition of Proliferation in Human Breast Cancer MCF7 Cells Transfected with Androgen Receptor. Endocrinology. 1999. v. 138 (4). pp. 1406-1412.

Raffo et al. Overexpression of bcl-2 Protects Prostate Cancer Cells from Apoptosis in Vitro and Confers Resistance to Androgen Depletion in Vivo. Cencer Research. 1995. v. 55. 4438-4445.

Office Action of Aug. 11, 2009 from U.S. Patent and Trademark Office for U.S. Appl. No. 10/583,280.

Presentation of Charles Sawyers, Prostate Cancer Foundation Scientific Retreat, Scottsdale, Arizona, Sept. 29 - Oct. 1, 2005.

Abstract submitted by Samedy Ouk, Prostate Cancer Foundation Scientific Retreat, Scottsdale, Arizona, Sept. 29 - Oct. 1, 2005.

CHARACTERISTICS OF Bicalutimide, RD37, RD131 AND RD162

| NAME | STRUCTURE | IC$_{50}$ [nM] | LogP | C$_{SS}$,10mpk [µM] | C$_{SS}$,25mpk [µM] | C$_{SS}$,50mpk [µM] |
|------|-----------|----------------|------|---------------------|---------------------|---------------------|
| Bic. | 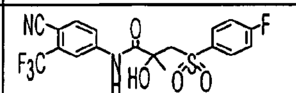 | 1000 | 2.91 | 10.0 | 11.4 | 11.9 |
| RD37 | 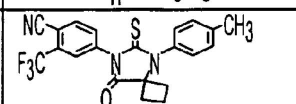 | 124 | 4.20 | NA | NA | NA |
| RD131 | 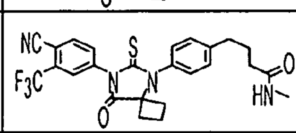 | 92 | 3.44 | 0.39 | 0.43 | 0.40 |
| RD162 | 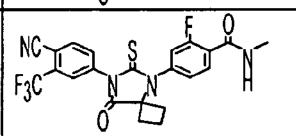 | 122 | 3.20 | 9.9 | 10.7 | 10.2 |

DIARYLHYDANTOIN COMPOUNDS

FIELD OF THE INVENTION

The present invention relates to diaryihydantoin compounds including diarylthiohydantoins and methods for synthesizing them and using them in the treatment of hormone refractory prostate cancer. This application claims the benefit of U.S. Provisional Application No. 60/786,837, filed Mar. 29, 2006, U.S. Provisional Application No. 60/756,552, filed Jan. 6, 2006, U.S. Provisional Application No. 60/750,351, filed Dec. 15, 2005, and U.S. Provisional Application No. 60/680,835, filed May 13, 2005, which are hereby incorporated by reference in their entirety.

This invention was made with United States Government support under National Institutes of Health SPORE grant number 5 P50 CA092131 and Department of Defense (Army) grant number W81XWH-04-1-0129. The Government has certain rights in the invention.

BACKGROUND OF THE INVENTION

Prostate cancer is the most common incidence of cancer and the second leading cause of cancer death in Western men. When the cancer is confined locally, the disease can be cured by surgery or radiation. However, 30% of such cancer relapses with distant metastatic disease and others have advanced disease at diagnoses. Advanced disease is treated by castration and/or administration of antiandrogens, the so-called androgen deprivation therapy. Castration lowers the circulating levels of androgens and reduces the activity of androgen receptor (AR). Administration of antiandrogens blocks AR function by competing away androgen binding, therefore, reducing the AR activity. Although initially effective, these treatments quickly fail and the cancer becomes hormone refractory.

Recently, overexpression of AR has been identified and validated as a cause of hormone refractory prostate cancer. See Chen, C. D., Welsbie, D. S., Tran, C., Baek, S. H., Chen, R., Vessella, R., Rosenfeld, M. G., and Sawyers, C. L., Molecular determinants of resistance to an antiandrogen therapy, Nat. Med., 10: 33-39, 2004, which is hereby incorporated by reference. Overexpression of AR is sufficient to cause progression from hormone sensitive to hormone refractory prostate cancer, suggesting that better AR inhibitors than the current drugs can slow the progression of prostate cancer. It was demonstrated that AR and its ligand binding are necessary for growth of hormone refractory prostate cancer, indicating that AR is still a target for this disease. It was also demonstrated that overexpression of AR converts anti-androgens from antagonists to agonists in hormone refractory prostate cancer (an AR antagonist inhibits AR activity and an AR agonist stimulates AR activity). Data from this work explains why castration and anti-androgens fail to prevent prostate cancer progression and reveals unrecognized properties of hormone refractory prostate cancer.

Bicalutamide (brand name: Casodex) is the most commonly used anti-androgen. While it has an inhibitory effect on AR in hormone sensitive prostate cancer, it fails to suppress AR when cancer becomes hormone refractory. Two weaknesses of current antiandrogens are blamed for the failure to prevent prostate cancer progression from the hormone sensitive stage to the hormone refractory disease and to effectively treat hormone refractory prostate cancer. One is their weak antagonistic activities and the other is their strong agonistic activities when AR is overexpressed in hormone refractory prostate cancer. Therefore, better AR inhibitors with more potent antagonistic activities and minimal agonistic activities are needed to delay disease progression and to treat the fatal hormone refractory prostate cancer.

Nonsteroidal anti-androgens, such as bicalutamide, have been preferred over steroidal compounds for prostate cancer because they are more selective and have fewer side effects. This class of compounds has been described in many patents such as U.S. Pat. No. 4,097,578, U.S. Pat. No. 5,411,981, U.S. Pat. No. 5,705,654, PCT International Applications WO 97/00071 and WO 00/17163, and U.S. Published Patent Application No. 2004/0009969, all of which are hereby incorporated by reference.

U.S. Pat. No. 5,434,176 includes broad claims which encompass a very large number of compounds, but synthetic routes are only presented for a small fraction of these compounds and pharmacological data are only presented for two of them, and one skilled in the art could not readily envision other specific compounds.

Because the mechanism of hormone refractory prostate cancer was not known, there was no biological system to test these compounds described in these patents for their effect on hormone refractory prostate cancer. Particularly, the ability of AR overexpression in hormone refractory prostate cancer to switch inhibitors from antagonists to agonists was not recognized. Some new properties of hormone refractory prostate cancer are reported in PCT applications US04/42221 and US05/05529, which are hereby incorporated by reference. PCT International Application US05/05529 presented a methodology for identifying androgen receptor antagonist and agonist characteristics of compounds. However, for each compound produced, the time consuming process of determining the antagonist and agonist characteristics of a compound must be determined. That is, there is no method to accurately predict characteristics relevant to treating prostate cancer from the chemical structure of a compound alone.

There is a need for new thiohydantoin compounds having desirable pharmacological properties, and synthetic pathways for preparing them. Because activities are sensitive to small structural changes, one compound may be effective in treating prostate cancer, whereas a second compound may be ineffective, even if it differs from the first compound only slightly, say by the replacement of a single substituent.

Identification of compounds which have high potency to antagonize the androgen activity, and which have minimal agonistic activity should overcome hormone refractory prostate cancer (HRPC) and avoid or slow down the progression of hormone sensitive prostate cancer (HSPC). Therefore, there is a need in the art for the identification of selective modulators of the androgen receptor, such as modulators which are non-steroidal, non-toxic, and tissue selective.

SUMMARY OF THE INVENTION

The invention provides a series of compounds having strong antagonistic activities with minimal agonistic activities against AR. These compounds inhibit the growth of hormone refractory prostate cancer.

The invention includes a compound having the formula

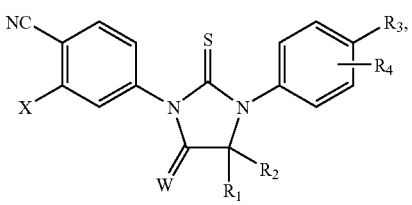

wherein X is selected from the group consisting of trifluoromethyl and iodo, wherein W is selected from the group consisting of O and NR5, wherein R5 is selected from the group consisting of H, methyl, and

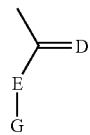

wherein D is S or O and E is N or O and G is alkyl, aryl, substituted alkyl or substituted aryl; or D is S or O and E-G together are C1-C4 lower alkyl, wherein R1 and R2 together comprise eight or fewer carbon atoms and are selected from the group consisting of alkyl, substituted alkyl including haloalkyl, and, together with the carbon to which they are linked, a cycloalkyl or substituted cycloalkyl group, wherein R3 is selected from the group consisting of hydrogen, halogen, methyl, C1-C4 alkoxy, formyl, haloacetoxy, trifluoromethyl, cyano, nitro, hydroxyl, phenyl, amino, methylcarbamoyl, methoxycarbonyl, acetamido, methanesulfonamino, methanesulfonyl, 4-methanesulfonyl-1-piperazinyl, piperazinyl, and C1-C6 alkyl or alkenyl optionally substituted with hydroxyl, methoxycarbonyl, cyano, amino, amido, nitro, carbamoyl, or substituted carbamoyl including methylcarbamoyl, dimethylcarbamoyl, and hydroxyethylcarbamoyl, wherein R4 is selected from the group consisting of hydrogen, halogen, alkyl, and haloalkyl, and wherein R3 is not methylaminomethyl or dimethylaminomethyl.

R5 may be

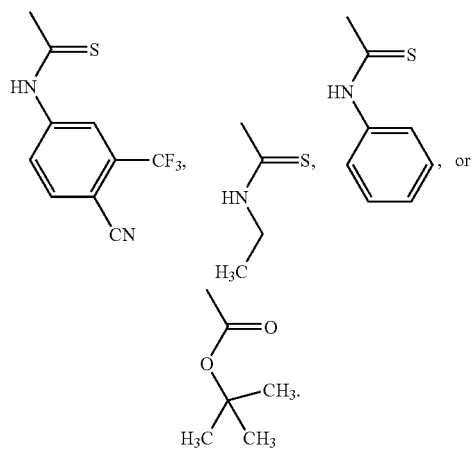

The compound may have the formula

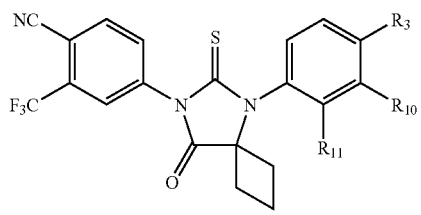

wherein R3 is selected from the group consisting of hydroxy, methylcarbamoyl, methylcarbamoylpropyl, methylcarbamoylethyl, methylcarbamoylmethyl, methylsulfonecarbamoylpropyl, methylaminomethyl, dimethylaminomethyl, methylsulfonyloxymethyl, carbamoylmethyl, carbamoylethyl, carboxymethyl, methoxycarbonylmethyl, methanesulfonyl, 4-cyano-3-trifluoromethylphenylcarbamoylpropyl, carboxypropyl, 4-methanesulfonyl-1-piperazinyl, piperazinyl, methoxycarbonyl, 3-cyano-4-trifluoromethylphenylcarbamoyl, hydroxyethylcarbamoylethyl, and hydroxyethoxycarbonylethyl, and wherein R10 and R11 are both H or, respectively, F and H, or H and F. In certain embodiments, R10 and R11 may both be H or, respectively, F and H, R3 may be methylcarbamoyl.

In some embodiments, R1 and R2 are independently methyl or, together with the carbon to which they are linked, a cycloalkyl group of 4 to 5 carbon atoms, and R3 is selected from the group consisting of carbamoyl, alkylcarbamoyl, carbamoylalkyl, and alkylcarbamoylalkyl, and R4 is H or F or R4 is 3-fluoro.

In other embodiments, R1 and R2 are independently methyl or, together with the carbon to which they are linked, a cycloalkyl group of 4 to 5 carbon atoms, R3 is selected from the group consisting of cyano, hydroxy, methylcarbamoyl, methylcarbamoyl-substituted alkyl, methylsulfonecarbamoyl-substituted alkyl, methylaminomethyl, dimethylaminomethyl, methylsulfonyloxymethyl, methoxycarbonyl, acetamido, methanesulfonamido, carbamoyl-substituted alkyl, carboxymethyl, methoxycarbonylmethyl, methanesulfonyl, 4-cyano-3-trifluoromethylphenylcarbamoyl-substituted alkyl, carboxy-substituted alkyl, 4-(1,1-dimethylethoxy)carbonyl)-1-piperazinyl, 4-methanesulfonyl-1-piperazinyl, piperazinyl, hydroxyethylcarbamoyl-substituted alkyl, hydroxyethoxycarbonyl-substituted alkyl, and 3-cyano-4-trifluoromethylphenylcarbamoyl, and R4 is F.

Compounds of the invention may have the formula

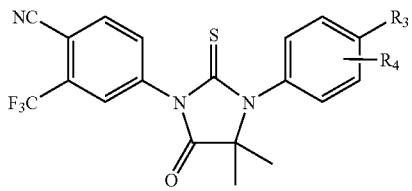

wherein R3 is selected from the group consisting of methylcarbonyl, methoxycarbonyl, acetamido, and methanesulfonamido, and R4 is selected from the group consisting of F and H.

Compounds of the invention may have the formula

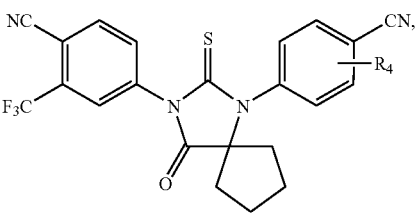

wherein R4 is selected from the group consisting of F and H.

In embodiments of the invention, wherein R1 and R2 together with the carbon to which they are linked are

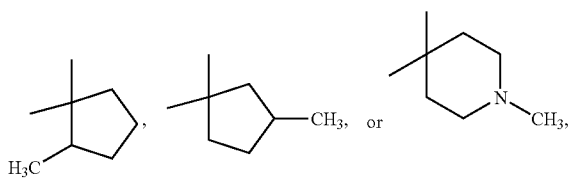

Compounds of the invention may be those listed in Tier 1, Tier 2, Tier 3, and/or Tier 4, below. Particular compounds of the invention include

[RD162]
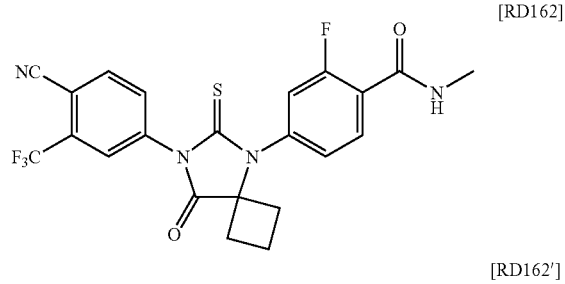

[RD162']
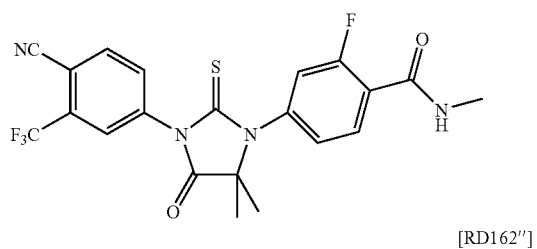

[RD162'']
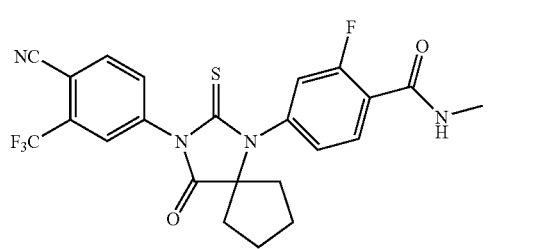

[RD169]
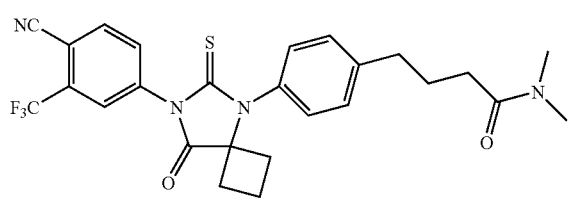

[RD170]
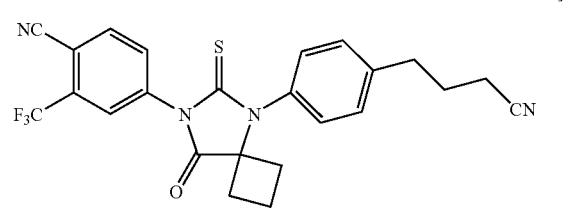

The invention also provides a pharmaceutical composition comprising a therapeutically effective amount of a compound according to any of the preceding compounds or a pharmaceutically acceptable salt thereof, and a pharmaceutically acceptable carrier or diluent.

The invention encompasses a method for treating a hyperproliferative disorder comprising administering such a pharmaceutical composition to a subject in need of such treatment, thereby treating the hyperproliferative disorder. The hyperproliferative disorder may be hormone refractory prostate cancer. The dosage may be in the range of from about 0.001 mg per kg body weight per day to about 100 mg per kg body weight per day, about 0.01 mg per kg body weight per day to about 100 mg per kg body weight per day, about 0.1 mg per kg body weight per day to about 10 mg per kg body weight per day, or about 1 mg per kg body weight per day.

The compound may be administered by intravenous injection, by injection into tissue, intraperitoneally, orally, or nasally. The composition may have a form selected from the group consisting of a solution, dispersion, suspension, powder, capsule, tablet, pill, time release capsule, time release tablet, and time release pill.

The administered compound may be selected from the group consisting of RD162', RD162'', RD 169, or RD170, or a pharmaceutically acceptable salt thereof. The administered compound may be RD162 or a pharmaceutically acceptable salt thereof.

The invention provides a method of synthesizing a diaryl compound of formula:

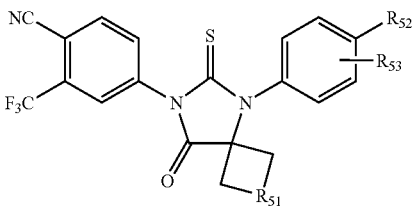

comprising mixing Compound I

Compound I
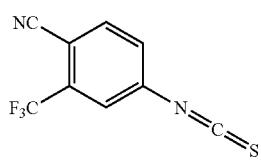

with Compound II

Compound II
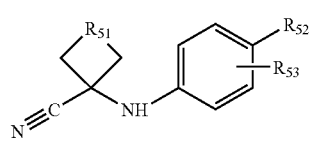

in a first polar solvent to form a mixture, heating the mixture, adding a second polar solvent, the same as or different from the first polar solvent, and an aqueous acid to the mixture, refluxing the mixture, cooling the mixture and combining with water, and separating the diaryl compound from the mixture, wherein R51 comprises an alkyl chain of from 1 to 4 carbon atoms, R52 is selected from the group consisting of cyano, hydroxy, methylcarbamoyl, methylcarbamoyl-substituted alkyl, methylsulfonecarbamoyl-substituted alkyl, methylaminomethyl, dimethylaminomethyl, methylsulfonyloxymethyl, methoxycarbonyl, 3-cyano-4-trifluoromethylphenylcarbamoyl, carbamoyl-substituted alkyl, carboxymethyl, methoxycarbonylmethyl, methanesulfonyl, 4-cyano-3-trifluoromethylphenylcarbamoyl-substituted alkyl, carboxy-substituted alkyl, 4-methanesulfonyl-1-piperazinyl, piperazinyl, hydroxyethylcarbamoyl-substituted alkyl, and hydroxyethoxycarbonyl-substituted alkyl, and R53 is selected from the group consisting of F and H.

R51 may comprise an alkyl chain of from 1 to 2 carbon atoms, R52 may be selected from the group consisting of carbamoyl and methylcarbamoyl, and R53 may be F.

The invention provides methods of synthesizing a compound of formula:

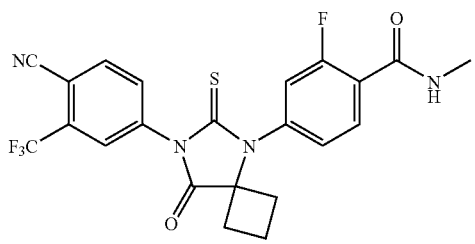

[RD162]

comprising mixing 4-isothiocyanato-2-trifluoromethylbenzonitrile and N-methyl-4-(1-cyanocyclobutylamino)-2-fluorobenzamide in dimethylformamide to form a first mixture, heating the first mixture to form a second mixture, adding alcohol and acid to the second mixture to form a third mixture, refluxing the third mixture to form a fourth mixture, cooling the fourth mixture, combining the fourth mixture with water and extracting an organic layer; isolating the compound from the organic layer.

Likewise, the invention provides a method of synthesizing RD162' comprising mixing N-Methyl-2-fluoro-4-(1,1-dimethyl-cyanomethyl)-aminobenzamide and 4-Isothiocyanato-2-trifluoromethylbenzonitrile in DMF and heating to form a first mixture, and processing as above.

The invention also provides a method of synthesizing RD162", comprising mixing N-Methyl-2-fluoro-4-(1-cyanocyclopentyl)aminobenzamide, 4-isothiocyanato-2-trifluoromethyl benzonitrile, and DMF and heating under reflux to form a first mixture, and processing as above.

The invention further provides a method of synthesizing RD169, comprising mixing N,N-Dimethyl 4-[4-(1-cyanocyclobutylamino)phenyl]butanamide, 4-isothiocyanato-2-trifluoromethyl benzonitrile, and DMF and heating under reflux to form a first mixture; and processing as above.

The invention provides a method of synthesizing RD170, comprising mixing DMSO, dichloromethane, and oxalyl chloride to form a first mixture, adding 4-(4-(7-(4-Cyano-3-(trifluoromethyl)phenyl)-8-oxo-6-thioxo-5,7-diazaspiro[3.4]octan-5-yl)phenyl)butanamide to the first mixture to form a second mixture; adding triethylamine to the second mixture to form a third mixture; warming the third mixture and quenching with aqueous NH$_4$Cl to form a fourth mixture; extracting an organic layer from the fourth mixture; and isolating the compound from the organic layer.

Further compounds according to the invention have the formula

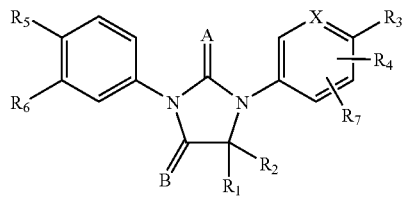

wherein R5 is CN or NO$_2$ or SO2R11, wherein R6 is CF3, alkyl, substituted alkyl, alkenyl, substituted alkenyl, alkynyl, substituted alkynyl, halogenated alkyl, halogenated alkenyl, halogenated akynyl, halogen, wherein A is sulfur (S) or oxygen (O), wherein B is O or S or NR8, wherein R8 is selected from the group consisting of H, methyl, aryl, substituted aryl, alkyl, substituted alkyl, alkenyl, substituted alkenyl, alkynyl, substituted alkynyl, arylalkyl, arylalkenyl, arylalkynyl, heterocyclic aromatic or non-aromatic, substituted heterocyclic aromatic or non-aromatic, cycloalkyl, substituted cycloalkyl, SO2R11, NR11R12, (CO)OR11, (CO)NR11R12, (CO)R11, (CS)R11, (CS)NR11R12, (CS)OR11,

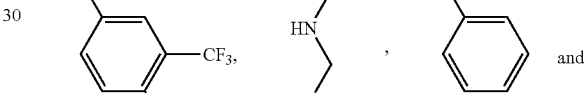

wherein D is S or O and E is N or O and G is alkyl, aryl, substituted alkyl or substituted aryl; or D is S or O and E-G together are C1-C4 lower alkyl, wherein R1 and R2 are independently alkyl, haloalkyl, hydrogen, aryl, substituted alkyl, alkenyl, substituted alkenyl, alkynyl, substituted alkynyl, halogenated alkenyl, halogenated akynyl, arylalkyl, arylalkenyl, arylalkynyl, heterocylic aromatic or non-aromatic, substituted heterocyclic aromatic or non-aromatic, cycloalkyl, substituted cycloalkyl, or R1 and R2 are connected to form a cycle which can be heterocyclic, substituted heterocyclic, cycloalkyl, substituted cycloalkyl,

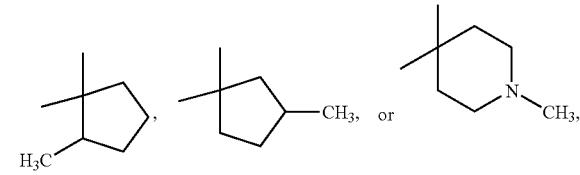

wherein X is carbon or nitrogen and can be at any position in the ring, and wherein R3, R4, and R7 are independently selected from the group consisting of hydrogen, halogen, methyl, methoxy, formyl, haloacetoxy, trifluoromethyl, cyano, nitro, hydroxyl, phenyl, amino, methylcarbamoyl, methylcarbamoyl-substituted alkyl, dimethylcarbamoyl-substituted alkyl, methoxycarbonyl, acetamido, methanesulfonamino, carbamoyl-substituted alkyl, methanesulfonyl, 4-methanesulfonyl-1-piperazinyl, piperazinyl, hydroxyethylcarbamoyl-substituted alkyl, hydroxyl-substituted alkyl, hydroxyl-substituted alkenyl, carbamoyl-substituted alkenyl, methoxycarbonyl-substituted alkyl, cyano-substituted alkyl,

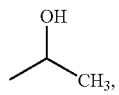

aryl, substituted aryl, alkyl, substituted alkyl, alkenyl, substituted alkenyl, alkynyl, substituted alkynyl, halogenated alkenyl, halogenated alkynyl, SO2R11, NR11R12, NR12(CO)OR11, NH(CO)NR11R12, NR12 (CO)R11, O(CO)R11, O(CO)OR11, O(CS)R11, NR12 (CS)R11, NH(CS)NR11R12, NR12 (CS)OR11, arylalkyl, arylalkenyl, arylalkynyl, heterocyclic aromatic or non-aromatic, substituted heterocyclic aromatic or non-aromatic, cycloalkyl, substituted cycloalkyl, haloalkyl, methylsulfonecarbamoyl-substituted alkyl, methylaminomethyl, dimethylaminomethyl, methylsulfonyloxymethyl, methoxycarbonyl, acetamido, methanesulfonamido, carbamoyl-substituted alkyl, carboxymethyl, methoxycarbonylmethyl, methanesulfonyl, 4-cyano-3-trifluoromethylphenylcarbamoyl-substituted alkyl, carboxy-substituted alkyl, 4-(1,1-dimethylethoxy)carbonyl)-1-piperazinyl, hydroxyethylcarbamoyl-substituted alkyl, hydroxyethoxycarbonyl-substituted alkyl, 3-cyano-4-trifluoromethylphenylcarbamoyl, wherein R11 and R12 are independently hydrogen, aryl, aralkyl, substituted aralkyl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, or substituted cycloalkyl, or R11 and R12 can be connected to form a cycle which can be heterocyclic aromatic or non-aromatic, substituted heterocyclic aromatic, cycloalkyl, or substituted cycloalkyl.

Such compounds have substantial androgen receptor antagonist activity and no substantial agonist activity on hormone refractory prostate cancer cells.

The invention encompasses a method comprising providing at least one such compound, measuring inhibition of androgen receptor activity for the compound and determining if the inhibition is above a first predetermined level, measuring stimulation of androgen receptor activity in hormone refractory cancer cells for the compound and determining if the stimulation is below a second predetermined level, and selecting the compound if the inhibition is above the first predetermined level and the stimulation is below the second predetermined level. The predetermined levels may be those of bicalutamide. The step of measuring inhibition may comprise measuring inhibitory concentration (IC50) in an AR response reporter system or a prostate specific antigen secreting system. The step of measuring stimulation may comprise measuring fold induction by increasing concentrations in an AR response reporter system or a prostate specific antigen secreting system. The method of measuring inhibition and/or stimulation may comprise measuring an effect of the compound on tumor growth in an animal.

BRIEF DESCRIPTION OF THE DRAWINGS

The following Figures present the results of pharmacological examination of certain compounds.

FIG. 6. Inhibition on growth of AR-overexpressed LNCaP cells. Androgen starved LNCaP cells with overexpressed AR were treated with increasing concentrations of DMSO as vehicle or test substances in the presence of 100 pM of R1881. After 4 days of incubation, cell growth was measured by MTS assay.

FIG. 7. Inhibitory effect on growth of AR-overexpressed LNCaP xenograft model. Mice with established LN-AR xenograft tumors were randomized and treated with indicated compounds orally once daily. Tumor size was measured by caliber. (A), mice were treated with 1 mg per kg of bicalutamide, example 7-3b, or vehicle for 44 days. (B), mice were treated with vehicle, 0.1, 1, or 10 mg per kg of example 7-3b for 44 days.

FIG. 8. Inhibitory effect on PSA expression of AR-overexpressed LNCaP xenograft model. Mice were treated with vehicle, 0.1, 1, or 10 mg per kg of example 7-3b for 44 days orally once daily. The tumors were taken out from the mice after 44 days of treatment, tumor lysate was extracted, and PSA level in tissue lysate was determined by ELISA.

FIG. 9. Inhibitory effect on growth and PSA of hormone refractory LAPC4 xenograft model. Mice with established tumors were randomized and treated with 1 mg per kg of bicalutamide, example 7-3b, or vehicle for 17 days orally once daily. (A), tumor size was measured by caliber. (B), the tumors were taken out from the mice after 17 days of treatment, tumor lysate was extracted, and PSA level in tissue lysate was determined by ELISA.

FIG. 10. Inhibitory effect on growth of hormone sensitive prostate cancer cells. Androgen starved LNCaP cells were treated with increasing concentrations of DMSO as vehicle or test substances in the presence of 1 pM of R1881. After 4 days of incubation, cell growth was measured by MTS assay.

FIG. 12 depicts experimental results of tumor size. At day 18, the animals were imaged via an optical CCD camera, 3 hours after last dose of treatment. A ROI was drawn over the tumor for luciferase activity measurement in photon/second. The night panels is a representation of the ROIs measurements.

Figure 13:
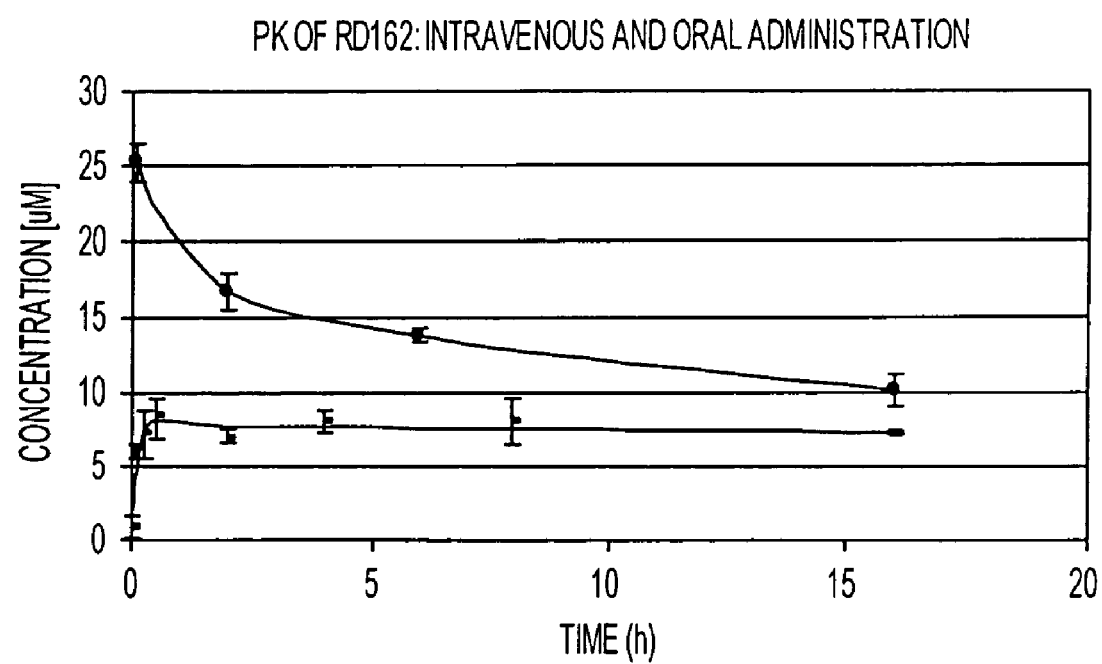

FIG. 13 is a graph depicting the pharmacokinetic curves of RD162 from intravenous (upper curve) and oral administration (lower curve).

Figure 14:
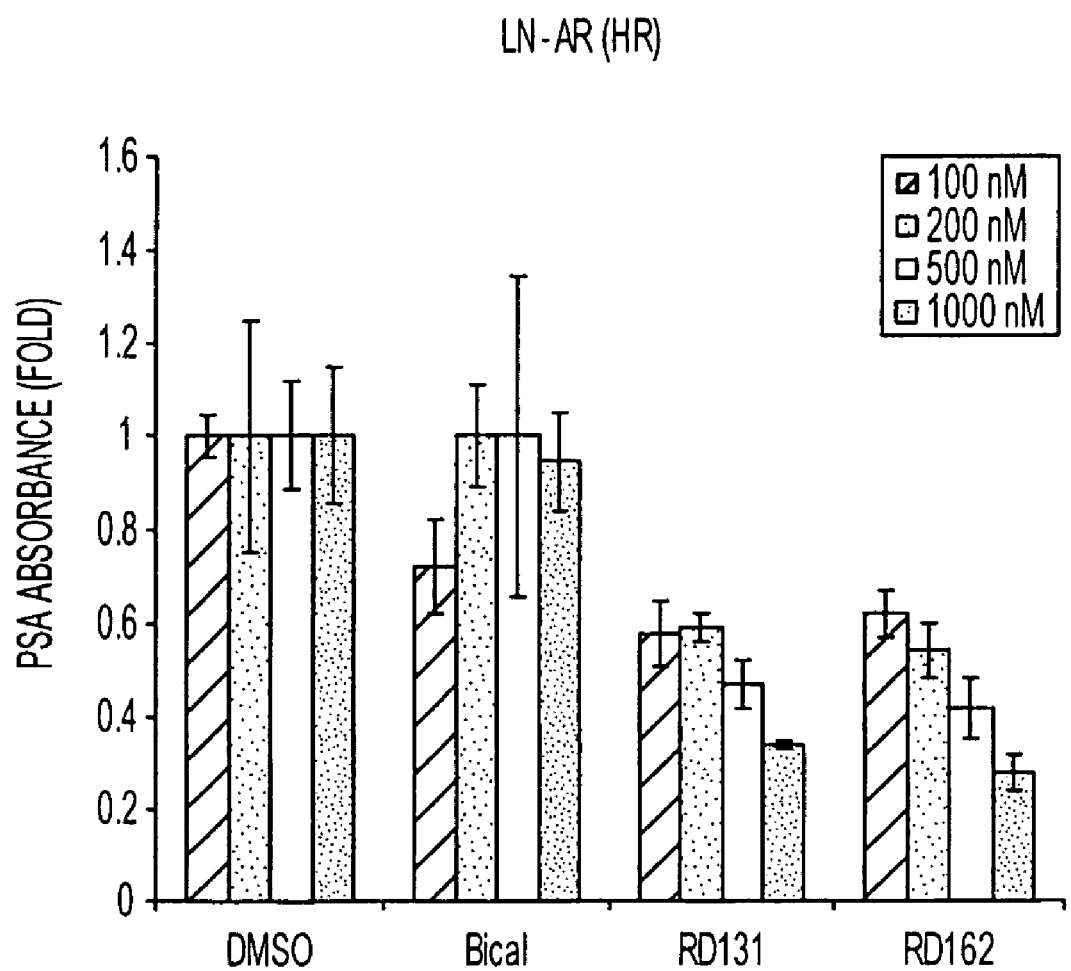

FIG. 14 is a graph depicting PSA absorbance measured for LN-AR cells after treatment with various doses of several compounds.

Figures 15A, 15B:
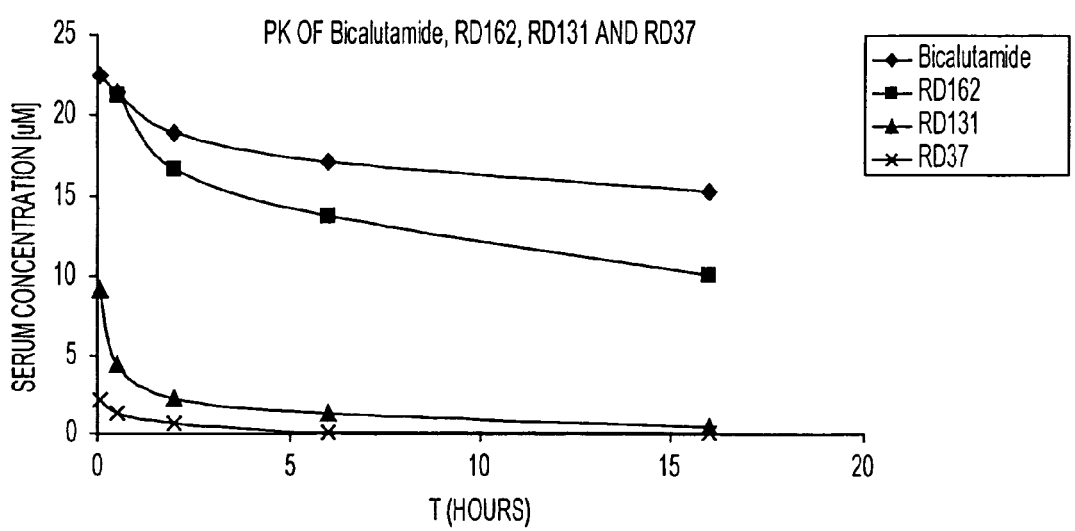

FIG. 15 presents a table providing several characteristics of compounds. FIG. 15 also presents a graph providing the pharmacokinetic characteristics of several compounds in terms of compound serum concentration as a function of time.

Figure 16:
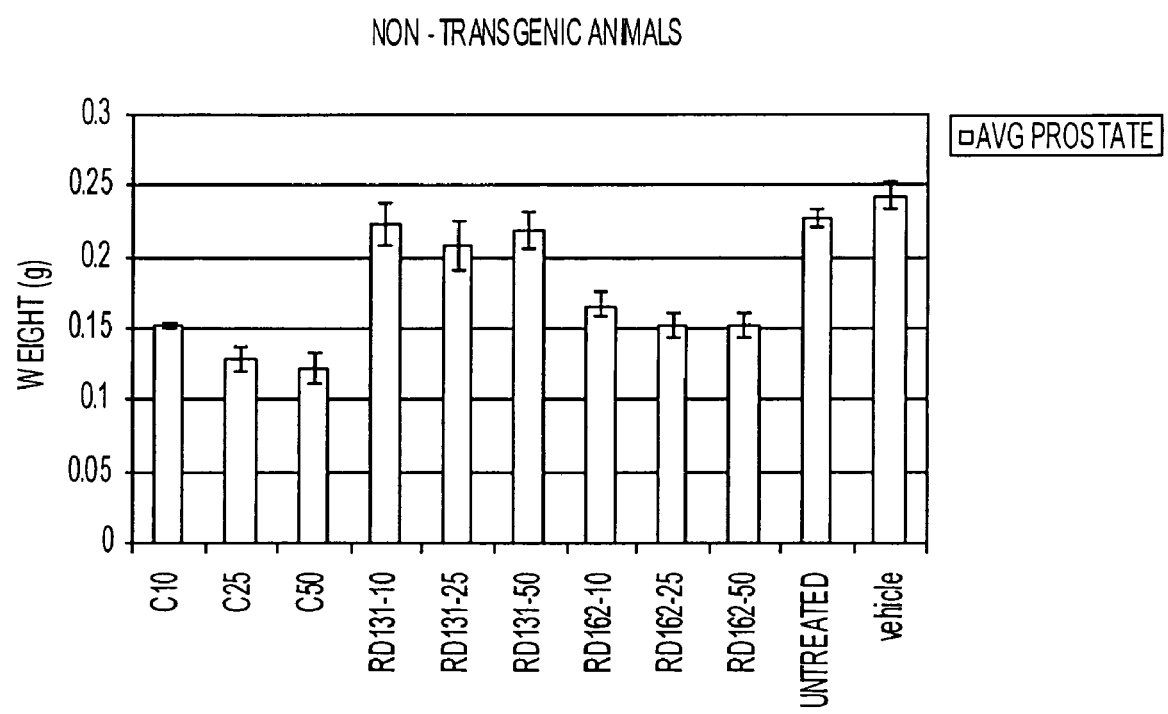

FIG. 16 is a chart depicting prostate weight after treatment with various compounds. 10, 25, or 50 mg of compound per kilogram body weight were administered per day, as indicated by the label of a bar. The compounds were administered to healthy FVB mice. After treatment with compound for 14 days, the urogenital tract weight was determined by removing and weighing the semi-vesicles, prostate, and bladder. Three mice were administered a given compound to obtain the data presented by a bar in the chart. A set of mice was not treated with a compound: data are presented in the bar labeled "untreated". Another set of mice was treated only with vehicle solution: data are presented in the bar labeled "vehicle".

Figure 6:
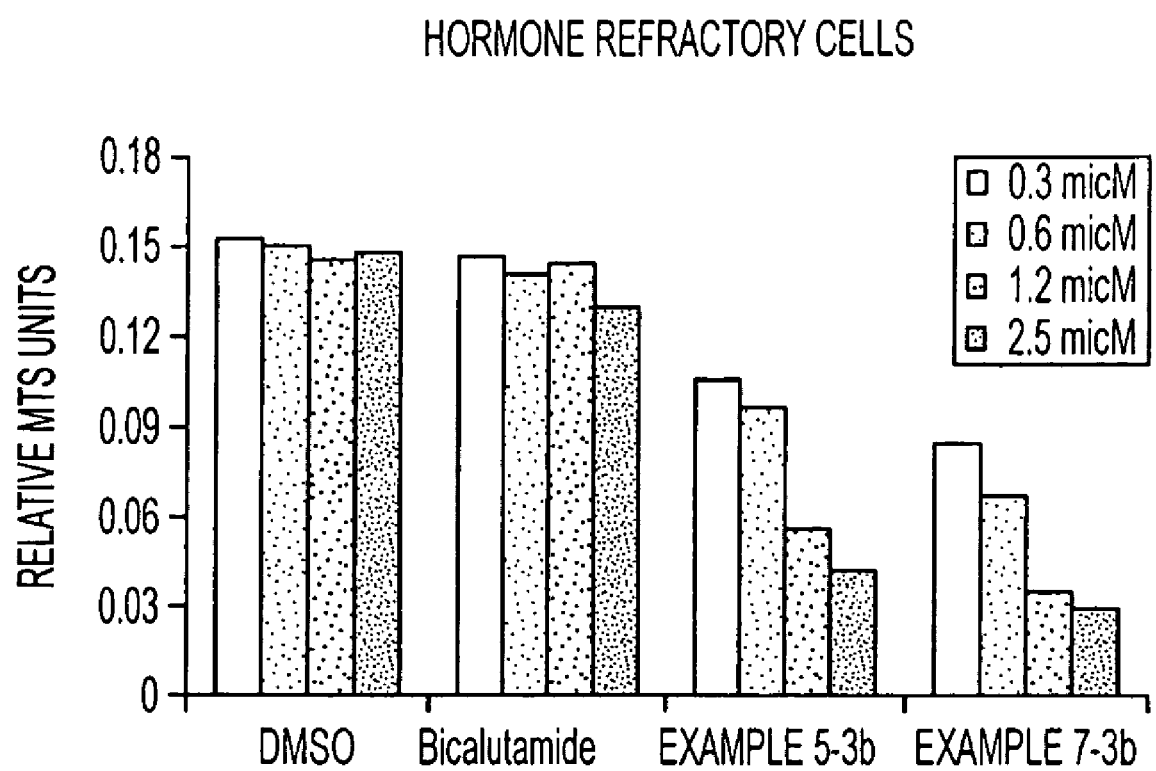
In FIGS. 6-10, example 5-3b is RD7 and example 7-3b is RD37.
Figure 17:
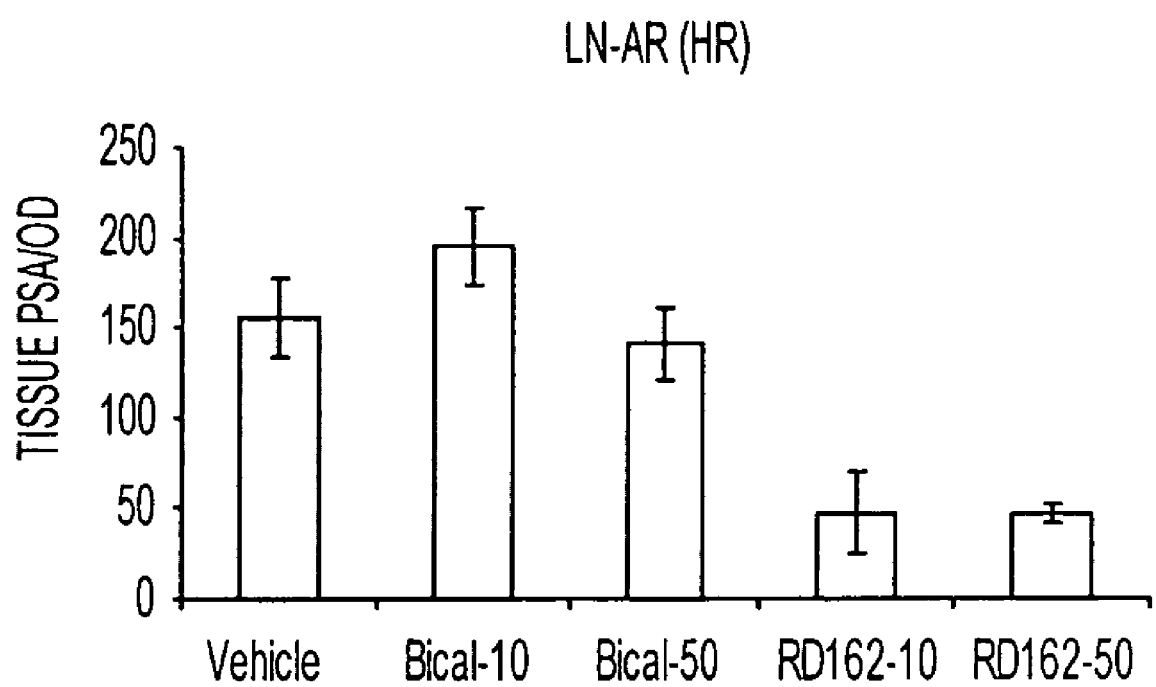

FIG. 17 is a graph presenting a PSA assay performed along with the experimental protocol presented in FIG. 6.

Figure 18:
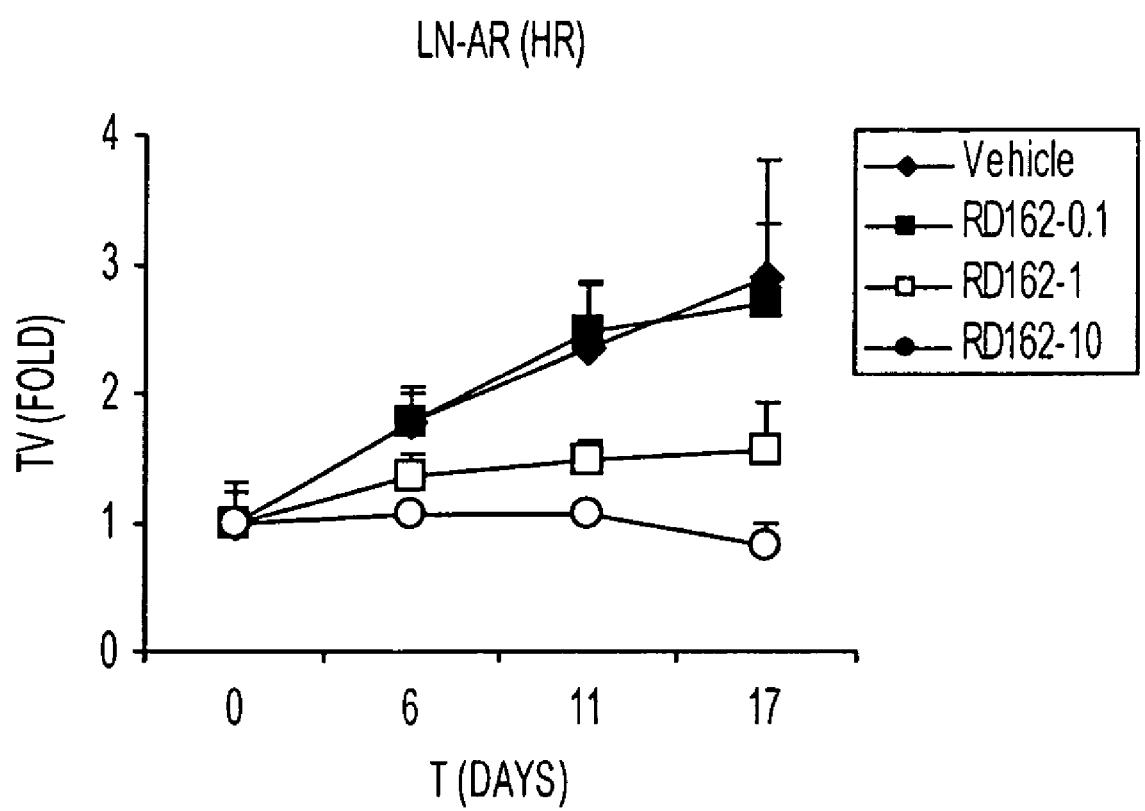

FIG. 18 is a graph presenting the effect of various dose regimens of RD162 on tumor volume.

Figure 19A:
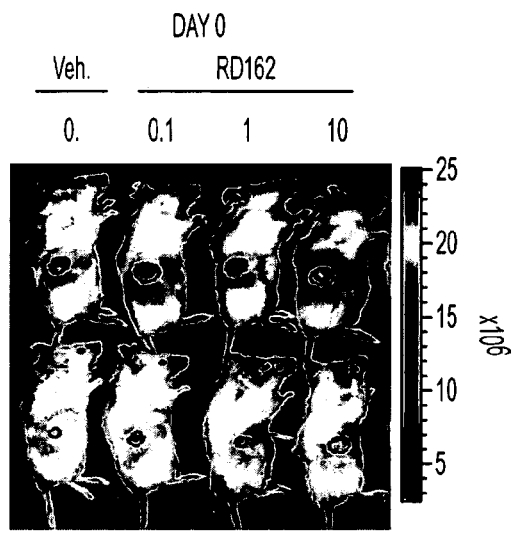
Figure 19B:
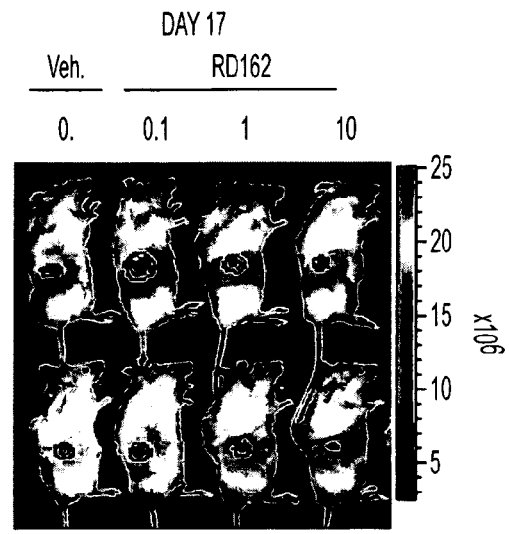
Figure 19C:
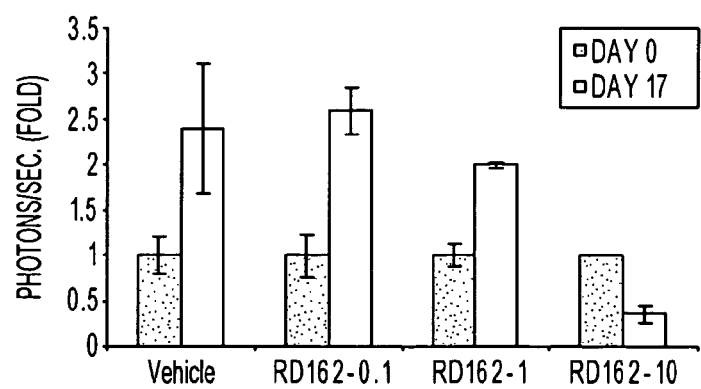

FIG. 19 is a graph presenting the rate of photon emission associated with luciferase activity at day 17 relative to the rate at day 0 after treatment with RD162 at doses of 0.1, 1, and 10 mg per kilogram body weight per day and without treatment with RD162.

Figure 20A:
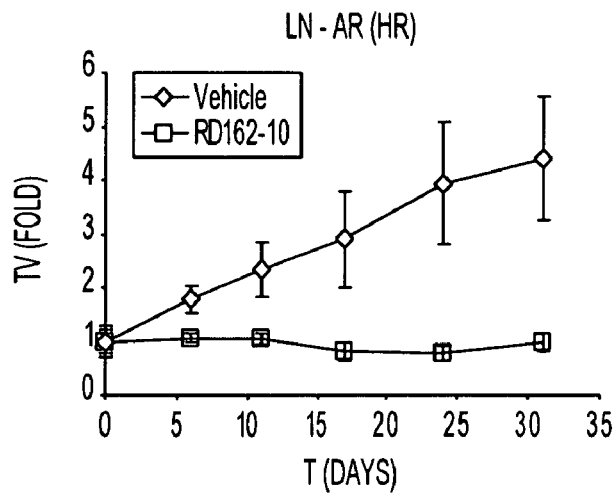
Figure 20B:
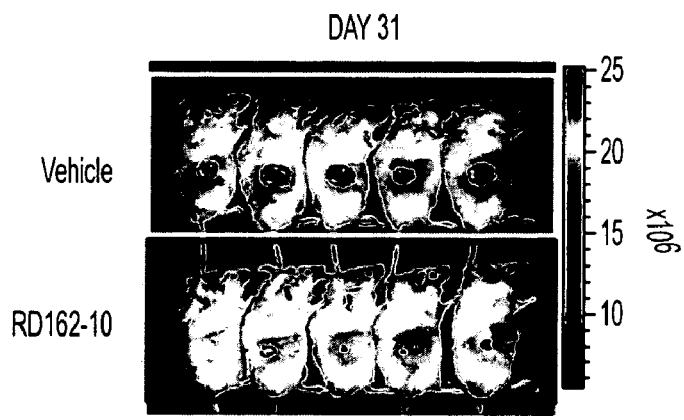
Figure 20C:
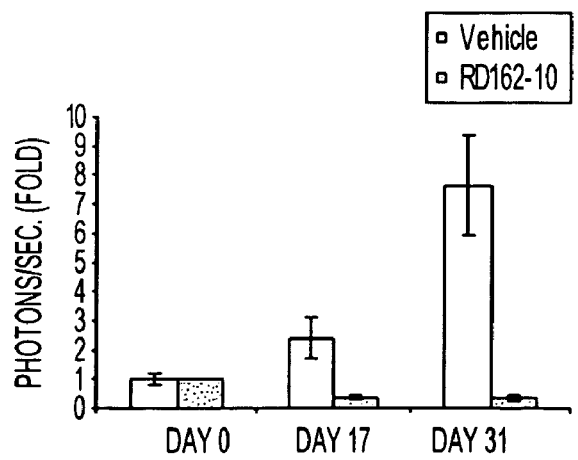

FIG. 20 presents the results of an experiment in which SCID mice were injected with the LN-AR (HR) cell line to induce tumor growth. One set of mice were treated with the compound RD162 at a dose of 10 mg per kilogram body weight per day; the other set of mice were treated only with vehicle solution. (A) The relative tumor volume as a function of time shown for each set of mice. (B) Images of each set of mice with photon emission associated with luciferase activity at day 31 shown as color contours. (C) Rate of photon emission associated with luciferase activity shown at several times for each set of mice.

Figure 21A:
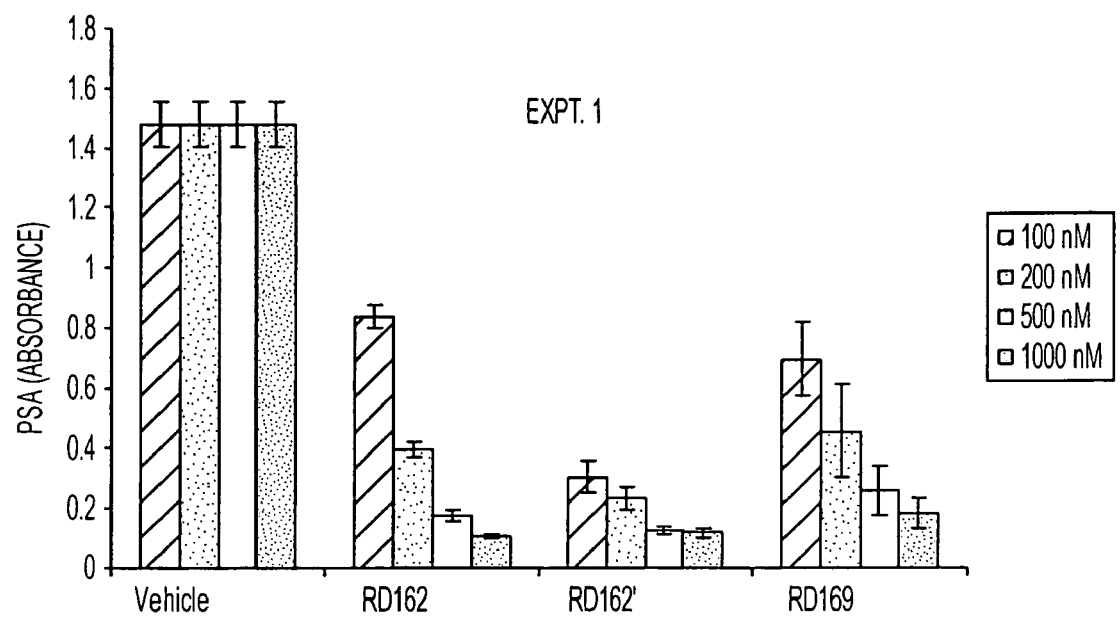
Figure 21B:
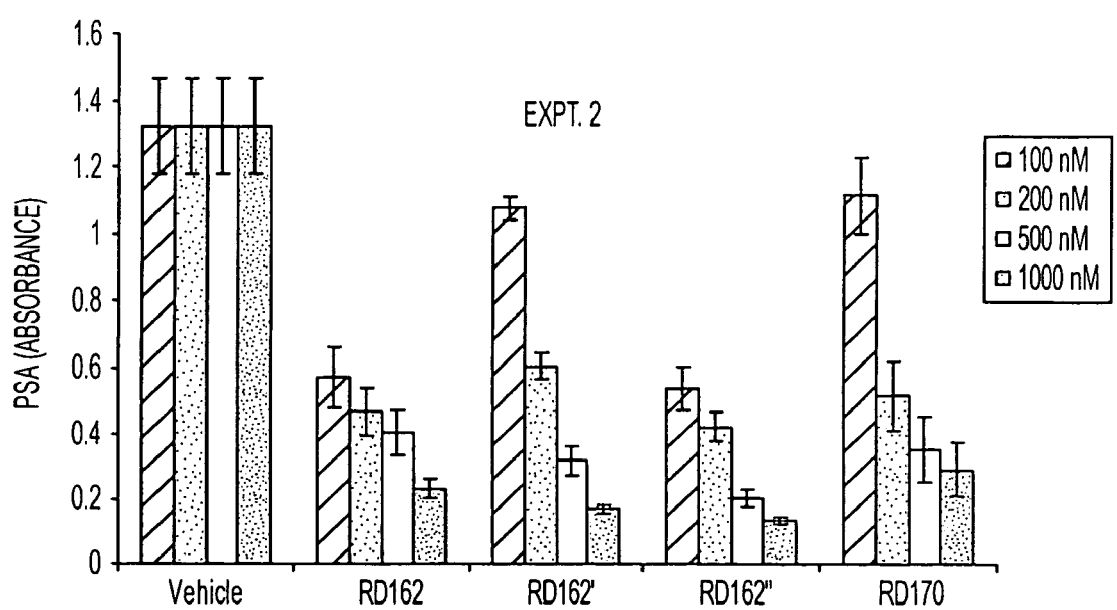

FIG. 21 is a graph presenting PSA absorbance associated with LN-AR cells treated with various concentrations of RD162, RD162', RD162", and RD170 and vehicle solution.

Figure 22:
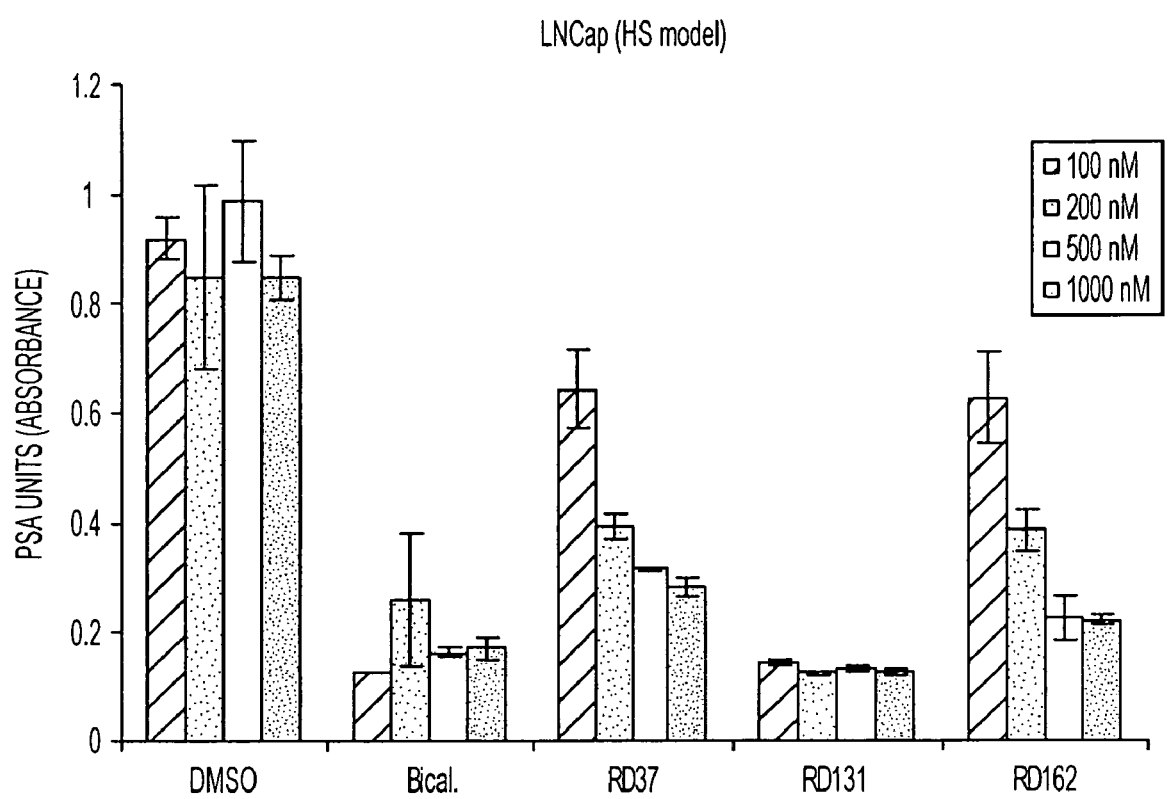

FIG. 22 is a graph presenting PSA absorbance associated with LN-CaP cells treated with various concentrations of RD37, RD131, RD162, bicalutamide, and DMSO.

Figure 23A:
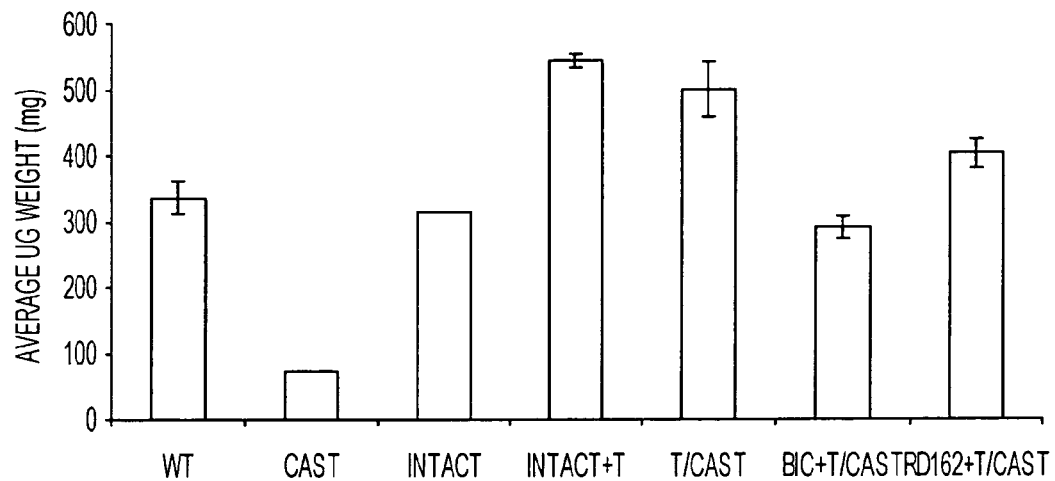
Figure 23B:
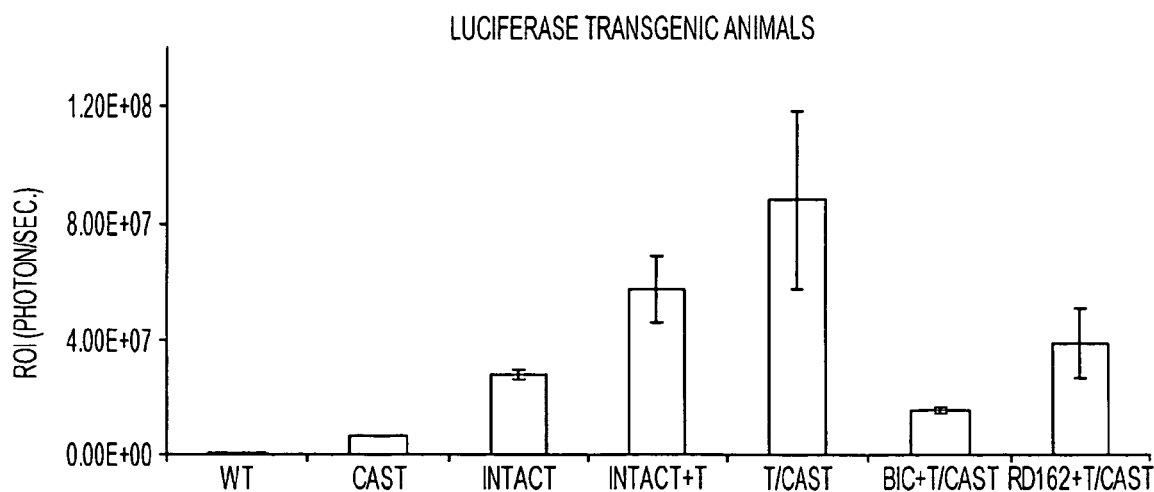

FIG. 23 presents results of an experiment conducted with wild type nontransgenic mice (WT), castrated luciferase transgenic mice (Cast), and non-castrated luciferase transgenic mice (Intact). Data are shown for castrated luciferase transgenic mice treated with an implanted testosterone pellet yielding 12.5 mg per kilogram body weight with a 90 day release period (T/Cast), and data are shown for non-castrated luciferase transgenic mice treated with an implanted testosterone pellet yielding 12.5 mg per kilogram body weight with a 90 day release period (Intact+T). Data are shown for castrated luciferase transgenic mice treated with the implanted testosterone pellet and with bicalutamide (BIC+T/Cast) or with RD162 (RD162+T/Cast) at 10 mg per kilogram body weight per day. (A) Urogenital tract weight at 14 days. (B) Photon emission rate at 14 days. In all cases, a hormone refractory disease state was not induced.

Figure 24:
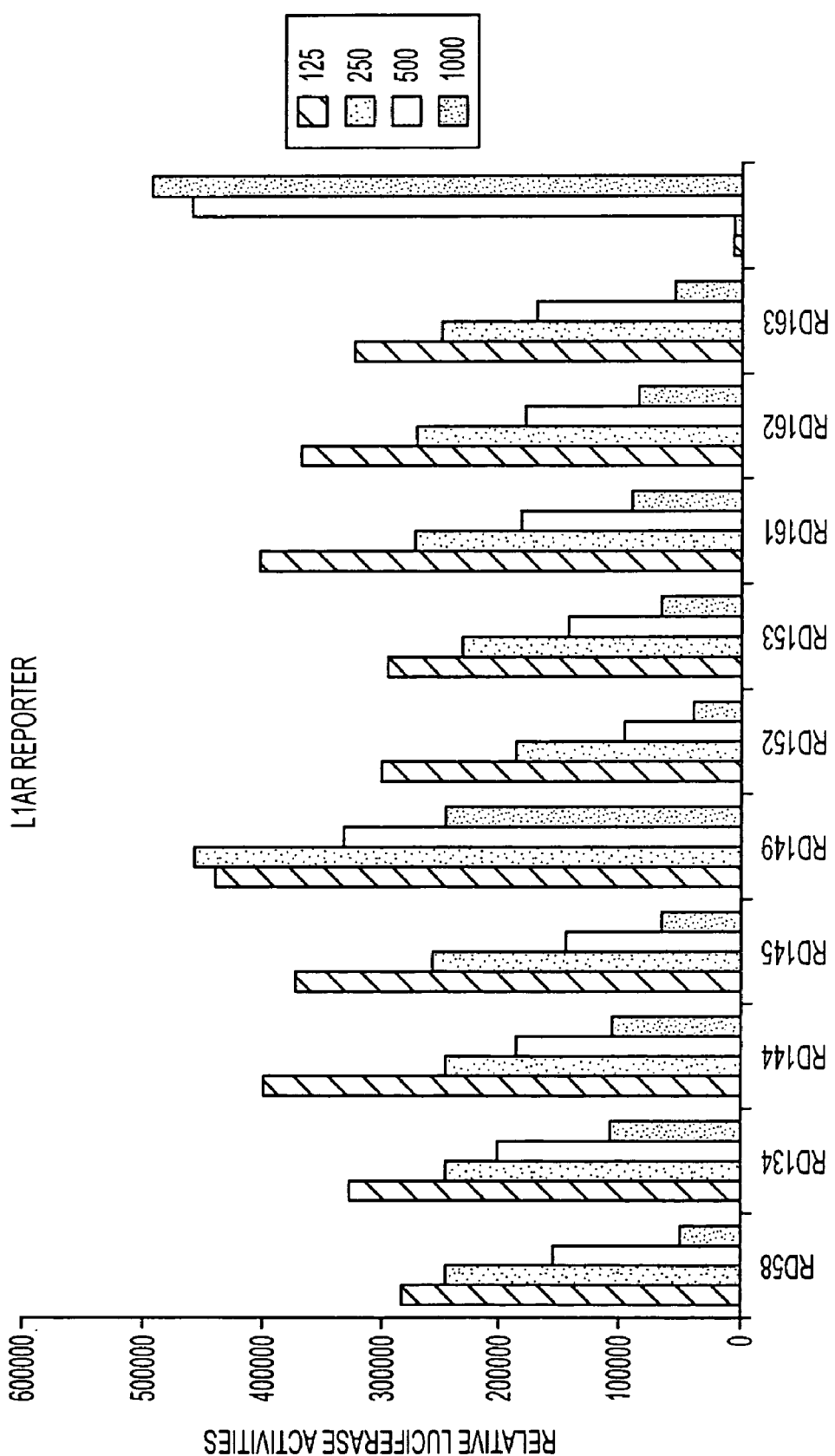

FIG. 24 is a graph of luciferase activity of the LIAR cell line dosed with various compounds administered at concentrations ranging from 125 nmol to 1000 nmol.

Figure 25:
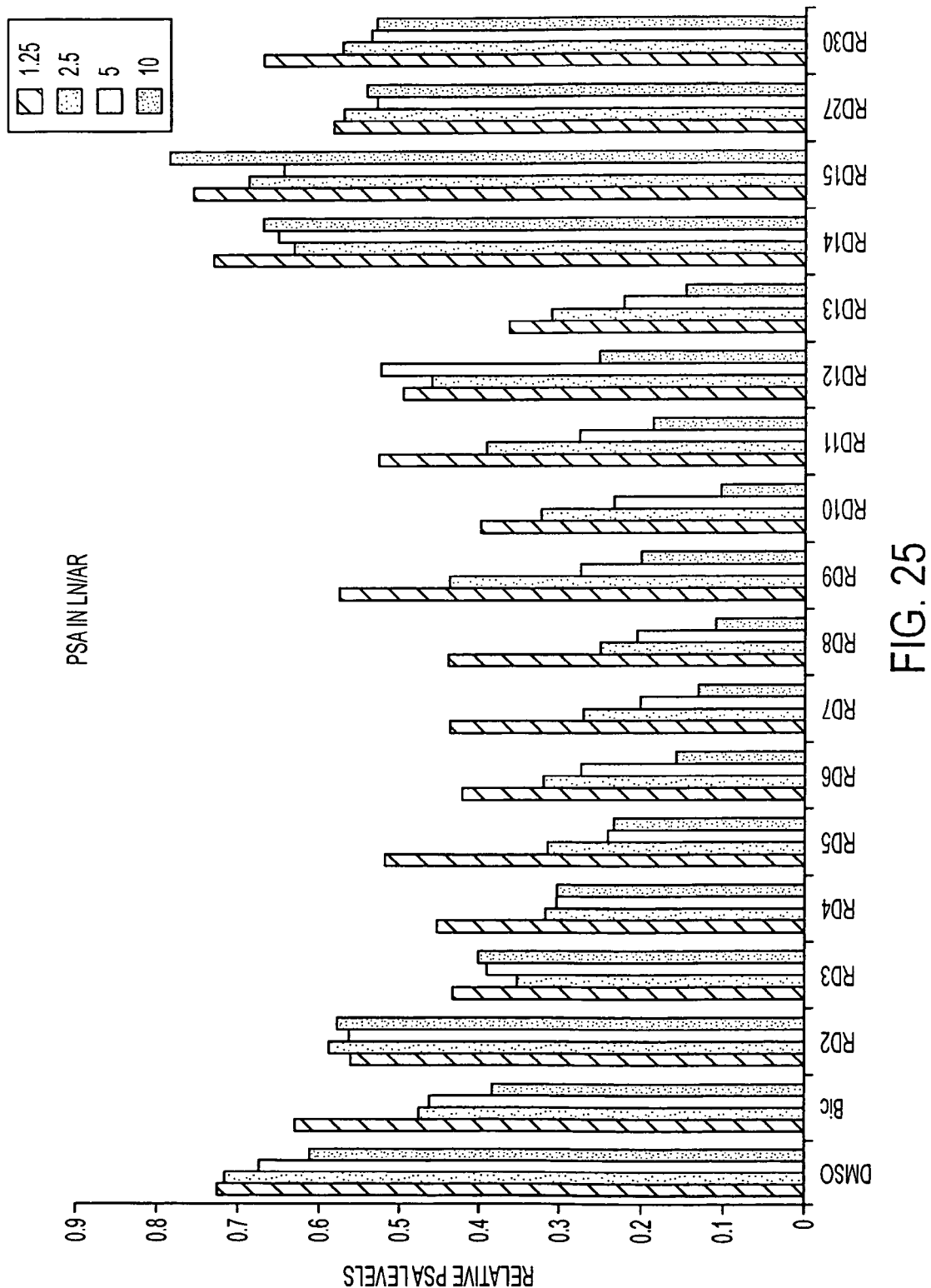

FIG. 25 is a graph of luciferase activity for the LN/AR cell line for various compounds administered at concentrations ranging from 1.25 to 10 μmol.

Figure 26:
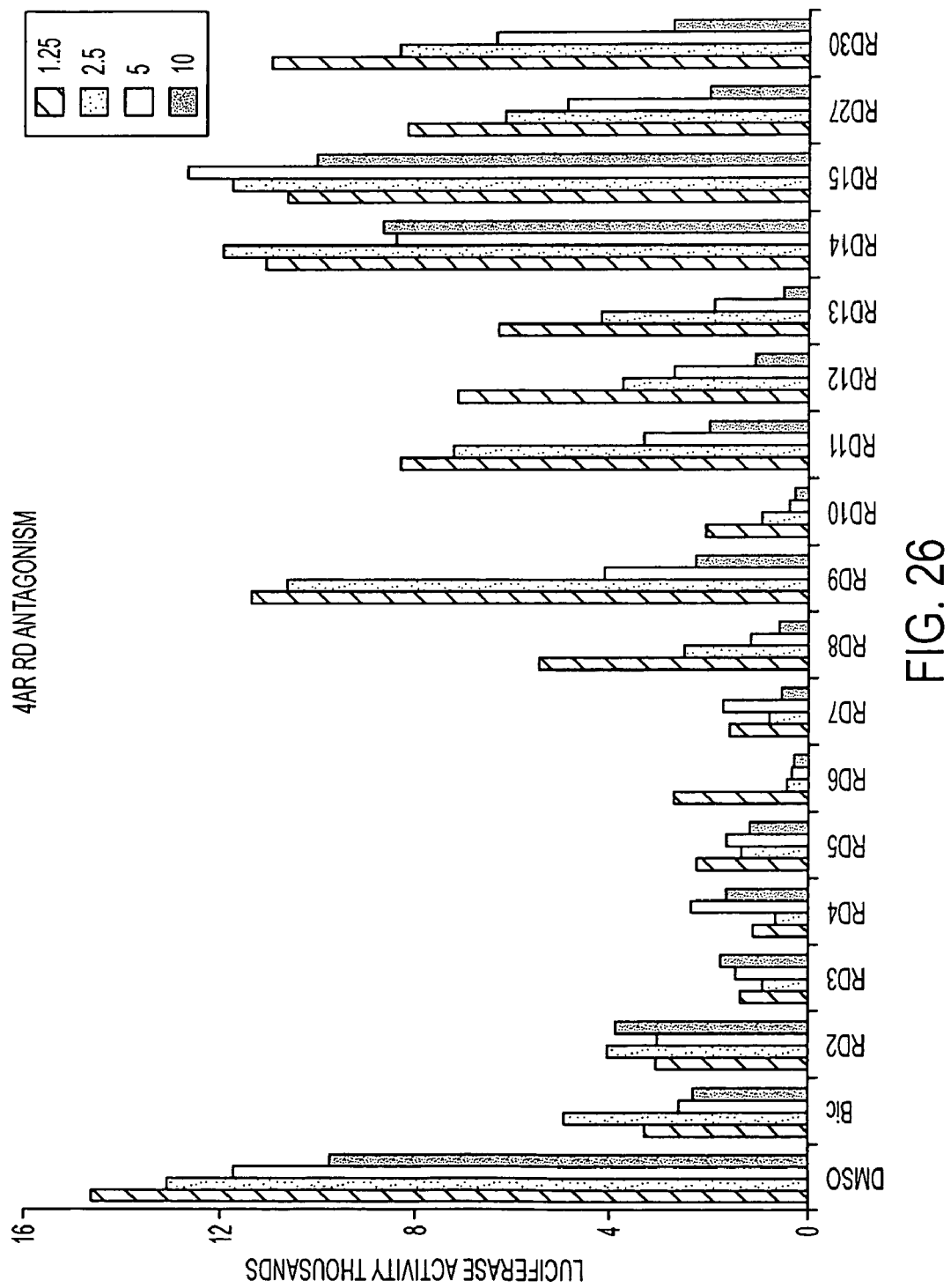

FIG. 26 is a graph of luciferase activity for the 4AR cell line for various compounds administered at concentrations ranging from 1.25 to 10 μmol.

Figure 27:
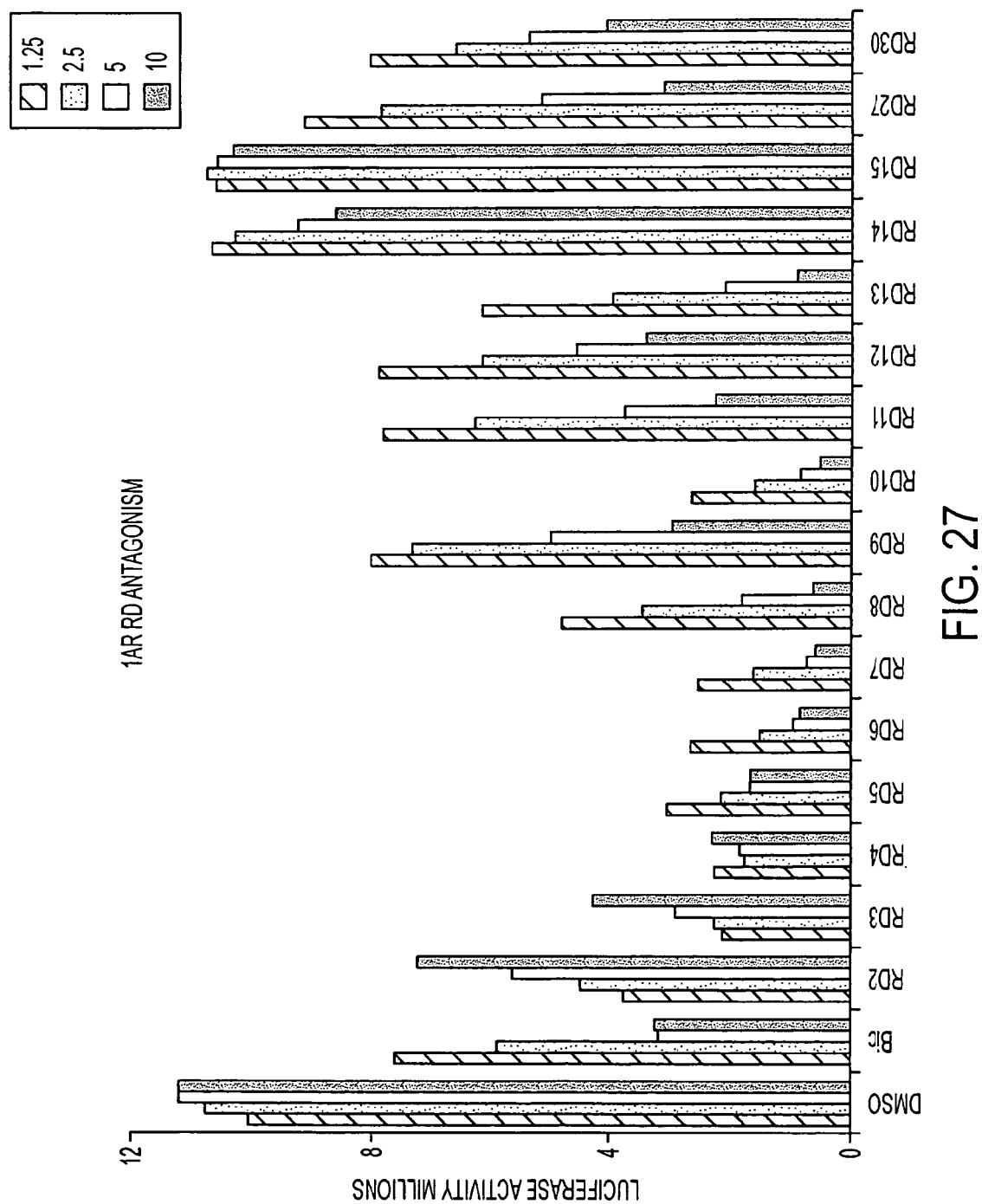

FIG. 27 is a graph of PSA levels for the 1AR cell line for various compounds administered at concentrations ranging from 1.25 to 10 μmol.

Figure 28:
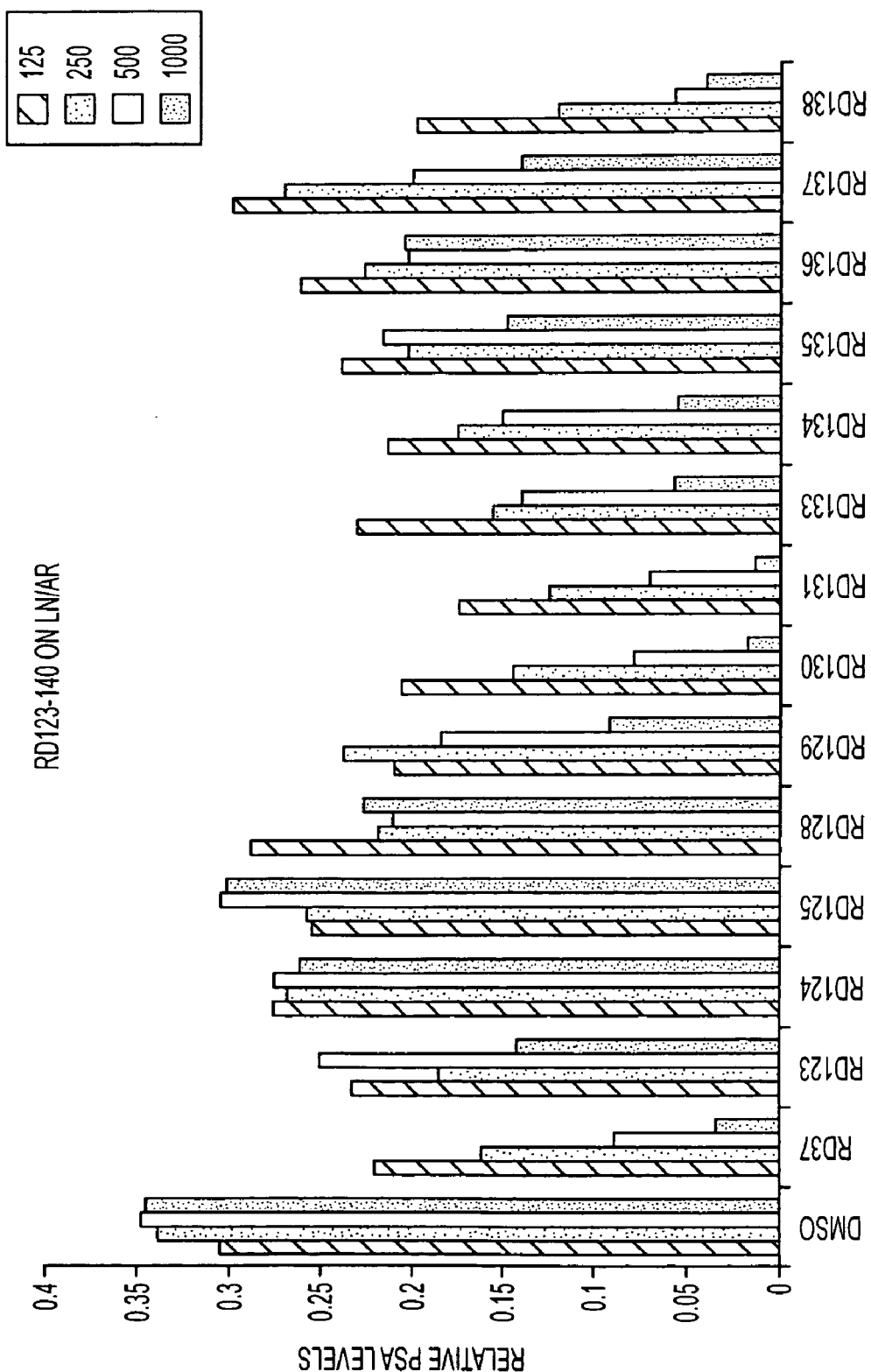

FIG. 28 is a graph of PSA levels for the LN/AR cell line for various compounds administered at concentrations ranging from 125 nmol to 1000 nmol.

Figure 29:
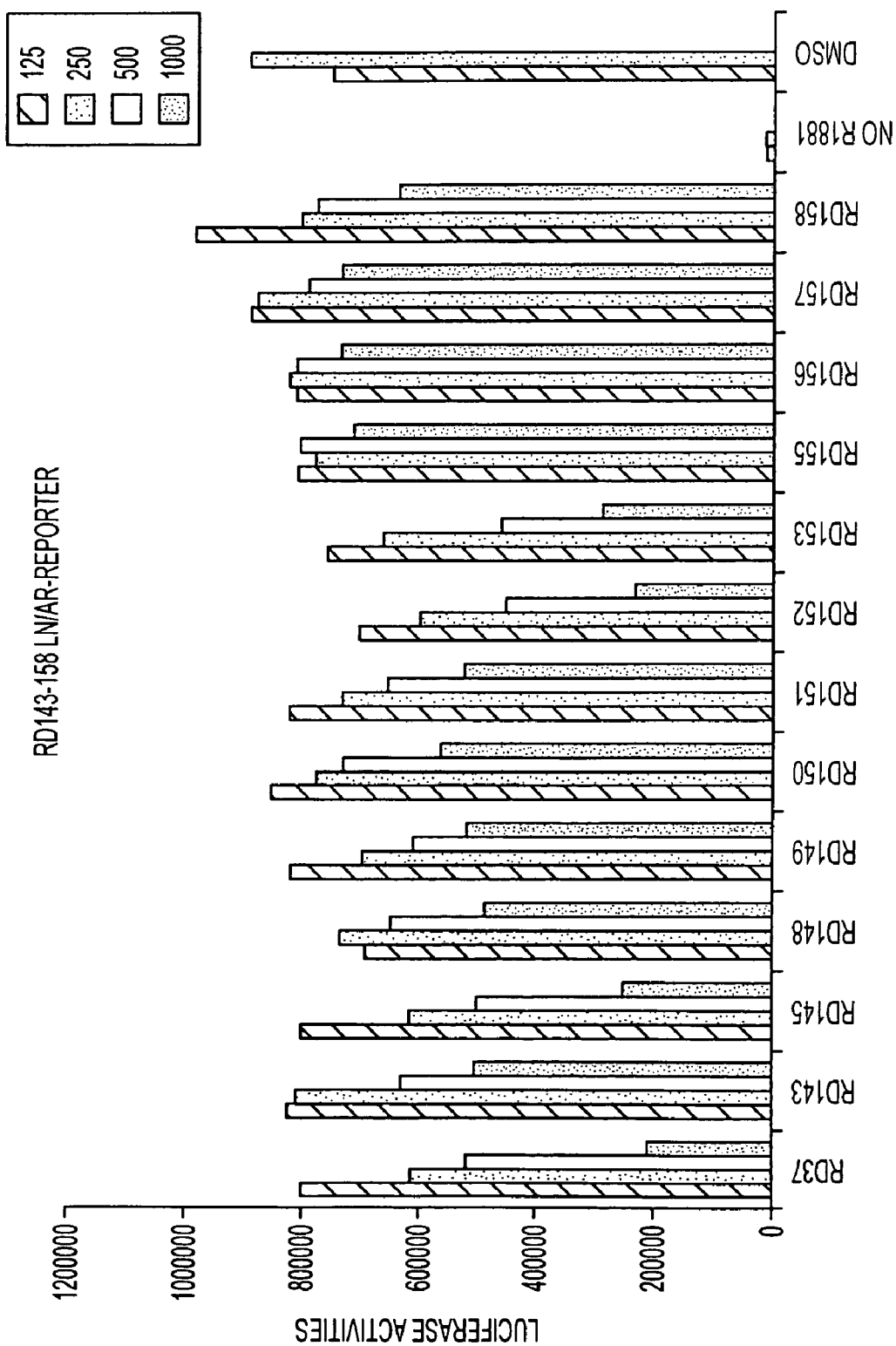

FIG. 29 is a graph of luciferase activity for various compounds administered at concentrations ranging from 125 nmol to 1000 nmol.

DETAILED DESCRIPTION

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

Synthesis of Diarylhydantoin Compounds

The invention provides for synthesis of diarylthiohydantoin compound having the formula

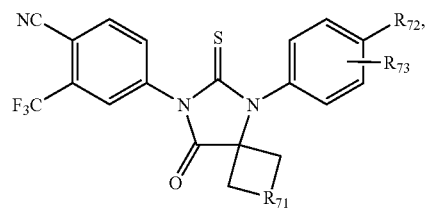

with R71 including an alkyl chain of from 1 to 4 carbon atoms. For example, R72 can be carbamoyl, e.g., —(CO)NH$_2$, or methylcarbamoyl, e.g., —(CO)NHCH$_3$. An amide group bonded at the carbon atom of the carbonyl to another structure is termed a carbamoyl substituent. For example, R73 can be a fluorine or a hydrogen atom. That is, a fluorine atom can be attached to any one of the carbons of the right-hand aryl ring which are not bonded to the R72 substituent or the nitrogen atom. Alternatively, no fluorine atom can be attached to the carbons of the right-hand aryl ring which are not bonded to the R72 substituent or the nitrogen atom. For example, a hydrogen atom can be attached to each of the carbons of the right-hand aryl ring which are not bonded to the R72 substituent or the nitrogen atom.

For example, as further presented below (see, for example, FIGS. 3, 5, 11-13), the compound having the formula

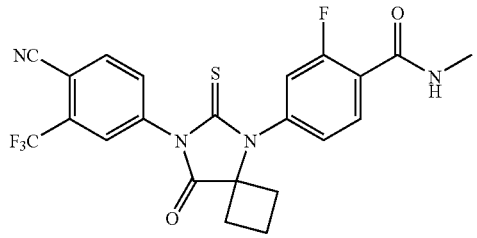

[RD162]

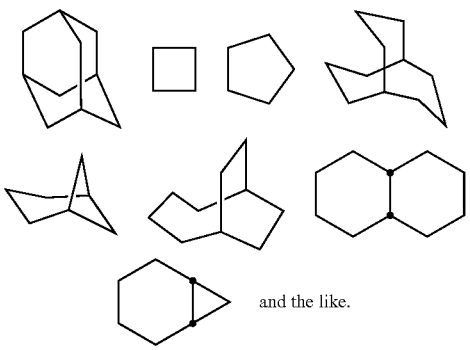

and the like.

exhibited surprisingly potent antagonistic activities with minimal agonistic activities for overexpressed AR in hormone refractory prostate cancer.

A list of several compounds according to this invention is presented in Tables 5-11. The compounds are grouped into tiers, with Tier 1 to Tier 3 compounds being expected to be superior to bicalutamide for the treatment of prostate cancer, Tier 4 compounds being comparable to bicalutamide in effectiveness, and Tier 5 and Tier 6 compounds being worse than bicalutamide for the treatment of prostate cancer. A more detailed description of the protocol used to rank the compounds into tiers is presented below.

Definitions

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which may be attached to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl. "Substituted cycloalkyl" includes a cycloalkyl group optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included in the definition of "substituted alkyl." For example, and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The term "halogen" or "halo" as used herein alone or as part of another group refers to chlorine, bromine, fluorine, and iodine.

The terms "halogenated alkyl", "halogenated alkenyl" and "alkynyl" as used herein alone or as part of another group refers to "alkyl", "alkenyl" and "alkynyl" which are substituted by one or more atoms selected from fluorine, chlorine, bromine, fluorine, and iodine.

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings).

"Substituted aryl" includes an aryl group optionally substituted with one or more functional groups, such as halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heterocyclic" or "heterocycle", as used herein, represents an unsubstituted or substituted stable 5- to 10-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. The term "heterocyclic aromatic" as used here in alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents. such as the substituents included above in the definition of "substituted alkyl" and "substituted cycloalkyl." Examples of heteroaryl groups include the following:

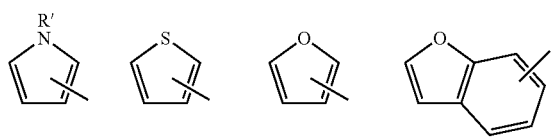

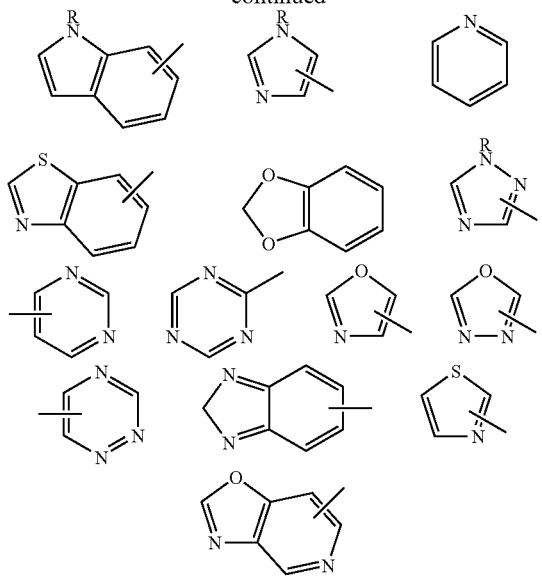

and the like.

EXAMPLE 1

4-isothiocyanato-2-trifluoromethylbenzonitrile, (1a)

4-Amino-2-trifluoromethylbenzonitrile, (2.23 g, 12 mmol) was added portionwise over 15 minutes into the well-stirred heterogeneous mixture of thiophosgene (1 ml, 13 mmol) in water (22 ml) at room temperature. Stirring was continued for an additional 1 h. The reaction medium was extracted with chloroform (3×15 ml). The combined organic phase was dried over $MgSO_4$ and evaporated to dryness under reduced pressure to yield desired product, 4-isothiocyanato-2-trifluoromethylbenzonitrile, (1a), as brownish solid and was used as such for the next step (2.72 g, 11.9 mmol, 99%).

EXAMPLE 2

2-1). (4-aminophenyl)carbamic acid tert-butyl ester, (2a)

An aqueous solution of potassium carbonate (1.52 g, 11 mmol in 5 ml of water) was added to a solution of 1,4-diaminobenzene (3.24 g, 30 mmol) in THF (30 ml) and DMF (10 ml). To this mixture was added di-tert-butyl pyrocarbonate, $Boc_2O$ (2.18 g, 10 mmol), dropwise over 0.5 h. The reaction mixture was stirred for an additional 4 h at room temperature. The mixture was then poured into cold water (40 ml) and extracted with chloroform (3×50 ml). The combined organic phase was dried over $MgSO_4$ and concentrated to yield a brown residue which was subjected to flash chromatography (dichloromethane/acetone, 4:1) to afford (4-aminophenyl)carbamic acid tert-butyl ester, (2a) as a yellow solid (1.98 g, 9.5 mmol, 95%) (yield based on $Boc_2O$).

2-2). {4-[(1-cyano-1-methylethyl)amino] phenyl}carbamic acid tert-butyl ester, 2b The mixture of 2a (0.83 g, 4 mmol), acetone cyanohydrin (4 ml) and $MgSO_4$ (2 g) was heated to 80° C. and stirred over 2.5 h. After cooling down to room temperature, compound 2b was crystallized into water (30 ml). The solid was filtered and dried to yield {4-[(1-cyano-1-methylethyl)amino]phenyl}carbamic acid tert-butyl ester, 2b (1.08 g, 3.9 mmol, 98%).

2-3). {4-[3-(4-cyano-3-trifluoromethylphenyl)-4-imino-5,5-dimethyl-2-thioxo-imidazolidin-1-yl]phenyl}carbamic acid tert-butyl ester, (2c)

Triethylamine (0.202 g, 2 mmol) was added to a solution of 1a (0.456 g, 2 mmol) and 2b (0.57 g, 2 mmol) in dry THF (5 ml). The reaction mixture was stirred at room temperature for 15 h and then concentrated to yield a dark residue which was subjected to flash chromatography (ethyl ether/acetone, 97:3) to afford {4-[3-(4-cyano-3-trifluoromethylphenyl)-4-imino-5,5-dimethyl-2-thioxo-imidazolidin-1-yl]phenyl}carbamic acid tert-butyl ester, (2c) (0.15 g, 0.3 mmol, 15%).

2-4). 4-[3-(4-aminophenyl)-4,4-dimethyl-5-oxo-2-thioxoimidazolidin-1-yl]-2-trifluoromethylbenzonitrile, 2d, [RD9]

The mixture of 2c (0.15 g, 0.3 mmol) in HCl aq, 3N. (1 ml) and methanol (4 ml) was heated to reflux for 2 h. After being cooled to room temperature, the reaction mixture was poured into cold water (5 ml) and extracted with dichloromethane (8 ml). The organic layer was dried over $MgSO_4$, concentrated and chromatographed (dichloromethane/acetone, 9:1) to yield 4-[3-(4-aminophenyl)-4,4-dimethyl-5-oxo-2-thioxoimidazolidin-1-yl]-2-trifluoromethylbenzonitrile, 2d, [RD9] (0.118 g, 0.29 mmol, 97%) as a yellow solid.

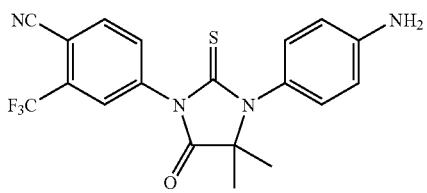

$^1$H NMR (400 MHz, $CDCl_3$) δ 1.54 (s, 6H), 6.73-6.75 (m, 2H), 7.00-7.03 (m, 2H), 8.02 (dd, $J_1$=8.2 Hz, $J_2$=1.8 Hz, 1H), 8.16 (d, J=1.8 Hz, 1H), 8.20 (d, J=8.2 Hz, 1H); $^{13}$C NMR (100 MHz, $CDCl_3$) δ 22.7, 66.2, 109.1, 114.3, 114.9, 120.4, 122.0 (q, J=272.5 Hz), 127.0 (q, J=4.9 Hz), 130.4, 132.5 (q, J=33.0 Hz), 133.4, 135.6, 138.5, 149.2, 175.3, 180.4.

2-5). 4-[3-(4-azidophenyl)-4,4-dimethyl-5-oxo-2-thioxoimidazolidin-1-yl]-2-trifluoromethylbenzonitrile, 2e, [RD10]

An aqueous solution of sulfuric acid (25% wt, 1 ml) was added to a solution of 2d (0.10 g, 0.15 mmol) in acetone (1 ml) at −5° C. An aqueous solution of $NaNO_2$ (0.024 g, 0.35 mmol, in 0.5 ml of water) was added slowly the above mixture over 0.1 h. The reaction mixture was allowed to stir at −5° C. for an additional 1 h and then an aqueous solution of $NaN_3$ (0.02 g, 0.3 mmol in 0.3 ml of water) was added dropwise. Upon completion of the addition, the reaction medium was warmed to room temperature and stirred for an additional 3 h. The product was extracted with dichloromethane (3×5 ml). The combined organic layer was dried over $MgSO_4$, concentrated and chromatographed (dichloromethane) to yield 4-[3-(4-azidophenyl)-4,4-dimethyl-5-oxo-2-thioxoimidazolidin-1-yl]-2-trifluoromethylbenzonitrile, 2e, [RD10] (0.08 g, 0.18 mmol, 72%) as a yellowish solid.

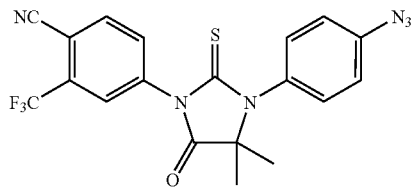

$^1$H NMR (400 MHz, $CDCl_3$) δ 1.54 (s, 6H), 7.17-7.20 (m, 2H), 7.27-7.30 (m, 2H), 7.84 (dd, $J_1$=8.3 Hz, $J_2$=1.8 Hz, 1H), 7.96 (d, J=1.8 Hz, 1H), 7.97 (d, J=8.3 Hz, 1H); $^{13}$C NMR (100 MHz, $CDCl_3$) δ 23.7, 66.4, 110.1, 114.8, 120.4, 122.1 (q, J=272.5 Hz), 127.0 (q, J=4.7 Hz), 131.1, 131.5, 132.3, 133.3 (q, J=33.0 Hz), 135.3, 137.1, 141.7, 174.8, 180.1. MS for $C_{19}H_{13}F_3N_6OS$, calculated 430.4, found 430.1.

EXAMPLE 3

3-1). 2-(4-hydroxyphenylamino)-2-methylpropanenitrile, 3a

A mixture of 4-aminophenol (1.09 g, 10 mmol), acetone cyanohydrin (10 ml) and MgSO4 (2 g) was heated to 80° C. and stirred for 4 h. After concentration of the medium under vacuum, compound 3a was crystallized from water (20 ml). The solid was filtered and dried to yield 2-(4-hydroxyphenylamino)-2-methylpropanenitrile, 3a (1.69 g, 9.6 mmol, 96%).

3-2). 4-[3-(4-hydroxyphenyl)-5-imino-4,4-dimethyl-2-thioxoimidazolidin-1-yl]-2-trifluoromethylbenzonitrile, 3b Triethylamine (0.101 g, 1 mmol) was added to a solution of 1a (0.456 g, 2 mmol) and 3a (0.352 g, 2 mmol) in dry THF (5 ml). The reaction mixture was stirred at 0° C. for 48 h and then concentrated to yield a dark residue which was subjected to flash chromatography (dichloromethane/acetone, 85:15) to afford 4-[3-(4-hydroxyphenyl)-5-imino-4,4-dimethyl-2-thioxoimidazolidin-1-yl]-2-trifluoromethylbenzonitrile, 3b (0.274 g, 0.68 mmol, 34%).

3-3). 4-[3-(4-hydroxyphenyl)-4,4-dimethyl-5-oxo-2-thioxoimidazolidin-1-yl]-2-trifluoromethylbenzonitrile 3c, [RD8]

A mixture of 3b (0.202 g, 0.5 mmol) in HCl aq., 2N (2 ml) and methanol (5 ml) was heated to reflux for 2 h. After being cooled to room temperature, the reaction mixture was poured into cold water (10 ml) and extracted with ethyl acetate (10 ml). The organic layer was dried over $MgSO_4$, concentrated and chromatographed (dichloromethane/acetone, 9:1) to yield 4-[3-(4-hydroxyphenyl)-4,4-dimethyl-5-oxo-2-thioxoimidazolidin-1-yl]-2-trifluoromethylbenzonitrile, 3c, [RD8] (0.198 g, 0.49 mmol, 98%) as a white powder.

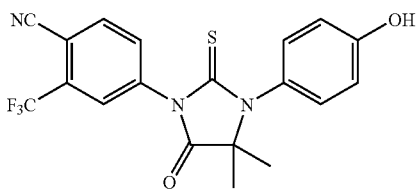

$^1$H NMR ($CDCl_3$, 400 MHz) δ 1.57 (s, 6H), 6.26 (s, OH), 6.90-6.93 (m, 2H), 7.11-7.14 (m, 2H), 7.84 (dd, $J_1$=8.3 Hz, $J_2$=1.8 Hz, 1H), 7.95-7.98 (m, 2H); $^{13}$C NMR ($CDCl_3$, 100

MHz) δ 23.6, 66.5, 109.9, 114.9, 115.7, 116.8, 121.9 (q, J=272.7 Hz), 127.2 (q, J=4.7 Hz), 130.6, 132.3, 133.5 (q, J=33.2 Hz), 135.3, 137.2, 157.0, 175.3, 180.2.

EXAMPLE 4

Chloroacetic acid 4-[3-(4-cyano-3-trifluoromethylphenyl)-5,5-dimethyl-4-oxo-2-thioxoimidazolidin-1-yl]phenyl ester, 4a, [RD13]

Chloroacetyl chloride (0.045 g, 0.4 mmol) was added to a mixture of 3c (0.101 g, 0.25 mmol) and triethylamine (0.041 g, 0.41 mmol) in dry THF (1.5 ml). The mixture was stirred at room temperature for 4 h. Triethylamine hydrochloride was filtered off. The filtrate was concentrated and chromatographed (dichloromethane/acetone, 95:5) to yield 84% of Chloroacetic acid 4-[3 -(4-cyano-3-trifluoromethylphenyl)-5,5-dimethyl-4-oxo-2-thioxoimidazolidin-1-yl]phenyl ester, 4a, [RD13] (0.101 g, 0.21 mmol) as white powder.

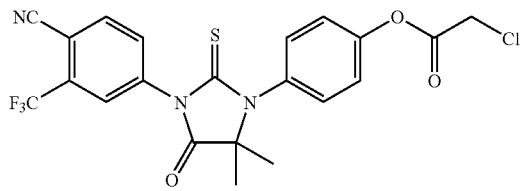

$^1$H NMR (CDCl$_3$, 400 MHz) δ 1.58 (s, 6H), 4.32 (s, 2H), 7.33 (s, 4H), 7.83 (dd, J$_1$=8.3 Hz, J$_2$=1.9 Hz, 1H), 7.95-7.97 (m, 2H); $^{13}$C NMR (CDCl$_3$, 100 MHz) δ 23.7, 40.8, 66.5, 110.1, 114.8, 121.9 (q, J=272.5 Hz), 122.7, 127.1 (q, J=4.7 Hz), 130.9, 132.3, 132.9, 133.5 (q, J=33.2 Hz), 135.3, 137.1, 150.9, 165.5, 174.8, 180.0.

EXAMPLE 5

5-1a). 2-methyl-2-(4-methylphenyl)-aminopropanenitrile, 5a

A mixture of p-toluidine (1.07 g, 10 mmol) and acetone cyanohydrin (10 ml) was heated to 80° C. and stirred for 4 h. The medium was concentrated and dried under vacuum to yield 2 -methyl-2-(4-methylphenyl)aminopropanenitrile, 5a (1.72 g, 9.9 mmol, 99%) as brown solid.

5-1b). 2-methyl-2-(4-methylphenyl)-aminopropanenitrile, 5a

Sodium cyanide (0.735 g, 15 mmol) was added to a mixture of p-toluidine (1.07 g, 10 mmol) and acetone (1.16 g, 20 mmol) in 90% acetic acid (10 ml). The reaction mixture was stirred at room temperature for 12 h and then ethyl acetate (50 ml) was added. The organic layer was washed with water (4×30 ml), dried over magnesium sulfate and concentrated under vacuum to dryness to yield 2-methyl-2-(4-methylphenyl)aminopropanenitrile, 5a (1.65 g, 9.5 mmol, 95%) as a brown solid.

5-2). 4-[3-(4-methylphenyl)-5-imino-4,4-dimethyl-2-thioxoimidazolidin-1-yl]-2-trifluoromethylbenzonitrile, 5b Triethylamine (0.101 g, 1 mmol) was added to a solution of 1a (0.456 g, 2 mmol) and 5a (0.348 g, 2 mmol) in dry THF (3 ml). The reaction mixture was stirred at 0° C. for 2 days and then concentrated to yield a dark residue which was subjected to flash chromatography (dichloromethane/acetone, 95:5) to afford 4-[3-(4-methylphenyl)-5-imino-4,4-dimethyl-2-thioxoimidazolidin-1-yl]-2-trifluoromethylbenzonitrile, 5b (0.136 g, 0.34 mmol, 17%).

5-3a). 4-[3-(4-methylphenyl)-4,4-dimethyl-5-oxo-2-thioxoimidazolidin-1-yl]-2-trifluoromethylbenzonitrile, 5c A mixture of 5b (0.121 g, 0.3 mmol) in HCl aq., 2N (2 ml) and methanol (5 ml) was heated to reflux for 2 h. After being cooled to room temperature, the reaction mixture was poured into cold water (10 ml) and extracted with ethyl acetate (10 ml). The organic layer was dried over MgSO$_4$, concentrated and chromatographed (dichloromethane) to yield 4-[3-(4-methylphenyl)-4,4-dimethyl-5-oxo-2-thioxoimidazolidin-1-yl]-2-trifluoromethylbenzonitrile, 5c (0.118 g, 0.294 mmol, 98%) as a white powder.

5-3b). 4-[3-(4-methylphenyl)-4,4-dimethyl-5-oxo-2-thioxoimidazolidin-1-yl]-2-trifluoromethyl-benzonitrile, 5c, [RD7]

A mixture of 1a (0.547 g, 2.4 mmol) and 5a (0.348 g, 2 mmol) in dry DMF (0.6 ml) was stirred for 36 h. To this mixture were added methanol (20 ml) and 2N HCl (5 ml). The second mixture was refluxed for 6 h. After being cooled to room temperature, the reaction mixture was poured into cold water (30 ml) and extracted with ethyl acetate (40 ml). The organic layer was dried over MgSO$_4$, concentrated and chromatographed (dichloromethane) to yield 4-[3-(4-methylphenyl)-4,4 -dimethyl-5-oxo-2-thioxoimidazolidin-1-yl]-2-trifluoromethyl-benzonitrile, 5c, [RD7] (0.596 g, 1.48 mmol, 74%) as a white powder.

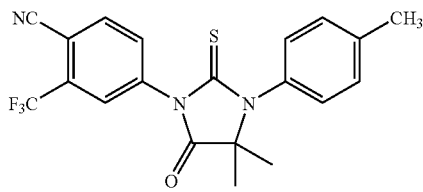

$^1$H NMR (CDCl$_3$, 400 MHz) δ 1.61 (s, 6H), 2.44 (s, 3H), 7.17-7.20 (m, 2H), 7.33-7.36 (m, 2H), 7.86 (dd, J$_1$=8.3 Hz, J$_2$=1.8 Hz, 1H), 7.96-7.98 (m, 2H); $^{13}$C NMR (CDCl$_3$, 100 MHz) δ 21.3, 23.6, 66.4, 110.0, 114.9, 121.9 (q, J=272.6 Hz), 127.1 (q, J=4.7 Hz), 129.2, 130.6, 132.2, 132.3, 133.4 (q, J=33.2 Hz), 135.2, 137.2, 140.1, 175.1, 179.9.

EXAMPLE 6

6-1). 2-methyl-2-phenylaminopropanenitrile, 6a

A mixture of aminobenzene (0.931 g, 10 mmol) and acetone cyanohydrin (2 ml) was heated to reflux and stirred for 20 h. After being cold to room temperature, the reaction mixture was poured into ethyl acetate (40 ml) and washed with cold water (2×30 ml). The organic layer was dried over MgSO$_4$, concentrated under vacuum to dryness to yield 2-methyl-2-phenylaminopropanenitrile, 6a (1.51 g, 9.4 mmol, 94%) as slurry brown liquid.

6-2). 4-[3-phenyl-4,4-dimethyl-5-oxo-2-thioxoimidazolidin-1-yl]-2-trifluoromethylbenzonitrile, 6b, [RD10]

A mixture of 1a (0.274 g, 1.2 mmol) and 6a (0.160 g, 1 mmol) in dry DMF (0.2 ml) was stirred for 48 h. To this mixture were added methanol (10 ml) and 2N HCl (3 ml). The second mixture was refluxed for 6 h. After being cooled to room temperature, the reaction mixture was poured into cold water (20 ml) and extracted with ethyl acetate (20 ml). The organic layer was dried over MgSO$_4$, concentrated and chromatographed (dichloromethane) to yield 4-[3-phenyl-4,4-dimethyl-5-oxo-2-thioxoimidazolidin-1-yl]-2-trifluoromethylbenzonitrile, 6b, [RD10] (0.276 g, 0.71 mmol, 71%) as a white powder.

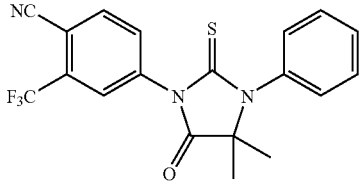

$^1$H NMR (CDCl$_3$, 400 MHz) δ 1.60 (s, 6H), 7.28-7.31 (m, 2H), 7:50-7.58 (m, 3H), 7.85 (dd, J$_1$=8.3 Hz, J$_2$=1.8 Hz, 1H), 7.96-7.99 (m, 2H); $^{13}$C NMR (CDCl$_3$, 100 MHz) δ 23.7, 66.4, 110.2, 114.8, 121.9 (q, J=272.6 Hz), 127.1 (q, J=4.7 Hz), 129.5, 129.8, 129.9, 132.2, 133.4 (q, J=33.2 Hz), 135.1, 135.2, 137.2, 175.0, 179.9.

EXAMPLE 7

7-1a). 1-(4-methylphenyl)aminocyclobutanenitrile, 7a

Sodium cyanide (0.147 g, 3 mmol) was added to a mixture of p-toluidine (0.214 g, 2 mmol) and cyclobutanone (0.21 g, 3 mmol) in 90% acetic acid (3 ml). The reaction mixture was stirred at room temperature for 12 h and then 20 ml of ethyl acetate was added. The organic layer was washed with water (3×10 ml), dried over magnesium sulfate and concentrated under vacuum to dryness to yield 1-(4-methylphenyl)aminocyclobutanenitrile, 7a (0.343 g, 1.84 mmol, 92%) as a brown solid.

7-1b). 1-(4-methylphenyl)aminocyclobutanenitrile, 7a

Trimethylsilyl cyanide (0.93 ml, 7 mmol) was added dropwise to a mixture of p-toluidine (0.535 g, 5 mmol) and cyclobutanone (0.42 g, 6 mmol). The reaction mixture was stirred at room temperature for 6 h and then concentrated under vacuum to obtain a brown liquid which was subjected to chromatography (dichloromethane) to yield 1-(4-methylphenyl)aminocyclobutanenitrile, 7a (0.912 g, 4.9 mmol, 98%) as a yellowish solid.

7-2). 4-(8-imino-6-thioxo-5-(4-methylphenyl)-5,7-diazaspiro[3.4]oct-7-yl)-2-trifluoromethylbenzonitrile, 7b To a solution of 1a (2.28 g, 10 mmol) in dry DMF (3 ml) was added progressively, over 20 hours, a solution of 7a (1.764 g, 9 mmol) in dry DMF (3 ml) at room temperature. The medium was stirred for an additional 4 h. After DMF being evaporated, the residue was chromatographed (dichloromethane/acetone, 95:5) to afford 4-(8-imino-6-thioxo-5-(4-methylphenyl)-5,7-diazaspiro[3.4]oct-7-yl)-2-trifluoromethylbenzonitrile, 7b (1.937 g, 4.68 mmol, 52%).

7-3a). 4-(8-oxo-6-thioxo-5-(4-methylphenyl)-5,7-diazaspiro[3.4]oct-7-yl)-2-trifluoromethylbenzonitrile, 7c [RD37]

A mixture of 7b (0.041 g, 0.1 mmol) in HCl aq., 2N (3 ml) and methanol (1 ml) was heated to reflux for 2 h. After being cooled to room temperature, the reaction mixture was poured into cold water (5 ml) and extracted with ethyl acetate (6 ml). The organic layer was dried over MgSO$_4$, concentrated and chromatographed (dichloromethane) to yield 4-(8-oxo-6-thioxo-5-(4-methylphenyl)-5,7-diazaspiro[3.4]oct-7-yl)-2-trifluoromethylbenzonitrile, 4-(8-oxo-6-thioxo-5-(4-methylphenyl)-5,7-diazaspiro[3.4]oct-7-yl)-2-trifluoromethylbenzonitrile, 7c (0.04 g, 0.096 mmol, 96%) as a white powder.

7-3b). 4-(8-oxo-6-thioxo-5-(4-methylphenyl)-5,7-diazaspiro[3.4]oct-7-yl)-2-trifluoromethylbenzonitrile, 7c, [RD37]

A mixture of 1a (0.912 g, 4 mmol) and 7a (0.558 g, 3 mmol) in dry DMF (0.5 ml) was stirred at room temperature for 24 h. To this mixture were added methanol (30 ml) and HCl aq. 2N (6 ml). The second mixture was refluxed for 6 h. After being cooled to room temperature, the reaction mixture was poured into cold water (50 ml) and extracted with ethyl acetate (60 ml). The organic layer was dried over MgSO$_4$, concentrated and chromatographed (dichloromethane) to yield 4-(8-oxo-6-thioxo-5-(4-methylphenyl)-5,7-diazaspiro[3.4]oct-7-yl)-2-trifluoromethylbenzonitrile, 7c (0.959 g, 2.31 mmol, 77%) as a white powder.

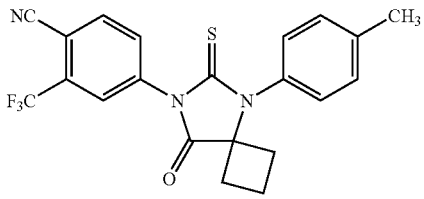

$^1$H NMR (CDCl$_3$, 400 MHz) δ 1.62-1.69 (m, 1H), 2.16-2.22 (m, 1H), 2.46 (s, 3H), 2.55-2.66 (m, 4H), 7.19-7.26 (m, 2H), 7.36-7.42 (m, 2H), 7.86 (dd, J$_1$=8.3 Hz, J$_2$=1.8 Hz, 1H), 7.96 (d, J=8.3 Hz, 1H), 7.99 (d, J=1.8 Hz, 1H); $^{13}$C NMR (CDCl$_3$, 100 MHz) δ 13.7, 21.3, 31.4, 67.4, 109.9, 114.9, 121.9 (q, J=272.6 Hz), 127.1 (q, J=4.7 Hz), 129.5, 130.8, 132.2, 132.4, 133.3 (q, J=33.2 Hz), 135.2, 137.3, 140.1, 175.0, 180.0.

EXAMPLE 8

8-1). 1-(4-methylphenyl)aminocyclopentanenitrile, 8a

Trimethylsilyl cyanide (0.865 ml, 7 mmol) was added dropwise to a mixture of p-toluidine (0.535 g, 5 mmol) and cyclopentanone (0.589 g, 7 mmol). The reaction mixture was stirred at room temperature for 6 h and then concentrated under vacuum to obtain a brown liquid which was subjected to chromatography (dichloromethane) to yield 1-(4-methylphenyl)aminocyclopentanenitrile, 8a (0.981 g, 4.9 mmol, 98%) as a yellowish solid.

8-2). 4-(4-Oxo-2-thioxo-1-(4-methylphenyl)-1,3-diazaspiro[4.4]non-3-yl)-2-trifluoromethylbenzonitrile, 8b, [RD35]

A mixture of 1a (0.296 g, 1.3 mmol) and 8a (0.2 g, 1 mmol) in dry DMF (0.2 ml) was stirred for 48 h. To this mixture were added methanol (10 ml) and HCl aq. 2N (3 ml). The second mixture was refluxed for 6 h. After being cooled to room temperature, the reaction mixture was poured into cold water (20 ml) and extracted with ethyl acetate (30 ml). The organic layer was dried over MgSO$_4$, concentrated and chromatographed (dichloromethane) to yield 4-(4-Oxo-2-thioxo-1-(4-methylphenyl)-1,3-diazaspiro[4.4]non-3-yl)-2-trifluoromethylbenzonitrile, 8b, [RD35] (0.3 g, 0.7 mmol, 70%) as a white powder.

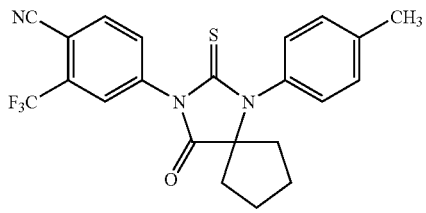

$^1$H NMR (CDCl$_3$, 400 MHz) δ 1.47-1.57 (m, 2H), 1.81-1.92 (m, 2H), 2.20-2.24 (m, 2H), 2.27-2.34 (m, 2H), 2.43 (s, 3H), 7.18-7.22 (m, 2H), 7.33-7.36 (m, 2H), 7.86 (dd, J$_1$=8.2 Hz, J$_2$=1.8 HZ, 1H), 7.96 (d, J=8.2 Hz, 1H), 7.98 (d, J=1.8 Hz, 1H); $^{13}$C NMR (CDCl$_3$, 100 MHz) δ 21.3, 25.2, 36.3, 75.1, 110.0, 114.9, 121.9 (q, J=272.5 Hz), 127.1 (q, J=4.7 Hz), 129.5, 130.7, 123.2, 133.0, 133.4 (q, J=33.2 Hz), 135.1, 137.4, 140.0, 176.3, 180.2.

EXAMPLE 9

9-1). 1-(4-methylphenyl)aminocyclohexanenitrile, 9a

Sodium cyanide (0.147 g, 3 mmol) was added to a mixture of p-toluidine (0.214 g, 2 mmol) and cyclohexanone (0.294 g, 3 mmol) in acetic acid 90% (3 ml). The reaction mixture was stirred at room temperature for 12 h and then 20 ml of ethyl acetate was added. The organic layer was washed with water (3×10 ml), dried over magnesium sulfate and concentrated under vacuum to dryness to yield 14-methylphenyl)aminocyclohexanenitrile, 9a (0.398 g, 1.86 mmol, 93%) as a brown solid.

9-2). 4-(4-imino-2-thioxo-1-(4-methylphenyl)-1,3-diazaspiro[4.5]dec-3-yl)-2-trifluoromethylbenzonitrile, 9b Triethylamine (0.05 g, 0.5 mmol) was added to a solution of 1a (0.228 g, 1 mmol) and 9a (0.214 g, 1 mmol) in dry THF (2 ml). The reaction mixture was stirred at room temperature for 2 days and then concentrated to yield a dark residue which was subjected to flash chromatography (dichloromethane/acetone, 95:5) to afford 4-(4-imino-2-thioxo-1-(4-methylphenyl)-1,3-diazaspiro[4.5]dec-3-yl)-2-trifluoromethylbenzonitrile, 9b (0.035 g, 0.08 mmol, 8%).

9-3). 4-(4-Oxo-2-thioxo-1-(4-methylphenyl)-1,3-diazaspiro[4.5]dec-3-yl)-2-trifluoromethylbenzonitrile, 9c, [RD48]

A mixture of 9b (0.035 g, 0.08 mmol) in HCl aq., 2N (1 ml) and methanol (3 ml) was heated to reflux for 2 h. After being cooled to room temperature, the reaction mixture was poured into cold water (5 ml) and extracted with ethyl acetate (6 ml). The organic layer was dried over MgSO$_4$, concentrated and chromatographed (dichloromethane) to yield 4-(4-Oxo-2-thioxo-1-(4 -methylphenyl)-1,3-diazaspiro[4.5]dec-3-yl)-2-trifluoromethylbenzonitrile, 9c, [RD48](0.034 g, 0.076 mmol, 95%) as a white powder.

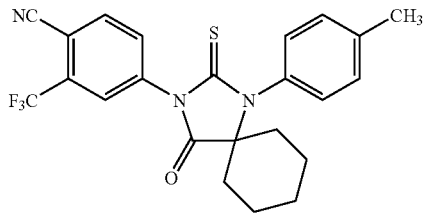

$^1$H NMR (CDCl$_3$, 400 MHz) δ 1.02-1.05 (m, 1H), 1.64-1.76 (m, 4H), 2.03-2.12 (m, 5H), 2.44 (s, 3H), 7.12-7.15 (m, 2H), 7.33-7.36 (m, 2H), 7.85 (dd, J$_1$=8.2 Hz, J$_2$=1.8 Hz, 1H), 7.96 (d, J=8.3 Hz, 1H), 7.97 (d, J=1.8 Hz, 1H); $^{13}$C NMR (CDCl$_{100}$ MHz) 20.7, 21.3, 24.0, 32.6, 67.4, 109.9, 114.9, 122.0 (q, J=272.5 Hz), 127.3 (q, J=4.6 Hz), 130.0, 130.5, 132.0, 132.5, 133.3 (q, J=33.2 Hz), 135.2, 137.3, 140.1, 174.1, 180.1.

EXAMPLE 10

10-1). 1-(4-methylphenyl)aminocyclohexanenitrile, 10a

Sodium cyanide (0.147 g, 3 mmol) was added to a mixture of p-toluidine (0.214 g, 2 mmol) and cycloheptanone (0.337 g, 3 mmol) in acetic acid 90% (3 ml). The reaction mixture was stirred at room temperature for 12 h and then 20 ml of ethyl acetate was added. The organic layer was washed with water (3×10 ml), dried over magnesium sulfate and concentrated under vacuum to dryness to yield 1-(4-methylphenyl)aminocyclohexanenitrile, 10a (0.438 g, 1.92 mmol, 96%) as a brown solid.

10-2). 4-(4-imino-2-thioxo-1-(4-methylphenyl)-1,3-diazaspiro[4.5]undec-3-yl)-2-trifluoromethylbenzonitrile, 10b Triethylamine (0.05 g, 0.5 mmol) was added to a solution of 1a (0.228 g, 1 mmol) and 9a (0.228 g, 1 mmol) in dry THF (2 ml). The reaction mixture was stirred at room temperature for 2 days and then concentrated to yield a dark residue which was subjected to flash chromatography (dichloromethane/acetone, 95:5) to afford 4-(4-imino-2-thioxo-1-(4-methylphenyl)-1,3-diazaspiro[4.5]undec-3-yl)-2-trifluoromethylbenzonitrile, 10b (0.036 g, 0.08 mmol, 8%).

10-3). 4-(4-oxo-2-thioxo-1-(4-methylphenyl)-1,3-diazaspiro[4.5]undec-3-yl)-2-trifluoromethylbenzonitrile, 10c, [RD49]

A mixture of 9b (0.036 g, 0.08 mmol) in HCl aq., 2N (1 ml) and methanol (3 ml) was heated to reflux for 2 h. After being cooled to room temperature, the reaction mixture was poured into cold water (5 ml) and extracted with ethyl acetate (6 ml). The organic layer was dried over MgSO$_4$, concentrated and chromatographed (dichloromethane) to yield 10c (0.034 g, 0.075 mmol, 94%) as a white powder.

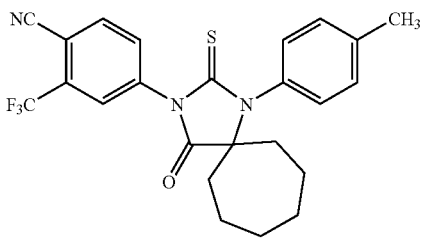

¹H NMR (CDCl₃, 400 MHz) δ 1.24-134 (m, 2H), 1.37-1.43 (m, 2H), 1.53-1.60 (m, 2H), 1.74-1.82 (m, 2H), 2.19-2.25 (m, 4H), 2.44 (s, 3H), 7.16-7.19 (m, 2H), 7.32-7.35 (m, 2H), 7.83 (dd, J₁=8.2 Hz, J₂=1.8 Hz, 1H), 7.95-7.97 (m, 2H); ¹³C NMR (CDCl₃, 100 MHz) δ 21.4, 22.2, 30.9, 36.3, 71.1, 110.0, 114.9, 121.9 (q, J=272.5 Hz), 127.2 (q, J=4.6 Hz), 129.6, 130.5, 132.3, 133.0, 133.2 (q, J=33.2 Hz), 135.1, 137.4, 140.0, 175.9, 179.7.

EXAMPLE 11

11-1). 1-(4-hydroxyphenyl)aminocyclobutanenitrile, 11a

Trimethylsilyl cyanide (0.93 ml, 7 mmol) was added dropwise to a mixture of 4-hydroxyaniline (0.545 g, 5 mmol) and cyclobutanone (0.42 g, 6 mmol). The reaction mixture was stirred at room temperature for 6 h and then concentrated under vacuum to obtain a brown liquid which was subjected to chromatography (dichloromethane:acetone, 98:2) to yield 11a (0.903 g, 4.8 mmol, 96%) as a yellowish solid.

11-2). 4-(8-oxo-6-thioxo-5-(4-hydroxyphenyl)-5,7-diazaspiro[3.4]oct-7-yl)-2-trifluoromethylbenzonitrile, 11b, [RD58]

A mixture of 1a (0.57 g, 2.5 mmol) and 7a (0.376 g, 2 mmol) in dry DMF (0.5 ml) was stirred at room temperature for 40 h. To this mixture were added methanol (30 ml) and HCl aq. (5 ml). The second mixture was refluxed for 6 h. After being cooled to room temperature, the reaction mixture was poured into cold water (40 ml) and extracted with ethyl acetate (50 ml). The organic layer was dried over MgSO₄, concentrated and chromatographed (dichloromethane:acetone, 98:2) to yield 11b (0.659 g, 1.58 mmol, 79%) as a white powder.

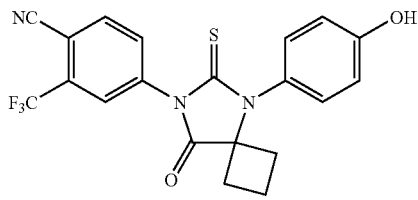

¹H NMR (CDCl₃, 400 MHz) δ 1.55-1.63 (m, 1H), 2.01-2.09 (m, 1H), 2.50-2.65 (m, 4H), 6.97-7.01 (m, 2H), 7.20-7.24 (m, 2H), 8.02 (dd, J₁=8.3 Hz, J₂=1.8 Hz, 1H), 8.14 (d, J=1.8 Hz, 1H), 8.21 (d, J=8.3 Hz, 1H); ¹³C NMR (Acetone-d₆, 100 MHz) δ 13.4, 31.3, 67.5, 108.9, 114.8, 116.1, 123.5 (q, J=271.5 Hz), 127.4 (q, J=4.9 Hz), 131.3, 131.8 (q, J=32.7 Hz), 133.3, 135.5, 136.2, 138.5, 158.1, 175.1, 180.7.

EXAMPLE 12

12-1). 1-(4-biphenylamino)cyclobutanecarbonitrile, 12a

Trimethylsilyl cyanide (0.2 ml, 1.5 mmol) was added dropwise to a mixture of 4-biphenylamine (0.169 g, 1 mmol) and cyclobutanone (0.098 g, 1.4 mmol). The reaction mixture was stirred at room temperature for 6 h and then concentrated under vacuum to obtain a brown liquid which was subjected to chromatography (dichloromethane) to yield 12a (0.24 g, 0.97 mmol, 97%) as a white solid.

12-2). 4-(8-oxo-6 thioxo-5-(4-biphenyl)-5,7-diazaspiro[3.4]oct-7-yl)-2-trifluoromethylbenzonitrile, 12b [RD57]

A mixture of 1a (0.137 g, 0.6 mmol) and 12a (0.124 g, 0.5 mmol) in dry DMF (0.2 ml) was stirred at room temperature for 3 days. To this mixture were added methanol (5 ml) and HCl aq. 2N (1 ml). The second mixture was refluxed for 6 h. After being cooled to room temperature, the reaction mixture was poured into cold water (10 ml) and extracted with ethyl acetate (15 ml). The organic layer was dried over MgSO₄, concentrated and chromatographed (dichloromethane) to yield 12b (0.162 g, 0.34 mmol, 68%) as a white powder.

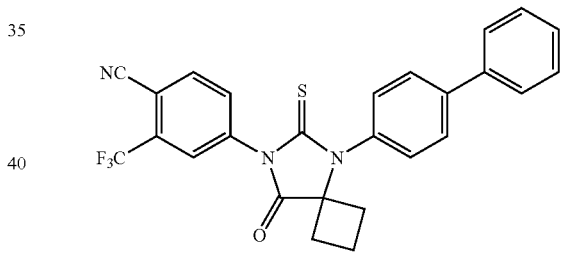

¹H NMR (CDCl₃, 400 MHz) δ 1.67-1.76 (m, 1H), 2.19-2.31 (m, 1H), 2.59-2.74 (m, 4H), 7.40-7.44 (m, 3H), 7.47-7.53 (m, 2H), 7.64-7.67 (m, 2H), 7.79-7.82 (m, 2H), 7.88 (dd, J₁=8.3 Hz, J₂=1.8 Hz, 1H), 7.97 (d, J=8.2 Hz, 1H), 8.02 (d, J=1.8 Hz, 1H); ¹³C NMR (CDCl₃, 100 MHz) δ 13.7, 31.5, 67.5, 110.0, 114.9, 122.0 (q, J=272.6 Hz), 127.1 (q, J=4.7 Hz), 127.3, 128.1, 128.7, 129.0, 130.2, 132.3, 133.5 (q, J=33.2 Hz), 134.2, 135.2, 137.2, 139.6, 142.8, 174.9, 179.9.

EXAMPLE 13

13-1). 1-(2-naphthylamino)cyclobutanecarbonitrile, 13a

Trimethylsilyl cyanide (0.27 ml, 2 mmol) was added dropwise to a mixture of 2-aminonaphthalene (0.143 g, 1 mmol) and cyclobutanone (0.098 g, 1.4 mmol). The reaction mixture was stirred at room temperature for 12 h and then concentrated under vacuum to obtain a brown liquid which was subjected to chromatography (dichloromethane) to yield 13a (0.209 g, 0.94 mmol, 94%) as a yellow solid.

13-2). 4-(8-oxo-6 thioxo-5-(4-biphenyl)-5,7-diaza-spiro[3.4]oct-7-yl)-2-trifluoromethylbenzonitrile, 12b, [RD85]

A mixture of 1a (0.137 g, 0.6 mmol) and 13a (0.111 g, 0.5 mmol) in dry DMF (0.2 ml) was stirred at room temperature for 3 days. To this mixture were added methanol (5 ml) and HCl aq. (1 ml). The second mixture was refluxed for 6 h. After being cooled to room temperature, the reaction mixture was poured into cold water (10 ml) and extracted with ethyl acetate (15 ml). The organic layer was dried over MgSO$_4$, concentrated and chromatographed (dichloromethane) to yield 12b (0.146 g, 0.325 mmol, 65%) as a white powder.

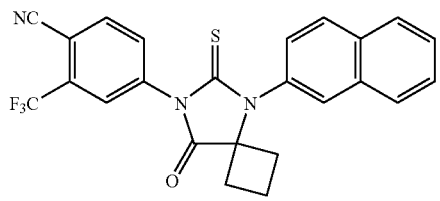

$^1$H NMR (CDCl$_3$, 400 MHz) δ 158-1.68 (m, 1H), 2.17-2.29 (m, 1H), 2.61-2.75 (m, 4H), 7.40 (dd, J$_1$=8.6 Hz, J$_2$=2.0 Hz, 1H), 7.58-7.65 (m, 2H), 7.86-8.00 (m, 5H), 8.04 (J=1.8 Hz, 1H), 8.06 (d, J=8.6 Hz, 1H); $^{13}$C NMR(CDCl$_3$, 100 MHz)δ 13.7, 31.6, 67.7, 110.0, 114.9, 122.0 (q, J=272.6 Hz), 126.8, 127.1 (q, J=4.8 Hz), 127.2, 127.7, 128.0, 128.3, 129.1, 130.2, 132.2, 132.5, 133.4, 133.5 (q, J=33.1 Hz), 133.6, 135.2, 137.2, 175.0, 180.1.

EXAMPLE 14

14-1). 2-(4-methyl-2-pyridinamino)-2-methylpropanenitrile, 14a

Trimethylsilyl cyanide (0.27 ml, 2 mmol) was added dropwise to a mixture of 2-amino-4-methylpyridine (0.108 g, 1 mmol) and acetone (0.58 g, 10 mmol). The reaction mixture was stirred at room temperature for 6 days and then concentrated under vacuum to obtain a brown liquid which was subjected to chromatography (dichloromethane:acetone, 60:40) to yield 14a (0.133 g, 0.76 mmol, 76%) as a white solid.

14-2). 4-[4,4-dimethyl-3-(4-methylpyridin-2-yl)-5-oxo-2-thioxoimidazolidin-1-yl]-2-trifluoromethylbenzonitrile, 14b, [RD83]

A mixture of 1a (0.91 g, 0.4 mmol) and 14a (0.053 g, 0.3 mmol) in dry DMF (0.2 ml) was stirred at room temperature for 6 days. To this mixture were added methanol (5 ml) and HCl aq. (1 ml). The second mixture was refluxed for 5 h. After being cooled to room temperature, the reaction mixture was poured into cold water (10 ml) and extracted with ethyl acetate (15 ml). The organic layer was dried over MgSO$_4$, concentrated and chromatographed (dichloromethane) to yield 14b (0.07 g, 0.174 mmol, 58%) as a white powder.

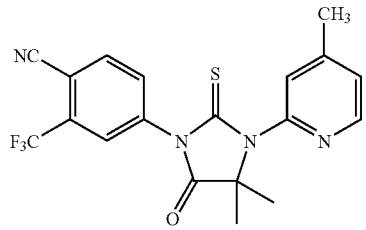

$^1$H NMR (CDCl$_3$, 400 MHz) δ 1.70 (s, 6H), 2.44 (s, 3H), 7.19 (d, J=4.4 Hz, 1H), 7.45 (t, J=0.6 Hz, 1H), 7.82 (dd, J$_1$=8.2 Hz, J$_2$=1.8 Hz, 1H), 7.95 (d, J=1.8 Hz, 1H), 7.97 (d, J=8.2 Hz, 1H), 8.47 (d, J=5.0 Hz, 1H); $^{13}$C NMR (CDCl$_3$, 100 MHz) δ 21.1, 24.1, 67.1, 110.2, 114.8, 121.9 (q, J=272.6 Hz), 124.4, 125.1, 127.3 (q, J=4.8 Hz), 132.4, 133.5 (q, J=33.2 Hz), 135.3, 137.1, 149.2, 149.5, 150.0, 175.2, 179.0.

EXAMPLE 15

15-1). 2-(2-pyridinamino)-2-methylpropanenitrile, 15a

Trimethylsilyl cyanide (0.27 ml, 2 mmol) was added dropwise to a mixture of 2-aminopyridine (0.094 g, 1 mmol) and acetone (0.58 g, 10 mmol). The reaction mixture was stirred at room temperature for 6 days and then concentrated under vacuum to obtain a brown liquid which was subjected to chromatography (dichloromethane:acetone, 60:40) to yield 15a (0.131 g, 0.81 mmol, 81%) as a white solid.

15-2). 4-[4,4-dimethyl-3-(pyridin-2-yl)-5-oxo-2-thioxoimidazolidin-1-yl]-2-trifluoromethylbenzonitrile, 15b, [RD82]

A mixture of 1a (0.91 g, 0.4 mmol) and 15a (0.048 g, 0.3 mmol) in dry DMF (0.3 ml) was stirred at room temperature for 10 days. To this mixture were added methanol (5 ml) and of HCl aq. (1 ml). The second mixture was refluxed for 5 h. After being cooled to room temperature, the reaction mixture was poured into cold water (10 ml) and extracted with ethyl acetate (15 ml). The organic layer was dried over MgSO$_4$, concentrated and chromatographed (dichloromethane) to yield 15b (0.059 g, 0.153 mmol, as a white powder.

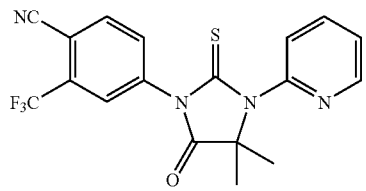

$^1$H NMR (CDCl$_3$, 400 MHz) δ 1.73 (s, 6H), 7.38 (dd, J$_1$=7.3 Hz, J$_2$=5.4 Hz, 1H), 7.71 (d, J=8.0 Hz, 1H), 7.87 (dd, J$_1$=8.2 Hz, J$_2$=1.8 Hz, 1H), 7.95 (td, J$_1$=7.8 Hz, J$_2$=1.8 Hz, 1H), 7.95 (d, J=1.3 Hz, 1H), 7.98 (d, J=8.2 Hz, 1H), 8.62 (dd, J$_1$=4.7 Hz, J$_2$=1.3 Hz, 1H); $^{13}$C NMR (CDCl$_3$, 100 MHz) δ 24.2, 67.1, 110.3, 114.8, 121.9 (q, J=272.6 Hz), 123.7, 123.8, 127.3 (q, J=4.8 Hz), 132.4, 133.6 (q, J=33.2 Hz), 135.3, 137.1, 138.2, 149.5, 149.6, 175.1, 179.0.

EXAMPLE 16

16-1). 1-(5-methyl-2H-pyrazol-3-ylamino)-cyclobutanecarbonitrile, 16a

Trimethylsilyl cyanide (0.532 ml, 4.0 mmol) was added dropwise to the mixture of 3-amino-5-methylpyrazole (0.194 g, 2.0 mmol) and cyclobutanone (0.154 g, 2.2 mmol). The reaction mixture was stirred at room temperature for 40 h and then concentrated under vacuum to obtain a dark liquid which was subjected to chromatography (dichloromethane) to yield 16a (0.267 g, 1.52 mmol, 76%) as a off-white powder.

16-2). 4-[5-(5-methyl-2H-pyrazol-3-yl)-8-oxo-6-thioxo-5,7-diaza-spiro[3.4]oct-7-yl]-2-trifluoromethyl-benzonitrile, 16b, [RD84]

A mixture of 1a (0.0684 g, 0.3 mmol) and 16a (0.053 g, 0.3 mmol) in dry DMF (0.2 ml) was stirred at room temperature for 4 days. To this mixture were added methanol (10 ml) and HCl aq. 2N (2 ml). The second mixture was refluxed for 5 h. After being cooled to room temperature, the reaction mixture was poured into cold water (30 ml) and extracted with ethyl acetate (30 ml). The organic layer was dried over MgSO4, concentrated and chromatographed (dichloromethane:acetone, 97:3) to yield 16b (0.0826 g, 0.2 mmol, 67%) as a white powder.

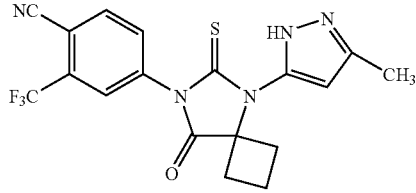

$^1$H NMR (acetone d$_6$, 400 MHz) δ 1.66-1.76 (m, 1H), 2.00-2.07 (m, 1H), 3.35 (s, 3H), 2.56-2.63 (m, 2H), 2.85-2.93 (m, 2H), 8.04 (dd, J$_1$=8.2 Hz, J$_2$=1.6 Hz, 1H), 8.18 (d, J=1.6 Hz, 1H), 8.22 (d, J=8.2 Hz, 1H), 11.99 (s, 1H); $^{13}$C NMR (acetone d$_6$, 100 MHz) δ 10.2, 13.1, 31.1, 67.4, 102.5, 109.1, 114.8, 122.5 (q, J=271.4 Hz), 127.8 (q, J=4.8 Hz), 131.9 (q, J=33.6 Hz), 133.6, 135.6, 138.4, 139.9, 145.0, 175.0, 179.6.

EXAMPLE 17

4-[3-(4-hydroxyphenyl)-4,4-dimethyl-2,5-dithioxo-imidazolidin-1-yl]-2-trifluoromethylbenzonitrile, 17a, [RD59]

A mixture of 3c (0.081 g, 0.2 mmol) and Lawesson reagent (0.097 g, 0.24 mmol) in toluene (3 ml) was heated to reflux for 15 h. After being cooled to room temperature, the reaction mixture was poured into cold water (10 ml) and extracted with ethyl acetate (10 ml). The organic layer was dried over MgSO$_4$, concentrated and chromatographed (dichloromethane:pentane, 9:1) to yield 17a (0.0185 g, 0.044 mmol, 22%) as a white powder.

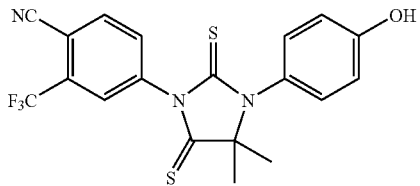

$^1$H NMR (CDCl$_3$, 400 MHz) δ 1.65 (s, 6H), 6.95-6.97 (m, 2H), 7.15-7.18 (m, 2H), 7.75 (d, J=8.2 Hz, 1H), 7.86 (d, J=1.8 Hz, 1H), 7.98 (dd, J$_1$=8.2 Hz, J$_2$=1.8 Hz, 1H); $^{13}$C NMR (CDCl$_3$, 100 MHz) a 27.9, 77.8, 110.9, 114.7, 116.7, 121.9 (q, J=272.6 Hz), 128.1 (q, J=4.8 Hz), 129.1, 130.7, 133.3, 133.5 (q, J=33.2 Hz), 135.5, 140.3, 156.8, 179.9, 207.9.

EXAMPLE 18

4-[3-(4-hydroxyphenyl)-4,4-dimethyl-2,5-dioxoimidazolidin-1-yl]-2-trifluoromethylbenzonitrile, 18a, [RD60]

Hydrogen peroxide, 30% (3 ml, 26 mmol) was added dropwise to a solution of of 3c (0.121 g, 0.4 mmol) in glacial acetic acid (3 ml). The mixture was stirred at room temperature for 12 h and then 20 ml of ethyl acetate was added. The organic layer was washed with water (3×15 ml), dried over magnesium sulfate, concentrated and chromatographed (dichloromethane) to yield 18a (0.102 g, 0.261 mmol, 87%) as a white powder.

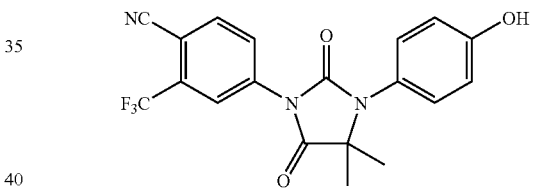

$^1$H NMR (CDCl, 400 MHz) δ 1.52 (s, 6H), 6.70-6.73 (m, 2H), 7.01-7.04 (m, 2H), 7.92 (d, J=8.4 Hz, 1H), 8.00 (dd, J$_1$=8.4 Hz, J$_2$=1.8 Hz, 1H), 8.15 (d, J=1.8 Hz, 1H); $^{13}$C NMR (CDCl$_3$, 100 MHz) δ 23.7, 63.7, 108.4, 115.0, 116.7, 121.9 (q, J=272.6 Hz), 123.5 (q, J=4.8 Hz), 124.0, 128.5, 130.5, 133.6 (q, J=33.2 Hz), 135.5, 136.2, 153.4, 157.2, 174.5.

EXAMPLE 19

19-1). 3-fluoro-2-methyl-2-(4-methylphenyl)amino-propionitrile, 19a

Trimethylsilyl cyanide (0.146 ml, 1.1 mmol) was added dropwise to the mixture of p-toluidine (0.107 g, 1 mmol) and fluoroacetone (0.082 g, 1.1 mmol). The reaction mixture was stirred at room temperature for 12 h and then concentrated under vacuum to obtain a brown liquid which was subjected to chromatography (dichloromethane) to yield 19a (0.179 g, 0.93 mmol, 93%) as a yellowish solid.

19-2). 4-(4 fluoromethyl-4-methyl-5-oxo-2-thioxo-3-(4-methylphenyl)imidazolidin-1-yl)-2-trifluoromethylbenzonitrile, 19b, [RD68]

A mixture of 1a (0.16 g, 0.7 mmol) and 19a (0.096 g, 0.5 mmol) in dry DMF (0.3 ml) was stirred at room temperature for 48 h. To this mixture were added methanol (10 ml) and HCl aq. 2N (2 ml). The second mixture was refluxed for 6 h. After being cooled to room temperature, the reaction mixture was poured into cold water (30 ml) and extracted with ethyl acetate (30 ml). The organic layer was dried over MgSO$_4$, concentrated and chromatographed (dichloromethane) to yield 19b (0.168 g, 0.4 mmol, 80%) as a white powder.

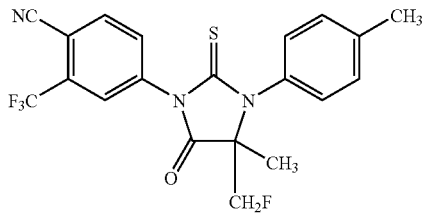

$^1$H NMR (CDCl$_3$, 400 MHz) δ 1.49 (s, 3H), 2.44 (s, 3H), 4.35 (dd, J$_1$=47.2 Hz, J$_2$=10.0 Hz, 1H), 4.71 (dd, J$_1$=45.2 Hz, J$_2$=10 Hz, 1H), 7.22-7.26 (m, 2H), 7.35-7.39 (m, 2H), 7.82 (dd, J$_1$=8.2 Hz, J$_2$=1.8 Hz, 1H), 7.93 (d, J=1.8 Hz, 1H), 7.98 (d, J=8.2 Hz, 1H); $^{13}$C NMR (CDCl$_3$, 100 MHz) δ 17.0 (d, J=4.6 Hz), 21.3, 69.3 (d, J=18.3 Hz), 81.9 (d, J=179.5 Hz), 109.9, 114.8, 121.8 (q, J=272.6 Hz), 127.2 (q, J=4.7 Hz), 129.3, 130.9, 131.6, 132.3, 133.3 (q, J=33.2 Hz), 135.3, 137.0, 140.5, 174.1, 181.4; $^{19}$F NMR (CDCl$_3$, 376 MHz) δ −62.5, 110.9.

EXAMPLE 20

20-1). 2-methyl-2-(4-trifluoromethylphenyl)amino-propanenitrile, 20a

A mixture of 4-trifluoromethylaniline (1.61 g, 10 mmol), acetone cyanohydrin (5 ml) and magnesium sulfate (2 g) was heated to 80° C. and stirred for 12 h. To the medium was added ethyl acetate (50 ml) and then washed with water (3×30 ml). The organic layer was dried over MgSO$_4$ and concentrated under vacuum to dryness to yield 20a (2.166 g, 9.5 mmol, 95%) as brown solid.

20-2). 4-(4,4-dimethyl-5-oxo-2-thioxo-3-(4-trifluoromethylphenyl)imidazolidin-1-yl)-2-trifluoromethylbenzonitrile, 20b, [RD66]

A mixture of 1a (0.114 g, 0.5 mmol) and 20a (0.092 g, 0.4 mmol) in dry DMF (0.3 ml) was stirred at room temperature for 48 h. To this mixture were added methanol (10 ml) and HCl aq. (3 ml). The second mixture was refluxed for 6 h. After being cooled to room temperature, the reaction mixture was poured into cold water (20 ml) and extracted with ethyl acetate (20 ml). The organic layer was dried over MgSO$_4$, concentrated and chromatographed (dichloromethane) to yield 20b (0.117 g, 0.256 mmol, 64%) as a white powder.

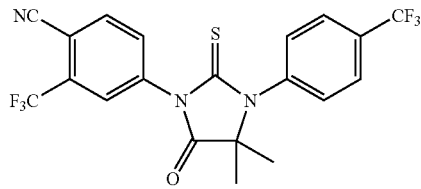

$^1$H NMR (CDCl$_3$, 400 MHz) δ 1.61 (s, 6H), 7.45-7.49 (m, 2H), 7.80-7.83 (m, 2H), 7.85 (dd, J$_1$=8.3 Hz, J$_2$=1.8 Hz, 1H), 7.97 (d, J=1.8 Hz, 1H), 7.99 (d, J=8.2 Hz, 1H); $^{13}$C NMR (CDCl$_3$, 100 MHz) δ 23.8, 66.6, 110.3, 114.8, 121.8 (q, J=272.6 Hz), 123.5 (q, J=271.1 Hz), 127.0 (q, J=4.6 Hz), 127.1 (q, J=4.7 Hz), 130.3, 131.9 (q, J=32.9 Hz), 132.2, 133.5 (q, J=33.3 Hz), 135.3, 136.9, 138.4, 174.6, 179.9.

EXAMPLE 21

21-1). 3-chloro-2-chloromethyl-2-(4-methylphenyl)aminopropanenitrile, 21a

Trimethylsilyl cyanide (0.27 ml, 2 mmol) was added dropwise to a mixture of p-toluidine (0.107 g, 1 mmol) and 1,3-dichloroacetone (0.254 g, 2 mmol). The reaction mixture was heat to 80° C. and stirred for 6 h. To the mixture was added 20 ml of ethyl acetate and then wash with water (2×20 ml). The organic layer was dried over MgSO$_4$, concentrated and chromatographed (dichloromethane) to yield 21a (0.192 g, 0.79 mmol, 79%) as a brown powder.

21-2). 4-(4,4-bischloromethyl-5-oxo-2-thioxo-3-(4-methylphenyl)imidazolidin-1-yl)-2-trifluoromethyl-benzonitrile, 21b, [RD67]

A mixture of 1a (0.16 g, 0.7 mmol) and 21a (0.122 g, 0.5 mmol) in dry DMF (0.5 ml) was stirred at room temperature for 10 days. To this mixture were added methanol (10 ml) and of HCl aq. 2N (2 ml). The second mixture was refluxed for 6 h. After being cooled to room temperature, the reaction mixture was poured into cold water (20 ml) and extracted with ethyl acetate (30 ml). The organic layer was dried over MgSO$_4$, concentrated and chromatographed (dichloromethane) to yield 21b (0.09 g, 0.19 mmol, 38%) as a white powder.

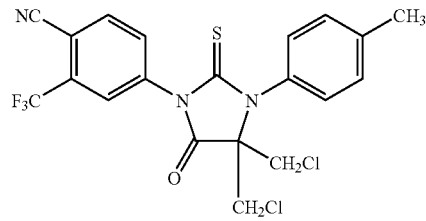

$^1$H NMR (CDCl$_3$, 400 MHz) δ 2.44 (s, 3H), 3.54 (d, J=11.8 Hz, 2H), 3.93 (d, J=11.8 Hz, 2H), 7.37-7.40 (m, 2H), 7.48-7.51 (m, 2H), 7.79 (dd, J$_1$=8.2 Hz, J$_2$=1.8 Hz, 1H), 7.88 (d, J=1.8 Hz, 1H), 7.98 (d, J=8.2 Hz, 1H); $^{13}$C NMR (CDCl$_3$, 100 MHz) δ 21.4, 42.8, 74.3, 110.7, 114.7, 121.7 (q, J=272.6 Hz), 127.2 (q, J=4.7 Hz), 128.8, 131.0, 131.1, 132.4, 133.8 (q, J=33.2 Hz), 135.5, 136.9, 140.9, 169.5, 182.5.

EXAMPLE 22

22-1). 1-(4-methylphenyl)aminocyclo-hexanenitrile, 22a

Sodium cyanide (0.245 g, 5 mmol) was added to a mixture of anthranilic acid (0.411 g, 3 mmol) and acetone (1 ml, 13.6 mmol) in acetic acid 90% (3 ml). The reaction mixture was stirred at room temperature for 12 h and then 50 ml of ethyl acetate was added. The organic layer was washed with brine (3×30 ml). The organic layer was dried over magnesium sulfate, concentrated and chromatographed (dichloromethane:acetone, 90:10) to yield 22a (0.551 g, 2.7 mmol, 90%) as a brown solid.

22-2). 2-[3-(4-cyano-3-trifluoromethylphenyl)-5,5-dimethyl-4-oxo-2-thioxoimidazolidin-1-yl]benzoic acid, 22b, [RD65]

A mixture of 1a (0.114 g, 0.0 mmol) and 22a (0.103 g, 0.5 mmol) in dry DMF (0.5 ml) was stirred at room temperature for 3 days. To this mixture were added methanol (10 ml) and HCl aq. 2N, (3 ml). The second mixture was refluxed for 6 h. After being cooled to room temperature, the reaction mixture was poured into cold water (20 ml) and extracted with ethyl acetate (30 ml). The organic layer was dried over MgSO$_4$, concentrated and chromatographed (ethyl acetate:pentane, 2:1) to yield 22b (0.143 g, 0.33 mmol, 66%) as a white powder.

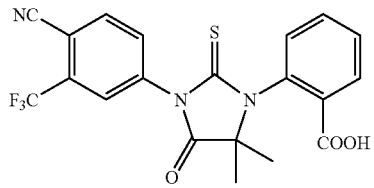

$^1$H NMR (CDCl$_3$, 400 MHz) δ 1.47 (s, 3H), 1.78 (s, 3H), 7.39 (d, J=7.7 Hz, 1H), 7.63 (t, J=7.7 Hz, 1H) 7.76-7.82 (m, 2H), 7.90-7.98 (m, 2H), 8.22 (d, J=6.8 Hz, 1H), 8.96 (bs, 1H); $^{13}$C NMR (CDCl$_3$, 100 MHz) δ 20.6, 26.2, 67.6, 110.1, 114.8, 121.9 (q, J=272.6 Hz), 127.2 (q, J=4.7 Hz), 128.9, 131.0, 130.2, 132.5, 133.2 (q, J=33.3 Hz), 133.7, 134.7, 135.4, 135.8, 137.3, 169.8, 175.3, 180.7.

EXAMPLE 23

23-1). 1-(2-methylphenyl)aminocyclobutanenitrile, 23a

Trimethylsilyl cyanide (0.66 ml, 5 mmol) was added dropwise to the mixture of p-toluidine (0.321 g, 3 mmol) and cyclobutanone (0.28 g, 4 mmol). The reaction mixture was stirred at room temperature for 6 h and then concentrated under vacuum to obtain a brown liquid which was subjected to chromatography (dichloromethane) to yield 23a (0.541 g, 2.91 mmol, 97%) as a yellowish solid.

23-2). 4-(8-oxo-6-thioxo-5-(2-methylphenyl)-5,7-diazaspiro[3.4]oct-7-yl)-2-trifluoromethylbenzonitrile, 23b, [RD71]

A mixture of 1a (0.114 g, 0.5 mmol) and 23a (0.093 g, 0.5 mmol) in dry DMF (0.3 ml) was stirred at room temperature for 3 days. To this mixture were added methanol (10 ml) and HCl aq. 2N, (3 ml). The second mixture was refluxed for 6 h. After being cooled to room temperature, the reaction mixture was poured into cold water (20 ml) and extracted with ethyl acetate (30 ml). The organic layer was dried over MgSO$_4$, concentrated and chromatographed (dichloromethane) to yield 23b (0.116 g, 0.28 mmol, 56%) as a white powder.

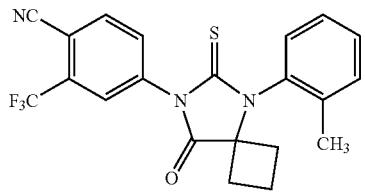

$^1$H NMR (CDCl$_3$, 400 MHz) δ 1.63-1.69 (m, 1H), 2.26 (s, 3H), 2.28-2.41 (m, 2H), 2.58-2.76 (m, 3H), 7:21 (d, J=7.6 Hz, 1H), 7.39-7.49 (m, 3H), 7.89 (dd, J$_1$=8.2 Hz, J$_2$=1.8 Hz, 1H), 7.97 (d, J=8.2 Hz, 1H), 8.00 (d, J=1.8 Hz, 1H); $^{13}$C NMR (CDCl$_3$, 100 MHz) δ 14.2, 18.0, 30.7, 32.2, 67.6, 109.9, 114.9, 121.9 (q, J=272.6 Hz), 127.0 (q, J=4.7 Hz), 127.5, 129.8, 130.2, 131.9, 132.3, 133.4, 133.5 (q, J=34.3 Hz), 135.2, 135.8, 137.1, 138.0, 175.3, 178.7.

EXAMPLE 24

24-1). 1-aminocyclopentanecarbonitrile, 24a

Ammonia anhydrous was bubble into a mixture of cyclopentanone (0.452 g) and trimethylsilyl cyanide (0.66 ml, 5 mmol). The excess of ammonia was refluxed by a dry ice-acetone condenser. After 1 h of reflux, the ammonia was allowed to degas form the medium and then the remaining mixture was concentrated under vacuum to yield 24a (0.522 g, 4.75 mmol, 95%) as a colorless liquid.

24-2). 4-(4-imino-2-thioxo-1,3-diazaspiro[4.4]non-3-yl)-2-trifluoromethylbenzonitrile, 24b Triethylamine (0.101 g, 0.1 mmol) was added to a solution of 1a (0.684 g, 3 mmol) and 24a (0.33 g, 3 mmol) in dry THF (5 ml). The reaction mixture was stirred at room temperature for 5 h and then concentrated to yield a brown residue which was subjected to flash chromatography (dichloromethane/acetone, 93:7) to afford 24b (0.741 g, 2.19 mmol, 73%).

24-3). 4-(4-oxo-2-thioxo-1,3-diazaspiro[4.4]non-3-yl)-2-trifluoromethylbenzonitrile, 24c, [RD77]

A mixture of 24b (0.741 g, 2.19 mmol) in HCl aq., 2N (4 ml) and methanol (20 ml) was heated to reflux for 1 h. After being cooled to room temperature, the reaction mixture was poured into cold water (20 ml) and extracted with ethyl acetate (40 ml). The organic layer was dried over MgSO$_4$, concentrated and chromatographed (dichloromethane) to yield 24c (0.72 g, 2.12 mmol, 97%) as a white powder.

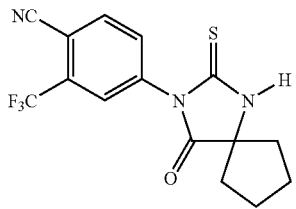

$^1$H NMR (CDCl$_3$, 400 MHz) δ 1.86-190 (m, 2H), 1.96-2.05 (m, 4H), 2.26-2.30 (m, 2H), 7.80 (dd, J$_1$=8.2 Hz, J$_2$=1.8 Hz, 1H), 7.92 (d, J=1.8 Hz, 1H), 7.97 (d, J=8.2 Hz, 1H) 8.20 (bs, NH); $^{13}$C NMR(CDCl$_3$, 100 MHz) δ 25.3, 38.1, 71.0, 110.1, 114.8, 121.8 (q, J=272.7 Hz), 126.8 (q, J=4.7 Hz), 131.9, 133.6 (q, J=34.3 Hz), 135.3, 136.7, 176.1, 179.8.

EXAMPLE 25

25). 4-[1-(4-nitrophenyl)-4-oxo-2-thioxo-1,3-diaza-spiro[4.4]non-3-yl]-2-trifluoromethylbenzonitrile, 25a, [RD55]

A mixture of 25c (0.0678 g, 0.2 mmol), 1,8-Diazabicyclo[5.4.0]undec-7-ene (0.05 g, 0.33 mmol) and 4-fluoronitrobenzene (0.056 g, 0.4 mmol) in dimethylformamide (0.5 ml) was placed under argon in a sealed-tube and heated to 130° C. for 40 h. The reaction mixture was poured into ethyl acetate (5 ml) and washed with water (2×10 ml). The organic layer was dried over MgSO₄, concentrated and chromatographed (dichloromethane) to yield 25a (0.038 g, 0.084 mmol, 42%) as a white powder.

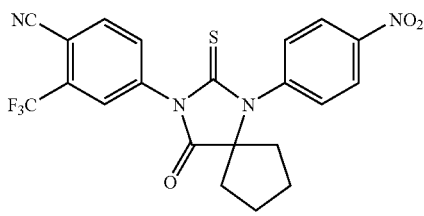

¹H NMR (CDCl₃, 400 MHz) δ 1.53-1.56 (m, 2H), 1.90-1.93 (m, 2H), 2.14-2.18 (m, 2H), 2.37-2.40 (m, 2H), 7.54-7.57 (m, 2H), 7.85 (dd, J₁=8.2 Hz, J₂=1.8 Hz, 1H), 7.97 (d, J=1.8 Hz, 1H), 7.98 (d, J=8.2 Hz, 1H), 8.39-8.43 (m, 2H); ¹³C NMR (CDCl₃, 100 MHz) 25.2, 36.5, 75.3, 110.3, 114.8, 121.8 (q, J=272.6 Hz), 125.2, 127.0 (q, J=4.7 Hz), 131.4, 132.1, 133.6 (q, J=34.3 Hz), 135.3, 136.9, 141.7, 148.1, 175.6, 180.2.

EXAMPLE 26

26). 4-[1-(4-cyanophenyl)-4-oxo-2-thioxo-1,3-diaza-spiro[4.4]non-3-yl]-2-trifluoromethylbenzonitrile, 26a, [RD54]

A mixture of 24c (0.0678 g, 0.2 mmol), 1,8-diazabicyclo[5.4.0]undec-7-ene (0.061 g, 0.4 mmol) and 4-fluorocyanobenzene (0.048 g, 0.4 mmol) in dimethylformamide (0.5 ml) was placed under argon in a sealed-tube and heated to 140° C. for 5 days. The reaction mixture was poured into ethyl acetate (5 ml) and washed with water (2×10 ml). The organic layer was dried over MgSO₄, concentrated and chromatographed (dichloromethane) to yield 26a (0.023 g, 0.052 mmol, 26%) as a white powder.

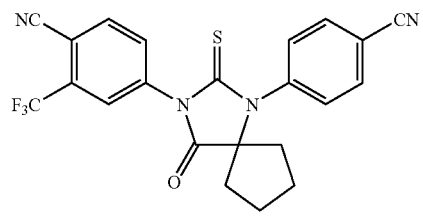

¹H NMR (CDCl₃, 400 MHz) δ 1.51-1.55 (m, 2H), 1.90-1.93 (m, 2H), 2.12-2.16 (m, 2H), 2.33-2.38 (m, 2H), 7.47-7.50 (m, 2H), 7.81-7.87 (m, 3H), 7.95-7.99 (m, 2H); ¹³C NMR (CDCl₃, 100 MHz) δ 25.2, 36.5, 75.3, 110.3, 113.9, 114.7, 117.5, 121.8 (q, J=272.6 Hz), 127.0 (q, J=4.8 Hz), 131.2, 132.1, 133.6 (q, J=34.3 Hz), 133.8, 135.3, 136.9, 140.0, 175.6, 180.1.

EXAMPLE 27

27-1). 1-methyl-4-(4-methylphenylamino)piperidine-4-carbonitrile, 27a

Sodium cyanide (0.318 g, 6.5 mmol) was added to a mixture of p-toluidine (0.535 g, 5 mmol) and 1-methyl-4-piperidinone (0.678 g, 6 mmol) in acetic acid 90% (5 ml). The reaction mixture was stirred at room temperature for 6 h and then 100 ml of dichloromethane was added. The organic layer was washed with a solution NaOH, 2N (2×50 ml), dried over magnesium sulfate, concentrated and chromatographed (DCM and then acetone) to obtained 27a (0.722 g, 3.15 mmol, 63%).

27.2). 4-(4-imino-8-methyl-2-thioxo-1-(4-methylphenyl)-1,3,8-triazaspiro[4.5]dec-3-yl)-2-trifluoromethylbenzonitrile, 27b Triethylamine (0.02, 0.2 mmol) was added to a solution of 1a (0.228 g, 1 mmol) and 27a (0.114 g, 0.5 mmol) in dry THF (2 ml). The reaction mixture was stirred at room temperature for 20 h and then concentrated to yield a dark residue which was subjected to flash chromatography (dichloromethane/acetone, 90:10, and then acetone) to afford 27b (0.059 g, 0.13 mmol, 26%).

27-3). 4-(8-methyl-4-oxo-2-thioxo-1-(4-methylphenyl)-1,3,8-triazaspiro[4.5]dec-3-yl)-2-trifluoromethylbenzonitrile, 27c, [RD53]

A mixture of 27b (0.059 g, 0.13 mmol) in HCl aq., 2N (1 ml) and methanol (3 ml) was heated to reflux for 2 h. After being cooled to room temperature, the reaction mixture was poured into cold water (5 ml) and extracted with ethyl acetate (10 ml). The organic layer was dried over MgSO₄, concentrated and chromatographed (dichloromethane:acetone, 60:40) to yield 27c (0.055 g, 0.012 mmol, 92%) as a white powder.

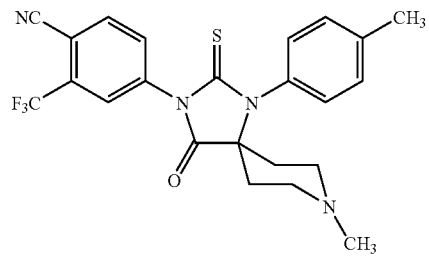

¹H NMR (Acetone-d₆, 400 MHz) δ 1.93-1.99 (m, 1H), 2.00-2.04 (m, 1H), 2.18 (s, 3H), 2.24-2.28 (m, 2H), 2.38 (s, 3H), 2.61-2.72 (m, 4H), 7.18-7.20 (m, 2H), 7.32-7.35 (m, 2H), 8.03 (dd, J₁=8.2 Hz, J₂=1.8 Hz, 1H), 8.16 (d, J=1.8 Hz, 1H), 8.22 (d, J=8.2 Hz, 1H); ¹³C NMR (Acetone-d₆, 100 MHz) δ 20.3, 31.4, 45.1, 49.8, 65.1, 109.1, 114.8, 122.4 (q, J=275.1 Hz), 127.7 (q, J=4.8 Hz), 130.0, 130.5, 131.9 (q, J=32.6 Hz), 132.6, 133.5, 135.6, 138.3, 139.4, 174.0, 180.6.

EXAMPLE 28

4-(8-methyl-4-oxo-2-thioxo-1,3,8-triazaspiro[4.5]dec-3-yl)-2-trifluoromethylbenzonitrile, 28a, [RD52]

Compound 28a was synthesized according to the procedure described in patent U.S. Pat. No. 5,958,936.

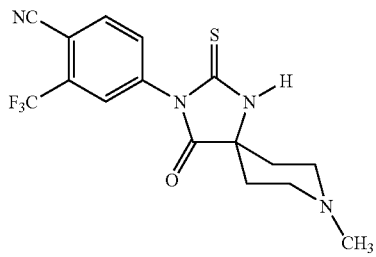

$^1$H NMR (Acetone-$d_6$, 400 MHz) δ 1.93-2.00 (m, 2H), 2.09-2.16 (m, 2H), 2.25 (s, 3H), 2.42-2.49 (m, 2H), 2.75-2.80 (m, 2H), 7.97 (dd, $J_1$=8.2 Hz, $J_2$=1.8 Hz, 1H), 8.11 (d, J=1.8 Hz, 1H), 8.20 (d, J=8.2 Hz, 1H), 9.80 (bs, NH); $^{13}$C NMR (Acetone-$d_6$, 100 MHz) δ 32.9, 45.4, 50.1, 62.3, 109.1, 114.8, 122.4 (q, J=271.6 Hz), 127.5 (q, J=4.8 Hz), 131.8 (q, J=32.7 Hz), 133.2, 135.6, 135.6, 138.0, 175.2, 180.4.

EXAMPLE 29

4-[3-(4-hydroxybutyl)-4,4-dimethyl-5-oxo-2-thioxoimidazolidin-1-yl]-2-trifluoromethylbenzonitrile, RU 59063

Compound RU 59063 was synthesized according to the procedure described by Teutsch et al [*J. Steroid. Biochem. Molec. Biol.* 1994, 48(1), 111-119].

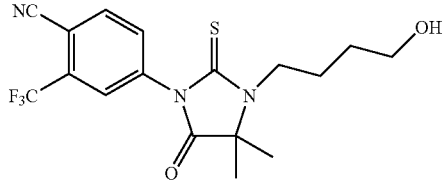

$^1$H NMR (CDCl$_3$, 400 MHz) δ 1.55 (s, 6H), 1.58-1.62 (m, 2H), 1.86-1.89 (m, 2H), 2.25 (bs, OH), 3.65-3.71 (m, 4H), 7.74 (dd, $J_1$=8.0 Hz, $J_2$=1.8 Hz, 1H), 7.92 (d, J=1.8 Hz, 1H), 7.98 (d, J=8.0 Hz, 1H); $^{13}$C NMR (CDCl$_3$, 100 MHz) δ 23.1, 24.7, 29.6, 43.9, 61.7, 65.2, 109.7, 114.9, 121.9 (q, J=272.6 Hz), 127.1 (q, J=4.8 Hz), 132.2, 133.7 (q, J=34.3 Hz), 135.2, 137.2, 175.3, 178.2.

EXAMPLE 30

30-1). 1-methylaminocyclobutanecarbonitrile, 30a

Methylamine was bubbled into a refrigerated mixture of cyclobutanone (0.21 g, 3 mmol) and trimethylsilyl cyanide (0.396 g, 4 mmol) until the volume doubled. The mixture was stirred 3 h and then concentrated to dryness to obtain 30a (0.33 g, quantitative).

30-2). 4-(5-methyl-8-oxo-6-thioxo-5,7-diazaspiro[3.4]oct-7-yl)-2-trifluoromethylenzonitrile, 30b, [RD73]

A mixture of 1a (0.114 g, 0.5 mmol) and 30a (0.055 g, 0.5 mmol) in dry DMF (0.2 ml) was stirred at room temperature for 0.5 h. To this mixture were added 10 ml of methanol and 2 ml of 2N HCl. The second mixture was refluxed for 2 h. After being cooled to room temperature, the reaction mixture was poured into cold water (20 ml) and extracted with ethyl acetate (30 ml). The organic layer was dried over MgSO$_4$, concentrated and chromatographed (dichloromethane) to yield 30b (0.148 g, 0.435 mmol, 87%) as a white powder.

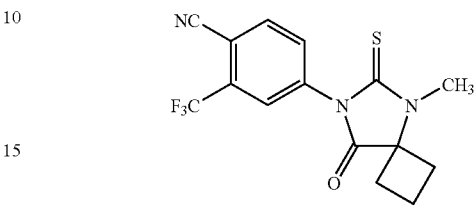

$^1$H NMR (CDCl$_3$, 400 MHz) δ 1.95-2.06 (m, 1H), 2.21-2.32 (m, 1H), 2.58-2.71 (m, 4H), 3.44 (s, 3H), 7.77 (dd, $J_1$=8.2 Hz, $J_2$=2.0 Hz, 1H), 7.89 (d, J=2.0 Hz, 1H), 7.93 (d, J=8.2 Hz, 1H); $^{13}$C NMR (CDCl$_3$, 100 MHz) & 13.7, 30.3, 30.4, 66.1, 109.7, 114.9, 121.9 (q, J=272.6 Hz), 126.9 (q, J=4.8 Hz), 132.1, 133.2 (q, J=34.3 Hz), 135.2, 137.3, 175.1, 178.7.

30-3). 4-(5-methyl-6,8-dioxo-5,7-diazaspiro[3.4]oct-7-yl)-2-trifluoromethylbenzonitrile, 30c, [RD74]

Hydrogen peroxide (2 ml, 30%) was added to the mixture of 30b (0.068 g, 0.2 mmol) in glacial acetic acid (3 ml). After being stirred at room temperature for 10 h, the reaction mixture was poured into ethyl acetate (20 ml) and then washed with water (2×20 ml). The organic layer was dried over MgSO$_4$, concentrated and chromatographed (dichloromethane:acetone) to yield 30c (0.057 g, 0.176 mmol, 88%) as a white powder.

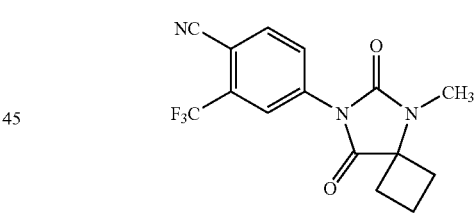

$^1$H NMR (CDCl$_3$, 400 MHz) δ 1.91-2.35 (m, 1H), 2.21-2.31 (m, 1H), 2.50-2.61 (m, 4H), 3.12 (s, 3H), 7.89 (d, J=8.2 Hz, 1H), 7.97 (dd, $J_1$=8.2 Hz, $J_2$=2.0 Hz, 1H), 8.12 (d, J=2.0 Hz, 1H),; $^{13}$C NMR (CDCl$_3$, 100 MHz) δ 13.9, 25.4, 29.3, 63.4, 108.1, 115.1, 121.6 (q, J=272.6 Hz), 122.9 (q, J=4.8 Hz), 127.9, 133.5 (q, J=34.3 Hz), 135.3, 136.5, 152.7, 174.4.

EXAMPLE 31

31-1). 1-methylaminocyclopentanecarbonitrile, 31a

Methylamine was bubbled into a refrigerated mixture of cyclopentanone (0.252 g, 3 mmol) and trimethylsilyl cyanide (0.396 g, 4 mmol) until the volume doubled. The mixture was stirred 3 h and then concentrated to dryness to obtain 31a (0.372 g, quantitative).

31-2). 4-(1-methyl-4-oxo-2-thioxo-1,3-diazaspiro[4.4]non-3-yl)-2-trifluoromethylbenzonitrile, 31b, [RD75]

A mixture of 1a (0.114 g, 0.5 mmol) and 31a (0.062 g, 0.5 mmol) in dry DMF (0.2 ml) was stirred at room temperature for 0.5 h. To this mixture were added 10 ml of methanol and 2 ml of 2N HCl. The second mixture was refluxed for 2 h. After being cooled to room temperature, the reaction mixture was poured into cold water (20 ml) and extracted with ethyl acetate (30 ml). The organic layer was dried over MgSO$_4$, concentrated and chromatographed (dichloromethane) to yield 31b (0.159 g, 0.45 mmol, 90%) as a white powder.

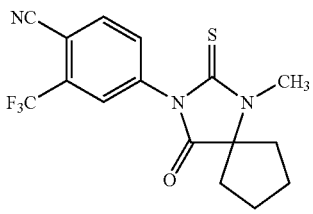

$^1$H NMR (CDCl$_3$, 400 MHz) δ 1.91-2.05 (m, 6H), 2.16-2.21 (m, 2H), 3.27 (s, 3H), 7.77 (dd, J$_1$=8.2 Hz, J$_2$=1.8 Hz, 1H), 7.89 (d, J=1.8 Hz, 1H), 7.91 (d, J=8.2 Hz, 1H); $^{13}$C NMR (CDCl$_3$, 100 MHz) δ 26.4, 30.3, 35.4, 73.2, 109.5, 114.9, 121.9 (q, J=272.6 Hz), 126.9 (q, J=4.8 Hz), 132.2, 133.2 (q, J=34.3 Hz), 135.2, 137.5, 176.8, 178.5.

31-3). 4-(1-methyl-2,4-dioxo-1,3-diaza-spiro[4.4]non-3-yl)-2-trifluoromethylbenzonitrile, 31c, [RD76]

Hydrogen peroxide (2 ml, 30%) was added to the mixture of 31b (0.07 g, 0.2 mmol) in glacial acetic acid (3 ml). After being stirred at room temperature for 10 h, the reaction mixture was poured into ethyl acetate (20 ml) and then washed with water (2×20 ml). The organic layer was dried over MgSO$_4$, concentrated and chromatographed (dichloromethane:acetone) to yield 31c (0.057 g, 0.168 mmol, 84%) as a white powder.

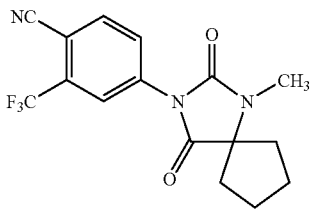

$^1$H NMR (CDCl$_3$, 400 MHz) δ 1.88-1.99 (m, 6H), 2.12-2.17 (m, 2H), 2.98 (s, 3H), 7.88 (d, J=8.2 Hz, 1H), 7.97 (dd, J$_1$=8.2 Hz, J$_2$=1.8 Hz, 1H), 8.12 (d, J=1.8 Hz, 1H); $^{13}$C NMR (CDCl$_3$, 100 MHz) δ 25.2, 26.5, 34.8, 70.1, 108.0, 115.1, 122.0 (q, J=272.5 Hz), 122.9 (q, J=4.9 Hz), 127.9, 133.5 (q, J=32.9 Hz), 135.3, 136.6, 152.7, 176.1.

EXAMPLE 32

4-(8-methylimino-6-thioxo-5-p-tolyl-5,7-diaza-spiro[3.4]oct-7-yl)-2-trifluoromethyl-benzonitrile, 32a, [RD90]

A mixture of 7b (0.042 g, 0.1 mmol), DBU (0.023 g, 0.15 mmol) and iodomethane (0.073 g, 0.5 mmol) in DMF (0.3 ml) was stirred for 15 h at room temperature. After DMF being evaporated, the medium was chromatographed (dichloromethane) to yield 32a (0.011 g, 0.026 mmol, 26%) as white powder.

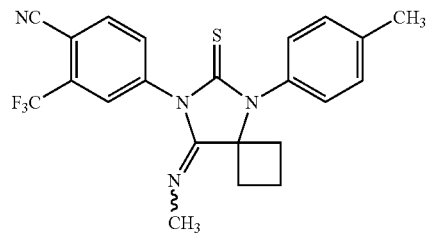

$^1$H NMR (CDCl$_3$, 400 MHz) δ 1.58-1.65 (m, 1H), 2.04-2.13 (m, 1H), 2.45 (s, 3H), 2.70-2.77 (m, 2H), 3.06-3.10 (m, 2H), 3.58 (s, CH$_3$—N, major isomer) [2.70 (s, CH$_3$—N, minor isomer)], 7.20-7.34 (m, 4H), 7.75-7.91 (m, 3H); (CDCl$_3$, 100 MHz) δ 12.6, 21.4, 30.2, 33.7 (35.3 for the other isomer), 66.9, 109.1, 115.2, 122.1 (q, J=272.5 Hz), 128.5 (q, J=4.9 Hz), 129.8, 130.4, 130.6, 132.8, 133.2 (q, J=32.9 Hz), 133.5, 134.9, 139.8, 157.0, 180.2.

EXAMPLE 33

1-[3-(4-cyano-3-trifluoromethyl-phenyl)-5,5-dimethyl-2-thioxo-1-p-tolyl-imidazolidin-4-ylidene]-3-ethyl-thiourea, 33a, [RD91]

A mixture of 5b (0.06 g, 0.149 mmol), ethylthioisocyanate (0.087 g, 1 mmol) and CuI (0.01 g, 0.05 mmol) in DMF (0.1 ml) was heated under microwave for 45 minutes. Then the medium was washed with brine and extracted with ethyl acetate. The organic layer was dried over MgSO$_4$, concentrated and chromatographed (HPLC, alumina column) to yield 33a (0.054 g, 0.108 mmol, 72%) as white powder.

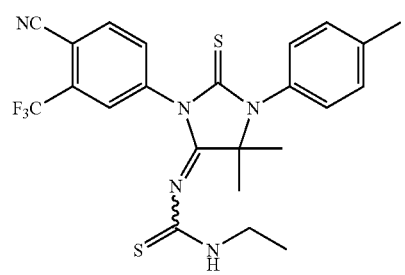

$^1$H NMR (CDCl$_3$, 400 MHz) δ 1.15 (t, J=7.23 Hz, 3H), 1.70 [1.75 minor isomer] (s, 6H), 2.42 (s, 3H), 3.28-3.39 (m, 2H) [3.15-3.22 (m, 2H), minor isomer], 6.50 (bs, 1H) [6.93 (bs, 1H), minor isomer], 7.14-7.18 (m, 2H), 7.32-7.35 (m, 2H), 7.77-7.94 (m, 3H); $^{13}$C NMR (CDCl$_3$, 100 MHz) δ 13.31 (13.83 minor), 21.3, 25.22 (24.89 minor), 40.31 (40.67 minor), 68.1, 109.9, 114.9, 122.3 (q, J=272.5 Hz), 127.6 (q, J=4.9 Hz), 129.1, 129.59 (129.55 minor), 130.52 (130.57 minor), 132.27 (132.15 minor), 132.9 (q, J=32.9 Hz), 134.27 (134.15 minor), 134.9, 135.2, 156.33 (156.06 minor), 180.28 (180.06 minor), 187.24 (186.63 minor).

EXAMPLE 34

1-[7-(4-cyano-3-trifluoromethyl-phenyl)-6-thioxo-5-p-tolyl-5,7-diaza-spiro[3.4]oct-8-ylidene]-3-phenyl-thiourea, 34a, [RD92]

A mixture of 7b (0.021 g, 0.05 mmol) and phenylthioisocyante (0.027 g, 0.2 mmol) in DMF (0.3 ml) was stirred for 2 days at 60° C. After DMF being evaporated, the medium was chromatographed (dichloromethane) to yield 34a (0.015 g, 0.028 mmol, 57%) as white powder.

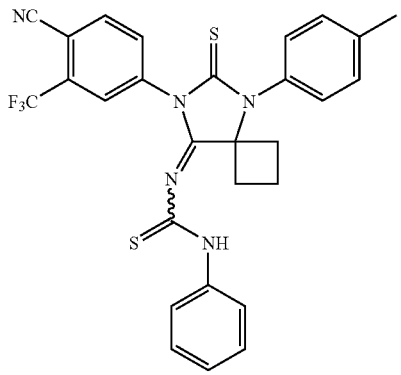

$^1$H NMR (CDCl$_3$, 400 MHz) δ 1.59-1.67 (m, 1H), 2.12-2.22 (m, 1H), 2.45 (s, 3H), 2.61-2.71 (m, 2H), 2.81-2.87 (m, 2H), 7.18-7.27 (m, 6H), 7.33-7.41 (m, 5H), 7.60-7.62 (m, 1H), 8.40 (bs, 1H); $^{13}$C NMR (CDCl$_3$, 100 MHz) δ 13.6, 21.4, 32.3, 69.6, 110.7, 114.8, 121.6, 122.0 (q, J=272.5 Hz), 126.3, 128.0 (q, J=4.9 Hz), 128.9, 129.4, 130.7, 132.5, 133.2 (q, J=32.9 Hz), 134.1, 134.9, 137.7, 139.2, 140.2, 154.8, 180.3, 185.5.

EXAMPLE 35

1-(4-Cyano-3-trifluoromethyl-phenyl)-3-[7-(4-cyano-3-trifluoromethyl-phenyl)-6-thioxo-5-p-tolyl-5,7-diaza-spiro[3.4]oct-8-ylidene]-thiourea, 35a, [RD93]

A mixture of 1a (0.5.02 g, 2.2 mmol) and 7a (0.186 g, 1 mmol) in DMF (1 ml) was stirred at room temperature. After 20 hours of stirring, the mixture was concentrated under reduced pressure to yield an orange viscous liquid, which was chromatographed (dichloromethane:acetone, 99:1) to yield 35a (0.269 g, 0.42 mmol, 42%) as a yellow powder.

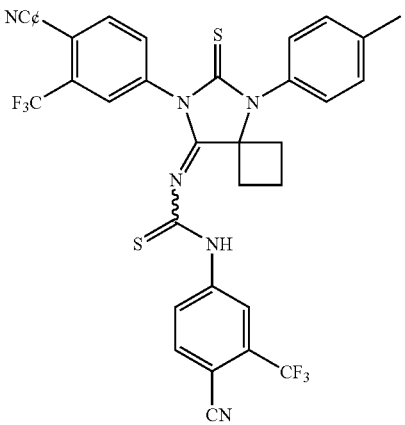

-continued

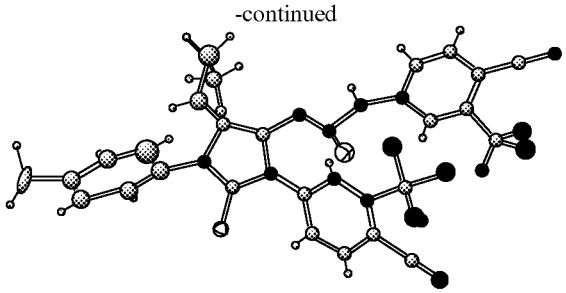

X-ray structure of 35a

EXAMPLE 36

36-1). 1-(4-hydroxymethylphenylamino)-cyclobutanecarbonitrile, 36a

Trimethylsilyl cyanide (0.66 ml, 5 mmol) was added dropwise to a mixture of 4-aminobenzoic acid (0.492 g, 4 mmol) and cyclobutanone (0.35 g, 5 mmol) in dichloromethane (10 ml). The reaction mixture was stirred at room temperature for 6 h and then concentrated under vacuum to obtain a brown liquid which was subjected to chromatography (dichloromethane) to yield 36a (0.677 g, 3.36 mmol, 84%) as a brown solid.

36-2). 4-[8-(4-hydroxymethylphenyl)-5-oxo-7-thioxo-6-azaspiro[3.4]oct-6-yl]-2-trifluoromethyl-benzonitrile, 36b, [RD110]

A mixture of 1a (0.342 g, 1.5 mmol) and 36a (0.21 g, 1 mmol) in dry DMF (0.5 ml) was stirred at room temperature for 24 h. To this mixture were added methanol (20 ml) and HCl aq. 2N (5 ml). The second mixture was refluxed for 6 h. After being cooled to room temperature, the reaction mixture was poured into cold water (40 ml) and extracted with ethyl acetate (60 ml). The organic layer was dried over MgSO$_4$, concentrated and chromatographed (dichloromethane:acetone, 90:10) to yield 36b (0.296 g, 0.69 mmol, 69%) as a white powder.

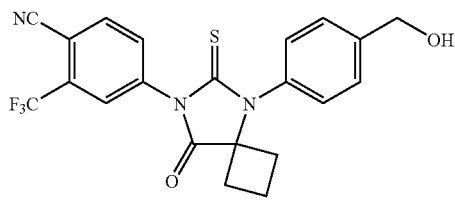

$^1$H NMR (CDCl$_3$, 400 MHz) δ 1.63-1.68 (m, 1H), 2.17-2.26 (m, 1H), 2.52-2.68 (m, 4H), 4.75 (s, 2H), 7.30 (d, J=8.1 Hz, 2H), 7.58 (d, J=8.1 Hz, 2H), 7.88 (dd, J$_1$=8.3 Hz, J$_2$=1.8 Hz, 1H), 7.95-7.98 (m, 2H); $^{13}$C NMR (CDCl$_3$, 100 MHz) δ 13.7, 31.5, 64.4, 67.5, 109.9, 114.9, 121.9 (q, J=272.6 Hz), 127.1 (q, J=4.7 Hz), 128.3, 130.0, 132.2, 133.3, 133.4 (q, J=33.2 Hz), 134.2, 137.2, 142.9, 174.9, 179.9.

EXAMPLE 37

4-[5-(4-formylphenyl)-8-oxo-6-thioxo-5,7-diaza-spiro[3.4]oct-7-yl]-2-trifluoromethyl-benzonitrile, 37a, [RD114]

To a mixture of 36b (0.303 g, 0.7 mmol) and Dess-Martin periodinane (0.417 g, 1 mmol) in dichloromethane (5 ml) was added pyridine (1.01 g, 1 mmol). The mixture was stirred for 2 hours at room temperature and then ethyl ether (10 ml) was added to precipitate the by-product of the reaction. After filtration and concentration under reduced pressure, the mixture was chromatographed (dichloromethane:acetone, 95:5) to yield 37a (0.24 g, 0.56 mmol, 80%) as white powder.

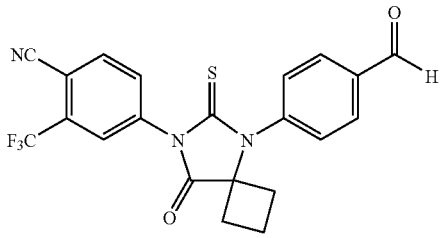

$^1$H NMR (CDCl$_3$, 400 MHz) δ 1.62-1.73 (m, 1H), 2.24-2.30 (m, 1H), 2.50-2.58 (m, 2H), 2.69-2.75 (m, 2H), 7.53 (d, J=8.1 Hz, 2H), 7.85 (dd, J$_1$=8.3 Hz, J$_2$=1.8 Hz, 1H), 7.97-7.99 (m, 2H), 8.11 (d, J=8.1 Hz, 2H), 10.12 (s, 1H); $^{13}$C NMR (CDCl$_3$, 100 MHz) δ 13.7, 31.7, 67.5, 110.2, 114.8, 121.9 (q, J=272.6 Hz), 127.0 (q, J=4.7 Hz), 129.1, 131.0, 131.2, 132.2, 133.3 (q, J=33.2 Hz), 135.3, 136.9, 140.5, 174.5, 179.8, 190.8.

EXAMPLE 38

4-{5-[4-(1-hydroxyethyl)-phenyl]-8-oxo-6-thioxo-5,7-diazaspiro[3.4]oct-7-yl}-2-trifluoromethyl-benzonitrile, 38a [RD116]

The mixture of 37a (0.043 g, 0.1 mmol) and dry THF (1 ml) in a flamed-dried flash was placed under argon and cooled to −78° C. Then, methylmagnesium iodide (1.1 ml, 0.1 M) was added. The mixture was stirred at −78° C. for 30 minutes and warmed slowly to room temperature. The medium was washed with water (3 ml) and extracted with ethyl acetate (10 ml). The organic layer was dried over MgSO$_4$, concentrated and chromatographed (dichloromethane:acetone, 95:5) to yield 38a (0.037 g, 0.032 mmol, 82%) as a white powder.

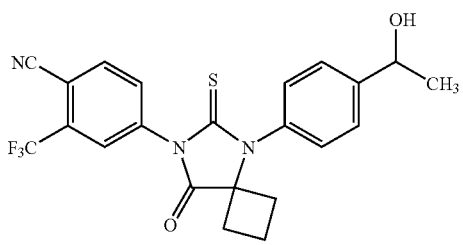

$^1$H NMR (CDCl$_3$, 400 MHz) δ 1.57 (d, J=6.5 Hz, 3H), 1.61-1.71 (m, 1H), 2.09 (d, J=3.2 Hz, OH), 2.16-2.28 (m, 1H), 2.52-2.60 (m, 2H), 2.63-2.69 (m, 2H), 5.00 (dd, J$_1$=6.5 Hz, q, J$_2$=3.1 Hz, 1H), 7.29 (d, J=8.3 Hz, 2H), 7.60 (d, J=8.2 Hz, 2H), 7.85 (dd, J$_1$=8.3 Hz, J$_2$=1.8 Hz, 1H), 7.95-7.98 (m, 2H); $^{13}$C NMR (CDCl$_3$, 100 MHz) δ 13.7, 25.3, 31.5, 67.4, 69.8, 110.0, 114.9, 121.9 (q, J=272.6 Hz), 127.0 (q, J=4.7 Hz), 127.1, 129.9, 132.2, 133.4 (q, J=33.2 Hz), 134.1, 135.2, 137.1, 147.6, 174.9, 179.9.

EXAMPLE 39

3-{4-[7-(4-cyano-3-trifluoromethylphenyl)-8-oxo-6-thioxo-5,7-diazaspiro[3.4]oct-5-yl]-phenyl}-acrylic acid ethyl ester, 39a [RD117]

A mixture of 37a (0.043 g, 0.1 mmol) and (carbethoxyethylidene)triphenylphosphorane (0.039 g, 0.12 mmol) in dichloromethane (2 ml) was stirred at room temperature for 10 hours. The medium was concentrated and chromatographed (dichloromethane) to yield 39a (0.048 g, 0.096 mmol, 96%) as white powder.

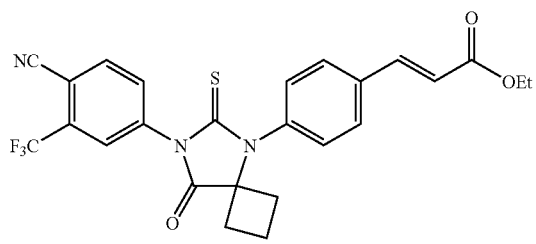

$^1$H NMR (CDCl$_3$, 400 MHz) δ 1.35 (t, J=7.1 Hz, 3H), 1.66-1.70 (m, 1H), 2.19-2.65 (m, 1H), 2.51-2.69 (m, 2H), 2.66-2.72 (m, 2H), 4.28 (q, J=7.1 Hz, 2H), 6.51 (d, J=16.1 Hz 1H) 7.35 (d, J=8.3 Hz, 2H), 7.72 (d, J=8.3 Hz, 2H), 7.73 (d, J=16.1 Hz, 1H), 7.85 (dd, J$_1$=8.3 Hz, J$_2$=1.8 Hz, 1H), 7.96-7.98 (m, 2H); $^{13}$C NMR (CDCl$_3$, 100 MHz) δ 13.7, 14.3, 31.6, 60.8, 67.5, 110.0, 114.9, 120.5, 121.8 (q, J=272.6 Hz), 127.0 (q, J=4.7 Hz), 129.5, 130.5, 132.2, 133.4 (q, J=33.2 Hz), 135.2, 136.0, 136.5, 137.0, 142.7, 166.5, 174.7, 179.8.

EXAMPLE 40

4-{5-[4-(3-hydroxypropenyl)-phenyl]-8-oxo-thioxo-5,7-diazaspiro[3.4]oct-7-yl}-2-trifluoromethylbenzonitrile, 40a [RD120]

To a mixture of 39a (0.05 g, 0.1 mmol) in dichloromethane (2 ml) at −78° C. WAS added a solution of diisobutylaluminum hydride in THF (0.11 ml, 1M, 0.11 mmol). The mixture was stirred at −78° C. for 3 hours. After being warmed to room temperature, the mixture was washed with an aqueous solution of sodium thiosulfate and extracted with ethyl acetate. The organic layer was dried over MgSO$_4$, concentrated and chromatographed (dichloromethane:acetone, 95:5) to yield 40a (0.040 g, 0.089 mmol, 89%) as a white powder.

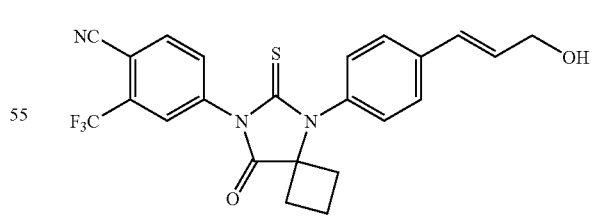

$^1$H NMR (CDCl$_3$, 400 MHz) δ 1.57-1.68 (m, 1H), 2.17-2.39 (m, 1H), 2.55-2.61 (m, 2H), 2.61-2.67 (m, 2H), 4.39 (d, J=4.7 Hz, 2H), 6.47 (dt, J$_1$=16.0 Hz, J$_2$=5.3 Hz, 1H), 6.70 (d, J=16.0 Hz, 1H), 7.29 (d, J=8.3 Hz, 2H), 7.59 (d, J=8.3 Hz, 2H), 7.85 (dd, J$_1$=8.3 Hz, J$_2$=1.8 Hz, 1H), 7.96-7.98 (m, 2H); $^{13}$C NMR (CDCl$_3$, 100 MHz) δ 13.7, 31.5, 63.4, 67.4, 110.0, 114.8, 120.5, 121.8 (q, J=272.6 Hz), 127.0 (q, J=4.7 Hz), 127.9, 129.2, 130.1, 131.1, 132.1, 133.4 (q, J=33.2 Hz), 135.2, 137.1, 138.4, 174.8, 179.9.

EXAMPLE 41

41-1) 3-[4-(1-cyanocyclobutylamino)-phenyl]-propionic acid, 41a (41-1)

Trimethylsilyl cyanide (0.4 g, 4 mmol) was added dropwise to a mixture of 3-(4-aminophenyl)-propionic acid (0.33 g, 2 mmol), cyclobutanone (0.35 g, 5 mmol) and sodium sulfate (1 g) in 1,4-dioxane (5 ml). The mixture was stirred for 15 hours. After filtration to eliminate sodium sulfate, the medium was concentrated under vacuum to obtain a brown liquid which was subjected to chromatography (dichloromethane:acetone, 50:50) to yield 41a (0.472 g, 1.93 mmol, 97%) as a yellowish solid.

41-2) 3-{4-[7-(4-cyano-3-trifluoromethylphenyl)-8-oxo-6-thioxo-5,7-diazaspiro[3.4]oct-5-yl]-phenyl}-propionic acid methyl ester, 41b (41-2) [RD128]

A mixture of 1a (0.661 g, 2.9 mmol) and 41a (0.472 g, 1.93 mmol) in dry DMF (2 ml) was stirred at room temperature for 15 hours. To this mixture were added methanol (10 ml) and HCl aq. (5 ml, 2M). The second mixture was refluxed for 3 h. After being cooled to room temperature, the reaction mixture was poured into cold water (10 ml) and extracted with ethyl acetate (3×30 ml). The organic layer was dried over MgSO$_4$, concentrated and chromatographed (dichloromethane) to yield 41b (0.582 g, 1.19 mmol, 62%) as a white powder.

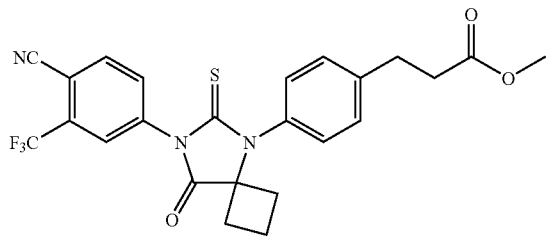

$^1$H NMR (CDCl$_3$, 400 MHz) δ 1.60-1.70 (m, 1H), 2.14-2.26 (m, 1H), 2.51-2.56 (m, 2H), 2.58-2.67 (m, 2H), 2.71 (t, J=7.8 Hz, 2H), 3.05 (t, J=7.8 Hz, 2H), 3.69 (s, 3H), 7.23 (d, J=8.2 Hz, 2H), 7.41 (d, J=8.2 Hz, 2H), 7.85 (dd, J$_1$=8.3 Hz, J$_2$=1.8 Hz, 1H), 7.95 (d, J=8.3 Hz, 1H), 7.98 (d, J=1.8 Hz, 1H); $^{13}$C NMR (CDCl$_3$, 100 MHz) δ 13.7, 30.5, 31.4, 35.1, −51.8, 67.5, 109.9, 114.9, 121.9 (q, J=272.7 Hz), 127.1 (q, J=4.7 Hz), 129.9, 130.0, 133.2, 132.3, 133.3 (q, J=33.2 Hz), 135.7, 137.2, 142.5, 173.1, 174.9, 179.9.

41-3) 3-{4-[7-(4-cyano-3-trifluoromethylphenyl)-8-oxo-6-thioxo-5,7-diaza-spiro[3.4]oct-5-yl]-phenyl}-propionic acid, 41c (41-3) [RD132]

A mixture of 41b (0.487 g, 1 mmol) in methanol (10 ml) and solution of sodium hydroxide (10 ml, 2M) was stirred at room temperature for 5 hours. Methanol was evaporated. The residue was adjusted to pH=5 by HCl aq. (2M) and then extracted with ethyl acetate (3×50 ml). The organic layer was dried over MgSO$_4$ and concentrated to dryness to obtain 41c (0.472 g, 0.99 mmol, 99%).

41-4) 3-{4-[7-(4-cyano-3-trifluoromethylphenyl)-8-oxo-6-thioxo-5,7-diaza-spiro[3.4]oct-5-yl]-phenyl}-propionamide, 41d (41-4) [RD133]

To a suspension of 41c (0.094 g, 0.2 mmol) in THF (10 ml) at −5° C. was added thionyl chloride (0.019 ml, 0.26 mmol). The medium was stirred at −5° C. for one hour. Then ammonia was bubbled into the mixture. The excess of ammonia was condensed by reflux condenser at −78° C. for 30 minutes and then was allowed to evaporate. The medium was filtered. The filtrate was concentrated and chromatographed (dichloromethane:acetone, 70:30) to yield 41 d (0.09 g, 0.19 mmol, 95%) as an off-white powder.

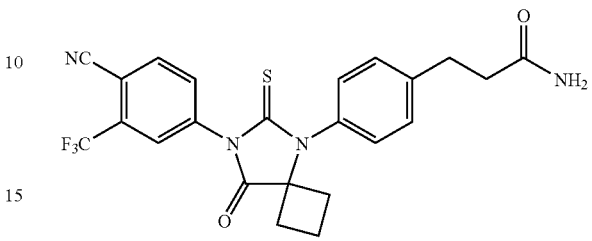

$^1$H NMR (acetone-d$_6$, 400 MHz) δ 1.52-160 (m, 1H), 2.01-2.09 (m, 1H), 2.49-2.58 (m, 4H), 2.61-2.67 (m, 2H), 2.98 (t, J=7.5 Hz, 2H), 6.20 (bs, 1H), 6.78 (bs, 1H), 7.31 (d, J=8.2 Hz, 2H), 7.44 (d, J=8.2 Hz, 2H), 8.03 (dd, J$_1$=8.3 Hz, J$_2$=1.8 Hz, 1H), 8.15 (d, J=1.8 Hz, 1H), 8.22 (d, J=8.3 Hz, 1H); $^{13}$C NMR (acetone-d$_6$, 100 MHz)δ 13.4, 30.7, 31.2, 36.4, 67.5, 109.0, 114.8, 122.5 (q, J=271.5 Hz), 127.5 (q, J=4.7 Hz), 129.5, 130.0, 131.8 (q, J=32.5 Hz), 133.3, 133.8, 135.6, 138.4, 143.2, 171.6, 174.9, 178.0.

41-5) 3-{4-[7-(4-Cyano-3-trifluoromethylphenyl)-8-oxo-6-thioxo-5,7-diaza-spiro[3.4]oct-5-yl]-phenyl}-N-methyl-propionamide, 41e (41-5) [RD134]

To a suspension of 41c (0.094 g, 0.2 mmol) in THF (10 ml) at −5° C. was added thionyl chloride (0.019 ml, 0.26 mmol). The medium was stirred at −5° C. for one hour. Then methylamine was bubbled into the mixture at −5° C. for 30 minutes. The medium was filtered. The filtrate was concentrated and chromatographed (dichloromethane:acetone, 75:25) to yield 41e (0.092 g, 0.19 mmol, 95%) as an off-white powder.

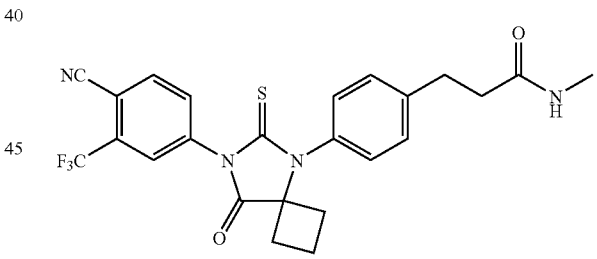

$^1$H NMR (acetone-d$_6$, 400 MHz) δ 1.51-1.60 (m, 1H), 2.01-2.11 (m, 1H), 2.48-2.58 (m, 4H), 2.61-2.67 (m, 2H), 2.77 (d, J=4.6 Hz, 3H), 2.98 (t, J=7.5 Hz, 2H), 7.03 (bs, NH), 7.33 (d, J=8.2 Hz, 2H), 7.42 (d, J=8.2 Hz, 2H), 8.01 (dd, J$_1$=8.3 Hz, J$_2$=1.8 Hz, 1H), 8.13 (d, J=1.8 Hz, 1H), 8.20 (d, J=8.3 Hz, 1H); $^{13}$C NMR (acetone-d$_6$, 100 MHz) δ 13.4, 25.3, 30.0, 31.2, 37.0, 67.6, 109.0, 114.8, 122.5 (q, J=271.5 Hz), 127.4 (q, J=4.7 Hz), 129.5, 130.0, 131.9 (q, J=32.5 Hz), 133.3, 133.8, 135.6, 138.4, 143.1, 171.7, 175.0, 178.0.

41-6) 3-{4-[7-(4-cyano-3-trifluoromethylphenyl)-8-oxo-6-thioxo-5,7-diaza-spiro[3.4]oct-5-yl]-phenyl}-N-(2-hydroxyethyl)-propionamide, 41f (41-6) [RD135]

To a suspension of 41c (0.094 g, 0.2 mmol) in THF (10 ml) at −5° C. was added thionyl chloride (0.019 ml, 0.26 mmol).

The medium was stirred at −5° C. for one hour. Then 2-aminoethanol (0.0183 g, 0.03 mmol) was added into the mixture at −5° C. After stirring of an additional 30 minutes, the medium was filtered. The filtrate was concentrated and chromatographed (dichloromethane:acetone, 50:50) to yield 41f (0.093 g, 0.18 mmol, 90%) as an off-white powder.

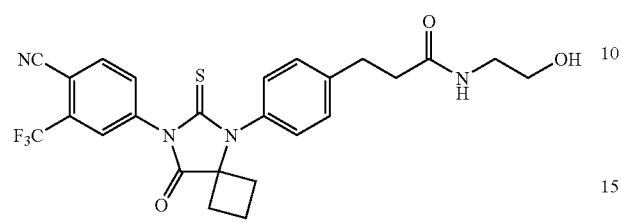

$^1$H NMR (acetone-$d_6$, 400 MHz) δ 1.51-161 (m, 1H), 2.01-2.11 (m, 1H), 2.49-2.66 (m, 6H), 2.99 (t, J=7.5 Hz, 2H), 3.27 (dd, $J_1$=11.2 Hz, $J_2$=5.6 Hz, 3H), 3.51 (dd, $J_1$=11.2 Hz, $J_2$=5.6 Hz, 2H), 3.87 (bs, OH), 7.20 (bs, NH), 7.33 (d, J=8.2 Hz, 2H), 7.43 (d, J=8.2 Hz, 2H), 8.02 (dd, $J_1$=8.3 Hz, $J_2$=1.8 Hz, 1H), 8.14 (d, J=1.8 Hz, 1H), 8.22 (d, J=8.3 Hz, 1H); $^{13}$C NMR (acetone-$d_6$, 100 MHz) δ 13.4, 31.0, 31.2, 37.1, 42.0, 61.2, 67.6, 109.0, 114.8, 122.5 (q, J=271.5 Hz), 127.4 (q, J=4.7 Hz), 129.6, 130.0, 131.9 (q, J=32.5 Hz), 133.3, 133.8, 135.6, 138.4, 143.0, 171.9, 175.0, 178.1.

42-1) 4-[4-(1-Cyanocyclobutylamino)-phenyl]-butyric acid, 42a

Trimethylsilyl cyanide (0.50 g, 5 mmol) was added dropwise to a mixture of 4-(4-aminophenyl)-butyric acid (0.537 g, 3 mmol), cyclobutanone (0.35 g, 5 mmol) and sodium sulfate (1 g) in 1,4-dioxane (10 ml). The mixture was stirred for 15 hours. After filtration to eliminate sodium sulfate, the medium was concentrated under vacuum to obtain a brown liquid which was subjected to chromatography (dichloromethane:acetone, 50:50) to yield 42a (0.665 g, 2.58 mmol, 86%) as a yellowish solid.

42-2) 4-{4-[7-(4-cyano-3-trifluoromethylphenyl)-8-oxo-6-thioxo-5,7-diazaspiro[3.4]oct-5-yl]-phenyl}-butyric acid methyl ester, 42b [RD129]

A mixture of 1a (0.547 g, 2.4 mmol) and 42a (0.342 g, 1.5 mmol) in dry DMF (2 ml) was stirred at room temperature for 15 hours. To this mixture were added methanol (10 ml) and HCl aq. (5 ml, 2M). The second mixture was refluxed for 3 h. After being cooled to room temperature, the reaction mixture was poured into cold water (10 ml) and extracted with ethyl acetate (3×30 ml). The organic layer was dried over MgSO$_4$, concentrated and chromatographed (dichloromethane) to yield 42b (0.594 g, 1.18 mmol, 79%) as a white powder.

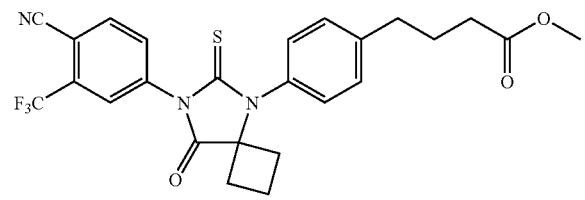

$^1$H NMR (CDCl$_3$, 400 MHz) δ 1.60-1.70 (m, 1H), 1.98-2.07 (m, 2H), 2.14-2.26 (m, 1H), 2.40 (t, J=7.4 Hz, 2H), 2.52-2.60 (m, 2H), 2.62-2.68 (m, 2H), 2.74 (t, J=7.4 Hz, 2H), 3.68 (s, 3H), 7.22 (d, J=8.2 Hz, 2H), 7.38 (d, J=8.2 Hz, 2H), 7.86 (dd, $J_1$=8.3 Hz, $J_2$=1.8 Hz, 1H), 7.95 (d, J=8.3 Hz, 1H), 7.98 (d, J=1.8 Hz, 1H); $^{13}$C NMR(CDCl$_3$, 100 MHz)δ 13.7, 26.1, 31.4, 33.5, 34.8, 51.7, 67.5, 109.9, 114.9, 121.9 (q, J=272.7 Hz), 127.1 (q, J=4.7 Hz), 129.7, 130.1, 132.3, 133.0, 133.3 (q, J=33.2 Hz), 135.2, 137.2, 143.5, 173.8, 175.0, 179.9.

42-3) 4-{4-[7-(4-cyano-3-trifluoromethylphenyl)-8-oxo-6-thioxo-5,7-diaza-spiro[3.4]oct-5-yl]-phenyl}-butyric acid, 42c [RD141]

A mixture of 42b (0.501 g, 1 mmol) in methanol (10 ml) and solution of sodium hydroxide (10 ml, 2M) was stirred at room temperature for 5 hours. The methanol was evaporated. The residue was adjusted to pH=5 by HCl aq. (2M) and then, the medium was extracted with ethyl acetate (3×50 ml). The organic layer was dried over MgSO$_4$ and concentrated to dryness to obtain 42c (0.482 g, 0.99 mmol, 99%), the structure of which is illustrated in Formula 5.

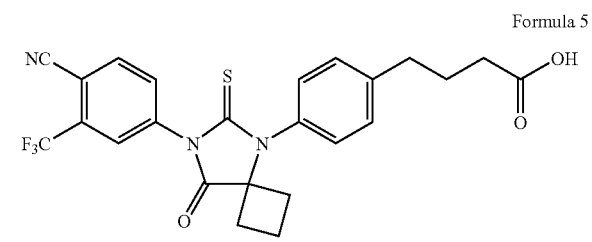

Formula 5

$^1$H NMR (CDCl$_3$, 400 MHz) δ 1.60-1.70 (m, 1H), 1.98-2.07 (m, 2H), 2.14-2.26 (m, 1H), 2.45 (t, J=7.3 Hz, 2H), 2.51-2.59 (m, 2H), 2.62-2.68 (m, 2H), 2.77 (t, J=7.3 Hz, 2H), 7.23 (d, J=8.1 Hz, 2H), 7.40 (dd, J=8.1 Hz, 2H), 7.85 (dd, J=8.3, 1.8 Hz, 1H), 7.95 (d, J=8.3 Hz, 1H), 7.97 (d, J=1.8 Hz, 1H); $^{13}$C NMR (CDCl$_3$, 100 MHz) δ 13.7, 25.9, 31.4, 33.4, 34.7, 67.5, 109.9, 114.9, 121.9 (q, J=272.6 Hz), 127.1 (q, J=4.7 Hz), 129.8, 130.1, 132.3, 133.0, 133.4 (q, J=33.1 Hz), 135.2, 137.2, 143.3, 174.9, 178.9, 179.9.

42-4) 4-{4-[7-(4-Cyano-3-trifluoromethylphenyl)-8-oxo-6-thioxo-5,7-diaza-spiro[3.4]oct-5-yl]-phenyl}-butyramide, 42d [RD130]

To a suspension of 42c (0.097 g, 0.2 mmol) in THF (10 ml) at −5° C. was added thionyl chloride (0.019 ml, 0.26 mmol). The medium was stirred at −5° C. for one hour. Then ammonia was bubbled into the mixture. The excess of ammonia was condensed by reflux condenser at −78° C. for 30 minutes and then was allowed to evaporate. The medium was filtered. The filtrate was concentrated and chromatographed (dichloromethane:acetone, 70:30) to yield 42d (0.093 g, 0.19 mmol, 95%) as an off-white powder.

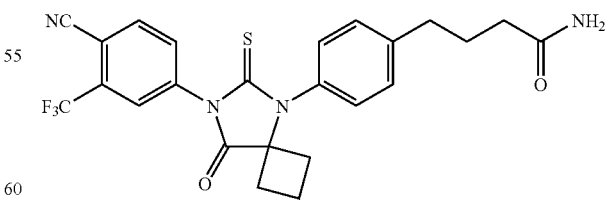

$^1$H NMR (CDCl$_3$, 400 MHz) δ 1.57-1.70 (m, 1H), 2.00-2.08 (m, 2H), 2.16-2.25 (m, 1H), 2.31 (t, J=7.3 Hz, 2H), 2.51-2.59 (m, 2H), 2.62-2.68 (m, 2H), 2.77 (t, J=7.3 Hz, 2H), 5.56 (bs, 1H), 5.65 (bs, 1H), 7.22 (d, J=8.2 Hz, 2H), 7.39 (d, J=8.2 Hz, 2H), 7.85 (dd, $J_1$=8.3 Hz, $J_2$=1.8 Hz, 1H), 7.95 (d, J=8.3 Hz, 1H), 7.97 (d, J=1.8 Hz, 1H); $^{13}$C NMR (CDCl$_3$, 100

MHz) δ 13.7, 26.5, 31.4, 34.8, 35.0, 67.5, 109.9, 114.9, 121.9 (q, J=272.7 Hz), 127.1 (q, J=4.7 Hz), 129.8, 130.1, 132.2, 133.0, 133.3 (q, J=33.2 Hz), 135.2, 137.2, 143.5, 173.8, 174.9, 179.9.

42-5) 4-{4-[7-(4-Cyano-3-trifluoromethylphenyl)-8-oxo-6-thioxo-5,7-diaza-spiro[3.4]oct-5-yl]-phenyl}-N-methyl-butyramide, 42e [RD131]

To a suspension of 42c (0.097 g, 0.2 mmol) in THF (10 ml) at −5° C. was added thionyl chloride (0.019 ml, 0.26 mmol). The medium was stirred at −5° C. for one hour. Then methylamine was bubbled into the mixture at −5° C. for 30 minutes. The medium was filtered. The filtrate was concentrated and chromatographed (dichloromethane:acetone, 75:25) to yield 42e (0.095 g, 0.19 mmol, 95%) as an off-white powder.

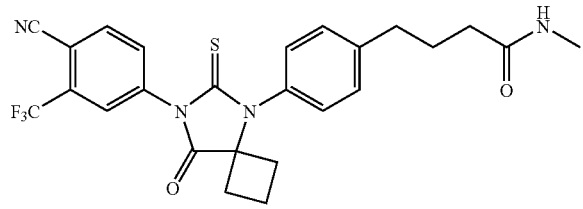

$^1$H NMR (CDCl$_3$, 400 MHz) δ 1.52-1.64 (m, 1H), 1.94-2.01 (m, 2H), 2.10-2.17 (m, 1H), 2.20 (t, J=7.3 Hz, 2H), 2.46-2.62 (m, 4H), 2.69 (t, J=7.3 Hz, 2H), 2.73 (d, J=4.7 Hz, 3H), 6.09 (bs, 1H), 7.16 (d, J=8.2 Hz, 2H), 7.33 (d, J=8.2 Hz, 2H), 7.82 (dd, J$_1$=8.3 Hz, J$_2$=1.8 Hz, 1H), 7.91 (d, J=8.3 Hz, 1H), 7.94 (d, J=1.8 Hz, 1H); $^{13}$C NMR (CDCl$_3$, 100 MHz) δ 13.7, 26.2, 26.8, 31.4, 35.0, 35.7, 67.5, 109.7, 114.9, 121.9 (q, J=272.7 Hz), 127.1 (q, J=4.7 Hz), 129.7, 130.0, 132.3, 133.8, 133.3 (q, J=33.2 Hz), 135.2, 137.3, 143.7, 173.3, 174.9, 179.8.

42-6) N-(4-{4-[7-(4-cyano-3-trifluoromethylphenyl)-8-oxo-6-thioxo-5,7-diaza-spiro[3,4]oct-5-yl]phenyl}-butanoyl)-methanesulfonamide, 42f [RD157]

A mixture of 4-{4-[7-(4-cyano-3-trifluoromethylphenyl)-8-oxo-6-thioxo-5,7-diaza-spiro[3.4]oct-5-yl]phenyl)butanoic acid (42c) (0.049 g, 0.1 mmol), 2,4,6-trichlorobenzoyl chloride (0.244 g, 1 mmol), 4-dimethylaminopyridine (0.122 g, 1 mmol) and methanesulfonamide (0.019 g, 0.2 mmol) in dichloromethane was stirred at room temperature for 20 hours. The mixture was concentrated and chromatographed (dichloromethane:acetone, 80:20) to yield N{4-{4-[7-(4-cyano-3-trifluoromethylphenyl)-8-oxo-6-thioxo-5,7-diaza-spiro[3.4]oct-5-yl]phenyl}-butanoyl)-methanesulfonamide (42f) [RD157] (0.053 g, 0.094 mmol, 94%), the structure of which is illustrated in Formula 8, as a white powder.

Formula 8

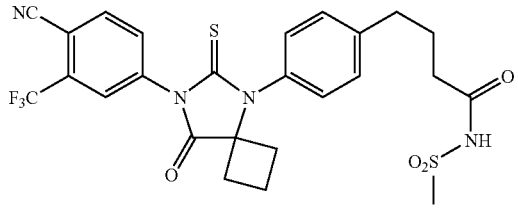

$^1$H NMR (acetone-d$_6$, 400 MHz) δ 1.51-160 (m, 1H), 1.96-2.11 (m, 3H), 2.49 (t, J=7.3 Hz, 2H), 2.51-2.57 (m, 2H), 2.61-2.67 (m, 2H), 2.75 (t, J=7.5 Hz, 2H), 2.94 (bs, 1H), 3.24 (s, 3H), 7.33 (d, J=8.3 Hz, 2H), 7.43 (d, J=8.2 Hz, 2H), 8.02 (dd, J=8.3, 1.6 Hz, 1H), 8.02 (d, J=1.6 Hz, 1H), 8.21 (d, J=8.3 Hz, 1H); $^{13}$C NMR (acetone-d$_6$, 100 MHz) δ 13.4, 25.8, 31.2, 34.3, 35.2, 40.6, 67.6, 109.0, 114.8, 122.5 (q, J=271.5 Hz), 127.5 (q, J=4.9 Hz), 129.6, 130.1, 131.9 (q, J=33.6 Hz), 133.3, 133.9, 135.6, 138.4, 143.1, 171.9, 175.0, 180.5.

42-7) N-methyl-4-{4-[7-(4-cyano-3-trifluoromethylphenyl)-6,8-dioxo-5,7-diazaspiro[3.4]oct-5-yl]-phenyl}butyramide, 42 g [RD158]

Hydrogen peroxide (30%, 0.4) was added dropwise to a solution of N-methyl-4 -{4-[7-(4-Cyano-3-trifluoromethylphenyl)-8-oxo-6-thioxo-5,7-diaza-spiro[3.4]oct-5-yl]phenyl}butanamide (42e) (0.032 g, 0.064 mmol) in glacial acetic acid (0.5 ml). The mixture was stirred at room temperature for 5 hours and then washed with water and extracted with ethyl acetate. The organic layer was dried over magnesium sulfate, concentrated and chromatographed (dichloromethane:acetone, 80:20) to yield N-methyl-4-[4-[7-(4-cyano-3-trifluoromethylphenyl)-6,8-dioxo-5,7-diazaspiro[3.4] oct-5-yl]-phenyl}butyramide (42 g) [RD158] (0.029 g, 0.06 mmol, 94%), the structure of which is illustrated in Formula 9, as a white powder.

Formula 9

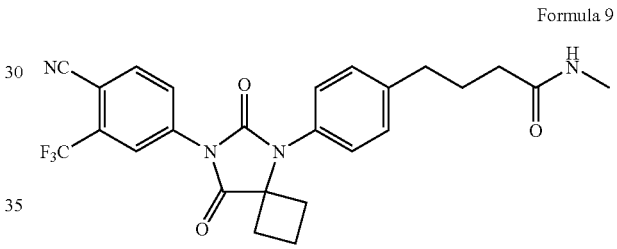

$^1$H NMR (CDCl$_3$, 400 MHz) δ 1.63-1.71 (m, 1H), 1.93-2.04 (m, 2H), 2.18-2.27 (m, 3H), 2.44-2.53 (m, H), 2.57-2.65 (m, 2H), 2.70 (t, J=7.3 Hz, 2H), 2.79 (d, J=4.8 Hz, 3H), 5.79 (bs, 1H), 7.21 (d, J=8.2 z, 2H), 7.34 (d, J=8.2 Hz, 2H), 7.92 (d, J=8.4 Hz, 1H), 8.03 (dd, J=8.3, 1.8 Hz, 1H), 8.18 (d, J=1.8 z, 1H).

EXAMPLE 43

43-1) 4-(4-aminophenyl)-piperazine-1-carboxylic acid tert-butyl ester, 43a

A mixture of 4-iodoaniline (0.654 g, 3 mmol), piperazine-1-carboxylic acid tert-butyl ester (0.67 g, 3.6 mmol), potassium phosphate (1.272 g, 6 mmol), ethylene glycol (0.33 ml) and copper iodide (0.03 g, 0.15 mmol) in 2-propanol (3 ml) was placed under argon in a sealed-tube and heated to 80° C. for 30 hours. After being cooled to room temperature, the medium was washed with water (50 ml) and extracted with ethyl acetate (100 ml). The organic layer was dried over MgSO$_4$, concentrated and chromatographed (dichloromethane:acetone, 70:30) to yield 43a (0.36 g, 1.3 mmol, 43%) as a yellow powder.

43-2) 4-[4-(1-cyanocyclobutylamino)phenyl]-piperazine-1-carboxylic acid tert-butyl ester, 43b Trimethylsilyl cyanide (0.3 g, 3 mmol) was added dropwise to a mixture of 43a (0.415 g, 1.5 mmol), cyclobutanone (0.21 g, 3 mmol) and sodium sulfate (1 g) in dichloromethane (5 ml). The mixture was stirred for 15 hours. After filtration to eliminate sodium sulfate, the medium was concentrated under vacuum to obtain a brown liquid which was subjected to chromatography (dichloromethane:acetone, 75:25) to yield 43b (0.448 g, 1.26 mmol, 84%) as a yellow solid.

43-3) 4-{4-[7-(4-cyano-3-trifluoromethylphenyl)-8-imino-6-thioxo-5,7-diazaspiro[3.4]oct-5-yl]-phenyl}-piperazine-1-carboxylic acid tert-butyl ester, 43c [RD139] and 4-{4-[7-(4-cyano-3-trifluoromethylphenyl)-8-(4-cyano-3-trifluoromethyl-phenylthiocarbamoylimino)-6-thioxo-5,7-diazaspiro[3.4]oct-5-yl]-phenyl}-piperazine-1-carboxylic acid tert-butyl ester, 43d [RD140]

A mixture of 1a (0.228 g, 1 mmol) and 43b (0.472 g, 0.63 mmol) in dry DMF (1 ml) was stirred at room temperature for 20 hours. The mixture was concentrated and chromatographed (dichloromethane:acetone, 90:10) to yield 43c (0.173 g, 0.296 mmol, 47%), the structure of which is illustrated in Formula 10, as a off-white powder and 43d (0.169 g, 0.21 mmol, 33%), the structure of which is illustrated in Formula 11, as a yellow powder.

Formula 10

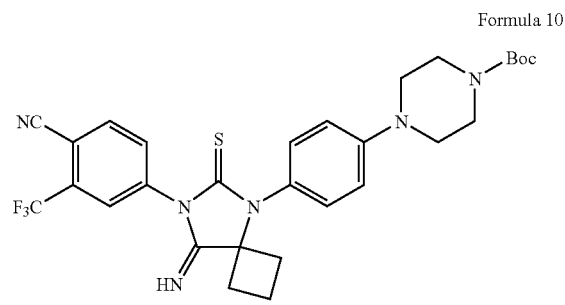

$^1$H NMR (CDCl$_3$, 400 MHz) δ 1.48, (s, 9H), 1.57-1.67 (m, 1H), 2.01-2.09 (m, 1H), 2.59-2.70 (m, 4H), 3.25 (t, J=5.1 Hz, 4H), 3.59 (t, J=4.9 Hz, 4H), 7.02 (d, J=8.9 Hz, 2H), 7.20 (d, J=8.9 Hz, 2H), 7.81 (d, J=7.4 Hz, 1H), 7.93 (s, 1H), 7.97 (d, J=8.1 Hz, 1H).

Formula 11

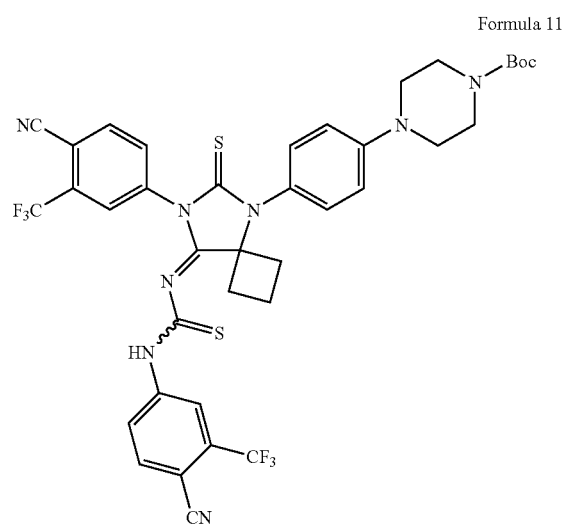

$^1$H NMR (CDCl$_3$, 400 MHz) δ 1.48, (s, 9H), 1.57-1.64 (m, 1H), 2.01-2.10 (m, 1H), 2.60-2.89 (m, 4H), 3.24 (t, J=5.1 Hz, 4H), 3.57 (t, J=4.9 Hz, 4H), 7.02 (d, J=8.9 Hz, 2H), 7.20 (d, J=8.9 Hz, 2H), 7.54-7.98 (m, 4H), 7.97 (d, J=8.1 Hz, 1H).

43-4) 4-[8-Oxo-5-(4-piperazin-1-yl-phenyl)-6-thioxo-5,7-diazaspiro[3.4]oct-7-yl]-2-trifluoromethylbenzonitrile, 43e [RD137]

A mixture of 43c (0.117 g, 0.2 mmol), methanol (5 ml) and HCl aq. (2 ml, 2M) was refluxed for 2 hours. After being cooled to room temperature, the reaction mixture was poured into cold water (10 ml) and extracted with ethyl acetate (3×30 ml). The organic layer was dried over MgSO$_4$, concentrated and chromatographed (dichloromethane:acetone, 50:50 and then methanol:acetone, 50:50) to yield 43e (0.089 g, 0.184 mmol, 92%) as a white powder.

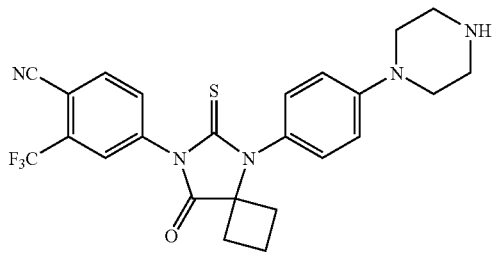

$^1$H NMR (CD$_3$OD, 400 MHz) δ 1.51-1.61 (m, 1H), 2.01-2.11 (m, 1H), 2.48-2.59 (m, 4H), 2.90-2.97 (m, 4H), 3.25-3.30 (m, 4H), 7.03 (d, J=8.9 Hz, 2H), 7.16 (d, J=8.9. Hz, 2H), 7.86 (dd, J$_1$=8.3 Hz, J$_2$=1.8 Hz, 1H), 8.02 (d, J=8.3 Hz, 1H), 8.07 (d, J=1.8 Hz, 1H); $^{13}$C NMR (CD$_3$OD, 100 MHz) δ 13.2, 30.9, 45.1, 48.9, 67.5, 108.9, 114.8, 115.9, 122.3 (q, J=271.7 Hz), 126.4, 127.3 (q, J=4.7 Hz), 130.4, 132.2 (q, J=33.2 Hz), 133.0, 135.4, 138.1, 152.1, 175.4, 180.4.

43-5) 4-{5-[4-(4-methanesulfonylpiperazin-1-yl)-phenyl]-8-oxo-6-thioxo-5,7-diazaspiro[3.4]oct-7-yl}-2-trifluoromethylbenzonitrile, 43f [RD138]

A mixture of 43e (0.049 g, 0.1 mmol), methanesulfonyl chloride (0.012 ml, 0.15 mmol) and triethylamine (0.15 ml) in dichloromethane was stirred at room temperature for 5 hours. The medium was filtered. The filtrate was concentrated and chromatographed (dichloromethane:acetone, 95:5) to yield 43f (0.042 g, 0.074 mmol, 74%) as a white powder.

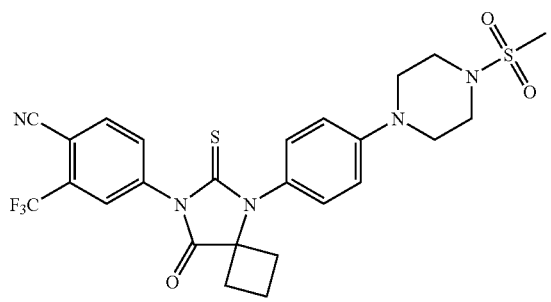

$^1$H NMR (CDCl$_3$, 400 MHz) δ 1.62-1.70 (m, 1H), 2.14-2.23 (m, 1H), 2.51-2.58 (m, 2H), 2.61-2.67 (m, 2H), 2.84 (s, 3H), 3.39 (s, 8H), 7.05 (d, J=8.9 Hz, 2H), 7.20 (d, J=8.9 Hz,

2H), 7.84 (dd, $J_1$=8.3 Hz, $J_2$=1.8 Hz, 1H), 7.95 (d, J=8.3 Hz, 1H), 7.97 (d, J=1.8 Hz, 1H); $^{13}$C NMR (CDCl$_3$, 100 MHz) δ 13.7, 31.4, 34.6, 45.7, 48.4, 67.5, 109.8, 114.9, 117.0, 121.9 (q, J=272.7 Hz), 126.8, 127.1 (q, J=4.7 Hz), 130.7, 132.3, 133.4 (q, J=33.2 Hz), 135.2, 137.3, 151.1, 175.0, 180.2.

EXAMPLE 44

44-1) 3-{4-(7-(4-Cyano-3-trifluoromethyl-phenyl)-8-oxo-6-thioxo-5,7-diaza-spiro[3.4]oct-5-yl]-phenyl}-acrylic acid, 44a A mixture of 39a (0.025 g, 0.05 mmol) in methanol (2 ml) and solution of sodium hydroxide (2 ml, 2M) was stirred at room temperature for 5 hours. Methanol was evaporated. The residue was adjusted to pH=5 by HCl aq. (2M) and then extracted with ethyl acetate (3×50 ml). The organic layer was dried over MgSO$_4$ and concentrated to dryness to obtain 44a (0.02 g, 0.042 mmol, 85%).

44-2) 3-{4-[7-(4-Cyano-3-trifluoromethyl-phenyl)-8-oxo-6-thioxo-5,7-diaza-spiro[3.4]oct-5-yl]-phenyl}-acrylamide, 44b [RD119]

To a suspension of 44b (0.02 g, 0.042 mmol) in THF (1 ml) at −5° C. was added thionyl chloride (0.007 ml, 0.1 mmol). The medium was stirred at −5° C. for one hour. Then ammonia was bubbled into the mixture. The excess of ammonia was condensed by reflux condenser at −78° C. for 30 minutes and then was allowed to evaporate. The medium was filtered. The filtrate was concentrated and chromatographed (dichloromethane:acetone, 70:30) to yield 44b (0.014 g, 0.03 mmol, 71%) as an off-white powder.

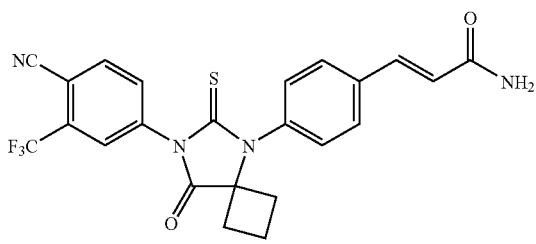

$^1$H NMR (DMSO-d$_6$, 400 MHz) δ 1.49-1.52 (m, 1H), 1.88-1.93 (m, 1H), 2.37-2.46 (m, 2H), 2.57-2.62 (m, 2H), 6.66 (d, J=15.9 Hz, 1H), 7.16 (bs, 1H), 7.43 (d, J=8.3 Hz, 2H), 7.47 (d, J=15.9 Hz, 1H), 7.58 (bs, 1H), 8.03 (dd, $J_1$=8.3 Hz, $J_2$=1.8 Hz, 1H), 8.23 (d, J=1.8 Hz, 1H), 8.34 (d, J=8.3 Hz, 1H).

EXAMPLE 45

RD145

Trimethylsilyl cyanide (0.4 g, 4 mmol) was added dropwise to a mixture of 4-methanesulfonylphenylamine hydrochloride (0.415 g, 2 mmol), cyclobutanone (0.28 g, 4-mmol) and sodium sulfate (1 g) in DMF (3 ml). The mixture was stirred for 15 hours at 120° C. After filtration to remove the sodium sulfate, the filtrate was washed with brine and extracted with ethyl acetate. The organic layer was concentrated and chromatographed (dichloromethane:acetone, 90:10) to yield 1-(4-methanesulfonylphenylamino)cyclobutanecarbonitrile (45a) (0.116 g, 0.44 mmol, 22%) as a yellowish solid. 4-methanesulfonylphenylamine (0.201 g, 1.17 mmol, 59%) was also recovered.

A mixture of 4-isothiocyanato-2-trifluoromethylbenzonitrile (1a) (0.0.141 g, 0.62 mmol) and 1-(4-methanesulfonylphenylamino)cyclobutanecarbonitrile (45a) (0.11 g, 0.42 mmol) in dry DMF (2 ml) was stirred at room temperature for 3 days. To this mixture were added methanol (10 ml) and aq. 2N HCl (5 ml). The second mixture was refluxed for 3 h. After being cooled to room temperature, the reaction mixture was poured into cold water (10 ml) and extracted with ethyl acetate (3×30 ml). The organic layer was dried over MgSO$_4$, concentrated and chromatographed (dichloromethane:acetone, 97:3) to yield 4-[5-(4-methanesulfonylphenyl)-8-oxo-6-thioxo-5,7-diazaspiro[3.4]oct-7-yl]-2-trifluoromethylbenzonitrile (45b) [RD145] (0.031 g, 0.065 mmol, 15%), the structure of which is illustrated in Formula 14, as a white powder.

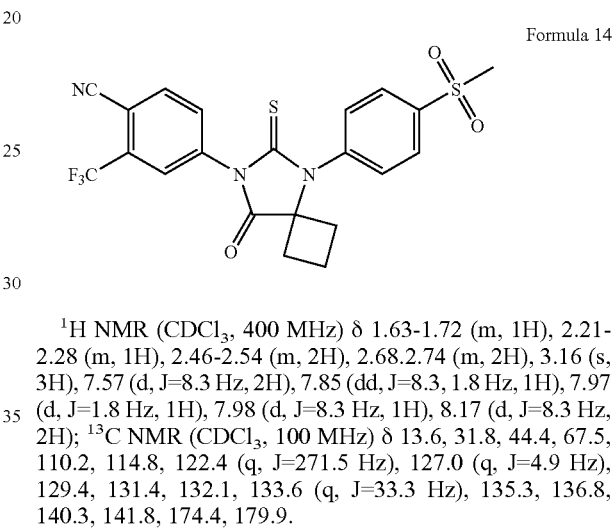

Formula 14

$^1$H NMR (CDCl$_3$, 400 MHz) δ 1.63-1.72 (m, 1H), 2.21-2.28 (m, 1H), 2.46-2.54 (m, 2H), 2.68.2.74 (m, 2H), 3.16 (s, 3H), 7.57 (d, J=8.3 Hz, 2H), 7.85 (dd, J=8.3, 1.8 Hz, 1H), 7.97 (d, J=1.8 Hz, 1H), 7.98 (d, J=8.3 Hz, 1H), 8.17 (d, J=8.3 Hz, 2H); $^{13}$C NMR (CDCl$_3$, 100 MHz) δ 13.6, 31.8, 44.4, 67.5, 110.2, 114.8, 122.4 (q, J=271.5 Hz), 127.0 (q, J=4.9 Hz), 129.4, 131.4, 132.1, 133.6 (q, J=33.3 Hz), 135.3, 136.8, 140.3, 141.8, 174.4, 179.9.

EXAMPLE 46

Trimethylsilyl cyanide (0.69 g, 7 mmol) was added dropwise to a mixture of 4-aminophenylacetic acid (0.755 g, 5 mmol) and cyclobutanone (0.49 g, 7 mmol) in dioxane (20 ml). The mixture was stirred for 8 hours at 80° C. The mixture was concentrated and chromatographed (dichloromethane:acetone, 60:40) to yield [4-(1-cyanocyclobutylamino)phenyl]acetic acid (46a) (1.138 g, 4.95 mmol, 99%) as a white solid.

46-1) RD146

A mixture of 4-isothiocyanato-2-trifluoromethylbenzonitrile (1a) (0.638 g, 2.8 mmol) and [4-(1-cyanocyclobutylamino)phenyl]acetic acid (46a) (0.46 g, 2.0 mmol) in DMF (5 ml) was stirred at room temperature for 15 hours. To this mixture were added methanol (20 ml) and aq. 2N HCl (10 ml). The second mixture was refluxed for 1 h. After being cooled to room temperature, the reaction mixture was poured into cold water (10 ml) and extracted with ethyl acetate (3×50 ml). The organic layer was dried over MgSO$_4$, concentrated and chromatographed (dichloromethane pure and then dichloromethane:acetone, 95:5) to yield (4-[7-(4-cyano-3-trifluoromethylphenyl)-8-oxo-6-thioxo-5,7-diaza-spiro[3.4] oct-5-yl]phenyl)acetic acid methyl ester (46b) [RD146] (0.532 g, 1.124 mmol, 56%), the structure of which is illustrated in Formula 15, as a white powder.

Formula 15

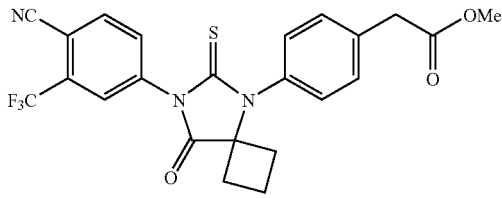

¹H NMR (CDCl₃, 400 MHz) δ 1.60-1.69 (m, 1H), 2.15-2.25 (m, 1H), 2.50-2.58 (m, 2H), 2.61-2.66 (m, 2H), 3.72 (bs, 5H), 7.27 (d, J=8.3 Hz, 2H), 7.50 (d, J=8.3 Hz, 2H), 7.84 (dd, J=8.3, 1.8 Hz, 1H), 7.94 (d, J=8.2 Hz, 1H), 7.97 (d, J=1.6 Hz, 1H); ¹³C NMR (CDCl₃, 100 MHz) δ 13.7, 31.4, 44.7, 52.3, 67.4, 109.9, 114.9, 122.0 (q, J=272.5 Hz), 127.0 (q, J=4.9 Hz), 130.0, 131.1, 132.3, 133.0 (q, J=33.3 Hz), 134.1, 135.2, 135.9, 137.2, 171.4, 174.9, 179.9.

46-2) RD147

A mixture of (4-[7-(4-cyano-3-trifluoromethylphenyl)-8-oxo-6-thioxo-5,7-diaza-spiro[3.4]oct-5-yl]phenyl}acetic acid methyl ester (46b) (0.095 g, 0.2 mmol) and a solution of sodium hydroxide (1 ml, 2M) in methanol (2 ml) was stirred at room temperature for 2 hours. The methanol was evaporated. The residue was adjusted to pH 5 by aq. 2M HCl and then the mixture was extracted with ethyl acetate (3×10 ml). The organic layer was dried over MgSO₄ and concentrated to dryness to obtain (4-[7-(4-cyano-3-trifluoromethylphenyl)-8-oxo-6-thioxo-5,7-diaza-spiro[3.4]oct-5-yl]phenyl)acetic acid (46c) [RD147](0.087 g, 0.19 mmol, 95%), the structure of which is illustrated in Formula 16.

Formula 16

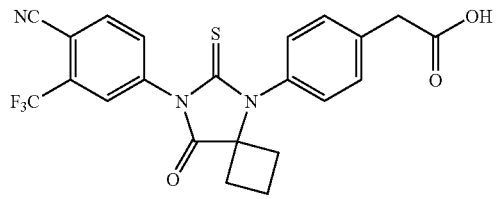

¹H NMR (CDCl₃, 400 MHz) δ 1.60-1.69 (m, 1H), 2.15-2.25 (m, 1H), 2.50-2.64 (m, 4H), 3.73 (s, 2H), 7.26 (d, J=8.3 Hz, 2H), 7.51 (d, J=8.3 Hz, 2H), 7.84 (dd, J=8.3, 1.8 Hz, 1H), 7.95 (d, J=8.2 Hz, 1H), 7.96 (d, J=1.6 Hz, 1H); ¹³C NMR (CDCl₃, 100 MHz) δ 13.7, 31.4, 40.2, 40.8, 67.4, 109.9, 114.9, 122.0 (q, J=272.5 Hz), 127.0 (q, J=4.9 Hz), 129.9, 131.2, 132.3, 133.3 (q, J=33.3 Hz), 133.9, 135.2, 136.1, 137.2, 14.1, 174.9, 179.9.

46-3) RD148

Thionyl chloride (0.238 g, 2 mmol) was added dropwise to a mixture of {4-[7-(4-cyano-3-trifluoromethylphenyl)-8-oxo-6-thioxo-5,7-diaza-spiro[3.4]oct-5-yl]phenyl}acetic acid (46c) (0.357 g, 0.777 mmol) in THF (5 ml) cooled to 0° C. The mixture was stirred for 1 hour at room temperature and then ammonia was bubbled into the mixture. The excess ammonia was condensed by a reflux condenser at −78° C. for 30 minutes and then was allowed to evaporate. The medium was filtered and the filtrate was concentrated and chromatographed (dichloromethane:acetone, 70:30) to yield 2-{4-[7-(4-cyano-3-trifluoromethylphenyl)-8-oxo-6-thioxo-5,7-diaza-spiro[3.4]oct-5-yl]phenyl}acetamide (46d) [RD148] (0.345 g, 0.75 mmol, 97%), the structure of which is illustrated in Formula 17, as an off-white powder.

Formula 17

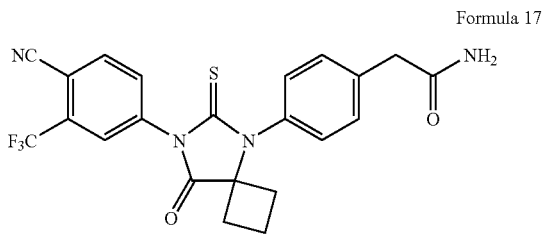

¹H NMR (CDCl₃, 400 MHz) δ 1.62-1.66 (m, 1H), 2.18.2.23 (m, 1H), 2.49-2.55 (m, 2H), 2.61-2.66 (m, 2H), 3.63 (s, 2H), 5.91 (bs, 1H), 6.10 (bs, 1H), 7.27 (d, J=8.1 Hz, 2H), 7.50 (d, J=8.1 Hz, 2H), 7.83 (dd, J=8.3, 1.8 Hz, 1H), 7.95 (d, J=8.2 Hz, 1H), 7.96 (d, J=1.6 Hz, 1H); ¹³C NMR (CDCl₃, 100 MHz) δ 13.7, 31.5, 42.5, 67.4, 109.9, 114.9, 121.9 (q, J=272.4 Hz), 127.1 (q, J=4.9 Hz), 130.2, 131.1, 132.2, 133.3 (q, J=33.3 Hz), 134.1, 135.2, 136.8, 137.2, 172.8, 174.8, 180.0.

46-4) RD149

Thionyl chloride (0.238 g, 2 mmol) was added dropwise to a mixture of {4-[7-(4-cyano-3-trifluoromethylphenyl)-8-oxo-6-thioxo-5,7-diaza-spiro[3.4]oct-5-yl]phenyl}acetic acid (46c) (0.357 g, 0.777 mmol) in THF (5 ml) cooled to 0° C. The mixture was stirred for 1 hour at room temperature and then methylamine (0.5 ml) was added into the mixture. The mixture was stirred for an additional 2 hours. The medium was filtered and the filtrate was concentrated and chromatographed (dichloromethane:acetone, 80:20) to yield N-methyl-2-{4-[7-(4-cyano-3-trifluoromethylphenyl)-8-oxo-6-thioxo-5,7-diaza-spiro[3.4]oct-5-yl]phenyl}acetamide (46e) [RD149] (0.348 g, 0.738 mmol, 95%), the structure of which is illustrated in Formula 18, as an off-white powder.

Formula 18

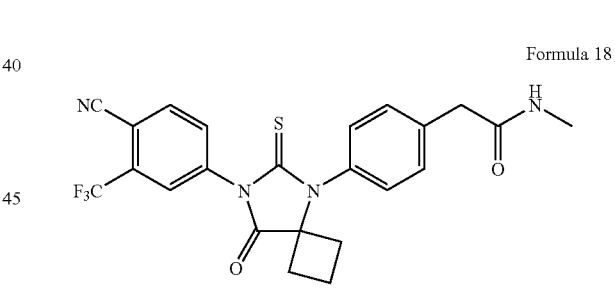

¹H NMR (CDCl₃, 400 MHz) δ 1.61-1.70 (m, 1H), 2.17-2.31 (m, 1H), 2.50-2.56 (m, 2H), 2.61-2.68 (m, 2H), 2.82 (d, J=4.8 Hz, 3H), 3.62 (s, 2H), 7.27 (d, J=8.3 Hz, 2H), 7.50 (d, J=8.3 Hz, 2H), 7.84 (dd, J=8.3, 1.8 Hz, 1H), 7.95 (d, J=8.2 Hz, 1H), 7.96 (d, J=1.6 Hz, 1H); ¹³C NMR (CDCl₃, 100 MHz) δ 13.7, 26.6, 31.5, 43.1, 67.4, 110.0, 114.9, 122.0 (q, J=272.5 Hz), 127.1 (q, J=4.9 Hz), 130.2, 131.0, 132.2, 133.3 (q, J=33.3 Hz), 134.1, 135.2, 137.0, 137.1, 170.1, 174.8, 179.9.

EXAMPLE 47

N-{4-[3-(4-cyano-3-trifluoromethylphenyl)-5,5-dimethyl oxo-2-thioxo-imidazolidin-1-yl]phenyl}methanesulfonamide (47a) [RD150]

A mixture of 4-[3-(4-aminophenyl)-4,4-dimethyl-5-oxo-2-thioxoimidazolidin-1-yl]-2-trifluoromethylbenzonitrile (2d) (0.02 g, 0.05 mmol), methanesulfonyl chloride (0.009 g, 0.075 mmol) and pyridine (0.006 g, 0.075 mmol) in dichloromethane (1 ml) was stirred at room temperature for 15 hours. The medium was washed with water (2 ml) and extracted with ethyl acetate (5 ml). The organic layer was dried over MgSO$_4$, concentrated and chromatographed (HPLC, alumina column) to yield N-{4-[3-(4-cyano-3-fluoromethylphenyl)-5,5-dimethyl-4-oxo-2-h-oxo-imidazolidin-1-yl]phenyl}methanesulfonamide (47a) [RD150] (0.009 g, 0.018 mmol, 36%), the structure of which is illustrated in Formula 2, as a white powder.

Formula 2

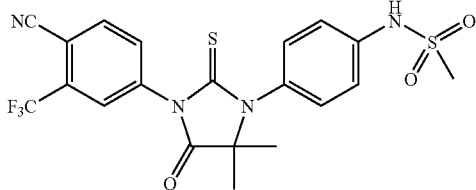

$^1$H NMR (DMSO-d$_6$, 400 MHz) δ 1.46 (s, 6H), 3.07 (s, 3H), 7.32 (s, 4H), 8.05 (dd, J=8.2, 1.2 Hz, 1H), 8.26 (d, J=1.2 Hz, 1H), 8.35 (d, J=8.2 Hz, 1H), 10.08 (bs, 1H); $^{13}$C NMR (DMSO-d$_6$, 100 MHz) δ 23.3, 40.4, 66.7, 109.0, 115.5, 119.9, 122.6 (q, J=272.2 Hz), 128.5 (q, J=4.7 Hz), 130.8, 131.2, 131.5 (q, J=32.3 Hz), 134.5, 136.6, 138.6, 139.5, 175.4, 180.4.

EXAMPLE 48

N-{4-[3-(4-cyano-3-trifluoromethylphenyl)-5,5-dimethyl-4-oxo-2-thioxo-imidazolidin-1-yl]phenyl}acetamide, 48a, [RD151]

A mixture of 4-[3-(4-aminophenyl)-4,4-dimethyl-4-oxo-2-thioxo-imidazolidin-1-yl]-2-trifluoromethylbenzonitrile (2d) [RD9] (0.008 g, 0.02 mmol), acetyl chloride (0.004 g, 0.03 mmol) and triethylamine (0.003 g, 0.03 mmol) in dichloromethane (1 ml) was stirred at 0° C. for 2 hours. The mixture was concentrated and chromatographed (dichloromethane: acetone, 90:10) to yield N-{4-[3-(4-cyano-3-trifluoromethylphenyl)-5,5-dimethyl-4-oxo-2-thioxo-imidazolidin-1-yl]phenyl}acetamide, 48a, [RD151] (0.007 g, 0.016 mmol, 80%), the structure of which is illustrated in Formula 3, as a white powder.

Formula 3

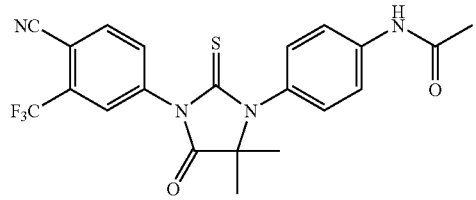

$^1$H NMR (CDCl$_3$, 400 MHz δ) 1.58 (s, 6H), 2.21 (s, 3H), 7.24 (d, J=8.6 Hz, 2H), 7.48 (bs, 1H), 7.69 (d, J=8.6 Hz, 2H), 7.83 (dd, J=8.2, 1.9 Hz, 1H), 7.96 (d, J=1.2 Hz, 1H), 7.97 (d, J=8.2 Hz, 1H); $^{13}$C NMR (CDCl$_3$, 100 MHz) δ 23.6, 53.4, 66.4, 110.0, 114.8, 120.7, 122.6 (q, J=272.2 Hz), 127.1 (q, J=4.7 Hz), 129.1, 130.2, 132.2, 133.5 (q, J=32.3 Hz), 135.2, 137.1, 139.2, 168.1, 175.0, 180.0.

EXAMPLE 49

Concentrated sulfuric acid was slowly added to a mixture of 4-aminobenzoic acid (4 g, 29.2 mmol) in methanol cooled to 0° C. After the addition, the mixture was stirred at room temperature for 5 hours. The mixture was washed with a saturated solution of sodium bicarbonate and extracted with ethyl acetate. The organic layer was dried over MgSO$_4$ and concentrated under vacuum to obtain 4-aminobenzoic acid methyl ester (49a) (4.22 g, 27.9 mmol, 96%) as an off-white solid.

A mixture of 4-aminobenzoic acid methyl ester (0.32 g, 2.12 mmol), acetonecyanohydrin (3 ml) and sodium sulfate (1 g) was refluxed for 15 hours. After filtration to remove the sodium sulfate, the filtrate was washed with brine and extracted with ethyl acetate. The organic layer was concentrated and chromatographed (dichloromethane:acetone, 60:40) to yield 4-[(cyanodimethylmethyl)-amino]-benzoic acid methyl ester (49b) (0.398 g, 1.95 mmol, 92%) as a white solid.

49-1) RD152

A mixture of 4-isothiocyanato-2-trifluoromethylbenzonitrile (1a) (0.228 g, 1 mmol) and 4-[(cyanodimethylmethyl)-amino]-benzoic acid methyl ester (49b) (0.14 g, 0.64 mmol) in DMF (2 ml) was heated under microwave irradiation at 60° C. for 12 hours. To this mixture were added methanol (6 ml) and an 2N HCl (2 ml). The second mixture was refluxed for 4 h. After being cooled to room temperature, the reaction mixture was poured into cold water (10 ml) and extracted with ethyl acetate (3×30 ml). The organic layer was dried over MgSO$_4$, concentrated and chromatographed (dichloromethane; dichloromethane:acetone, 75:25) to yield 4-[3-(4-cyano-3-trifluoromethylphenyl)-5,5-dimethyl-4-oxo-2-thioxo-imidazolidin-1-yl]benzoic acid methyl ester (49c) [RD152](0.18 g, 0.4 mmol, 63%), the structure of which is illustrated in Formula 19, as a white powder.

Formula 19

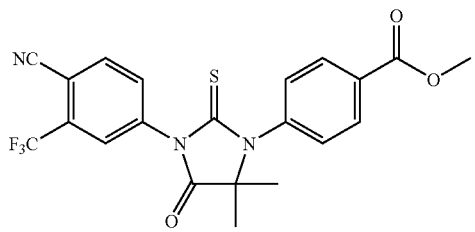

$^1$H NMR (CDCl$_3$, 400 MHz) δ 1.60 (s, 6H), 3.95 (s, 3H), 7.40 (d, J=8.6 Hz, 2H), 7.84 (dd, J=8.2, 1.9 Hz, 1H), 7.96 (d, J=1.2 Hz, 1H), 7.97 (d, J=8.2 Hz, 1H), 8.21 (d, J=8.6 Hz, 2H); $^{13}$C NMR (CDCl$_3$, 100 MHz) δ 23.8, 52.6, 66.6, 110.3, 114.8, 121.9 (q, J=272.7 Hz), 127.1 (q, J=4.7 Hz), 129.8, 131.2, 131.4, 132.2, 133.5 (q, J=32.3 Hz), 135.3, 137.0, 139.2, 165.9, 174.7, 179.7.

49-2) RD153

A mixture of 4-[3-(4-cyano-3-trifluoromethylphenyl)-5,5-dimethyl-4-oxo-2-thioxo-imidazolidin-1-yl]benzoic acid methyl ester (49c) (0.02 g, 0.0435 mmol) and methylamine (2 ml distilled from its 40% aqueous solution) was kept at −20° C. for 15 hours. After evaporation of the methylamine, the mixture was chromatographed (dichloromethane:acetone, 80:20) to yield 4-[3-(4-cyano-3-trifluoromethylphenyl)-5,5-dimethyl-4-oxo-2-thioxo-imidazolidin-1-yl]-N-methylbenzamide (49d) [RD153] (0.01 g, 0.0224, 51%), the structure of which is illustrated in Formula 20. The ester 4-[3-(4-cyano-3-trifluoromethylphenyl)-5,5-dimethyl-4-oxo-2-thioxo-imidazolidin-1-yl]benzoic acid methyl ester (49c) (0.08 g, 0.0179 mmol, 41%) was also recovered.

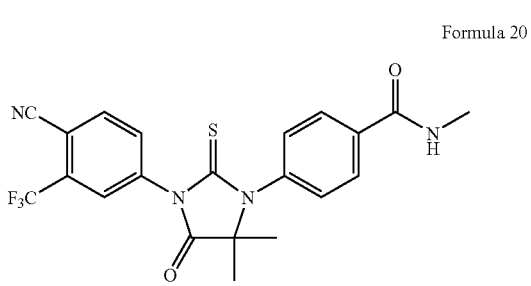

Formula 20

$^1$H NMR (Acetone-d$_6$, 400 MHz) δ 1.60 (s, 6H), 2.90 (d, J=4.6 Hz, 3H), 7.48 (d, J=8.6 Hz, 2H), 7.80 (bs, 1H), 7.99 (d, J=8.6 Hz, 2H), 8.06 (dd, J=8.2, 1.8 Hz, 1H), 8.18 (d, J=1.8 Hz, 1H), 8.25 (d, J=8.2 Hz, 1H); $^{13}$C NMR (Acetone-d$_6$, 100 MHz) δ 23.8, 54.0, 66.5, 110.3, 114.8, 121.9 (q, J=272.7 Hz), 127.1 (q, J=4.7 Hz), 128.2, 129.9, 133.5 (q, J=32.3 Hz), 135.7, 135.8, 138.2, 138.3, 139.2, 166.0, 174.9, 179.7.

EXAMPLE 50

50-1) RD154

A mixture of 4-[8-(4-hydroxymethylphenyl)-5-oxo-7-thioxo-6-azaspiro[3.4]oct-6-yl]-2-trifluoromethyl-benzonitrile (36b) (0.086 g, 0.2 mmol) and methanesulfonyl anhydride (0.07 g, 0.4 mmol) in dichloromethane (1 ml) was stirred at room temperature for 15 hours. The mixture was concentrated and chromatographed (dichloromethane:acetone, 98:2) to yield Methanesulfonic acid 4-[7-(4-cyano-3-trifluoromethylphenyl)-8-oxo-6-thioxo-5,7-diazaspiro[3.4]oct-5-yl]phenylmethyl ester (50a) [RD154] (0.089 g, 0.175 mmol, 88%), the structure of which is illustrated in Formula 22, as a white powder.

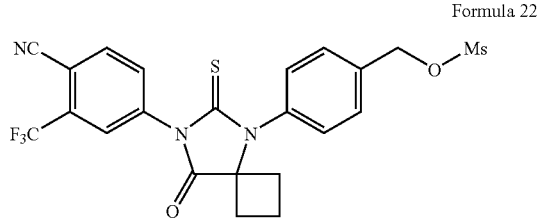

Formula 22

$^1$H NMR (CDCl$_3$, 400 MHz) δ 1.63-1.70 (m, 1H), 2.17-2.31 (m, 1H), 2.48-2.57 (m, 2H), 2.64-2.70 (m, 2H), 3.04 (s, 3H), 5.30 (s, 2H), 7.37 (d, J=8.3 Hz, 2H), 7.62 (d, J=8.3 Hz, 2H), 7.84 (dd, J=8.3, 1.8 Hz, 1H), 7.97 (d, J=8.2 Hz, 1H), 7.98 (d, J=1.6 Hz, 1H).

50-2) RD155

Methylamine (0.5 ml) was bubbled into a mixture of Methanesulfonic acid 4-[7-(4-cyano-3-trifluoromethylphenyl)-8-oxo-6-thioxo-5,7-diazaspiro[3.4]oct-5-yl]phenylmethyl ester (50a) (0.059 g, 0.115 mmol) in THF (3 ml) cooled to −78° C. After 1 hour of reaction at −78° C., the mixture was concentrated and chromatographed (dichloromethane:acetone, 95:5; methanol) to yield 4-[5-(4-methylaminomethylphenyl)-8-oxo-6-thioxo-5,7-diazaspiro[3.4]oct-7-yl]-2-trifluoromethylbenzonitrile (50b) [RD155] (0.042 g, 0.095 mmol, 82%), the structure of which is illustrated in Formula 23, as a white powder.

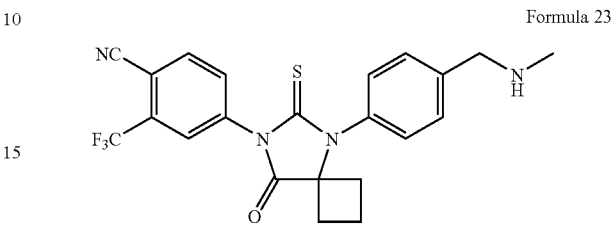

Formula 23

$^1$H NMR (CDCl$_3$, 400 MHz) δ 1.57-1.70 (m, 1H), 2.16-2.24 (m, 1H), 2.52 (s, 3H), 2.53-2.57 (m, 2H), 2.60-2.68 (m, 2H), 3.85 (s, 2H), 7.27 (d, J=8.3 Hz, 2H), 7.55 (d, J=8.3 Hz, 2H), 7.84 (dd, J=8.3, 1.8 Hz, 1H), 7.95 (d, J=8.2 Hz, 1H), 7.97 (d, J=1.6 Hz, 1H); $^{13}$C NMR (CDCl$_3$, 100 MHz) δ 13.7, 31.5, 36.4, 55.6, 67.4, 110.0, 114.9, 122.0 (q, J=272.5 Hz), 127.0 (q, J=4.9 Hz), 129.1, 129.6, 129.8, 132.2, 133.3 (q, J=33.3 Hz), 133.7, 135.2, 142.4, 174.8, 179.9.

50-3) RD156

A mixture of Methanesulfonic acid 4-[7-(4-cyano-3-trifluoromethylphenyl)-8-oxo-6-thioxo-5,7-diazaspiro[3.4]oct-5-yl]phenylmethyl ester (50a) (0.02 g, 0.039 mmol) and dimethylamine (0.5 ml; distilled from its 40% aqueous solution) in THF (1 ml) was stirred for 2 hours at −78° C. The mixture was concentrated and chromatographed (dichloromethane:acetone, 95:5; acetone) to yield 4-[5-(4-dimethylaminomethylphenyl)-8-oxo-6-thioxo-5,7-diazaspiro[3.4]oct-7-yl]-2-trifluoromethylbenzonitrile (50c) [RD156] (0.017 g, 0.037 mmol, 95%), the structure of which is illustrated in Formula 24, as a white powder.

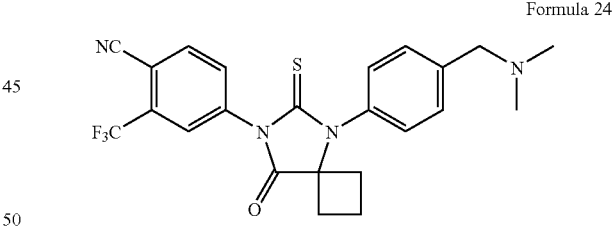

Formula 24

$^1$H NMR (CDCl$_3$, 400 MHz) δ 1.57-1.70 (m, 1H), 2.16-2.24 (m, 1H), 2.32 (s, 6H), 2.55-2.60 (m, 2H), 2.63-2.69 (m, 2H), 3.53 (s, 2H), 7.27 (d, J=8.3 Hz, 2H), 7.55 (d, J=8.3 Hz, 2H), 7.84 (dd, J=8.3, 1.8 Hz, 1H), 7.95 (d, J=8.2 Hz, 1H), 7.97 (d, J=1.6 Hz, 1H); $^{13}$C NMR (CDCl$_3$, 100 MHz) δ 13.7, 31.5, 45.5, 63.7, 67.4, 110.0, 114.9, 122.0 (q, J=272.5 Hz), 127.0 (q, J=4.9 Hz), 129.1, 129.6, 129.8, 132.2, 133.3 (q, J=33.3 Hz), 133.7, 135.2, 142.4, 174.8, 179.9.

EXAMPLE 51

Sodium cyanide (0.245 g, 5 mmol) was added to a mixture of 4-aminobenzoic acid (0.274 g, 2 mmol) and cyclobutanone (0.21 g, 3 mmol) in 90% acetic acid (4.5 ml). The reaction mixture was stirred at room temperature for 15 hours. The mixture was washed with aqueous HCl (pH 2) and extracted with ethyl acetate. The organic layer was dried over magnesium sulfate and concentrated to dryness under vacuum to yield 4-(1-cyanocyclobutylamino)benzoic acid (51a) (0.426 g, 1.97 mmol, 99%) as a white solid.

51-1) RD159 and RD160

A mixture of 4-isothiocyanato-2-trifluoromethylbenzonitrile (1a) (0.51 g, 2.22 mmol) and 4-(1-cyanocyclobutylamino)benzoic acid (51a) (0.343 g, 1.59 mmol) in DMF (2 ml) was heated under microwave irradiation at 60° C. and stirred for 16 hours. To this mixture were added methanol (10 ml) and aq. 2M HCl (5 ml). The second mixture was refluxed for 12 hours. After being cooled to room temperature, the reaction mixture was poured into cold water (20 ml) and extracted with ethyl acetate (3×30 ml). The organic layer was dried over MgSO$_4$, concentrated and chromatographed (dichloromethane:acetone, 95:5) to yield 4-[7-(4-cyano-3-trifluoromethylphenyl)-8-oxo-6-thioxo-5,7-diazaspiro[3.4]oct-5-yl]-benzoic acid methyl ester (51b) [RD159] (0.09 g, 0.196 mmol, 12%), the structure of which is illustrated in Formula 25, as a white powder and N-(3-cyano-4-trifluoromethylphenyl)$_4$-[7-(4-cyano-3-trifluoromethylphenyl)-8-oxo-6-thioxo-5,7-diazaspiro[3.4]oct-5-yl]benzamide (51b') [RD160] (0.28 g, 0.45 mmol, 29%), the structure of which is illustrated in Formula 26, as a white powder.

Formula 25

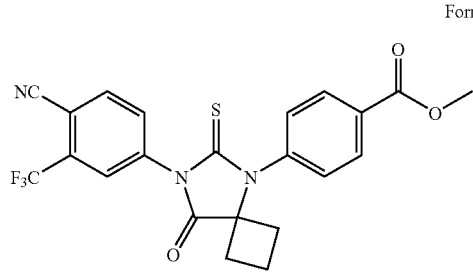

$^1$H NMR (CDCl$_3$, 400 MHz) δ 1.67-1.71 (m, 1H), 2.20-2.26 (m, 1H); 2.49-2.57 (m, 2H), 2.66-2.73 (m, 2H), 3.96 (s, 3H), 7.42 (d, J=8.4 Hz, 2H), 7.85 (dd, J=8.3, 1.7 Hz, 1H), 7.97 (d, J=8.3 Hz, 1H), 7.98 (d, J=1.7 Hz, 1H), 8.26 (d, J=8.3 Hz, 2H); $^{13}$C NMR (CDCl$_3$, 100 MHz) δ 13.7, 31.6, 52.6, 67.5, 110.1, 114.8, 121.8 (q, J=272.7 Hz), 127.0 (q, J=4.7 Hz), 130.2, 131.4, 131.5, 132.2, 133.4 (q, J=33.2 Hz), 135.2, 137.0, 139.2, 165.9, 174.6, 179.7.

Formula 26

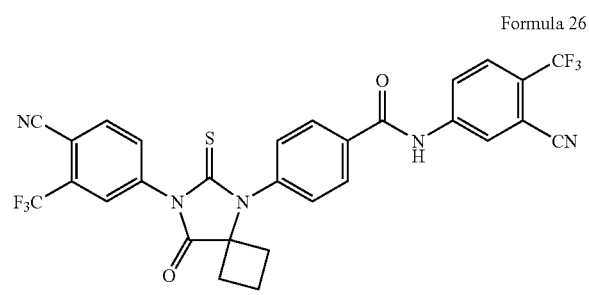

$^1$H NMR (CDCl$_3$, 400 MHz) δ 1.67-1.71 (m, 1H), 2.18-2.26 (m, 1H), 2.50-2.58 (m, 2H), 2.68-2.74 (m, 2H), 7.47 (d, J=8.5 Hz, 2H), 7.83 (d, J=8.7 Hz, 1H), 7.84 (dd, J=8.3, 1.9 Hz, 1H), 7.96 (d, J=8.0 Hz, 1H), 9.97 (d, J=1.9 Hz, 1H), 8.10-8.14 (m, 3H). 8.21 (d. J=1.9 Hz, 1H), 8.88, (s, 1H).

51-2) RD161

A mixture of 4-[7-(4-cyano-3-trifluoromethylphenyl)-8-oxo-6-thioxo-5,7-diazaspiro[3.4]oct-5-yl]-benzoic acid methyl ester (51b) (0.046 g, 0.1 mmol) and methylamine (1 ml distilled from its 40% aqueous solution) was kept at −20° C. for 15 hours. After evaporation of the methylamine, the mixture was chromatographed (dichloromethane:acetone, 80:20) to yield N-methyl-4-[7-(4-cyano-3-trifluoromethylphenyl)-8-oxo-6-thioxo-5,7-diazaspiro[3.4]oct-5-yl]benzamide (51c) [RD161] (0.041 g, 0.085, 84%), the structure of which is illustrated in Formula 27.

Formula 27

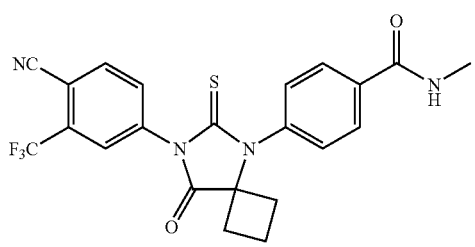

$^1$H NMR (CDCl$_3$, 400 MHz) δ 1.63-1.70 (m, 1H), 2.18-2.26 (m, 1H), 2.48-2.56 (m, 2H), 2.65-2.71 (m, 2H), 3.05 (d, J=4.8 Hz, 3H), 6.32 (bs, 1H), 7.39 (d, J=8.3 Hz, 2H), 7.84 (dd, J=8.3, 1.7 Hz, 1H), 7.95-7.98 (m, 4H); $^{13}$C NMR (CDCl$_3$, 100 MHz) δ 13.6, 27.0, 31.6, 67.4, 110.3, 114.8, 121.8 (q, J=272.7 Hz), 127.0 (q, J=4.7 Hz), 128.7, 130.3; 132.1, 133.3 (q, J=33.2 Hz), 135.2, 136.3, 137.0, 137.8, 167.2, 174.6, 179.8.

EXAMPLE 52

RD162

Thionyl chloride (2.38 g, 20 mmol) was added slowly to a solution of 2-fluoro-4-nitrobenzoic acid (2.97 g, 16 mmol) in DMF (50 ml) cooled at −5° C. The mixture was stirred for an additional 1 hour at −5° C. Methylamine (0.62 g, 20 mmol; freshly distilled from its 40% aqueous solution) was added to the reaction medium. The second mixture was stirred for an additional 1 hour. Ethyl acetate (300 ml) was added to the mixture, which was washed with brine (3×150 ml). The organic layer was dried over MgSO$_4$, and concentrated to yield N-methyl-2-fluoro-4-nitrobenzamide (52a) (2.89 g, 14.6 mmol, 91%) as a yellow solid. $^1$H NMR (Acetone d$_6$, 400 MHz) δ 3.05 (d, J=4.3 Hz, 3H), 6.31 (dd, J=13.5, 2.1 Hz, 1H), 6.40 (dd, J=8.5, 2.1 Hz, 1H), 7.64 (dd, J=8.6, 8.6 Hz, 1H).

A mixture of N-methyl-2-fluoro-4-nitrobenzamide (52a) (2.89 g, 14.6 mmol) and iron (5.04 g, 90 mmol) in ethyl acetate (40 ml) and acetic acid (40 ml) was refluxed for 1 hour. The solid particles were filtered off. The filtrate was washed with water and extracted with ethyl acetate. The organic layer was dried over MgSO$_4$, concentrated and chromatographed (dichloromethane:acetone, 95:5) to yield N-methyl-2-fluoro-4-aminobenzamide (52b) (2.3 g, 13.7 mmol, 94%) as an off-white solid.

$^1$H NMR (acetone-d$_6$, 400 MHz) δ 2.86 (d, J=4.3 Hz, 3H), 5.50 (bs, 2H), 6.37 (dd, J$_1$=14.7 Hz, J$_2$=2.1 Hz, 1H), 6.50 (dd, J=8.5, 2.1 Hz, 1H), 7.06 (bs, 1H), 7.68 (dd, J=8.8 8.8 Hz, 1H); $^{13}$C NMR (acetone-d$_6$, 100 MHz) δ 25.8, 99.6 (d, J=13.8 Hz), 109.2 (d, J=12.8 Hz), 110.0 (d, J=1.6 Hz), 132.5 (d, J=4.8 Hz), 153.5 (d, J=12.6 Hz), 162.2 (d, J=242.5 Hz), 164.0 (d, J=3.1 Hz).

Sodium cyanide (1.47 g, 30 mmol) was added to a mixture of N-methyl-2-fluoro-4-aminobenzamide (52b) (1.68 g, 10 mmol) and cyclobutanone (1.4 g, 20 mmol) in 90% acetic acid (20 ml). The reaction mixture was stirred at 80° C. for 24 hours. The mixture was washed with water and extracted with ethyl acetate. The organic layer was dried over magnesium sulfate and concentrated to dryness under vacuum. The solid was washed with a 50:50 mixture of ethyl ether and hexane (10 ml) to remove cyclobutanone cyanohydrin to afford after filtration N-methyl-4-(1 -cyanocyclobutylamino)-2-fluorobenzamide (52c) (2.19 g, 8.87 mmol, 89%). $^1$H NMR (CDCl$_3$, 400 MHz) δ 1.87-1.95 (m, 1H), 2.16-2.27 (m, 1H), 2.35-2.41 (m, 2H), 2.76-2.83 (m, 2H), 2.97 (d, J=4.4 Hz, 3H), 4.68 (bs, 1H), 6.29 (dd, J=14.3, 1.8 Hz, 1H), 6.48 (dd, J=8.3, 1.8 Hz, 1H), 6.75 (q, J=4.4 Hz, 1H), 7.90 (dd, J=8.3, 8.3 Hz, 1H); $^{13}$C NMR (CDCl$_3$, 100 MHz) δ 15.7, 26.7, 33.9, 49.4, 100.2 (d, J=29.5 Hz), 110.6, 111.0 (d, J=11.8 Hz), 133.1 (d, J=4.2 Hz), 148.4 (d, J=12.0 Hz), 162.0 (d, J=244.1 Hz), 164.4 (d, J=3.6 Hz).

A mixture of 4-isothiocyanato-2-trifluoromethylbenzonitrile (1a) (2.16 g, 9.47 mmol) and N-methyl-4-(1-cyanocyclobutylamino)-2-fluorobenzamide (52c) (1.303 g, 5.27 mmol) in DMF (20 ml) was heated under microwave irradiation at 80° C. for 16 hours. To this mixture was added methanol (50 ml) and aq. 2N HCl (20 ml). The second mixture was refluxed for 3 hours. After being cooled to room temperature, the reaction mixture was poured into cold water (100 ml) and extracted with ethyl acetate (150 ml). The organic layer was dried over MgSO$_4$, concentrated and chromatographed (dichloromethane:acetone, 95:5) to yield N-methyl-4-[7-(4-cyano-3-trifluoromethylphenyl)-8-oxo-6-thioxo-5,7-diazaspiro[3.4]oct-5-yl]-2-fluorobenzamide (52d) [RD162](1.43 g, 3.0 mmol, 57%), the structure of which is illustrated in Formula 28, as a yellow powder.

Formula 28

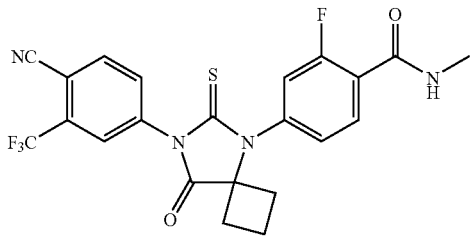

$^1$H NMR (CDCl$_3$, 400 MHz), 1.65-1.75 (m, 1H), 2.18-2.30 (m, 1H), 2.49-2.57 (m, 2H), 2.67-2.73 (m, 2H), 3.07 (d, J=4.4 Hz, 3H), 6.75 (q, J=4.6 Hz, 1H), 7.17 (dd, J=11.5, 1.9 Hz, 1H), 7.26 (dd, J=8.3, 1.9 Hz, 1H), 7.83 (dd, J=8.2, 2.0 Hz, 1H), 7.95 (d, J=1.8 Hz, 1H), 7.97 (d, J=8.3 Hz, 1H) 8.30 (dd, J=8.3, 8.3 Hz, 1H); $^{13}$C NMR (CDCl$_3$, 100 MHz) δ 13.6, 27.0, 31.7, 67.4, 110.3, 114.8, 118.2, 118.5, 121.9 (q, J=272.7 Hz), 126.6, 127.0 (q, J=4.8 Hz), 132.1, 133.3 (q, J=33.2 Hz), 133.8, 135.3, 136.8, 139.1 (d, J=10.9 Hz), 160.5 (d, J=249.1 Hz), 162.7 (d, J=3.3 Hz), 174.3, 179.8; $^{19}$F NMR (CDCl$_3$, 100 MHz) a −111.13, −62.58.

EXAMPLE 53

RD163

A mixture of 4-nitro-3-fluorophenol (0.314 g, 2 mmol) and iron (0.56 g, 10 mmol) in ethyl acetate (4 ml) and acetic acid (2 ml) was refluxed for 3 hour. The solid particles were filtered off. The filtrate was washed with water and extracted with ethyl acetate. The organic layer was dried over MgSO$_4$, concentrated to yield 4-amino-3-fluorophenol (53a) (0.25 g, 19.6 mmol, 98%) as a brown solid.

$^1$H NMR (CDCl$_3$, 400 MHz) δ 6.48-6.58 (m, 2H), 6.61-6.70 (m, 1H), 7.87 (bs, 3H).

Sodium cyanide (0.194 g, 4 mmol) was added to a mixture of 4-amino-3 -fluorophenol (0.29 g, 2.28 mmol) and cyclobutanone (0.175 g, 2.5 mmol) in 90% acetic acid (3 ml). The reaction mixture was stirred at room temperature for 15 hours. The medium was washed with water and extracted with ethyl acetate. The organic layer was dried over magnesium sulfate, concentrated and chromatographed (dichloromethane:acetone, 90:10) to yield 1-(2-fluoro-4 -hydroxyphenylamino)-cyclobutanecarbonitrile (53b) (0.271 g, 1.31 mmol, 58%) as an off-white solid. $^1$H NMR (CDCl$_3$, 400 MHz) b 2.13-2.20 (m, 2H), 2.36-2.41 (m, 2H), 2.70.2.75 (m, 2H), 4.00 (bs, 1H), 6.46 (bs, 1H), 6.52 (ddd, J$_1$=2.2 Hz, J$_2$=0.65 Hz, J$_3$=0.22 Hz, 1H), 6.57 (d, J=2.3 Hz), 6.62 (dd, J$_1$=3.0 Hz, J$_2$=0.67 Hz, 1H); $^{13}$C NMR (CDCl$_3$, 100 MHz) δ 15.7, 34.1, 50.9, 104.0 (d, J=21.9 Hz), 111.0 (d, J=3.4 Hz), 115.8 (d, J=3.7 Hz), 121.8, 125.3 (d, J=12.3 Hz), 150.1 (d, J-21.9 Hz), 111.0 (d, J=152.8 (d, J-239.3 Hz).

A mixture of 4-isothiocyanato-2-trifluoromethylbenzonitrile (1a) (0.228 g, 1.0 mmol) and 1-(2-fluoro-4-hydroxyphenylamino)-cyclobutanecarbonitrile (53b) (0.145 g, 0.7 mmol) in dry DMF (2 ml) was stirred at room temperature for 24 hours. To this mixture were added methanol (10 ml) and aq. 2M HCl (2 ml). The second mixture was refluxed for 1 hour. After being cooled to room temperature, the reaction mixture was poured into cold water (10 ml) and extracted with ethyl acetate (50 ml). The organic layer was dried over MgSO$_4$, concentrated and chromatographed (dichloromethane pure and then dichloromethane:acetone, 90:10) to yield 4-[5-(2-fluoro-4-hydroxyphenyl)-8-oxo-6-thioxo-5,7-diazaspiro [3.4]oct-7-yl]-2-trifluoromethylbenzonitrile (53c) [RD163] (0.17 g, 0.39 mmol, 56%), the structure of which is illustrated in Formula 29, as a off-white powder.

Formula 29

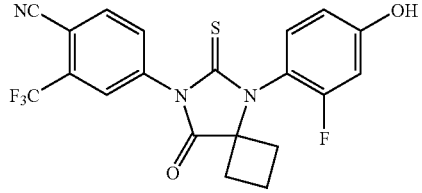

$^1$H NMR (CDCl$_3$, 400 MHz) δ 1.66-1.75 (m, 1H), 2.18-2.28 (m, 1H), 2.42-2.50 (m, 1H), 2.54-2.67 (m, 3H), 6.76 (d, J=2.2 Hz, 2H), 7.15 (t, J=2.1 Hz, 1H), 7.35 (bs, 1H), 7.87 (dd, J$_1$=8.2 Hz, J$_2$=1.8 Hz, 1H), 7.97 (d, J=8.2 Hz, 1H), 7.98 (d, J=1.8 Hz, 1H); $^{13}$C NMR (CDCl$_3$, 100 MHz) δ 13.8, 31.0, 67.6, 104.8 (d, J=22.3 Hz), 109.8, 112.6, 114.4 (d, J=13.1 Hz), 114.9, 121.9 (q, J=272.8 Hz), 127.1 (q, J=4.8 Hz), 132.0, 132.3, 133.5 (q, J=33.3 Hz), 135.3, 137.2, 159.3 (d, J=11.2 Hz), 159.6 (d, J=249.7 Hz), 175.2, 180.5; $^{19}$F NMR (CDCl$_3$, 100 MHz) δ −117.5, −62.49.

EXAMPLE 54

RD168

A mixture of 4-nitro-2-fluorobenzonitrile (1.83 g, 5 mmol) and iron (1.68 g, 6 mmol) in a mixture of acetic acid (40 ml) and ethyl acetate (40 ml) was refluxed for 2 hours. The solid was filtered off and the filtrate was washed with water and extracted with ethyl acetate. The organic layer was dried over magnesium sulfate, concentrated and chromatographed (dichloromethane:acetone, 95:5) to yield 4-amino-2-fluorobenzonitrile (54a) (0.653 g, 4.8 mmol, 96%).

Sodium cyanide (0.74 g, 15 mmol) was added to a mixture of 4-amino-2-fluorobenzonitrile (1.36 g, 10 mmol) and cyclopentanone (1.26 g, 15 mmol) in 90% acetic acid (10 ml). The reaction mixture was stirred at room temperature for 3 hours and then the medium was hearted to 80° C. and stirred for an additional 5 hours. The medium was washed with water and extracted with ethyl acetate. The organic layer was dried over magnesium sulfate, concentrated and chromatographed (dichloromethane:acetone, 97:3) to yield 4-(1-cyanocyclopentylamino)-2-fluorobenzonitrile (54b) (2.07 g, 9.03 mmol, 90%) as a yellow solid. $^1$H NMR (CDCl$_3$, 400 MHz) δ 1.69-1.91 (m, 4H), 2.13-2.18 (m, 2H), 2.37-2.42 (m, 2H), 5.08 (bs, 1H), 6.54-6.62 (m, 2H), 7.39 (t, J=7.3 Hz, 1H); $^{13}$C NMR (CDCl$_3$, 100 MHz) δ 23.7, 39.8, 56.8, 89.6 (d, J=15.8 Hz), 101.2 (d, J=23.8 Hz), 110.9, 115.2, 120.8, 134.1 (d, J=2.4 Hz), 150.3 (d, J=11.2 Hz), 164.5 (d, J=254.1 Hz).

A mixture of 4-isothiocyanato-2-trifluoromethylbenzonitrile (1a) (0.171 g, 0.75 mmol) and 441-cyanocyclopentylamino)-2-fluorobenzonitrile (54b) (0.115 g, 0.5 mmol) in dry DMF (1 ml) was heated under microwave irradiation at 60° C. for 48 hours. To this mixture were added methanol (3 ml) and aq 2M HCl (2 ml). The second mixture was refluxed for 1 hour. After being cooled to room temperature, the reaction mixture was poured into cold water (10 ml) and extracted with ethyl acetate (15 ml). The organic layer was dried over MgSO$_4$, concentrated and chromatographed (dichloromethane:acetone, 98:2) to yield 4-[1-(4-cyano-3-fluorophenyl)-4-oxo-2-thioxo-1,3-diazaspiro[4.4]non-3-yl]-2-trifluoromethylbenzonitrile (54c) [RD168] (0.017 g, 0.037 mmol, 7%), of which the structure is illustrated in Formula 30, as an off-white powder.

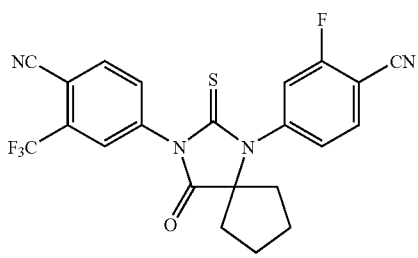

Formula 30

$^1$H NMR (CDCl$_3$, 400 MHz) δ 1.53-1.63 (m, 2H), 1.89-2.00 (m, 2H), 2.09-2.16 (m, 2H), 2.35-2.42 (m, 2H), 7.27-7.37 (m, 2H), 7.78-7.90 (m, 3H), 7.95 (d, J=1.8 Hz, 1H), 7.97 (d, J=8.3 Hz, 1H); $^{13}$C NMR (CDCl$_3$, 100 MHz) δ 25.2, 36.5, 75.3, 103.2 (d, J=15.3 Hz), 110.4, 112.8, 114.7, 119.2 (d, J=20.7 Hz), 121.9 (q, J=272.8 Hz), 127.0 (q, J=4.8 Hz), 132.1, 133.7 (q, J=33.2 Hz), 134.6, 135.3, 135.8, 136.8, 141.8 (d, J=9.5 Hz), 163.4 (d, J=261.5 Hz), 175.3, 180.1.

EXAMPLE 55

RD136 and RD142

Additional diarylhydantoin compounds can be synthesized, including the following compounds illustrated in Formulas 35 and 36.

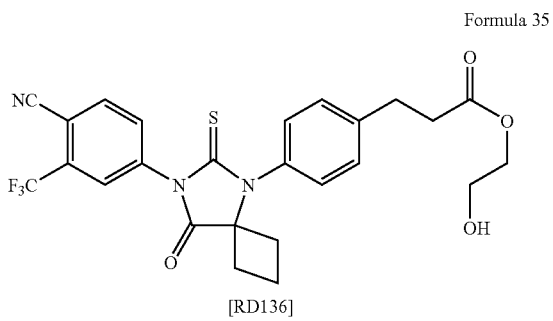

Formula 35

[RD136]

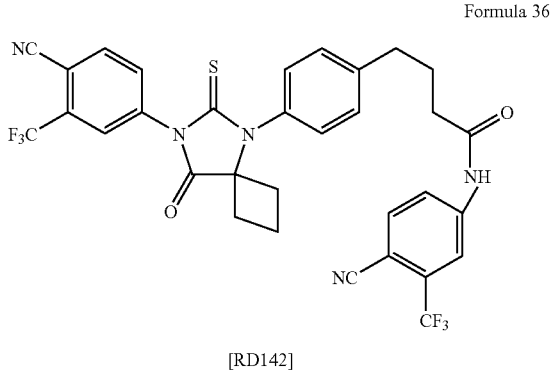

Formula 36

[RD142]

EXAMPLE 56

RD162

In the following, air or moisture sensitive reactions were conducted under argon atmosphere using oven-dried glassware and standard syringe/septa techniques. The reactions were monitored with a SiO$_2$ TLC plate under UV light (254 nm) followed by visualization with a p-anisaldehyde or ninhydrin staining solution. Column chromatography was performed on silica gel 60. $^1$H NMR spectra were measured at 400 MHz in CDCl$_3$ unless stated otherwise and data were reported as follows in ppm (δ) from the internal standard (TMS, 0.0 ppm): chemical shift (multiplicity, integration, coupling constant in Hz.).

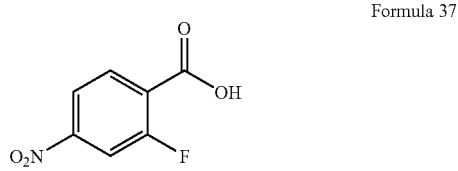

Formula 37

Periodic acid (1.69 g, 7.41 mmol) was dissolved in acetonitrile (25 mL) by vigorous stirring, and then chromium trioxide (0.16 g, 1.60 mmol) was dissolved into the solution. 2-Fluoro-4-nitrotoluene (0.33 g, 2.13 mmol) was added to the above solution with stirring. A white precipitate formed immediately with exothermic reaction. After 1 h of stirring, the supernatant liquid of the reaction mixture was decanted to a flask, and the solvent was removed by evaporation. The residues were extracted with methylene chloride (2×30 mL) and water (2×30 mL). The organic layer was dried over MgSO$_4$, and concentrated to give 2-Fluoro-4-nitrobenzoic acid (Formula 37) (0.32 mg, 81%) as a white solid. $^1$H NMR δ 8.06 (ddd, 1H, J=9.9, 2.2 and 0.3), 8.13 (ddd, 1H, J=8.6, 2.2 and 0.9), 8.25 (ddd, 1H, J=8.6, 7.0 and 0.3).

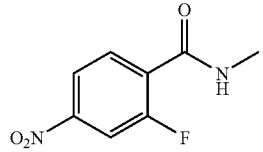

Formula 38

Thionyl chloride (0.15 g, 1.30 mmol) was added slowly to a solution of 2-fluoro-4-nitrobenzoic acid (Formula 37) (0.20 g, 1.10 mmol) in DMF (5 mL) cooled at −5° C. The mixture was stirred for an additional 1 hour at −5° C. Excess methylamine (freshly distilled from its 40% aqueous solution) was added to the reaction medium. The second mixture was stirred for an additional 1 hour. Ethyl acetate (50 mL) was added to the mixture, which was washed with brine (2×50 ml). The organic layer was dried over $MgSO_4$, and concentrated to yield N-Methyl-2-fluoro-4-nitrobenzamide (Formula 38) (0.18 g, 85%) as a yellowish solid. $^1$H NMR (acetone-$d_6$) δ 3.05 (d, 3H, J=4.3), 6.31 (dd, 1H, J=13.5 and 2.1), 6.40 (dd, 1H, J=8.6 and 2.1), 7.64 (dd, 1H, J=8.6 and 8.6).

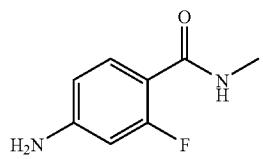

Formula 39

A mixture of N-Methyl-2-fluoro-4-nitrobenzamide (Formula 38) (0.18 g, 0.91 mmol) and iron (0.31 g, 5.60 mmol) in ethyl acetate (5 mL) and acetic acid (5 mL) was refluxed for 1 h. The solid particles were filtered off. The filtrate was washed with water and extracted with ethyl acetate. The organic layer was dried over $MgSO_4$, concentrated and the residue was purified with $SiO_2$ column chromatography (dichloromethane:acetone, 95:5) to give N-Methyl-2-fluoro-4-aminobenzamide (Formula 39) (0.14 g, 92%) as an off-white solid. $^1$H NMR (acetone-$d_6$) δ 2.86 (d, 3H, J=4.3), 5.50 (br s, 2H), 6.37 (dd, 1H, J=14.7 and 2.1), 6.50 (dd, 1H, J=8.6 and 2.1), 7.06 (br s, 1H), 7.68 (dd, 1H, J=8.8 and 8.8).

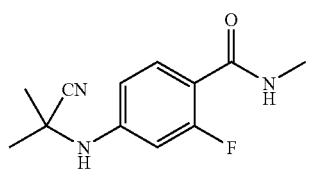

Formula 40

A mixture of N-Methyl-2-fluoro-4-aminobenzamide (Formula 39) (96 mg, 0.57 mmol), acetone cyanohydrin (0.3 mL, 3.14 mmol) and magnesium sulfate (50 mg) was heated to 80° C. and stirred for 12 h. To the medium was added ethyl acetate (25 mL) and then washed with water (2×25 mL). The organic layer was dried over $MgSO_4$ and concentrated and the residue was purified with $SiO_2$ column chromatography (dichloromethane:acetone, 95:5) to give N-Methyl-2-fluoro-4-(1,1-dimethyl-cyanomethyl)-aminobenzamide (Formula 40) (101 mg, 75%) as a white solid. $^1$H NMR δ 1.74 (s, 6H), 2.98 (dd, 3H, J=4.8 and 1.1), 6.58 (dd, 1H, J=14.6 and 2.3), 6.63 (dd, 1H, J=8.7 and 2.3), 6.66 (br s, 1H), 7.94 (dd, 1H, J=8.7 and 8.7).

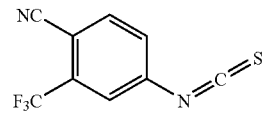

Formula 41

4-Amino-2-trifluoromethylbenzonitrile (2.23 g, 12 mmol) was added portionwise over 15 min into a well-stirred heterogeneous mixture of thiophosgene (1 mL, 13 mmol) in water (22 mL) at room temperature. Stirring was continued for an additional 1 h. The reaction medium was extracted with chloroform (3×15 ml). The combined organic phase was dried over $MgSO_4$ and evaporated to dryness under reduced pressure to yield desired product 4-Isothiocyanato-2-trifluoromethylbenzonitrile (Formula 41) as brownish solid and was used as such for the next step (2.72 g, 11.9 mmol, 99%) $^1$H NMR δ 7.49 (dd, 1H, J=8.3 and 2.1), 7.59 (d, 1H, J=2.1), 7.84 (d, 1H, J=8.3).

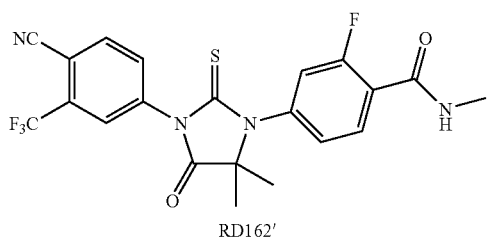

(Formula 42)

RD162'

56-1) RD162'

A mixture of N-Methyl-2-fluoro-4-(1,1-dimethyl-cyanomethyl)-aminobenzamide (Formula 40) (30 mg, 0.13 mmol) and 4-Isothiocyanato-2-trifluoromethylbenzonitrile (Formula 41) (58 mg, 0.26 mmol) in DMF (1 mL) was heated under microwave irradiation at 100° C. for 11 hours. To this mixture was added methanol (20 mL) and aq. 1 N HCl (5 mL). The second mixture was refluxed for 1.5 h. After being cooled to room temperature, the reaction mixture was poured into cold water (50 mL) and extracted with ethyl acetate (50 mL). The organic layer was dried over $MgSO_4$, concentrated and the residue was purified with $SiO_2$ column chromatography (dichloromethane:acetone, 95:5) to give RD162' (Formula 42) (15 mg, 25%) as a colorless crystal. $^1$H NMR δ 1.61 (s, 6H), 3.07 (d, 3H, J=4.1), 6.71 (m, 1H), 7.15 (dd, 1H, J=11.7 and 2.0), 7.24 (dd, 1H, J=8.4 and 2.0), 7.83 (dd, 1H, J=8.2 and 2.1), 7.95 (d, 1H, J=2.1), 7.99 (d, 1H, J=8.2), 8.28 (dd, 1H, J=8.4 and 8.4).

EXAMPLE 57

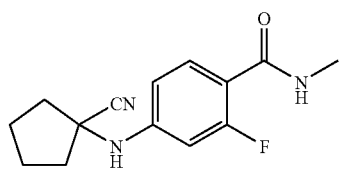

Formula 43

A mixture of N-Methyl-2-fluoro-4-aminobenzamide (Formula 39) (62 mg, 0.37 mmol), cyclopentanone (0.07 mL, 0.74 mmol) and TMSCN (0.1 mL, 0.74 mmol) was heated to 80° C. and stirred for 13 h. To the medium was added ethyl acetate (2×20 mL) and then washed with water (2×20 mL). The organic layer was dried over MgSO₄ and concentrated and the residue was purified with silica gel column chromatography (dichloromethane:acetone, 95:5) to give N-Methyl 2-fluoro-4-(1-cyanocyclopentyl)aminobenzamide (Formula 43) (61 mg, 63%) as a white solid. ¹H NMR δ 7.95 (dd, 1H, J=8.8, 8.8 Hz), 6.65 (br s, 1H), 6.59 (dd, 1H, J=8.8, 2.3 Hz), 6.50 (dd, 1H, J=14.6, 2.3 Hz), 4.60 (br s, 1H), 2.99 (dd, 3H, J=4.8, 1.1 Hz), 2.36-2.45 (m, 2H), 2.10-2.18 (m, 2H), 1.82-1.95 (m, 4H).

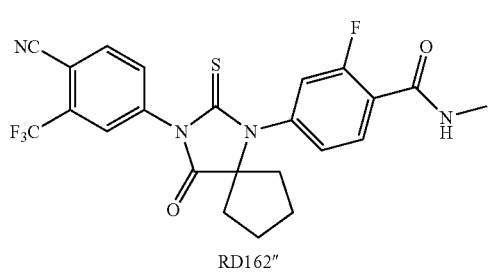

(Formula 44)

RD162″

57-1) RD162″

A mixture of N-Methyl 2-fluoro-4-(1-cyanocyclopentyl)aminobenzamide (Formula 43) (57 mg, 0.22 mmol) and 4-isothiocyanato-2-trifluoromethyl benzonitrile (0.15 g, 0.65 mmol) in DMF (3 mL) was heated under microwave irradiation (open vessel) at 130° C. for 12 hours. To this mixture was added methanol (20 mL) and aq. 1 N HCl (5 mL). The second mixture was refluxed for 1.5 h. After being cooled to room temperature, the reaction mixture was poured into cold water (50 mL) and extracted with ethyl acetate (50 mL). The organic layer was dried over MgSO₄, concentrated and the residue was purified with silica gel column chromatography (dichloromethane:acetone, 95:5) to give 4-(3-(4-Cyano-3-(trifluoromethyl)phenyl)-4-oxo-2-thioxo-1,3-diazaspiro[4.4]nonan-1-yl)-2-fluoro-N-methylbenzamide, RD162″ (Formula 44) (8 mg, 7%) as a pale yellowish solid. ¹H NMR δ 8.28 (dd, 1H, J=8.4, 8.4 Hz), 7.98 (d, 1H, J=8.3 Hz), 7.96 (d, 1H, J=1.8 Hz), 7.84 (dd, 1H, J=8.3, 1.8 Hz), 7.27 (dd, 1H, J=8.4, 1.8 Hz), 7.17 (dd, 1H, J=11.7, 1.8 Hz), 6.67-6.77 (m, 1H), 3.07 (d, 3H, J=4.3 Hz), 2.32-2.41 (m, 2H), 2.13-2.21 (m, 2H), 1.85-1.96 (m, 2H), 1.49-1.59 (m, 2H).

EXAMPLE 58

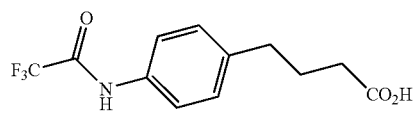

Formula 45

Trifluoroacetic anhydride (0.85 mL, 6.14 mmol) was added to a solution of 4-(4-aminophenyl)butyric acid (0.5 g, 2.79 mmol) in chloroform (10 mL) at 0° C. The mixture was warmed to room temperature and stirred for 3 hours. The mixture was partitioned with chloroform (20 mL) and water (20 mL). The organic layer was dried over MgSO₄, concentrated and the residue was purified with silica gel column chromatography (dichloromethane:acetone, 9:1) to give 4-[4-(2,2,2-Trifluoroacetylamino)phenyl]butanoic acid (Formula 45) (0.53 g, 69%). ¹H NMR δ 7.81 (br s, 1H), 7.48 (d, 2H, J=8.5 Hz), 7.22 (d, 2H, J=8.5 Hz), 2.68 (t, 2H, J=7.5 Hz), 2.38 (t, 2H, J=7.5 Hz), 1.96 (p, 2H, J=7.5 Hz).

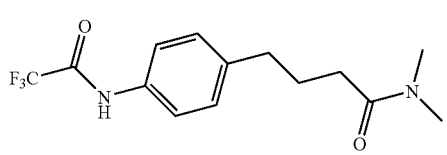

Formula 46

Thionyl chloride (71 mg, 0.60 mmol) was added slowly to a solution of 4-[4-(2,2,2-Trifluoroacetylamino)phenyl]butanoic acid (Formula 45) (0.15 g, 0.55 mmol) in DMF (5 mL) cooled at −5° C. The mixture was stirred for an additional 1 hour at −5° C. Excess dimethylamine (freshly distilled from its 40% aqueous solution) was added to the reaction medium. The second mixture was stirred for an additional 1 hour. Ethyl acetate (50 mL) was added to the mixture, which was washed with brine (2×50 ml). The organic layer was dried over MgSO₄, and concentrated to yield N,N-Dimethyl 4-[4-2,2,2-Trifluoroacetylamino)phenyl]butanamide (Formula 46) (0.17 g, quant.) as a yellowish solid. ¹H NMR δ 9.70 (br s, 1H), 7.55 (d, 2H, J=8.6 Hz), 7.11 (d, 2H, J=8.6 Hz), 2.91 (s, 3H), 2.89 (s, 3H), 2.60 (t, 2H, J=7.7 Hz), 2.27 (t, 2H, J=7.7 Hz), 1.89 (p, 2H, J=7.7 Hz).

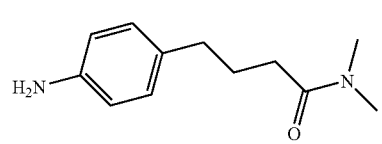

Formula 47

1 N NaOH solution (3 mL) was added to a solution of N,N-Dimethyl 4-[4-(2,2,2-Trifluoroacetylamino)phenyl]butanamide (Formula 46) (0.17 g, 0.55 mmol) in methanol (2 mL) at room temperature. The mixture was stirred for 14 hour. The mixture was partitioned with chloroform (25 mL) and water (25 mL). The organic layer was dried over MgSO₄, and concentrated and the residue was purified with silica gel column chromatography (dichloromethane:acetone, 9:1) to give N, N-Dimethyl 4-(4-aminophenyl)butanamide (Formula 47) (74 mg, 66%) as a white solid. ¹H NMR δ 6.97 (d, 2H, J=8.3 Hz), 6.61 (d, 2H, J=8.3 Hz), 3.56 (br s, 2H), 2.92 (s, 6H), 2.56 (t, 2H, J=7.7 Hz), 2.28 (t, 2H, J=7.7 Hz), 1.91 (p, 2H, J=7.7 Hz).

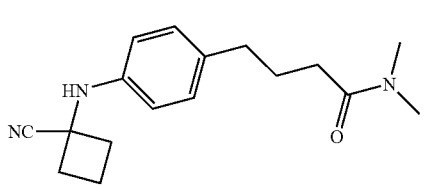

Formula 48

A mixture of N,N-Dimethyl 4-(4-aminophenyl)butanamide (Formula 47) (74 mg, 0.36 mmol), cyclobutanone (54 mg, 0.78 mmol) and TMSCN (77 mg, 0.78 mmol) was heated to 80° C. and stirred for 15 h. To the medium was added ethyl acetate (2×20 mL) and then washed with water (2×20 mL).

The organic layer was dried over MgSO$_4$ and concentrated and the residue was purified with silica gel column chromatography (dichloromethane:acetone, 9:1) to give N,N-Dimethyl 4-[4-(1-cyanocyclobutylamino)phenyl]butanamide (Formula 48) (58 mg, 57%) as a white solid. $^1$H NMR δ 7.07 (d, 2H, J=8.5 Hz), 6.59 (d, 2H, J=8.5 Hz), 3.94 (br s, 1H), 2.94 (s, 3H), 2.93 (s, 3H), 2.75-2.83 (m, 2H), 2.60 (t, 2H, J=7.6 Hz), 2.33-2.42 (m, 2H), 2.30 (t, 2H, J=7.6 Hz), 2.11-2.28 (m, 2H), 1.93 (p, 2H, J=7.6 Hz).

Formula 49

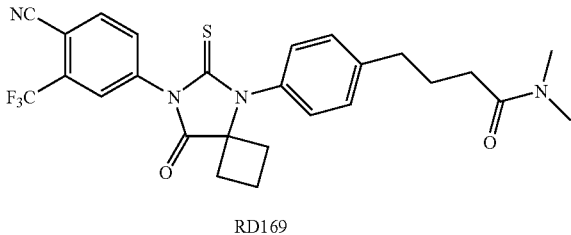

RD169

A mixture of N,N-Dimethyl 4-[4-(1-cyanocyclobutylamino)phenyl]butanamide (Formula 48) (58 mg, 0.20 mmol) and 4-isothiocyanato-2-trifluoromethyl benzonitrile (74 mg, 0.32 mmol) in DMF (3 mL) was heated under reflux for 2 hours. To this mixture was added methanol (20 mL) and aq. 1 N HCl (5 mL). The second mixture was refluxed for 1.5 h. After being cooled to room temperature, the reaction mixture was poured into cold water (50 mL) and extracted with ethyl acetate (50 mL). The organic layer was dried over MgSO$_4$, concentrated and the residue was purified with silica gel column chromatography (dichloromethane:acetone, 95:5) to give 4-(4-(7-(4-Cyano-3-trifluoromethyl)phenyl)-8-oxo-6-thioxo-5,7-diazaspiro[3.4]octan-5-yl)phenyl)-N,N-dimethylbutanamide, RD169 (Formula 49) (44 mg, 42%) as a pale yellowish solid. $^1$H NMR δ 7.98 (s, 1H), 7.97 (d, 1H, J=8.2 Hz), 7.86 (d, 1H, J=8.2 Hz), 7.42 (d, 2H, J=8.3 Hz), 7.22 (d, 2H, J=8.3 Hz), 2.99 (s, 3H), 2.96 (s, 3H), 2.78 (t, 2H, J=7.5 Hz), 2.62-2.70 (m, 2H), 2.52-2.63 (m, 2H), 2.40 (t, 2H, J=7.5 Hz), 2.15-2.30 (m, 1H), 2.04 (p, 2H, J=7.5 Hz), 1.62-1.73 (m, 1H);

EXAMPLE 59

Formula 50

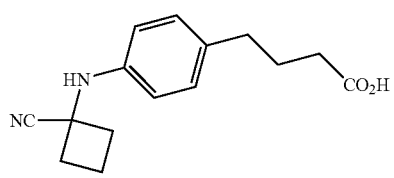

A mixture of 4-(4-aminophenyl)butyric acid (0.20 g, 1.12 mmol), cyclobutanone (0.17 mL, 2.23 mmol) and TMSCN (0.30 mL, 2.23 mmol) was heated to 80° C. and stirred for 13 h. To the medium was added ethyl acetate (2×30 mL) and then washed with water (2×30 mL). The organic layer was dried over MgSO$_4$ and concentrated and the residue was purified with silica gel column chromatography (dichloromethane:acetone, 9:1) to give 4-[4-(1-Cyanocyclobutylamino)phenyl]butanoic acid (Formula 50) (0.21 g, 74%) as a yellowish solid. $^1$H NMR δ 7.06 (d, 2H, J=8.6 Hz), 6.59 (d, 2H, J=8.6 Hz), 2.75-2.83 (m, 2H), 2.59 (t, 2H, J=7.5 Hz), 2.37 (t, 2H, J=7.5 Hz), 2.33-2.42 (m, 2H), 2.11-2.28 (m, 2H), 1.92 (p, 2H, J=7.5 Hz).

Formula 51

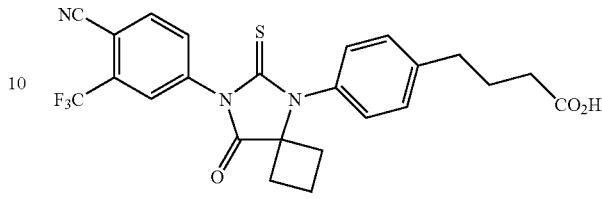

A mixture of 4-[4-(1-Cyanocyclobutylamino)phenyl]butanoic acid (Formula 50) (0.21 g, 0.83 mmol) and 4-isothiocyanato-2-trifluoro benzonitrile (0.25 g, 1.08 mmol) in toluene (10 mL) was heated under reflux for 1 hours. To this mixture was added aq. 1 N HCl (5 mL). The second mixture was refluxed for 1.5 h. After being cooled to room temperature, the reaction mixture was poured into cold water (50 mL) and extracted with ethyl acetate (50 mL). The organic layer was dried over MgSO$_4$, concentrated and the residue was purified with silica gel column chromatography (dichloromethane:acetone, 95:5) to give 4-(4-(7-(4-Cyano-3-(trifluoromethyl)phenyl)-8-oxo-6-thioxo-5,7-diazaspiro[3.4]octan-5-yl)phenyl)butanoic acid, RD141 (Formula 51) (60 mg, 15%). $^1$H NMR δ 7.98 (d, 1H, J=1.8 Hz), 7.97 (d, 1H, J=8.3 Hz), 7.86 (dd, 1H, J=8.3, 1.8 Hz), 7.42 (d, 2H, J=8.5 Hz), 7.24 (d, 2H, J=8.5 Hz), 2.79 (t, 2H, J=7.5 Hz), 2.62-2.68 (m, 2H), 2.51-2.59 (m, 2H), 2.47 (t, 2H, J=7.5 Hz), 2.14-2.26 (m, 1H), 2.06 (p, 2H, J=7.5 Hz), 1.60-1.70 (m, 1H).

EXAMPLE 60

Formula 52

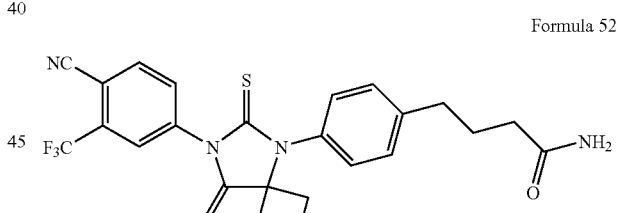

RD130

To a solution of 4-(4-(7-(4-Cyano-3-(trifluoromethyl)phenyl)-8-oxo-6-thioxo-5,7-diazaspiro[3.4]octan-5-yl)phenyl)butanoic acid, RD141 (Formula 51) (60 mg, 0.12 mmol) in DMF (3 mL) was added thionyl chloride (0.01 mL, 0.15 mmol) at 0° C. The mixture was stirred at 0° C. for 1 hour. Then ammonia was bubbled into the mixture. The mixture was partitioned with ethyl acetate (25 mL) and water (25 mL). The organic layer was dried over MgSO$_4$, concentrated and chromatographed (dichloromethane:acetone, 70:30) to yield 4-(4-(7-(4-Cyano-3-(fluoromethyl)phenyl)-8-oxo-6-thioxo-5,7-diazaspiro[3.4]octan-5-yl)phenyl)butanamide, RD130 (Formula 52) (37 mg, 61%) as a white powder. $^1$H NMR δ 7.97 (d, 1H, J=1.8 Hz), 7.95 (d, 1H, J=8.3 Hz), 7.85 (dd, 1H, J=8.3 Hz), 7.39 (d, 2H, J=8.3 Hz), 7.22 (d, 2H, J=8.3 Hz), 5.59 (br s, 2H), 2.77 (t, 2H, J=7.5 Hz), 2.62-2.68 (m, 2H), 2.51-2.59 (m, 2H), 2.31 (t, 2H, J=7.5 Hz), 2.16-2.25 (m, 1H), 2.05 (p, 2H, J=7.5 Hz), 1.57-1.70 (m, 1H).

EXAMPLE 61

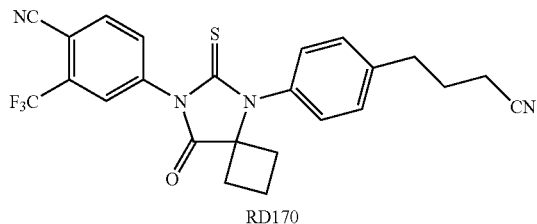

Formula 53

RD170

A solution of DMSO (0.01 mL, 0.12 mmol) in dry dichloromethane (1 mL) was added to a stirred solution of oxalyl chloride (0.01 mL, 0.09 mmol) in dry dichloromethane (2 mL) at −78° C. After 15 min, a dichloromethane solution of 4-(4-(7-(4-Cyano-3-(trifluoromethyl)phenyl)-8-oxo-6-thioxo-5,7-diazaspiro[3.4]octan-5-yl)phenyl)butanamide, RD130 (Formula 52) (35 mg, 0.07 mmol) was added to the reaction mixture. Stirring was continued for 20 min at −78° C., and then triethylamine (0.03 mL, 0.22 mmol) was added. After 30 min at −78° C., the reaction mixture was warmed to room temperature and then reaction was quenched with saturated aq. NH$_4$Cl solution. The reaction mixture was diluted with dichloromethane, and extracted with dichloromethane. The organic layer was dried over MgSO$_4$, concentrated and chromatographed (dichloromethane:acetone, 95:5) to yield 4-(5 -(4-(3-Cyanopropyl)phenyl)-8-oxo-6-thioxo-5,7-diazaspiro[3.4]octan-7-yl)-2-trifluoromethyl)benzonitrile, RD170 (Formula 53) (29 mg, 87%) as a viscous oil. $^1$H NMR δ 7.98 (d, 1H, J=1.8 Hz), 7.98 (d, 1H, J=8.3 Hz), 7.86 (dd, 1H, J=8.3, 1.8 Hz), 7.43 (d, 2H, J=8.4 Hz), 7.27 (d, 2H, J=8.4 Hz), 2.90 (t, 2H, J=7.3 Hz), 2.63-2.73 (m, 2H), 2.52-2.62 (m, 2H), 2.42 (t, 2H, J=7.3 Hz), 2.18-2.30 (m, 1H), 2.07 (p, 2H, J=7.3 Hz), 1.63-1.73 (m, 1H).

One skilled in the art could modify and/or combine the syntheses described herein to make other diarylhydantoin compounds.

Inventive compounds also include those with the following formulas.

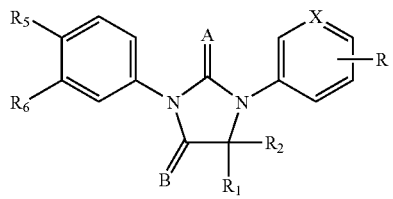

Where R is selected from hydrogen, aryl, substituted aryl, alkyl, substituted alkyl, alkenyl, substituted alkenyl, alkynyl, substituted alkynyl, halogenated alkyl, halogenated alkenyl, halogenated akynyl, arylalkyl, arylalkenyl, arylalkynyl, heterocylic aromatic or non-aromatic, substituted heterocyclic aromatic or non-aromatic, cycloalkyl, substituted cycloalkyl, halogen, SO$_2$R$_{11}$, NR$_{11}$R$_{12}$, NR$_{12}$(CO)OR$_{11}$, NH(CO) NR$_{11}$R$_{12}$, NR$_{12}$(CO)R$_{11}$, O(CO)R$_{11}$, O(CO)OR$_{11}$, O(CS) R$_{11}$, NR$_{12}$(CS)R$_{11}$, NH(CS)NR$_{11}$R$_{12}$, NR$_{12}$(CS)OR$_{11}$.

R$_1$ and R$_2$ are independently selected from hydrogen, aryl, alkyl, substituted alkyl, alkenyl, substituted alkenyl, alkynyl, substituted alkynyl, halogenated alkyl, halogenated alkenyl, halogenated akynyl, arylalkyl, arylalkenyl, arylalkynyl, heterocylic aromatic or non-aromatic, substituted heterocyclic aromatic or non-aromatic, cycloalkyl, substituted cycloalkyl.

R$_1$ and R$_2$ can be connected to form a cycle which can be heterocyclic, substituted heterocyclic, cycloakyl, substituted cycloalkyl.

R$_3$ is selected from aryl, substituted aryl, alkyl, substituted alkyl, alkenyl, substituted alkenyl, alkynyl, substituted alkynyl, arylalkyl, arylalkenyl, arylalkynyl, heterocyclic aromatic or non-aromatic, substituted heterocyclic aromatic or non-aromatic, cycloalkyl, substituted-cycloalkyl, SO$_2$R$_{11}$, R$_{12}$, (CO)OR$_{11}$, (CO)NR$_{11}$R$_{12}$, (CO)R$_{11}$, (CS)R$_{11}$, (CS)R$_{11}$, (CS) NR$_{11}$R$_{12}$, (CS)OR$_{11}$.

R$_5$ is CN or NO$_2$ or SO$_2$R$_{11}$

R$_6$ is CF$_3$, alkyl, substituted alkyl, alkenyl, substituted alkenyl, alkynyl, substituted alkynyl, halogenated alkyl, halogenated alkenyl, halogenated akynyl, halogen.

A is sulfur atom (S) or oxygen atom (O).

B is O or S or NR$_3$

X is carbon or nitrogen and can be at any position in the ring.

R$_{11}$, and R$_{12}$ are independently selected from hydrogen, aryl, aralkyl, substituted aralkyl, alkyl, substituted alkyl, alkenyl, substituted alkenyl, alkynyl, substituted alkynyl, halogenated alkyl, halogenated alkenyl, halogenated akynyl, arylalkyl, arylalkenyl, arylalkynyl, heterocyclic aromatic or non-aromatic, substituted heterocyclic aromatic or non-aromatic, cyclolakyl, substituted cycloalkyl.

R$_{11}$, and R$_{12}$ can be connected to form a cycle which can be heterocyclic aromatic or non-aromatic, substituted heterocyclic aromatic, cycloakyl, substituted cycloalkyl.

Pharmacological Examination of the Compounds

Compounds for which synthetic routes are described above were identified through screening on hormone refractory prostate cancer cells for antagonistic and agonistic activities against AR utilizing screening procedures similar to those in PCT applications US04/42221 and US05/05529, which are hereby incorporated by reference. A number of compounds exhibited potent antagonistic activities with minimal agonistic activities for over expressed AR in hormone refractory prostate cancer.

In Vitro Biological Assay

Effect of Compounds on AR by a Reporter Assay

Figure 1:
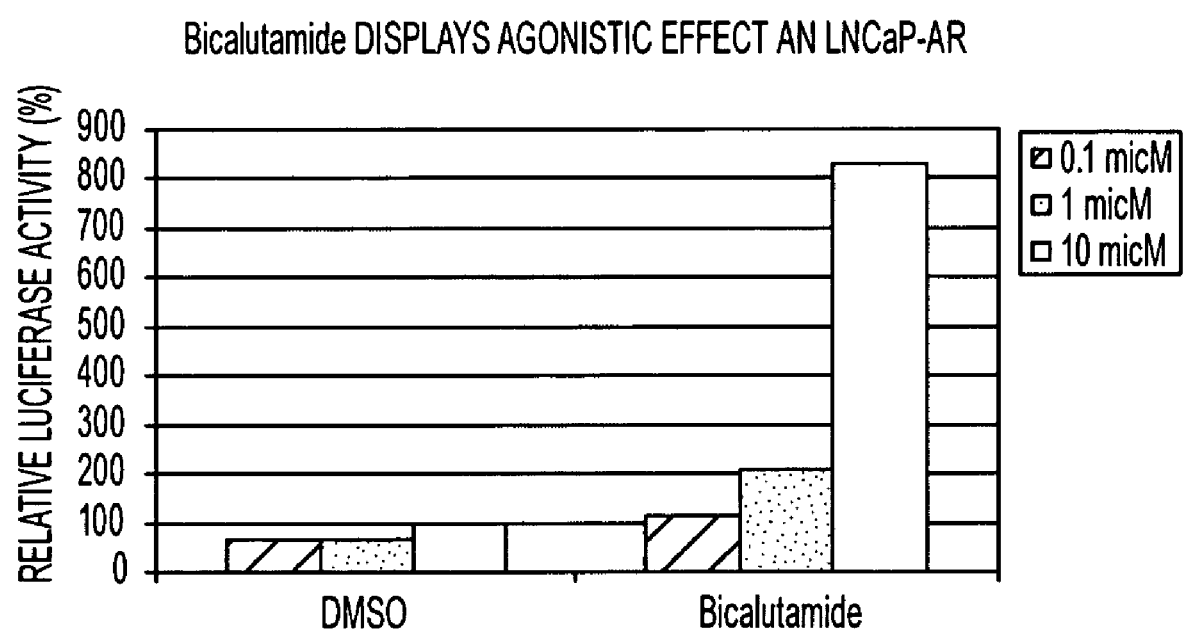
FIG. 1 is a graph depicting that bicalutamide displays an agonistic effect on LNCaP-AR. Agonistic activities of bicalutamide in AR-overexpressed hormone refractory prostate cancer. LNCaP cells with overexpressed AR were treated with increasing concentrations of DMSO as vehicle or bicalutamide in the absence of R1881. Activities of AR response reporter were measured.
Figure 2:
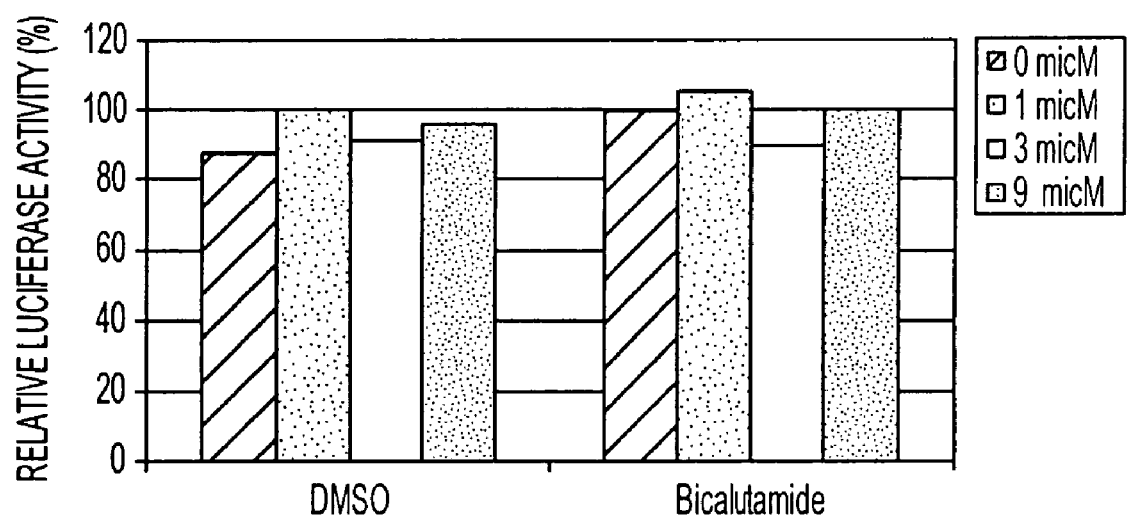
FIG. 2 is a graph depicting an antagonistic assay of bicalutamide on LNCaP-AR. Agonistic activities of bicalutamide in hormone sensitive prostate cancer. LNCaP cells were treated with increasing concentrations of DMSO as vehicle or bicalutamide in the absence of R1881. Activities of AR response reporter were measured.

The compounds were subjected to tests using an artificial AR response reporter system in a hormone refractory prostate cancer cell line. In this system, the prostate cancer LNCaP cells were engineered to stably express about 5-fold higher level of AR than endogenous level. The exogenous AR has similar properties to endogenous AR in that both are stabilized by a synthetic androgen R1881. The AR-over expressed cells were also engineered to stably incorporate an AR response reporter and the reporter activity of these cells shows features of hormone refractory prostate cancer. It responds to low concentration of a synthetic androgen R1881, is inhibited only by high concentrations of bicalutamide (see Table 1), and displays agonistic activity with bicalutamide (FIG. 1 and Table 2). Consistent with published data, bicalutamide inhibited AR response reporter and did not have agonistic activity in hormone sensitive prostate cancer cells (FIG. 2).

We examined the antagonistic activity of the compounds for which the synthesis is described above in the presence of 100 pM of R1881. Engineered LNCaP cells (LNCaP-AR, also abbreviated LN-AR) were maintained in Iscove's medium containing 10% fetal bovine serum (FBS). Two days prior to drug treatment, the cells were grown in Iscove's medium containing 10% charcoal-stripped FBS (CS-FBS) to deprive of androgen. The cells were split and grown in Iscove's medium containing 10% CS-FBS with 100 pM of R1881 and increasing concentrations of test compounds. After two days of incubation, reporter activities were assayed.

Table 1 lists the IC50 of these compounds to inhibit AR in hormone refractory prostate cancer. The control substance bicalutamide has an IC50 of 889 nM. Most of the compounds identified (diarylthiohydantoins) have IC50s between 100 to 200 nM in inhibiting AR in hormone refractory prostate cancer. In contrast, antiandrogenic compounds listed as examples in U.S. Pat. No. 5,705,654, such as examples 30-2, 30-3, 31-2, 31-3, and 24-3 (RD73-RD77) have no inhibitory activities on AR in this system.

TABLE 1

Antagonistic activities against AR in hormone refractory prostate cancer, measured by an AR response reporter and by endogenous PSA expression.

| Example | Name | IC50 (nM) Reporter | IC50 (nM) PSA |
|---|---|---|---|
| Bicalutamide Comparative | N-[4-cyano-3-(trifluoromethyl)phenyl]-3-[(4-fluorophenyl)sulfonyl]-2-hydroxy-2-methylpropanamide | 889 | >1000 |
| 29 Comparative | 4-[3-(4-hydroxybutyl)-4,4-dimethyl-5-oxo-2-thioxoimidazolidin-1-yl]-2-trifluoromethylbenzonitrile | No(*) | No |
| 6-2 (6b) [RD10] | 4-[3-phenyl-4,4-dimethyl-5-oxo-2-thioxoimidazolidin-1-yl]-2-trifluoromethylbenzonitrile | 149 | n/a(**) |
| 5-3b (5c) [RD7] | 4-[3-(4-methylphenyl)-4,4-dimethyl-5-oxo-2-thioxoimidazolidin-1-yl]-2-trifluoromethyl-benzonitrile | 125 | 132 |
| 3-3 (3c) [RD8] | 4-[3-(4-hydroxyphenyl)-4,4-dimethyl-5-oxo-2-thioxoimidazolidin-1-yl]-2-trifluoromethylbenzonitrile | 137 | 122 |
| 2-4 (2d) [RD9] | 4-[3-(4-aminophenyl)-4,4-dimethyl-5-oxo-2-thioxoimidazolidin-1-yl]-2-trifluoromethylbenzonitrile | 273 | n/a |
| 4 (4a) [RD13] | Chloroacetic acid 4-[3-(4-cyano-3-trifluoromethylphenyl)-5,5-dimethyl-4-oxo-2-thioxoimidazolidin-1-yl]phenyl ester | 131 | n/a |
| 8-2 (8b) [RD35] | 4-(4-Oxo-2-thioxo-1-(4-methylphenyl)-1,3-diazaspiro[4.4]non-3-yl)-2-trifluoromethylbenzonitrile | 147 | n/a |
| 7-3b (7c) [RD37] | 4-(8-oxo-6-thioxo-5-(4-methylphenyl)-5,7-diazaspiro[3.4]oct-7-yl)-2-trifluoromethylbenzonitrile | 124 | 128 |
| 9-3 (9c) [RD48] | 4-(4-Oxo-2-thioxo-1-(4-methylphenyl)-1,3-diazaspiro[4.5]dec-3-yl)-2-trifluoromethylbenzonitrile | 194 | n/a |
| 10-3 (10c) [RD49] | 4-(4-oxo-2-thioxo-1-(4-methylphenyl)-1,3-diazaspiro[4.5]undec-3-yl)-2-trifluoromethylbenzonitrile | 232 | n/a |
| 28 Comparative (28a) [RD52] | 4-(8-methyl-4-oxo-2-thioxo-1,3,8-triazaspiro[4.5]dec-3-yl)-2-trifluoromethylbenzonitrile | No | n/a |
| 27-3 (27c) [RD53] | 4-(8-methyl-4-oxo-2-thioxo-1-(4-methylphenyl)-1,3,8-triazaspiro[4.5]dec-3-yl)-2-trifluoromethylbenzonitrile | 638 | n/a |
| 26 (26a) [RD54] | 4-[1-(4-cyanophenyl)-4-oxo-2-thioxo-1,3-diazaspiro[4.4]non-3-yl]-2-trifluoromethylbenzonitrile | 469 | n/a |
| 25 (25a) [RD55] | 4-[1-(4-nitrophenyl)-4-oxo-2-thioxo-1,3-diazaspiro[4.4]non-3-yl]-2-trifluoromethylbenzonitrile | 498 | n/a |
| 12-2 (12b) [RD57] | 4-(8-oxo-6-thioxo-5-(4-biphenyl)-5,7-diazaspiro[3.4]oct-7-yl)-2-trifluoromethylbenzonitrile | 283 | n/a |
| 11-2 (11b) [RD58] | 4-(8-oxo-6-thioxo-5-(4-hydroxyphenyl)-5,7-diazaspiro[3.4]oct-7-yl)-2-trifluoromethylbenzonitrile | 162 | n/a |
| 17 (17a) [RD59] | 4-[3-(4-hydroxyphenyl)-4,4-dimethyl-2,5-dithioxoimidazolidin-1-yl]-2-trifluoromethylbenzonitrile | 278 | 287 |
| 18 (18a) [RD60] | 4-[3-(4-hydroxyphenyl)-4,4-dimethyl-2,5-dioxoimidazolidin-1-yl]-2-trifluoromethylbenzonitrile | 369 | 511 |
| 22-2 (22b) [RD65] | 2-[3-(4-cyano-3-trifluoromethylphenyl)-5,5-dimethyl-4-oxo-2-thioxoimidazolidin-1-yl]benzoic acid | 523 | >500 |
| 20-2 (20b) [RD66] | 4-(4,4-dimethyl-5-oxo-2-thioxo-3-(4-trifluoromethylphenyl)imidazolidin-1-yl)-2-trifluoromethylbenzonitrile | 143 | 144 |
| 21-2 (21b) [RD67] | 4-(4,4-bischloromethyl-5-oxo-2-thioxo-3-(4-methylphenyl)imidazolidin-1-yl)-2-trifluoromethylbenzonitrile | 521 | >500 |
| 19-2 (19b) [RD68] | 4-(4-fluoromethyl-4-methyl-5-oxo-2-thioxo-3-(4-methylphenyl)imidazolidin-1-yl)-2-trifluoromethylbenzonitrile | 126 | 129 |

TABLE 1-continued

Antagonistic activities against AR in hormone refractory prostate cancer, measured by an AR response reporter and by endogenous PSA expression.

| Example | Name | IC50 (nM) Reporter | IC50 (nM) PSA |
|---|---|---|---|
| 23-2 (23b) [RD71] | 4-(8-oxo-6-thioxo-5-(2-methylphenyl)-5,7-diazaspiro[3.4]oct-7-yl)-2-trifluoromethylbenzonitrile | 258 | 232 |
| 30-2 Comparative (30b) [RD73] | 4-(5-methyl-8-oxo-6-thioxo-5,7-diazaspiro[3.4]oct-7-yl)-2-trifluoromethylenzonitrile | No | No |
| 30-3 Comparative (30c) [RD74] | 4-(5-methyl-6,8-dioxo-5,7-diazaspiro[3.4]oct-7-yl)-2-trifluoromethylbenzonitrile | No | No |
| 31-2 Comparative (31b) [RD75] | 4-(1-methyl-4-oxo-2-thioxo-1,3-diazaspiro[4.4]non-3-yl)-2-trifluoromethylbenzonitrile | No | No |
| 31-3 Comparative (31c) [RD76] | 4-(1-methyl-2,4-dioxo-1,3-diaza-spiro[4.4]non-3-yl)-2-trifluoromethylbenzonitrile | No | No |
| 24-3 Comparative (24c) [RD77] | 4-(4-oxo-2-thioxo-1,3-diazaspiro[4.4]non-3-yl)-2-trifluoromethylbenzonitrile | No | No |
| 15-2 (15b) [RD82] | 4-[4,4-dimethyl-3-(4-pyridin-2-yl)-5-oxo-2-thioxoimidazolidin-1-yl]-2-trifluoromethylbenzonitrile | 723 | n/a |
| 14-2 (14b) [RD83] | 4-[4,4-dimethyl-3-(4-methylpyridin-2-yl)-5-oxo-2-thioxoimidazolidin-1-yl]-2-trifluoromethylbenzonitrile | 457 | n/a |
| 16-2 Comparative (16b) [RD84] | 4-[5-(5-methyl-2H-pyrazol-3-yl)-8-oxo-6-thioxo-5,7-diaza-spiro[3.4]oct-7-yl]-2-trifluoromethyl-benzonitrile | >1000 | n/a |
| 13-2 (12b) [RD85] | 4-(8-oxo-6-thioxo-5-(4-biphenyl)-5,7-diazaspiro[3.4]oct-7-yl)-2-trifluoromethylbenzonitrile | >1000 | n/a |
| 32 (32a) [RD90] | 4-(8-methylimino-6-thioxo-5-p-tolyl-5,7-diaza-spiro[3.4]oct-7-yl)-2-trifluoromethyl-benzonitrile | 222 | 421 |
| 33 (33a) [RD91] | 1-[3-(4-cyano-3-trifluoromethyl-phenyl)-5,5-dimethyl-2-thioxo-1-p-tolyl-imidazolidin-4-ylidene]-3-ethyl-thiourea | 157 | 239 |
| 34 (34a) [RD92] | 1-[7-(4-cyano-3-trifluoromethyl-phenyl)-6-thioxo-5-p-tolyl-5,7-diaza-spiro[3.4]oct-8-ylidene]-3-phenyl-thiourea | 176 | 276 |
| 35 (35a) [RD93] | 1-(4-Cyano-3-trifluoromethyl-phenyl)-3-[7-(4-cyano-3-trifluoromethyl-phenyl)-6-thioxo-5-p-tolyl-5,7-diaza-spiro[3.4]oct-8-ylidene]-thiourea | 144 | 158 |
| 36-2 (36b) [RD110] | 4-[8-(4-hydroxymethyl-phenyl)-5-oxo-7-thioxo-6-aza-spiro[3.4]oct-6-yl]-2-trifluoromethyl-benzonitrile | 311 | 337 |
| 37 (37a) [RD114] | 4-[5-(4-formylphenyl)-8-oxo-6-thioxo-5,7-diazaspiro[3.4]oct-7-yl]-2-trifluoromethyl-benzonitrile | n/a | 263 |
| 38 (38a) [RD116] | 4-{5-[4-(1-hydroxyethyl)-phenyl]-8-oxo-6-thioxo-5,7-diazaspiro[3.4]oct-7-yl}-2-trifluoromethyl-benzonitrile | n/a | 187 |
| 39 (39a) [RD117] | 3-{4-[7-(4-cyano-3-trifluoromethylphenyl)-8-oxo-6-thioxo-5,7-diazaspiro[3.4]oct-5-yl]-phenyl}-acrylic acid ethyl ester | n/a | 197 |
| 40 (40a) [RD120] | 4-{5-[4-(3-hydroxypropenyl)-phenyl]-8-oxo-6-thioxo-5,7-diazaspiro[3.4]oct-7-yl}-2-trifluoromethylbenzonitrile | n/a | 114 |
| 41-2 (41b) [RD128] | 3-{4-[7-(4-cyano-3-trifluoromethylphenyl)-8-oxo-6-thioxo-5,7-diazaspiro[3.4]oct-5-yl]-phenyl}-propionic acid methyl ester | No | n/a |
| 41-4 (41d) [RD133] | 3-{4-[7-(4-cyano-3-trifluoromethylphenyl)-8-oxo-6-thioxo-5,7-diaza-spiro[3.4]oct-5-yl]-phenyl}-propionamide | 224 | n/a |
| 41-5 (41e) [RD134] | 3-{4-[7-(4-Cyano-3-trifluoromethylphenyl)-8-oxo-6-thioxo-5,7-diaza-spiro[3.4]oct-5-yl]-phenyl}-N-methyl-propionamide | 234 | n/a |
| 41-6 (41f) [RD135] | 3-{4-[7-(4-cyano-3-trifluoromethylphenyl)-8-oxo-6-thioxo-5,7-diaza-spiro[3.4]oct-5-yl]-phenyl}-N-(2-hydroxyethyl)-propionamide | 732 | n/a |
| 42-2 (42b) [RD129] | 4-{4-[7-(4-cyano-3-trifluoromethylphenyl)-8-oxo-6-thioxo-5,7-diazaspiro[3.4]oct-5-yl]-phenyl}-butyric acid methyl ester | 432 | n/a |
| 42-4 (42d) [RD130] | 4-{4-[7-(4-Cyano-3-trifluoromethylphenyl)-8-oxo-6-thioxo-5,7-diaza-spiro[3.4]oct-5-yl]-phenyl}-butyramide | 112 | n/a |
| 42-5 (42e) [RD131] | 4-{4-[7-(4-Cyano-3-trifluoromethylphenyl)-8-oxo-6-thioxo-5,7-diaza-spiro[3.4]oct-5-yl]-phenyl}-N-methyl-butyramide | 92 | n/a |

TABLE 1-continued

Antagonistic activities against AR in hormone refractory prostate cancer, measured by an AR response reporter and by endogenous PSA expression.

| Example | Name | IC50 (nM) Reporter | IC50 (nM) PSA |
|---|---|---|---|
| 43-4 (43e) [RD137] | 4-[8-Oxo-5-(4-piperazin-1-yl-phenyl)-6-thioxo-5,7-diazaspiro[3.4]oct-7-yl]-2-trifluoromethylbenzonitrile | 718 | n/a |
| 43-5 (43f) [RD138] | 4-{5-[4-(4-methanesulfonylpiperazin-1-yl)-phenyl]-8-oxo-6-thioxo-5,7-diazaspiro[3.4]oct-7-yl}-2-trifluoromethylbenzonitrile | 138 | n/a |
| 44-2 (44b) [RD119] | 44-2) 3-{4-[7-(4-Cyano-3-trifluoromethyl-phenyl)-8-oxo-6-thioxo-5,7-diaza-spiro[3.4]oct-5-yl]-phenyl}-acrylamide, | | 113 |

(*)No: the compound did not inhibit AR response reporter;
(**)n/a: the compound was not examined in this assay.

One previously unrecognized property of AR overexpression in hormone refractory prostate cancer is its ability to switch antagonists to agonists. Therefore, only those compounds with minimal or no agonistic activities are qualified to be anti-androgens for this disease. To determine agonistic activities of different compounds, we examined their stimulating activities on AR using the AR response reporter as the measure in the LN-AR system in the absence of R1881. Table 2 lists the agonistic activities of different compounds. Consistent with previous results, bicalutamide activated AR in hormone refractory prostate cancer. The diarylthiohydantoin derivatives such as examples 7-3b (RD37), 33 (RD91), 34 (RD92), and 35 (RD93) have no agonistic activity. In contrast, RD59063, and other anti-androgenic compounds listed as examples in U.S. Pat. No. 5,705,654, such as examples 30-2, 30-3, 31-2, 31-3, and 24-3 (RD73-RD77) strongly activated AR in hormone refractory prostate cancer.

TABLE 2

Agonistic activities of selective test substances on AR response reporter in hormone refractory prostate cancer

| | | Fold induction by increasing concentrations of compounds | | |
|---|---|---|---|---|
| Example | Name | 0.1 µM | 1 µM | 10 µM |
| DMSO | Dimethyl sulfoxide | 1.00(*) | 1.00 | 1.00 |
| R1881 | methyltrienolone | 44.33 | n/a(**) | n/a |
| Bicalutamide | N-[4-cyano-3-(trifluoromethyl)phenyl]-3-[(4-fluorophenyl)sulfonyl]-2-hydroxy-2-methylpropanamide | 1.08 | 3.04 | 10.40 |
| 29 Comp. | 4-[3-(4-hydroxybutyl)-4,4-dimethyl-5-oxo-2-thioxoimidazolidin-1-yl]-2-trifluoromethylbenzonitrile | 10.99 | 20.84 | 34.62 |
| 7-3b (7c) [RD37] | 4-(8-oxo-6-thioxo-5-(4-methylphenyl)-5,7-diazaspiro[3.4]oct-7-yl)-2-trifluoromethylbenzonitrile | 0.87 | 1.19 | 0.89 |
| 33 (33a) [RD91] | 1-[3-(4-cyano-3-trifluoromethyl-phenyl)-5,5-dimethyl-2-thioxo-1-p-tolyl-imidazolidin-4-ylidene]-3-ethyl-thiourea | 1.30 | 1.18 | 1.28 |
| 34 (34a) [RD92] | 1-[7-(4-cyano-3-trifluoromethyl-phenyl)-6-thioxo-5-p-tolyl-5,7-diaza-spiro[3.4]oct-8-ylidene]-3-phenyl-thiourea | 1.19 | 1.41 | 1.17 |
| 35 (35a) [RD93] | 1-(4-Cyano-3-trifluoromethyl-phenyl)-3-[7-(4-cyano-3-trifluoromethyl-phenyl)-6-thioxo-5-p-tolyl-5,7-diaza-spiro[3.4]oct-8-ylidene]-thiourea | 1.26 | 1.10 | 1.30 |
| 30-2 Comp. (30b) [RD73] | 4-(5-methyl-8-oxo-6-thioxo-5,7-diazaspiro[3.4]oct-7-yl)-2-trifluoromethylenzonitrile | 14.88 | 19.41 | 35.22 |
| 30-3 Comp. (30c) [RD74] | 4-(5-methyl-6,8-dioxo-5,7-diazaspiro[3.4]oct-7-yl)-2-trifluoromethylbenzonitrile | 11.39 | 14.26 | 30.63 |
| 31-2 Comp. (31b) [RD76] | 4-(1-methyl-4-oxo-2-thioxo-1,3-diazaspiro[4.4]non-3-yl)-2-trifluoromethylbenzonitrile | 17.03 | 16.63 | 33.77 |

TABLE 2-continued

Agonistic activities of selective test substances on AR response reporter in hormone refractory prostate cancer

| Example | Name | Fold induction by increasing concentrations of compounds | | |
|---|---|---|---|---|
| | | 0.1 µM | 1 µM | 10 µM |
| 31-3 Comp. (31c) [RD76] | 4-(1-methyl-2,4-dioxo-1,3-diaza-spiro[4.4]non-3-yl)-2-trifluoromethylbenzonitrile | 11.99 | 19.77 | 38.95 |
| 24-3 Comp. (24c) [RD77] | 4-(4-oxo-2-thioxo-1,3-diazaspiro[4.4]non-3-yl)-2-trifluoromethylbenzonitrile | 14.88 | 22.48 | 37.09 |

(*)Fold induction: activities induced by a specific test substance over activities in DMSO vehicle;
(**)n/a: the compound was not examined in this assay.

To examine the specificity of AR inhibitors, selective compounds were tested in LNCaP cells with an over expression of glucocorticoid receptor (GR), the closest member of AR in the nuclear receptor family. These cells also carry a GR response reporter and the reporter activity was induced by dexamethasone, a GR agonist and the induction was blocked by RU486, a GR inhibitor. Example 7-3b (RD37) (4-(8-oxo-6-thioxo-5-(4-methylphenyl)-5,7-diazaspiro[3.4]oct-7-yl)-2-trifluoromethyl benzonitrile) had no effect on GR in this system.

Effect of Compounds on AR by Measuring Secreted Levels of Prostate Specific Antigen (PSA)

It is well established that PSA levels are indicators of AR activities in prostate cancer. To examine if the compounds affect AR function in a physiological environment, we determined secreted levels of endogenous PSA induced by R1881 in the AR-overexpressed LNCaP cells (LNCaP-AR, also abbreviated LN-AR). The LNCaP-AR cells are a line of lymph node carcinoma of prostate cells transduced with a plasmid that makes express androgen receptors. LNCaP-AR cells were maintained in Iscove's medium containing 10% FBS. Two days prior to drug treatment, the cells were grown in Iscove's medium containing 10% CS-FBS to deprive of androgens. The cells were split and grown in Iscove's medium containing 10% CS-FBS with appropriate concentrations of R1881 and the test compounds. After four days incubation, secreted PSA levels were assayed using PSA ELISA kits (American Qualex, San Clemente, Calif.)

The secreted PSA level of LNCaP-AR cells was strongly induced by 25 pM of R1881. In contrast, PSA was not induced in the parental LNCaP cells until concentration of R1881 reached 100 pM. This is consistent with our previous report that the AR in hormone refractory prostate cancer is hyper-sensitive to androgens. A dose-dependent inhibition on AR activity was carried out to determine the IC50s of different compounds in inhibiting PSA expression, and the results were listed in Table 1. IC50s of the selective compounds on PSA expression closely resemble those measured by the reporter assay, confirming that the diarylhydantoin derivatives are strong inhibitors of AR in hormone refractory prostate cancer.

We also examined agonistic activities of selective compounds on AR in hormone refractory prostate cancer using secreted PSA as the surrogate marker. To do this, androgen-starved AR over expressed LNCaP cells were incubated with increasing concentrations of the compounds for which a synthesis is described above in the absence of R1881 and secreted PSA in the culture medium was measured 4 days later.

Table 3 lists the agonistic activities of the selective compounds. Consistent with the results obtained from the reporter assay, the diarylthiohydantoin derivatives such as examples 7-3b (RD37), 33 (RD91), 34 (RD92), and 35 (RD93) have no agonistic activities. In contrast, RU59063, and other antiandrogenic compounds listed as examples in U.S. Pat. No. 5,705,654, such as examples 30-2 (RD73), 30-3 (RD74), and 31-2 (RD75) stimulated PSA expression in hormone refractory prostate cancer.

TABLE 3

Agonistic activities of selective test substances on endogenous PSA in hormone refractory prostate cancer

| Example | Name | Fold induction by increasing concentrations of compounds | | |
|---|---|---|---|---|
| | | 0.1 µM | 1 µM | 10 µM |
| DMSO | Dimethyl sulfoxide | 1.00(*) | 1.00 | 1.00 |
| R1881 | methyltrienolone | 20.69 | n/a(**) | n/a |
| Bicalutamide | N-[4-cyano-3-(trifluoromethyl)phenyl]-3-[4-fluorophenyl)sulfonyl]-2-hydroxy-2-methylpropanamide | 2.00 | 2.55 | 5.55 |
| 29 Comp. | 4-[3-(4-hydroxybutyl)-4,4-dimethyl-5-oxo-2-thioxoimidazolidin-1-yl]-2-trifluoromethylbenzonitrile | 6.88 | 11.50 | 21.50 |

TABLE 3-continued

Agonistic activities of selective test substances on endogenous PSA in hormone refractory prostate cancer
Fold induction by increasing concentrations of compounds

| Example | Name | 0.1 μM | 1 μM | 10 μM |
|---|---|---|---|---|
| 7-3b (7c) [RD37] | 4-(8-oxo-6-thioxo-5-(4-methylphenyl)-5,7-diazaspiro[3.4]oct-7-yl)-2-trifluoromethylbenzonitrile | 1.25 | 1.20 | 1.15 |
| 33 (33a) [RD91] | 1-[3-(4-cyano-3-trifluoromethyl-phenyl)-5,5-dimethyl-2-thioxo-1-p-tolyl-imidazolidin-4-ylidene]-3-ethyl-thiourea | 1.06 | 1.30 | 0.85 |
| 34 (34a) [RD92] | 1-[7-(4-cyano-3-trifluoromethyl-phenyl)-6-thioxo-5-p-tolyl-5,7-diaza-spiro[3.4]oct-8-ylidene]-3-phenyl-thiourea | 1.31 | 1.05 | 0.90 |
| 35 (35a) [RD93] | 1-(4-Cyano-3-trifluoromethyl-phenyl)-3-[7-(4-cyano-3-trifluoromethyl-phenyl)-6-thioxo-5-p-tolyl-5,7-diaza-spiro[3.4]oct-8-ylidene]-thiourea | 1.44 | 1.30 | 1.05 |
| 30-2 Comp. (30b) [RD73] | 4-(5-methyl-8-oxo-6-thioxo-5,7-diazaspiro[3.4]oct-7-yl)-2-trifluoromethylenzonitrile | 6.25 | 17.95 | 25.65 |
| 30-3 Comp. (30c) [RD74] | 4-(5-methyl-6,8-dioxo-5,7-diazaspiro[3.4]oct-7-yl)-2-trifluoromethylbenzonitrile | 7.50 | 15.20 | 23.75 |
| 31-2 Comp. (31b) [RD75] | 4-(1-methyl-4-oxo-2-thioxo-1,3-diazaspiro[4.4]non-3-yl)-2-trifluoromethylbenzonitrile | 8.13 | 18.20 | 17.50 |

(*)Fold induction: activities induced by a specific test substance over activities in DMSO vehicle;
(**)n/a: the compound was not examined in this assay.

Effect of Compounds on AR Mitochondrial Activity by MTS Assay

LNCaP-AR cells were maintained in Iscove's medium containing 10% FBS. The compounds were examined for their effect on growth of hormone refractory prostate cancer cells. Overexpressed LNCaP cells were used because these cells behave as hormone refractory prostate cancer cells in vitro and in vivo (1). We measured mitochondria activity by MTS assay, a surrogate for growth. LNCaP cells with overexpressed AR (LN-AR) were maintained in Iscove's medium containing 10% FBS. Two days prior to drug treatment, the cells were grown in Iscove's medium containing 10% CS-FBS to deprive of androgens. The cells were then split and grown in Iscove's medium containing 10% CS-FBS with appropriate concentrations of R1881 and increasing concentrations of the test compounds. After four days incubation, cell growth was monitored by MTS (Promega, Madison, Wis.).

Consistent with the reporter assay and PSA assay, growth of the AR-overexpressed LNCaP was stimulated by 25-microM of R1881, but the parental cells were not stimulated until R1881 concentration reached 100 microM. FIG. 2 shows the inhibitory effect of selected compounds on growth of hormone refractory prostate cancer in the presence of 100 pM of R1881. The current clinical drug bicalutamide did not inhibit hormone refractory prostate cancer. In contrast, example 5-3b (RD7) (4-[3-(4-methylphenyl)-4,4-dimethyl-5-oxo-2-thioxoimidazolidin-1-yl]-2-trifluoromethyl-benzonitrile) and example 7-3b (RD37) (4-(8-oxo-6-thioxo-5-(4-methylphenyl)-5,7-diazaspiro[3.4]oct-7-yl)-2-trifluoromethylbenzonitrile) inhibited hormone refractory prostate cancer with high potency.

We examined if growth inhibition in the MTS assay occurs by targeting AR, example 5-3b (RD7) (4-[3-(4-methylphenyl)-4,4-dimethyl-5-oxo-2-thioxoimidazolidin-1-yl]-2-trifluoromethyl-benzonitrile) and example 7-3b (RD37) (4-(8-oxo-6-thioxo-5-(4-methylphenyl)-5,7-diazaspiro[3.4]oct-7-yl)-2-trifluoromethylbenzonitrile) were tested in DU-145 cells, a prostate cancer cell line that lacks AR expression. These compounds had no growth inhibitory effect on DU-145 cells. The compounds did not inhibit cells other than AR-expressed prostate cancer cells, as they had no growth effect on MCF7 and SkBr3, two commonly used breast cancer cells, or 3T3, a normal mouse fibroblast cell line.

Figure 3:
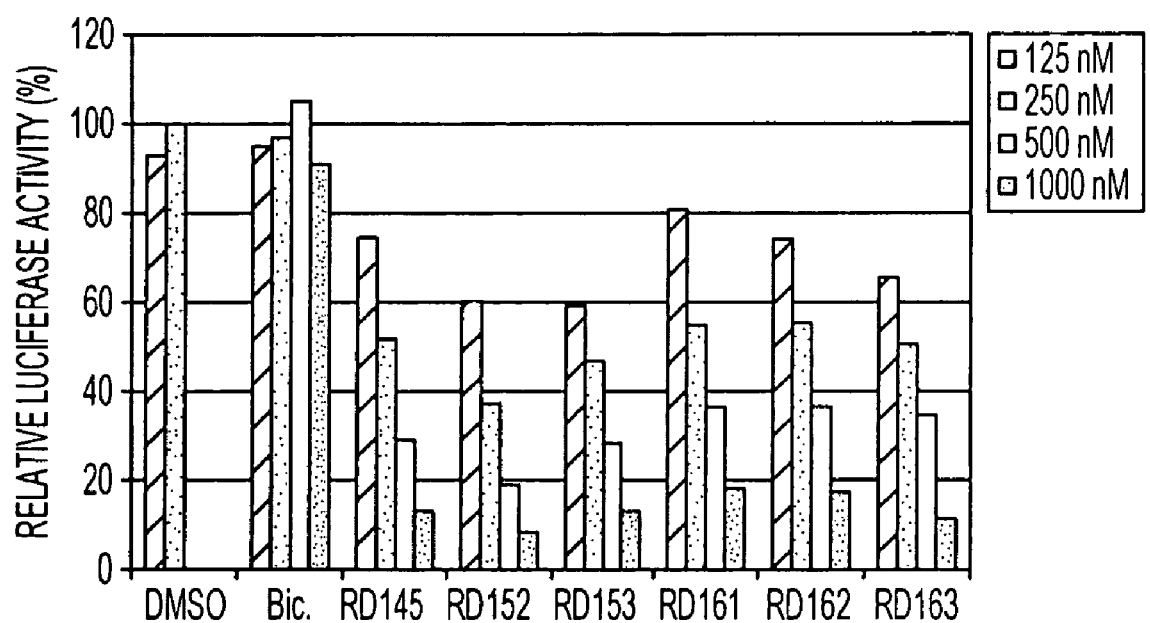
FIG. 3 is a graph depicting the effect of compounds on LNCaP-AR.
Figure 4:
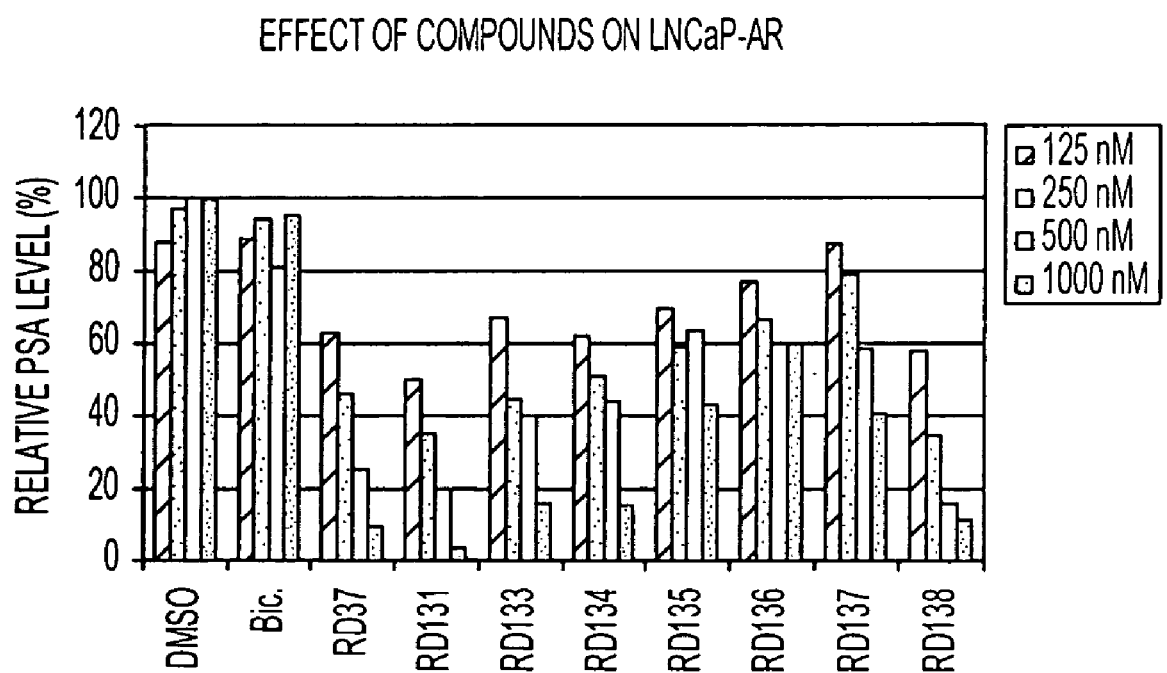
FIG. 4 is a graph depicting the effect of compounds on LNCaP-AR.
Figure 5:
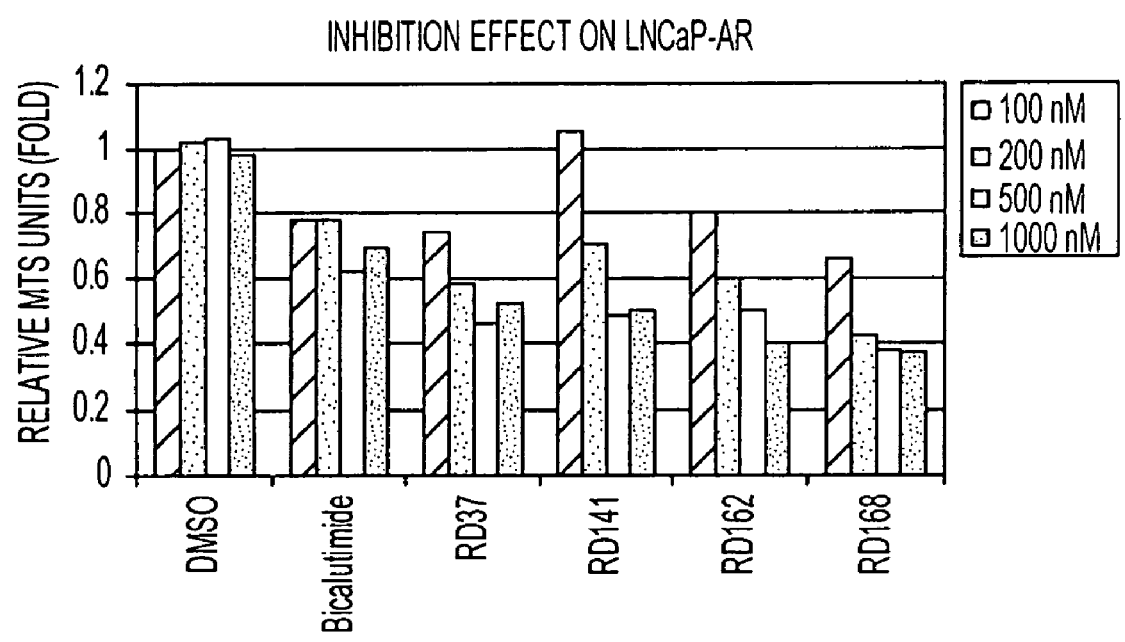
FIG. 5 is a graph depicting the inhibition effect on LNCaP-AR.

Examples of in vitro biological activity of diarylthiohydantoin derivatives are shown in the FIGS. 3, 4 and 5. For example, based on relative luciferase activity, FIG. 3 indicates that at a concentration of 500 nM the compounds ranked, in order of most active to least active as follows: RD152>RD153>RD145>RD163>RD161=RD162>bicalutamide. For example, based on relative PSA level, FIG. 4 indicates that at a concentration of 500 nM the compounds ranked, in order of most active to least active as follows: RD138>RD131>RD37>RD133>RD134>RD137>RD138>RD135>bicalutamide. For example, based on relative MTS units, FIG. 5 indicates that at a concentration of 500 nM the compounds ranked, in order of most active to least active as follows: RD168>RD37>RD141>RD162>bicalutamide.

Inhibitory Effect on Hormone Refractory Prostate Cancer Xenograft Tumors

Figure 7A:
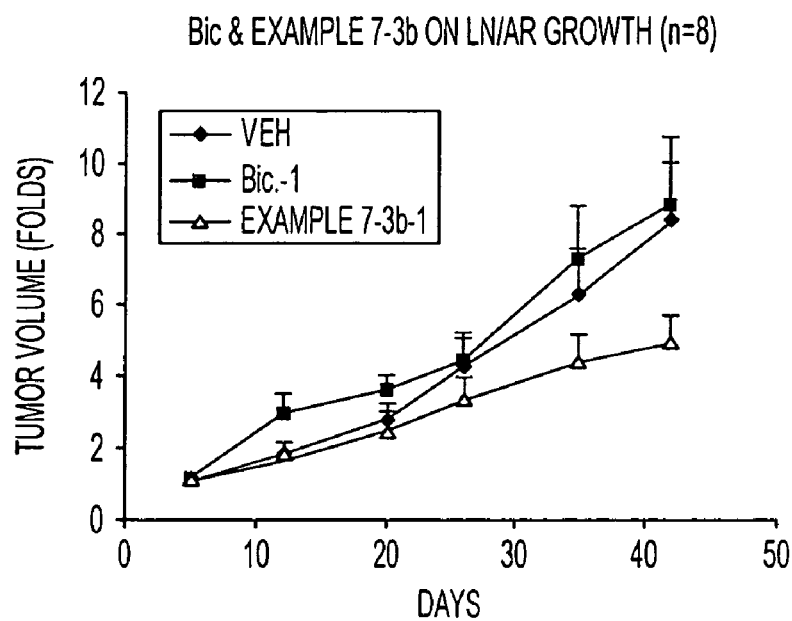
Figure 7B:
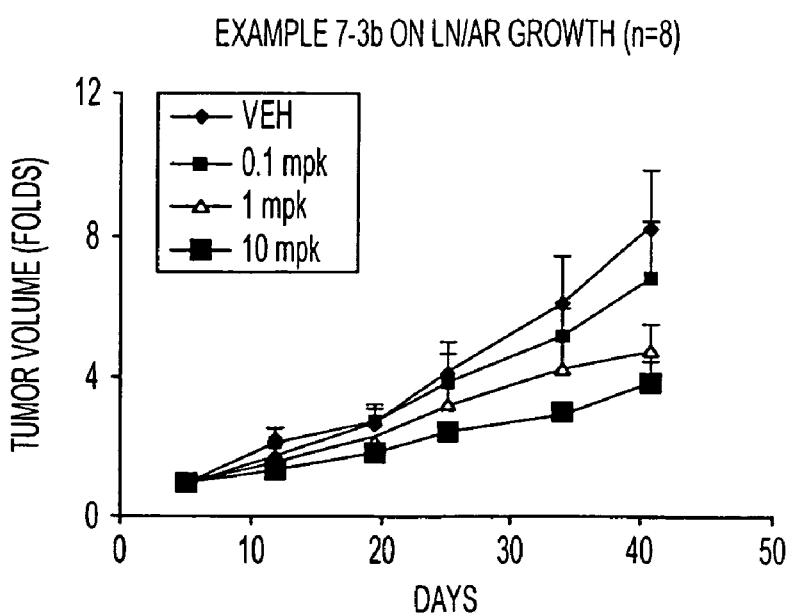
Figure 8:
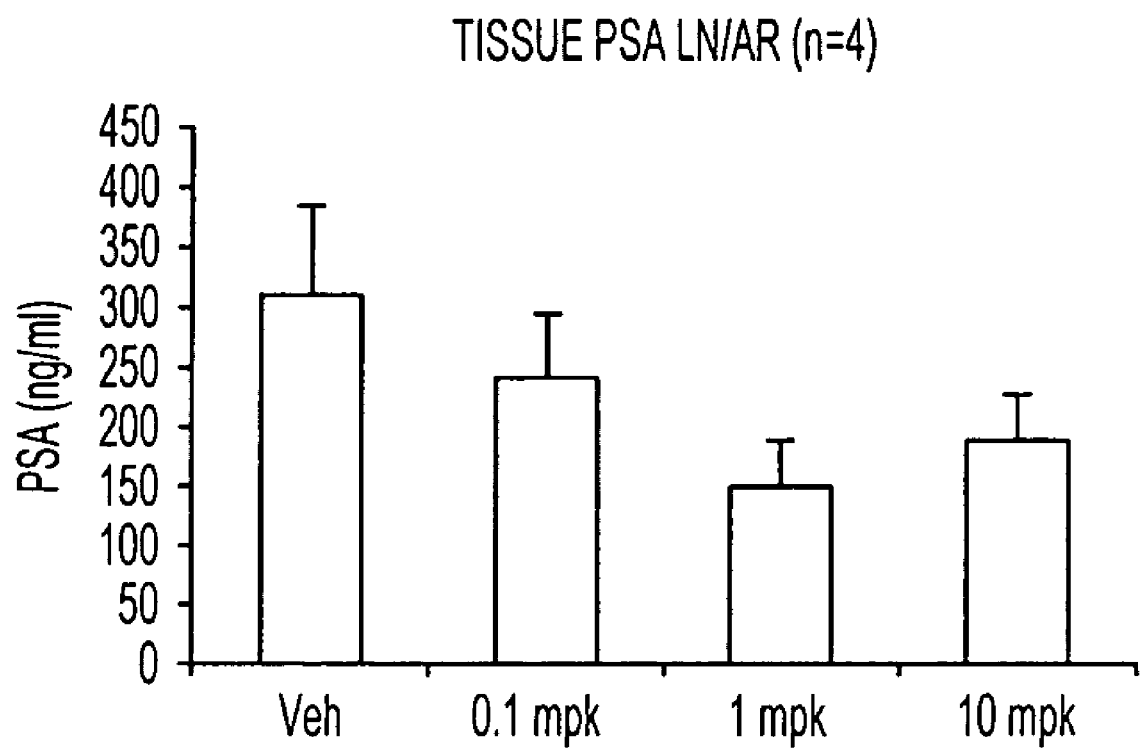

Example 7-3b (RD37) (4-(8-oxo-6-thioxo-5-(4-methylphenyl)-5,7-diazaspiro[3.4]oct-7-yl)-2-trifluoromethylbenzonitrile) was used to examine if the diarylhydantoin derivatives have in vivo effects on hormone refractory prostate cancer. First we examined this compound on xenograft tumors established from AR-overexpressed LNCaP cells. The engineered cells in Matrigel (Collaborative Biomedical) were injected subcutaneously into the flanks of the castrated male SCID mice. Tumor size was measured weekly in three dimensions using calipers. After xenograft tumors established (tumor size reached at least 40 mm³), mice with tumors were randomized and treated with different doses of compounds orally once daily. Consistent with clinical observation, current clinical drug bicalutamide did not inhibit growth of hormone refractory prostate cancer (same as vehicle) (FIG. 7a). In contrast, example 7-3b (RD37) (4-(8-oxo-6-thioxo-5-(4-methylphenyl)-5,7-diazaspiro[3.4]oct-7-yl)-2-trifluoromethylbenzonitrile) strongly inhibited growth of these tumors (FIG. 7a) and the inhibition is dose-dependent (FIG. 7b). Furthermore, example 7-3b (RD37) inhibited PSA expression (FIG. 8), the clinical marker for hormone refractory prostate cancer.

Figure 9A:
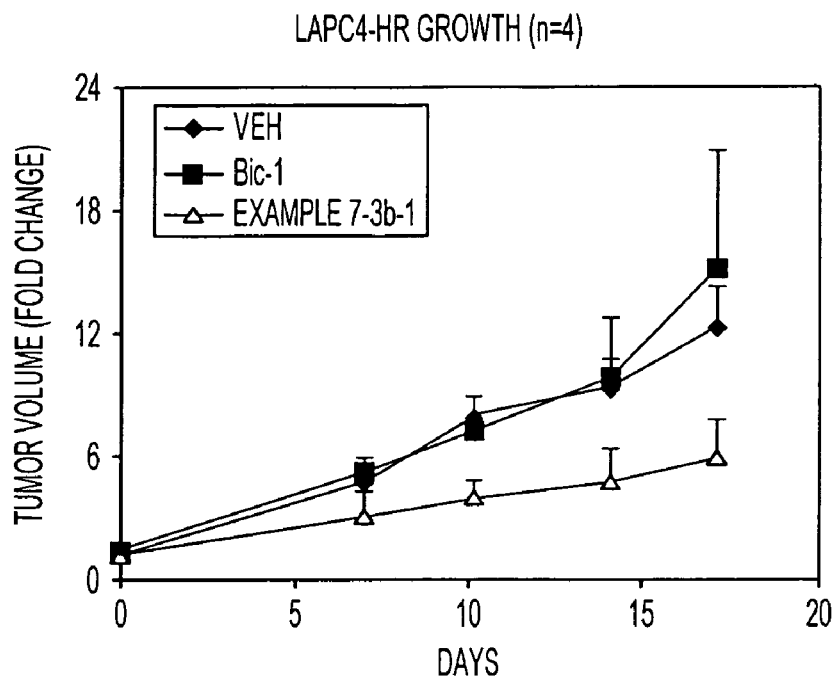
Figure 9B:
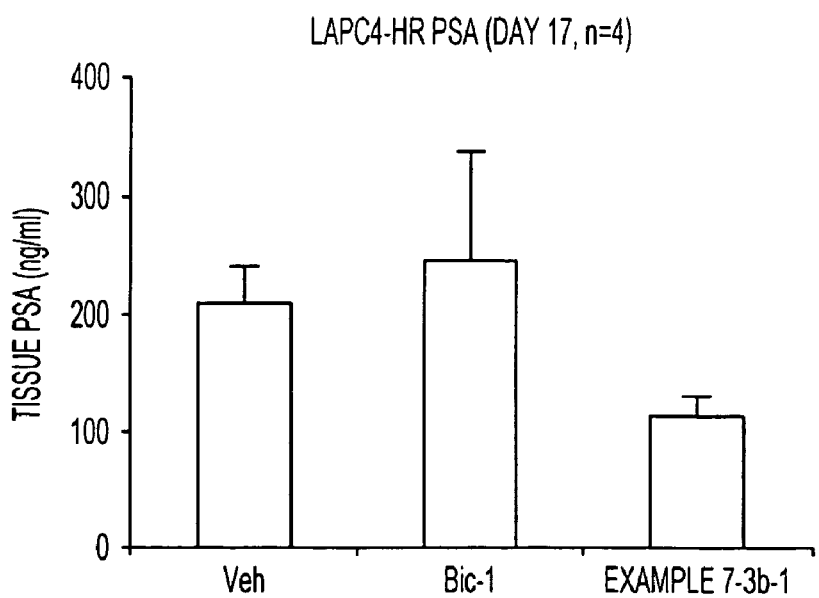

Example 7-3b (RD37) (4-(8-oxo-6-thioxo-5-(4-methylphenyl)-5,7-diazaspiro[3.4]oct-7-yl)-2-trifluoromethylbenzonitrile) was also tested in another xenograft model of hormone refractory prostate cancer, hormone refractory LAPC4. This model was established from passaging of hormone sensitive prostate cancer in castrated mice, which mimics the clinical progression of prostate cancer (2). Similar to the finding using AR-overexpressed LNCaP xenograft model, current clinical drug bicalutamide did not inhibit growth and PSA-expression in hormone refractory LAPC4 xenograft model (same as vehicle) (FIGS. 9a and 9b). In contrast, example 7-3b (RD37) strongly inhibited growth and PSA expression of these tumors (FIGS. 9a and 9b).

Inhibitory Effect on Growth of Hormone Sensitive Prostate Cancer Cells

Figure 10:
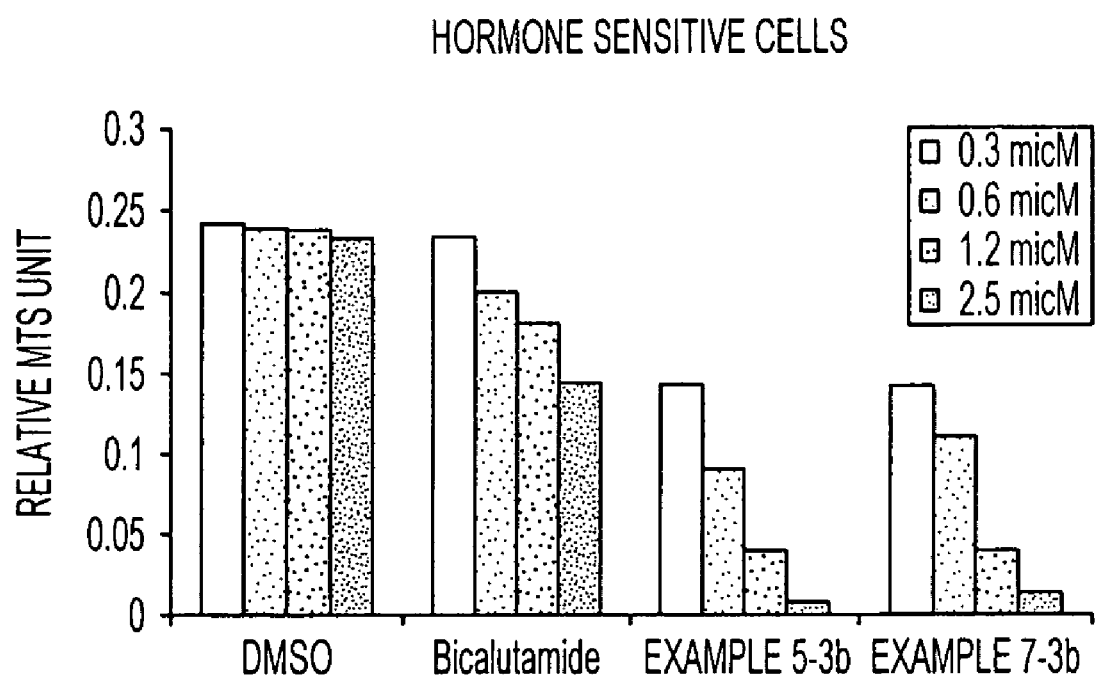

To determine if the diarylthiahydantoin derivatives also inhibit hormone sensitive prostate cancer cells, we tested some selective compounds on growth of LNCaP cells by measuring MTS of mitochondria activities. In contrast to have no effect on growth of hormone refractory prostate cancer, the current clinical drug bicalutamide mildly inhibited hormone sensitive LNCaP cells in a dose-dependent manner. Example 5-3b (RD7) (4-[3-(4-methylphenyl)-4,4-dimethyl-5-oxo-2-thioxoimidazolidin-1-yl]-2-trifluoromethyl-benzonitrile) and example 7-3b (RD37) (4-(8-oxo-6-thioxo-5-(4-methylphenyl)-5,7-diazaspiro[3.4]oct-7-yl)-2-trifluoromethylbenzonitrile) inhibited hormone sensitive prostate-cancer with a 10-fold higher potency than bicalutamide (FIG. 10).

In Vivo Biological Assay

Figure 11:
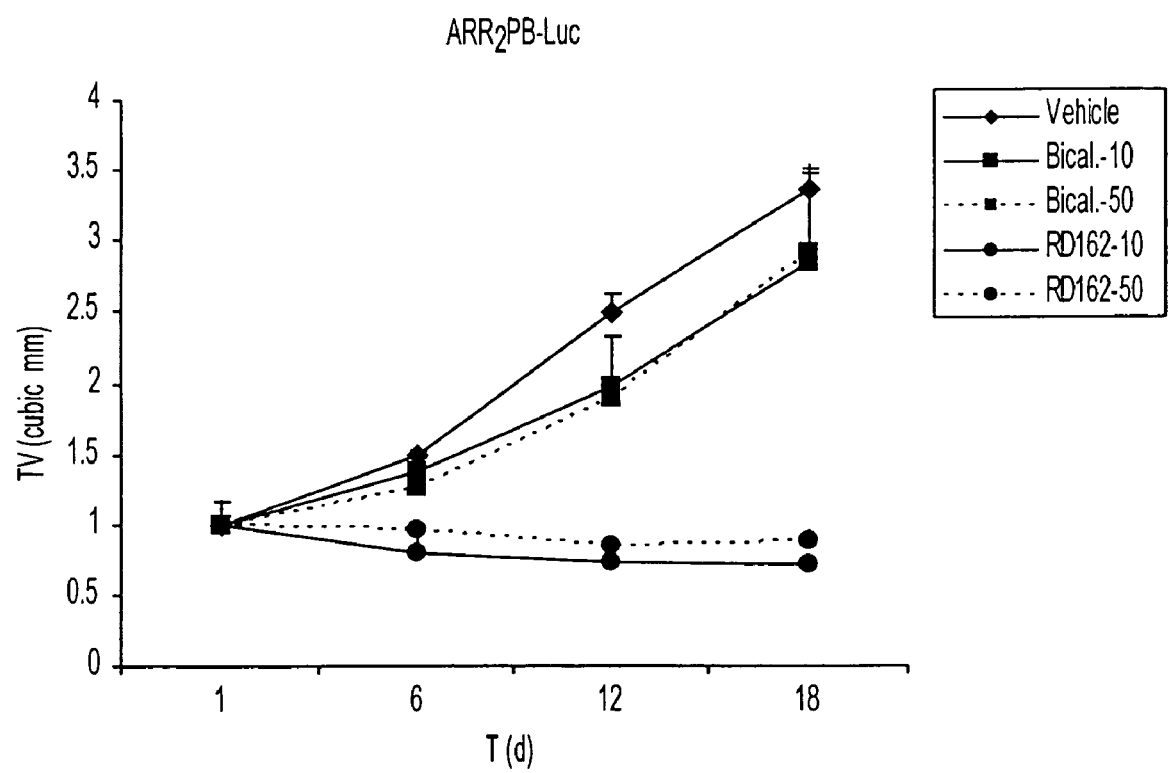
FIG. 11 is a graph of tumor size. AR overexpressing LNCaP cells were injected in the flanks of castrated SCID mice, subcutaneously. When tumors reached about 100 cubic mm, they were randomized into five groups. Each group had nine animals. After they reached this tumor volume, they were given orally with either vehicle, bicalutamide or RD162 at 10 or 50 mg/kg everyday. The tumors were measured three-dimensionally, width, length and depth, using a caliper.
Figure 12C:
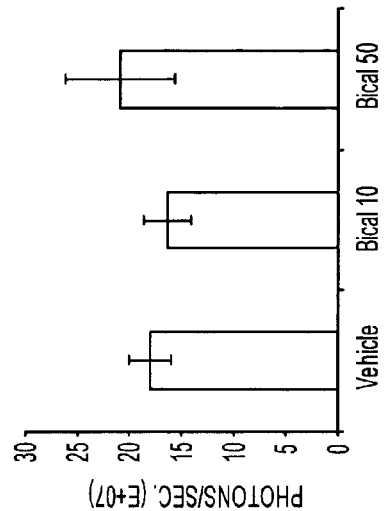
Figure 12D:
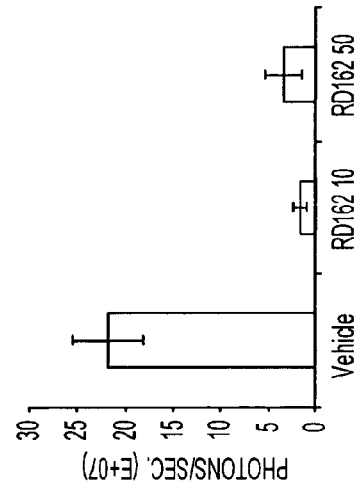
Figure 12A:
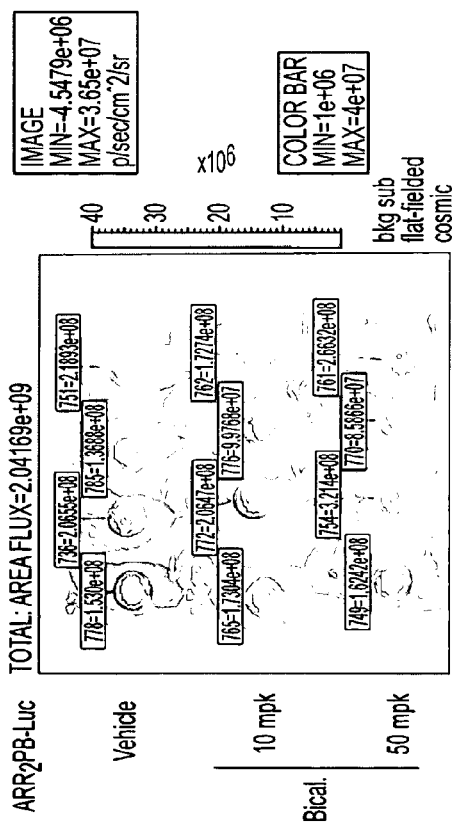
Figure 12B:
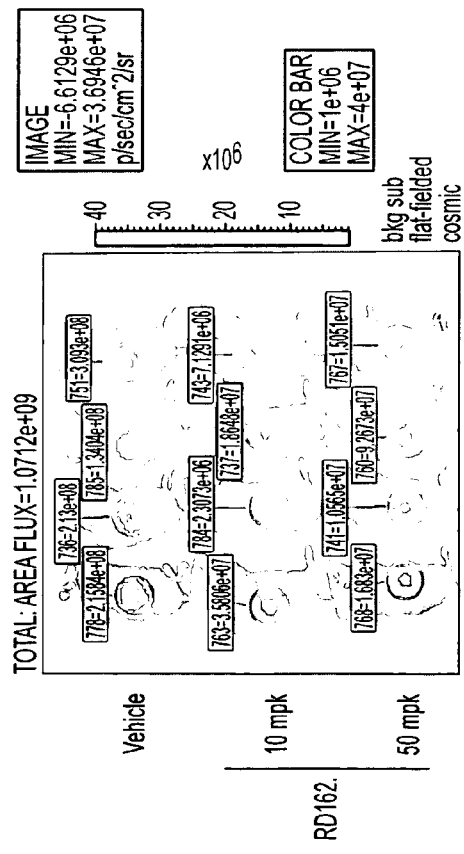

All animal experiments were performed in compliance with the guidelines of the Animal Research Committee of the University of California at Los Angeles. Animals were bought from Taconic and maintained in a laminar flow tower in a defined flora colony. LNCaP-AR and LNCaP-vector cells were maintained in RPMI medium supplemented with 10% FBS. $10^6$ cells in 100 µl of 1:1 Matrigel to RPMI medium were injected subcutaneously into the flanks of intact or castrated male SCID mice. Tumor size was measured weekly in three dimensions (length×width×depth) using calipers. Mice were randomized to treatment groups when tumor size reached approximately 100 mm³. Drugs were given orally every day at 10 mg/kg and 50 mg/kg. To obtain pharmacodynamic readout, the animals were imaged via an optical CCD camera, 3 hours after last dose of the treatment. A ROI is drawn over the tumor for luciferase activity measurement in photon/second. The right panels were a representation of the ROIs measurements. Data are shown in FIGS. 11 and 12. Over 18 days RD162 was effective to prevent tumor growth and even to cause tumor shrinkage, and was distinctly more effective than bicalutamide.

The pharmacokinetics of bicalutamide, 4-[7-(4-cyano-3-trifluoromethylphenyl)-8-oxo-6-thioxo-5,7-diaza-spiro[3.4]oct-5-yl]-toluene [RD37], N-methyl-4-{4-[7-(4-cyano-3-trifluoromethylphenyl)-8-oxo-6-thioxo-5,7-diaza-spiro[3.4]oct-5-yl]phenyl}butanamide [RD131], and N-methyl-4-[7-(4-cyano-3-trifluoromethylphenyl)-8-oxo-6-thioxo-5,7-diaza-spiro[3.4]oct-5-yl]-2-fluorobenzamide (52d) [RD162] were evaluated in vivo using 8 week-old FVB mice which were purchased from Charles River Laboratories. Mice were divided into groups of three for each time points. Two mice were not treated with drug and two other mice were treated with vehicle solution. Each group was treated with 10 mg per kilogram of body weight.

The drug was dissolved in a mixture 1:5:14 of DMSO:PEG400:$H_2O$. (Vehicle solution) and was administered into mice through the tail vein. The animals are warmed under a heat lamp for approximately 20 minutes prior to treatment to dilate their tail vein. Each mouse was placed into a mouse restrainer (Fisher Sci. Cat# 01-288-32A) and was injected with 200 µl of drug in vehicle solution into the dilated tail vein. After drug administration, the animals were euthanized via $CO_2$ inhalation at different timepoints: 5 nm, 30 nm, 2 h, 6 h, 16 h. Animals were immediately bleed after exposure to $CO_2$ via cardiac puncture (1 ml BD syringe+27G ⅝ needle). For oral dosage, the drug was dissolved in a mixture 50:10:1:989 of DMSO:Carboxymethylcellulose:Tween80:$H_2O$ before oral administration via a feeding syringe.

The serum samples were analyzed to determine the drug's concentration by the HPLC which (Waters 600 pump, Waters 600 controller and Waters 2487 detector) was equipped with an Alltima C18 column (3, 150 mm×4.6 mm). The RD37, RD131, and RD162 compounds were detected at 254 nm wave length and bicalutamide was detected at 270 nm wave length.

The samples for HPLC analysis were prepared according to the following procedure:

Blood cells were separated from serum by centrifugation.

To 400 µl of serum were added 80 µl of a 10 µsolution of an internal standard and 520 µl of acetonitrile. Precipitation occurred.

The mixture was vortexed for 3 minutes and then placed under ultrasound for 30 minutes.

The solid particles were filtered off or were separated by centrifugation.

The filtrate was dried under an argon flow to dryness. The sample was reconstructed to 80 µl with acetonitrile before analyzing by HPLC to determine the drug concentration.

Standard curve of drug was used to improve accuracy.

The concentration of RD162 in plasma as a function of time resulting from intravenous and from oral administration is shown in FIG. 13. The steady state concentration (Css) of bicalutamide, RD131, and RD162 is shown in Table 4. The concentration at steady state of RD162 is essentially as good as that of bicalutamide, and substantially better than RD131.

TABLE 4

Steady-state concentration of bicalutamide, RD131, and RD162 in mice plasma.

| Name | IC50 [nM] | LogP | Css, 10 mg/kg [µM] | Css, 25 mg/kg [µM] | Css, 50 mg/kg [µM] |
|---|---|---|---|---|---|
| Bic. | 1000 | 2.91 | 10.0 | 11.4 | 11.9 |
| RD131 | 92 | 3.44 | 0.39 | 0.43 | 0.40 |
| RD162 | 122 | 3.20 | 9.9 | 10.7 | 10.2 |

Ranking of Compounds in Tiers

Tables 5-10 present diarylhydantoin compounds grouped into Tiers 1-6. Table 11 presents diarylhydantoin compounds which have not been placed into a tier. The placement of compounds into tiers was based on available data coupled with analytical judgment. Data considered included in vitro assays (AR response reporter system in LNCaP cell line, PSA level measurement, MTS mitochondrial assay) and in vivo experiments (tumor size measured directly or by emission induced by luciferase reporter gene, pharmacokinetic assays based on blood plasma levels). Not every compound was subjected to each assay. Not all data that was generated is shown. Judgment was applied in ranking compounds relative to each other for their utility in treating prostate cancer, in particular when ranking two compounds for which the same experiments were not performed. Characteristics considered in establishing the ranking include AR antagonism activity, lack of AR agonism in hormone refractory cells, prevention of tumor growth, tumor shrinkage, and pharmacokinetic behavior, with a longer residence time in blood being advantageous.

Tier 1

Generally, Tier 1 compounds are diarylthiohydantoins with a disubstituted left hand aryl ring that are disubstituted on the right hydantoin carbon, and have either an oxygen or N substituent on the left hydantoin carbon. It is expected that the amido substituent hydrolyzes to an oxygen in aqueous solutions such as encountered in biological systems, in vitro and in vivo. RD100 has good activity with an iodine instead of a $CF_3$ substituent on the left hand aryl ring.

Tier 1 compounds (see Table 5) were judged to be much better than bicalutamide for treating prostate cancer. However, RD37 and RD131 were found to metabolize fast, that is, have a short residence time in blood. RD162 had desirable pharmacokinetics.

FIG. 17 shows that under treatment with bicalutamide, PSA levels for LNCaP cells stayed the same or increased relative to treatment with vehicle solution, whereas under treatment with RD162, PSA levels decreased. FIG. 18 illustrates that under treatment with vehicle solution, tumors continued to increase in size. By contrast, under treatment with RD162 at a dose of 1 mg per kg body weight per day, the rate of tumor increase decreased, and the size of the tumor appeared to be stabilizing after about 17 days. Under treatment with RD162 at a dose of 10 mg per kg body weight per day, tumor size decreased with time. FIG. 19 illustrates that under treatment with RD162 at a dose of 10 mg per kg body weight per day, photon emission associated with luciferase activity decreased. FIG. 20 shows that treatment with RD162 at this dose resulted in a decrease or stabilization of tumor size and a decrease in photon emission associated with luciferase activity.

FIG. 21 shows that under treatment with RD162, RD162', RD162", RD169, and RD170 at doses of 100, 200, 500, and 1000 nM, PSA levels of LN-AR cells decreased. Moreover, the higher the dose, the lower the PSA level. FIG. 23 presents urogenital tract weight and rate of photon emission associated with luciferase activity initially and after 14 days of treatment with bicalutamide or with RD162 for intact and castrated mice. The weight and rate of photon emission increased for both intact and castrated mice. Treatment of castrated mice with RD162 resulted in a decrease in weight and photon emission with respect to the untreated castrated mice, as did treatment with bicalutamide.

Thus, Tier 1 compounds are particularly advantageous for use as AR antagonists, and as therapeutic agents for hormone refractory prostate cancer. They may be useful to treat other AR related diseases or conditions such as benign prostate hyperplasia, hair loss, and acne. These and related compounds may also be useful as modulators of other nuclear receptors, such as glucocorticoid receptor, estrogen receptor, and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays e.g. as standards, or as intermediates or prodrugs.

TABLE 5

TIER 1 COMPOUNDS

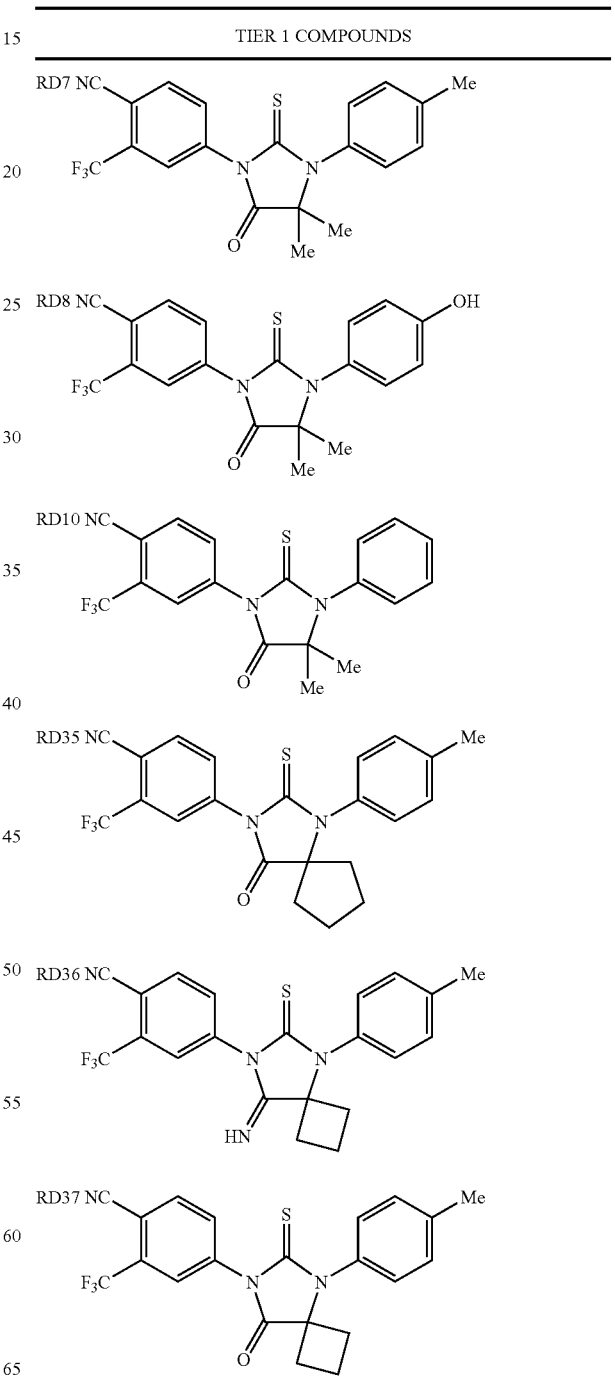

TABLE 5-continued

TIER 1 COMPOUNDS

RD57, RD58, RD90, RD91, RD92, RD93, RD94, RD95

TABLE 5-continued

TIER 1 COMPOUNDS

RD96, RD97, RD100, RD102, RD119, RD120, RD130, RD131, RD145, RD152, RD153, RD163, RD162

TABLE 5-continued

TIER 1 COMPOUNDS

RD162 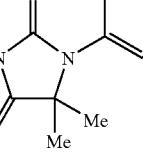

RD162″

RD168

RD169

RD170

Tier 2

Tier 2 compounds (see Table 6) were significantly better than bicalutamide for treating prostate cancer, although there were indications that RD54 could act as an agonist. FIG. 3 illustrates that compounds RD145, RD152, RD153, RD162, and RD163 in Tier 1 and RD161 in Tier 2 dosed at concentrations ranging from 125 nM to 1000 nM acted to reduce luciferase activity in LNCaP-AR cells whereas control solutions of DMSO and of bicalutamide had little or no effect. FIG. 4 illustrates, for example, that at concentrations of 1000 nM, compounds RD37 and RD131, in Tier 1, caused a greater decrease in PSA level of LNCaP-AR cells than RD133, RD134, and RD138 in Tier 2. FIG. 11 presents tumor volume over time, and illustrates that under treatment with bicalutamide or vehicle solution, tumors continued to grow, whereas under treatment with RD162, in Tier 1, tumors decreased in size. FIG. 12 illustrates that photon emission associated with luciferase activity remained about the same or increased under treatment with bicalutamide relative to treatment with vehicle solution, whereas photon emission decreased under treatment with RD162. FIG. 14 illustrates that under treatment with bicalutamide, there was little or no decrease in PSA levels, whereas under treatment with RD131 and RD162, PSA levels decreased. FIG. 15 illustrates that the $IC_{50}$ for RD37, RD131, and RD162, in Tier 1, was much lower than the $IC_{50}$ for bicalutamide.

Generally, Tier 2 compounds are structurally similar to Tier 1 compounds, but with different substituents on the right hand aryl ring. Tier 2 compounds are advantageous for use as AR antagonists, and as therapeutic agents for hormone refractory prostate cancer. They may be useful to treat other AR related diseases or conditions such as benign prostate hyperplasia, hair loss, and acne. These and related compounds may also be useful as modulators of other nuclear receptors, such as estrogen receptor and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays e.g. as standards, or as intermediates or prodrugs.

TABLE 6

TIER 2 COMPOUNDS

RD6 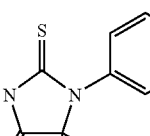

(comparative)

RD13 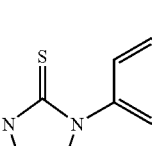

RD48

RD49 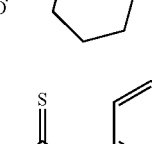

TABLE 6-continued

TIER 2 COMPOUNDS

RD51, RD53, RD54, RD55, RD63, RD66, RD68, RD71, RD87, RD103, RD110, RD111, RD114

TABLE 6-continued

TIER 2 COMPOUNDS

RD116

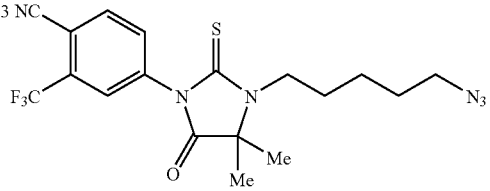

RD133

RD134

RD138

RD161

Tier 3

Tier 3 compounds (see Table 7) were judged to be slightly better than bicalutamide for treating prostate cancer. RD133, RD134, and RD138 (in Tier 2) caused a greater decrease in PSA level of LNCaP-AR cells than RD135 and RD137, in Tier 3. All of these compounds caused a greater decrease in PSA level than bicalutamide.

Other Tier 3 compounds (not shown) were not diarylthiohydantoins, and were comparable in activity to prior art monoarylhydantoin compounds RD2, RD4, and RD5.

Thus, Tier 3 compounds are useful as AR antagonists, and as therapeutic agents for hormone refractory prostate cancer. They may be useful to treat other AR related diseases or conditions such as benign prostate hyperplasia, hair loss, and acne. These and related compounds may also be useful as modulators of other nuclear receptors, such as estrogen receptor and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays e.g. as standards, or as intermediates or prodrugs.

TABLE 7

TIER 3 COMPOUNDS

RD3

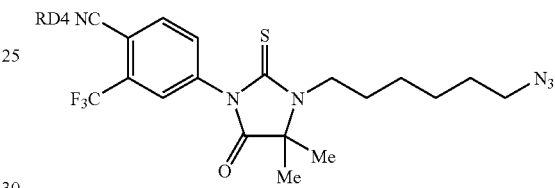

(comparative)

RD4

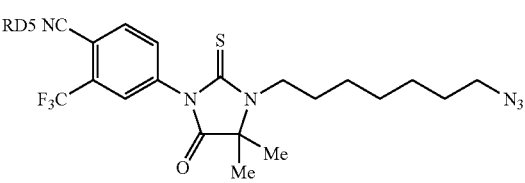

(comparative)

RD5

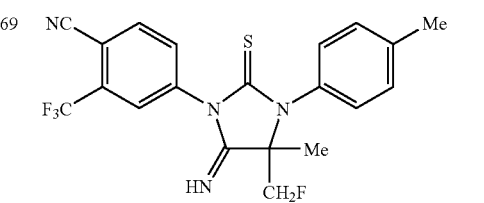

(comparative)

RD69

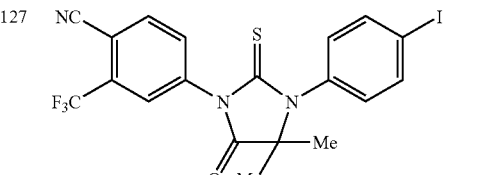

RD127

RD128

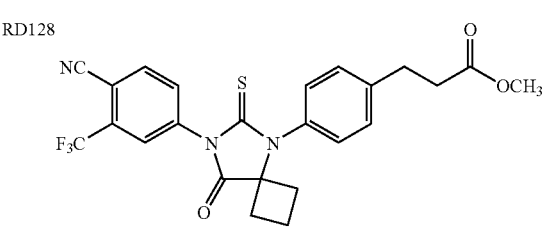

TABLE 7-continued

TIER 3 COMPOUNDS

RD129 

RD135 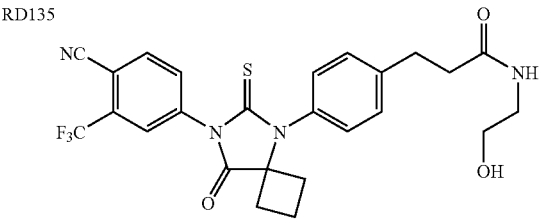

RD137 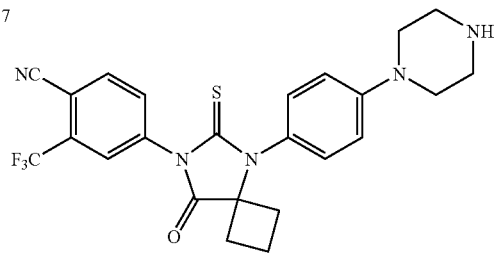

Tier 4 compounds (see Table 8) were judged to be no better than bicalutamide for treating prostate cancer. Tier 4 RD 39 and RD40 and Tier 1 RD37, for example, differ only in the substituent on the lower right carbon of the hydantoin ring. The substituents on the right hand aryl ring may also affect activity.

Some Tier 4 compounds (including those shown and others that are not shown) were not diaryl compounds (lacking the right hand aryl ring), were not thiohydantoins, were not disubstituted on the carbon on the lower right hand of the hydantoin ring, and/or had substituents other than oxygen or amido on the lower left hand carbon of the hydantoin ring. This provides evidence of the surprising advantages of diarylthiohydantoins that are disubstituted on the lower right hand carbon of the hydantoin ring and have oxygen or amido on the lower left hand carbon of the hydantoin ring.

Thus, Tier 4 compounds may be useful as AR antagonists, and as therapeutic agents for hormone refractory prostate cancer, at least to the extent that they are comparable to bicalutamide. They may be useful to treat other AR related diseases or conditions such as benign prostate hyperplasia, hair loss, and acne. These and related compounds may also be useful as modulators of other nuclear receptors, such as estrogen receptor and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays e.g. as standards, or as intermediates or prodrugs.

TABLE 8

TIER 4 COMPOUNDS

RD2 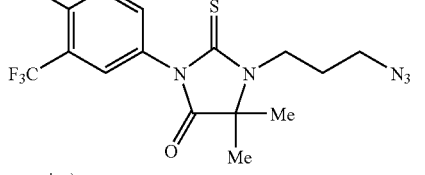
(comparative)

RD9 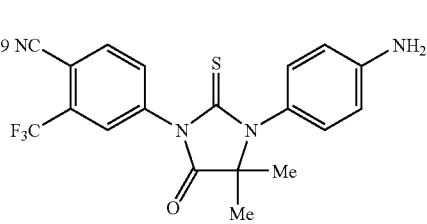

RD21 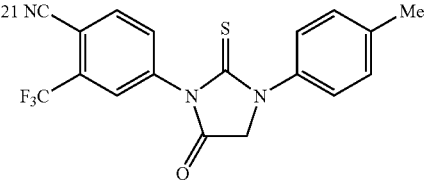

RD22 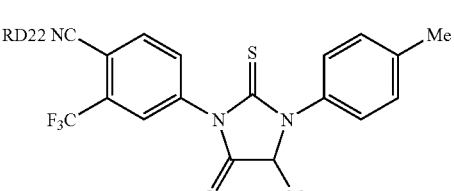

RD23 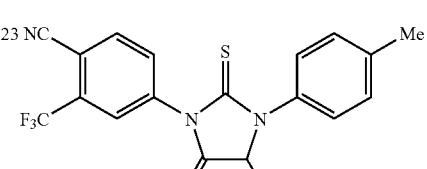

RD24 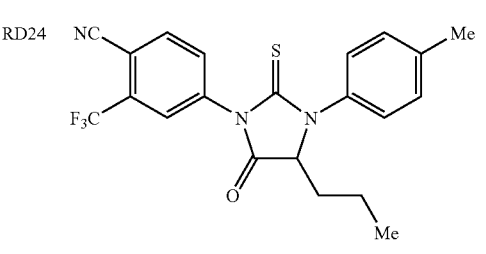

RD25 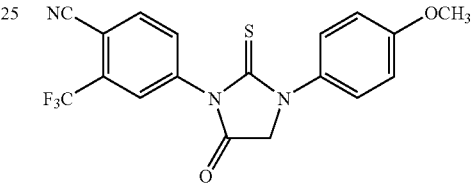

TABLE 8-continued

TIER 4 COMPOUNDS

RD26, RD27, RD30, RD31, RD39, RD40, RD44, RD59, RD60, RD67, RD82, RD83, RD117, RD118

TABLE 8-continued

TIER 4 COMPOUNDS

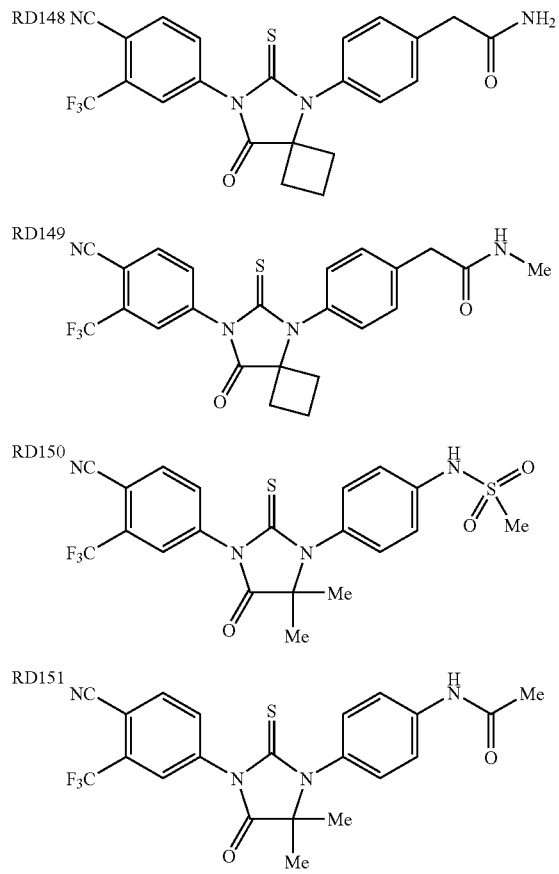

TABLE 9

TIER 5 COMPOUNDS

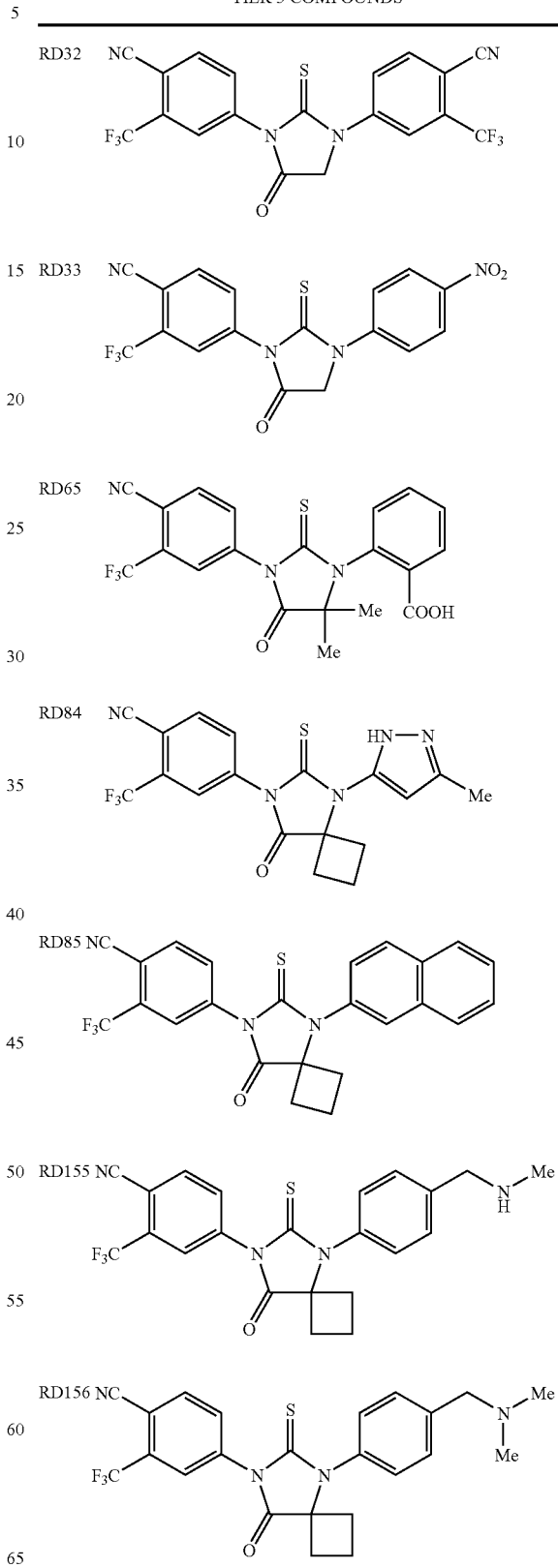

Tier 5

Tier 5 compounds (see Table 9) were inactive or nearly inactive, and thus, were worse than bicalutamide for treating prostate cancer. The substituents on the right hand aryl ring are important to determining activity.

Some Tier 5 compounds (some of which are shown and some that are not shown) were not diaryl compounds (lacking the right hand aryl ring), were not thiohydantoins, were not disubstituted on the carbon on the lower right hand of the hydantoin ring, and/or had substituents other than oxygen or amido on the lower left hand carbon of the hydantoin ring. This provides evidence of the surprising advantages of diarylthiohydantoins that are disubstituted on the lower right hand carbon of the hydantoin ring and have oxygen or amido on the lower left hand carbon of the hydantoin ring. In particular, the terminal substituent in RD155, RD156, and 158 ($CH_2NR_xR_y$, where $R_{x,y}$=H or methyl) is not seen as contributing to activity in these compounds.

Tier 5 compounds would not be desirable for treatment of prostate cancer or as AR antagonists, although these and related compounds may be useful as modulators of other nuclear receptors, such as estrogen receptor and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays e.g. as standards, or as intermediates or prodrugs.

TABLE 9-continued

TIER 5 COMPOUNDS

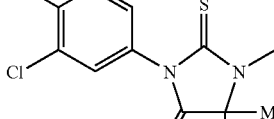

Tier 6

Tier 6 compounds (see Table 10) were inactive or nearly inactive, and furthermore were strong agonists, and thus were much worse than bicalutamide for treating prostate cancer. The comparative compounds ranked very poor relative to the inventive compounds. Notably, RD72 had very poor activity, with a chlorine substituent on the left hand aryl ring, whereas RD7, with a trifluoromethane, and RD100, with iodine, ranked in Tier 1. The results for the Tier 6 compounds provide evidence of the surprising advantages of diarylthiohydantoins that are disubstituted on the lower right hand carbon of the hydantoin ring and have oxygen or amido on the lower left hand carbon of the hydantoin ring, and have certain substituents on the left hand aryl ring.

Tier 6 compounds would not be desirable for treatment of prostate cancer or as AR antagonists.

TABLE 10

TIER 6 COMPOUNDS

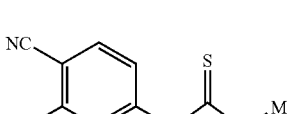

Untiered compounds

For several compounds, there was insufficient experimental data to rank them. These untiered compounds are presented in Table 11.

Based on the data and methods of the invention, and applying judgment based on review of many compounds, including some not shown here, one can make some observations about the untiered compounds. Comparative example RD1 is expected to be in Tier 3 with comparative examples RD3-RD5. RD89 is expected to hydrolyze to RD37 (Tier 1), and should therefore have comparable activity. RD104 is expected to hydrolyze to RD58 (Tier 1), and should therefore have comparable activity. RD105 is expected to hydrolyze to RD8 (Tier 1), and RD139 and RD140 are expected to hydrolyze to RD138 (Tier 2), and they should therefore have comparable activity.

TABLE 11

UNTIERED COMPOUNDS

RD1 (comparative)

RD19

RD52

RD79

RD80

RD81

RD89

TABLE 11-continued

UNTIERED COMPOUNDS

RD104

RD105

RD106

RD115

RD132

RD136

TABLE 11-continued

UNTIERED COMPOUNDS

RD139 [structure]

RD140 [structure]

RD141 [structure]

RD142 [structure]

RD146 [structure]

RD147 [structure]

TABLE 11-continued

UNTIERED COMPOUNDS

RD154 [structure]

In short, novel compounds which show evidence of being far superior to bicalutamide in treating prostate cancer were identified and produced.

Sensitivity of Anti-Cancer Activity of Compounds to Structural Differences

The inventors have determined that what might appear to be a small change in the structure of hydantoin compounds may result in a large change in that compound's performance in treating prostate cancer. For example, RD161 and RD162 differ only by a single fluorine substituent on an aryl ring, and RD162 is in Tier 1, while RD161 is in Tier 2, both being better than bicalutamide for the treatment of prostate cancer, but RD162 being superior. However, RD149, which differs from RD161 only in having an additional carbon atom between the methylcarbamoyl group and the aryl ring, is no better than bicalutamide for the treatment of prostate cancer and is ranked in Tier 4. The effect of RD161, RD162, and RD149 on luciferase activity can be seen in FIG. 24. At a given concentration of compound, the luciferase activity upon exposure to RD161 and RD162 is less than the luciferase activity upon exposure to RD149.

RD9 differs from RD8 only in that an amino group is substituted for a hydroxyl group. However, whereas RD8 is in Tier 1, much better than bicalutamide for the treatment of prostate cancer, RD9 is in Tier 4, no better than bicalutamide. The effect of RD8 and RD9 on luciferase activity in the 1AR cell line can be seen in FIG. 27. For a given dose, the luciferase activity upon exposure to RD8 is less than the luciferase activity upon exposure to RD9. The effect of RD8 and RD9 on luciferase activity in the 4AR cell line can be seen in FIG. 26. For a given dose, the luciferase activity upon exposure to RD8 is less than the luciferase activity upon exposure to RD9. The effect of RD8 and RD9 on PSA levels in the LN/AR cell line can be seen in FIG. 25. For a given dose, the PSA level upon exposure to RD8 is less than the PSA level upon exposure to RD9.

RD130 and RD131 differ from each other only by a methyl substituent on the end of a carbamoyl group and both compounds are ranked in Tier 1, although RD131 has been found to be particularly advantageous. RD129 is the same as RD130, with the exception of a methoxy group being substituted for an amino group. However, RD129 is ranked in Tier 3. RD128 is similar to RD129, but has one less carbon in the chain linking the ester group to the aryl ring; RD128 is ranked in Tier 3. The effect of RD130, RD131, RD128, and RD129 on PSA levels in the LN/AR cell line can be seen in FIG. 28. For a given concentration, the PSA level upon exposure to RD130 and RD131 is less than the PSA level upon exposure to RD128 and RD129.

RD153 and RD155 differ from each other in that the former has a methylcarbamoyl group attached to an aryl ring and a dimethyl substituent attached to the thiohydantoin group, whereas the latter has a methylamino group attached to the right hand aryl ring and a cyclobutyl substituent attached to the thiohydantoin group. Whereas RD153 is in Tier 1, much better than bicalutamide for the treatment of prostate cancer, RD155 is in Tier 5, inactive or nearly inactive in the treatment of prostate cancer. The effect of RD153 and RD155 on luciferase activity in the LN/AR cell-line can be seen in FIG. 29. For a given concentration, the luciferase activity upon exposure to RD153 is less than the luciferase activity upon exposure to RD155.

RD58 and RD60 differ from each other in the substitution of a thio for an oxo group and a dimethyl substituent for a cyclobutyl substituent. Whereas RD58 is in Tier 1, RD60 is in Tier 4.

Pharmaceutical Compositions and Administration

The compounds of the invention are useful as pharmaceutical compositions prepared with a therapeutically effective amount of a compound of the invention, as defined herein, and a pharmaceutically acceptable carrier or diluent.

The diarylhydantoin compounds of the invention can be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Thus, diarylhydantoin compounds of the invention may be systemically administered, e.g., orally, in combination with a pharmaceutically acceptable vehicle such as an inert diluent or an assimilable edible carrier; or by inhalation or insufflation. They may be enclosed in hard or soft shell gelatin capsules, may be compressed into tablets, or may be incorporated directly with the food of the patient's diet. For oral therapeutic administration, the diarylhydantoin compounds may be combined with one or more excipients and used in the form of ingestible tablets, buccal tablets, troches, capsules, elixirs, suspensions, syrups, wafers, and the like. The diarylhydantoin compounds may be combined with a fine inert powdered carrier and inhaled by the subject or insufflated. Such compositions and preparations should contain at least 0.1% diarylhydantoin compounds. The percentage of the compositions and preparations may, of course, be varied and may conveniently be between about 2% to about 60% of the weight of a given unit dosage form. The amount of diarylhydantoin compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the diarylhydantoin compounds may be incorporated into sustained-release preparations and devices. For example, the diarylhydantoin compounds may be incorporated into time release capsules, time release tablets, and time release pills.

The diarylhydantoin compounds may also be administered intravenously or intraperitoneally by infusion or injection. Solutions of the diarylhydantoin compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the diarylhydantoin compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the diarylhydantoin compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the diarylhydantoin compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the diarylhydantoin compounds can be dissolved or dispersed at effective levels, optionally with the aid of nontoxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the diarylhydantoin compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the diarylhydantoin compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of the diarylhydantoin compounds required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

The diarylhydantoin compounds are conveniently administered in unit dosage form; for example, containing 0.05 to 10000 mg, 0.5 to 10000 mg, 5 to 1000 mg, or about 100 mg of active ingredient per unit dosage form.

The diarylhydantoin compounds can be administered to achieve peak plasma concentrations of, for example, from about 0.5 to about 75 µM, about 1 to 50 µM, about 2 to about 30 µM, or about 5 to about 25 µM. Exemplary desirable plasma concentrations include at least or no more than 0.25, 0.5, 1, 5, 10, 25, 50, 75, 100 or 200 µM. For example, plasma levels may be from about 1 to 100 micromolar or from about 10 to about 25 micromolar. This may be achieved, for example, by the intravenous injection of a 0.05 to 5% solution of the diarylhydantoin compounds, optionally in saline, or orally administered as a bolus containing about 1-100 mg of the diarylhydantoin compounds. Desirable blood levels may be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of the diarylhydantoin compounds per kg of body weight.

The diarylhydantoin compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

A number of the above-identified compounds exhibit little or no agonistic activities with respect to hormone refractory prostate cancer cells. Because these compounds are strong AR inhibitors, they can be used not only in treating prostate cancer, but also in treating other AR related diseases or conditions such as benign prostate hyperplasia, hair loss, and acne. Because AR belongs to the family of nuclear receptors, these compounds may serve as scaffolds for drug synthesis targeting other nuclear receptors, such as estrogen receptor and peroxisome proliferator-activated receptor. Therefore, they may be further developed for other diseases such as breast cancer, ovarian cancer, diabetes, cardiac diseases, and metabolism related diseases, in which nuclear receptors play a role.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A compound selected from the group consisting of

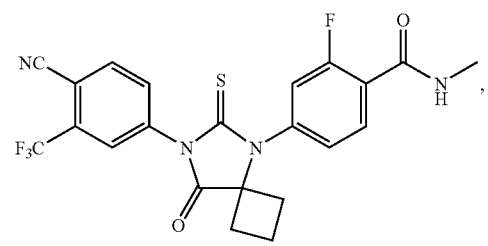

-continued

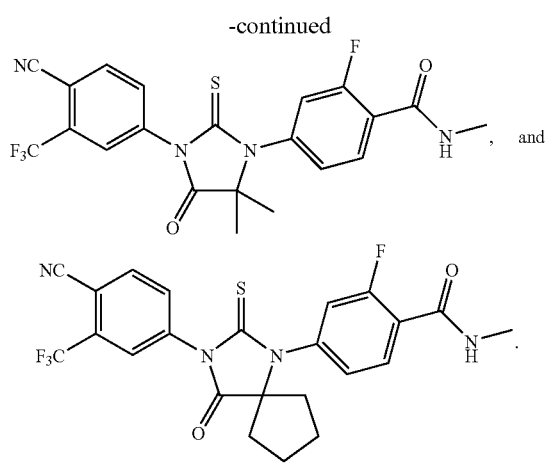

2. The compound of claim 1 having the formula

[RD162]

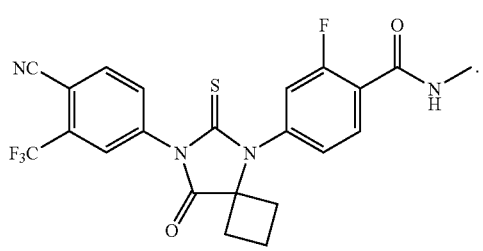

3. The compound of claim 1, having the formula

[RD162′]

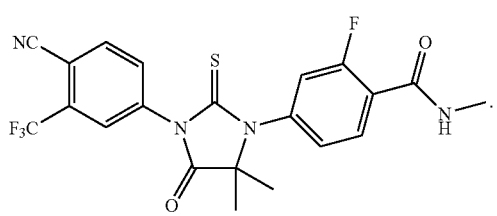

4. The compound of claim 1, having the formula

[RD162″]

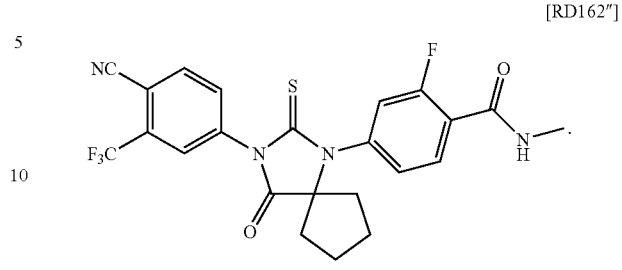

5. A pharmaceutical composition comprising a therapeutically effective amount of a compound according to claim 2, or a pharmaceutically acceptable salt thereof, and a pharmaceutically acceptable carrier or diluent.

6. A pharmaceutical composition comprising a therapeutically effective amount of a compound according to claim 3, or a pharmaceutically acceptable salt thereof, and a pharmaceutically acceptable carrier or diluent.

7. A pharmaceutical composition comprising a therapeutically effective amount of a compound according to claim 4, or a pharmaceutically acceptable salt thereof, and a pharmaceutically acceptable carrier or diluent.

8. A pharmaceutical acceptable salt of a compound according to claim 1.

9. A pharmaceutical composition comprising a therapeutically effective amount of a compound according to claim 1, or a pharmaceutically acceptable salt of a compound of claim 1, and a pharmaceutically acceptable carrier or diluent.

10. A pharmaceutical composition according to claim 9, wherein the compound is dissolved.

11. A pharmaceutical composition according to claim 9, comprising a solvent.

12. A pharmaceutical composition according to claim 9 comprising one or more of dimethylsulfoxide (DSMO), polyethylene glycol (PEG), and water.

13. A pharmaceutical composition according to claim 9, dimethylsulfoxide (DSMO), polyethylene glycol (PEG), and water.

* * * * *

UNITED STATES PATENT AND TRADEMARK OFFICE
CERTIFICATE OF CORRECTION

PATENT NO. : 7,709,517 B2  Page 1 of 2
APPLICATION NO. : 11/433829
DATED : May 4, 2010
INVENTOR(S) : Sawyers et al.

It is certified that error appears in the above-identified patent and that said Letters Patent is hereby corrected as shown below:

Title Page item 75

In the Inventors:

Delete "Derek Welsbie, Northridge, CA (US)"

Delete "Dongwon Yoo, Los Angeles, CA (US)"

Item 56

In the References Cited: FOREIGN PATENT DOCUMENTS:

On page 2, left column, 2nd citation from top of column, replace "EP 033123 A2" with --EP 0331232 A2--

On page 2, left column, 14th citation from top of column, replace "FR 2 845 348 A1 10/2002" with --FR 2 845 384 A1 4/2004--

In the References Cited: OTHER PUBLICATIONS:

On page 2, left column, 17th citation from top of section (leading with "Jones, *Genetics*..."), replace "85:12" with --85:23--

On page 4, right column, 22nd citation from top of column (leading with "Szelei, Androgen-Induced ..."), replace "1999" with --1997--

In the Claims:

Claim 12 should be corrected to the following:

12. A pharmaceutical composition according to claim 9, comprising one or more of dimethylsulfoxide (DSMO) DMSO, polyethylene glycol (PEG), and water.

Signed and Sealed this

Sixteenth Day of November, 2010

David J. Kappos
*Director of the United States Patent and Trademark Office*

CERTIFICATE OF CORRECTION (continued)
U.S. Pat. No. 7,709,517 B2

Claim 13 should be corrected to the following:

13. A pharmaceutical composition according to claim 9, <u>comprising</u> dimethylsulfoxide ~~(DSMO)~~ <u>(DMSO)</u>, polyethylene glycol (PEG), and water.

UNITED STATES PATENT AND TRADEMARK OFFICE
CERTIFICATE OF CORRECTION

PATENT NO. : 7,709,517 B2  Page 1 of 2
APPLICATION NO. : 11/433829
DATED : May 4, 2010
INVENTOR(S) : Sawyers et al.

It is certified that error appears in the above-identified patent and that said Letters Patent is hereby corrected as shown below:

Title Page item 75

In the Inventors:

Delete "Derek Welsbie, Northridge, CA (US)"

Delete "Dongwon Yoo, Los Angeles, CA (US)"

Item 56

In the References Cited: FOREIGN PATENT DOCUMENTS:

On page 2, left column, 2nd citation from top of column, replace "EP 033123 A2" with --EP 0331232 A2--

On page 2, left column, 14th citation from top of column, replace "FR 2 845 348 A1 10/2002" with --FR 2 845 384 A1 4/2004--

In the References Cited: OTHER PUBLICATIONS:

On page 2, left column, 17th citation from top of section (leading with "Jones, *Genetics*..."), replace "85:12" with --85:23--

On page 4, right column, 22nd citation from top of column (leading with "Szelei, Androgen-Induced ..."), replace "1999" with --1997--

In the Claims:

Column 116, lines 41-43,

Claim 12 should be corrected to the following:

12. A pharmaceutical composition according to claim 9, comprising one or more of dimethylsulfoxide ~~(DSMO)~~ DMSO, polyethylene glycol (PEG), and water.

This certificate supersedes the Certificate of Correction issued November 16, 2010.

Signed and Sealed this

Twenty-first Day of December, 2010

David J. Kappos
*Director of the United States Patent and Trademark Office*

CERTIFICATE OF CORRECTION (continued)
U.S. Pat. No. 7,709,517 B2

Column 116, lines 44-46,

Claim 13 should be corrected to the following:

13. A pharmaceutical composition according to claim 9, <u>comprising</u> dimethylsulfoxide <s>(DSMO)</s> <u>(DMSO)</u>, polyethylene glycol (PEG), and water.

UNITED STATES PATENT AND TRADEMARK OFFICE
CERTIFICATE OF CORRECTION

| | | |
|---|---|---|
| PATENT NO. | : 7,709,517 B2 | Page 1 of 1 |
| APPLICATION NO. | : 11/433829 | |
| DATED | : May 4, 2010 | |
| INVENTOR(S) | : Charles L. Sawyers et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 455 days.

Signed and Sealed this
Nineteenth Day of April, 2011

David J. Kappos
*Director of the United States Patent and Trademark Office*